United States Patent
Nakamura et al.

[11] Patent Number: 5,807,850
[45] Date of Patent: Sep. 15, 1998

[54] THERAPEUTIC AGENT FOR OSTEOPOROSIS AND TRIAZEPINE COMPOUND

[75] Inventors: Takeshi Nakamura; Yoshihisa Koga; Masanori Shindo, all of Takatsuki, Japan

[73] Assignee: Japan Tobacco, Inc., Tokyo, Japan

[21] Appl. No.: 836,243

[22] PCT Filed: Nov. 15, 1995

[86] PCT No.: PCT/JP95/02338

§ 371 Date: May 5, 1997

§ 102(e) Date: May 5, 1997

[87] PCT Pub. No.: WO96/16062

PCT Pub. Date: May 30, 1996

[30] Foreign Application Priority Data

Nov. 18, 1994 [JP] Japan .................... 6-309942

[51] Int. Cl.⁶ .................... C07D 487/04; C07D 401/06; C07D 409/12; A61K 31/55
[52] U.S. Cl. .................... 514/183; 540/501; 540/554
[58] Field of Search .................... 540/501, 554; 514/183

[56] References Cited

U.S. PATENT DOCUMENTS

| | | | |
|---|---|---|---|
| 4,094,871 | 6/1978 | Trepanier | 260/239.3 |
| 4,144,233 | 5/1979 | Brittan | 260/239.3 |
| 4,455,307 | 6/1984 | Hester, Jr. | 260/243.3 |
| 5,593,988 | 1/1997 | Tahara et al. | 514/219 |

FOREIGN PATENT DOCUMENTS

| | | |
|---|---|---|
| 0 638 560 A1 | 2/1995 | European Pat. Off. . |
| 50-50397 | 5/1975 | Japan . |
| 93/07129 | 4/1993 | WIPO . |

OTHER PUBLICATIONS

Richter, Pharmazie 46, 701–5 (1991).
P.H. Richter et al., "Synthese und Biologische Aktivität von 5–phenyl–1,3,4–benzotriazepinen", Pharmazie vol. 46, No. 10, Oct. 1991, pp. 701–705.

*Primary Examiner*—Mark L. Berch
*Attorney, Agent, or Firm*—Wenderoth, Lind & Ponack, L.L.P.

[57] ABSTRACT

Therapeutic agents for osteoporosis comprising, as an active ingredient, a triazepine compound of the formula [I]

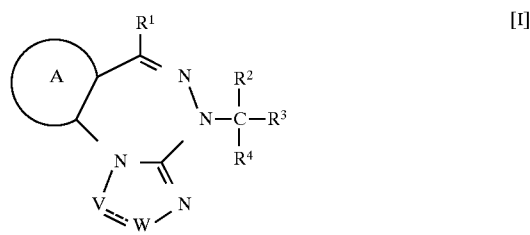

wherein $R^1$ is aryl or heteroaryl; $R^2$ is hydrogen atom, hydroxy, halogen atom or lower alkyl; $R^4$ is hydrogen atom or halogen atom, or $R^2$ and $R^4$ form carbonyl combinedly together with the carbon atom to which they bond; $R^3$ is hydrogen atom, lower alkyl, lower alkoxy, cycloalkyl, aryl, heteroaryl, —X—Y wherein X is —$(CH_2)_m$—, —CO—, —COCH$_2$—, —NH—, —NHCH$_2$—, —CH$_2$NH—, —CH$_2$NHCO—, —OCH$_2$—, —$(CH_2)_n$O— or —CH$_2$S— and Y is halogen atom, cycloallyl, aryl or heteroaryl; and A is benzene ring or thiophene ring, or a salt thereof, novel triazepine compounds, and intermediate triazepine compounds for producing these triazepine compounds. The triazepine compounds of the formula [I] have superior bone resorption-inhibitory action and are useful as therapeutic agents for osteoporosis.

32 Claims, No Drawings

THERAPEUTIC AGENT FOR OSTEOPOROSIS AND TRIAZEPINE COMPOUND

TECHNICAL FIELD

The present invention relates to therapeutic agents for osteoporosis containing, as an active ingredient, a certain triazepine compound having superior inhibitory effect on bone resorption, novel triazepine compounds and intermediate compounds useful for producing such triazepine compounds.

BACKGROUND ART

Osteoporosis is a syndrome representing symptoms wherein bone mass per unit volume decreases abnormally without changes in chemical composition (proportion between organic substance and inorganic substance) of the bone itself, and is physiologically characterized by a decrease in the amounts of protein, calcium and phosphorus in the bone. The bone mass also decreases due to the physiological aging. Osteoporosis is defined to be a disease which shows greater degree of decrease in bone mass than that caused by physiological aging, and which is associated with clinical symptoms such as dorsolumbar pain, pathologic fracture and deformation of vertebral body.

Osteoporosis increases in number with aging and generally affects vertebra to cause dorsolumbar pain and shortened stature. In particularly advanced cases, long bone is also affected to sometimes cause fracture. The cause of the femoral fracture found in aged people is said to be mostly caused by senile osteoporosis. The cause of the osteoporosis is divergent and examples thereof include abnormal endocrine including menopause, nutritional disorder and so on.

The therapeutic agents for osteoporosis heretofor known are vitamin preparations, calcium preparations, calcitonin preparations, bisphosphonate preparations and isoflavone preparations. These therapeutic agents are not necessarily satisfactory from the aspects of side-effects and the method of use. Accordingly, there is a strong demand for the development of a therapeutic agent for osteoporosis which can exhibit ensured effects, which is highly safe and which can be used easily.

A recent report teaches the usefulness, as therapeutic agents for osteoporosis, of benzothiadiazine derivatives and benzothiadiazepine derivatives having completely different chemical structures from the above-mentioned preparations (Japanese Patent Unexamined Publication No. 183572/1989). The inventors of the present invention also found the bone resorption-inhibitory action of triazolobenzothiadiazine derivatives and triazolobenzothiadiazepine derivatives and filed the finding as a patent application (Japanese Patent Application No. 357369/1992). In addition, the present inventors have found the bone resorption-inhibitory action of the compounds having a diazepine skeleton and filed a patent application thereto (W093/07129). Yet, these compounds are not satisfactory in terms of activity and are faced with difficulties in that they cannot fully meet the above-mentioned requirements, that optical resolution is difficult due to the presence of asymmetric carbon in the compound, and that they are associated with practical problems caused by long production steps.

On the other hand, certain compounds having a triazepine skeleton have been reported to have anticonvulsive action, muscle-relaxing action, sedative action, anti-anxiety action and ataractic action. However, a bone resorption-inhibitory action thereof has not been reported (U.S. Pat. Nos. 4,144,233, 5,091,381, 3,891,666 and 3,880,878).

DISCLOSURE OF THE INVENTION

It is therefore an object of the present invention to provide a novel therapeutic agent for osteoporosis.

It is another object of the present invention to provide a novel compound useful as an active ingredient of a therapeutic agent for osteoporosis.

It is still another object of the present invention to provide an intermediate compound for producing a compound useful as an active ingredient of a therapeutic agent for osteoporosis.

It is further object of the present invention to provide a method for treating osteoporosis and use of triazepine compounds.

The present inventors have investigated and now found that a triazepine compound of the following formula [I] has marked inhibitory action on bone resorption, which resulted in the completion of the present invention.

Accordingly, the present invention relates to a therapeutic agent for osteoporosis which contains, as an active ingredient, a triazepine compound of the following formula [I] or a pharmaceutically acceptable salt thereof. The present invention also relates to a novel triazepine compound of the following formula [I'] which is useful as such medicament and pharmaceutically acceptable salts thereof. The present invention moreover relates to an intermediate compound useful for producing these triazepine compounds.

The present invention further relates to a method for treating osteoporosis, comprising administering a triazepine compound of the following formula [I] and use of said triazepine compound for producing a therapeutic agent for osteoporosis. More particularly, the present invention provides the following (1) to (34).

(1) A therapeutic agent for osteoporosis, comprising, as an active ingredient, a triazepine compound of the formula [I]

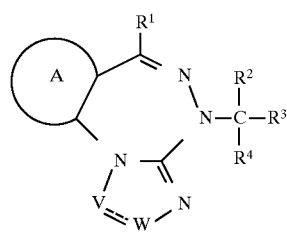

[I]

wherein $R^1$ is an optionally substituted aryl or an optionally substituted heteroaryl;

$R^2$ is a hydrogen atom, a hydroxy, a halogen atom or a lower alkyl;

$R^4$ is a hydrogen atom or a halogen atom, or $R^2$ and $R^4$ form carbonyl combinedly together with the carbon atom to which they are bonded;

$R^3$ is a hydrogen atom, a lower alkyl, a lower alkoxy, a cycloalkyl, an optionally substituted aryl, an optionally substituted heteroaryl, —$CR^5$=$CR^6R^7$ wherein $R^5$, $R^6$ and $R^7$ are the same or different and each is hydrogen atom, halogen atom, lower alkyl or optionally substituted aryl, a group of the formula

-continued

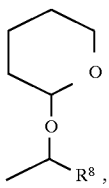

—COOR⁸, CONHR⁸,

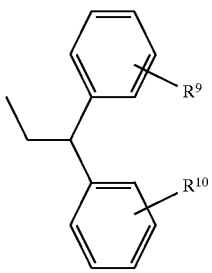

or

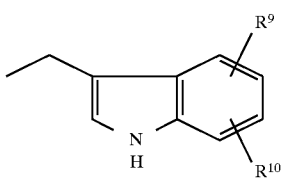

wherein R⁸ is hydrogen atom, lower alkyl, cycloalkyl, optionally substituted aryl, aralkyl or optionally substituted heteroaryl, and R⁹ and R¹⁰ are the same or different and each is hydrogen atom, lower alkyl, lower alkoxy, hydroxy, halogen atom, nitro or amino, —X—Y wherein X is —(CH₂)ₘ— wherein m is integer of 1 to 4, —CO—, —COCH₂—, —NH—, —NHCH₂—, —CH₂NH—, —CH₂NH—, —OCH₂—, —(CH₂)ₘO— wherein n is an integer of 1 to 4, or —CH₂S—, and Y is halogen atom, cycloalkyl, optionally substituted aryl or optionally substituted heteroaryl, or —OR¹⁸ wherein R¹⁸ is optionally substituted aryl;

ring A is a ring selected from the following rings

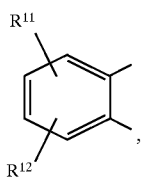

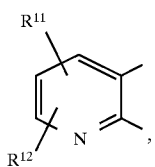

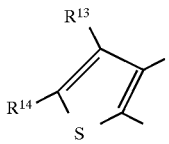

and

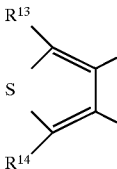

wherein R¹¹ and R¹² are the same or different and each is hydrogen atom, halogen atom, lower alkyl (said lower alkyl is optionally substituted by halogen atom, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl), lower alkenyl, aralkyl, aralkyl substituted by alkyl, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl, R¹³ and R¹⁴ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and

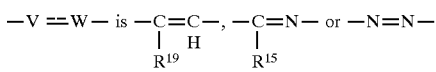

wherein R¹⁵ is lower alkyl and R¹⁹ is hydrogen atom or lower
alkyl, or a pharmaceutically acceptable salt thereof.

(2) A therapeutic agent for osteoporosis of the above (1), wherein, in the formula [I], the ring A is

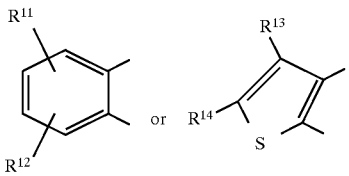

wherein R¹¹, R¹², R¹³ and R¹⁴ are as defined in the above (1).

(3) A therapeutic agent for osteoporosis of the above (2), wherein, in the formula [I],

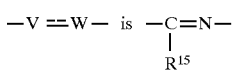

wherein R¹⁵ is a lower alkyl.

(4) A therapeutic agent for osteoporosis of the above (3), wherein, in the formula [I], R¹ is an optionally substituted aryl.

(5) A therapeutic agent for osteoporosis of the above (4), wherein, in the formula [I], R¹ is an optionally substituted phenyl.

(6) A therapeutic agent for osteoporosis of the above (5), wherein, in the formula [I], R² and R⁴ are both hydrogen atom.

(7) A therapeutic agent for osteoporosis of the above (1), comprising, as an active ingredient, a triazepine compound which is a member selected from the group consisting of 6-(4-chlorophenyl)-4-(4-methoxybenzyl)-1-methyl-4H-2,3,4,5,10b-pentaazabenz[e]azulene,
6-(4-chlorophenyl)-4-(3,4-dimethoxybenzyl)-1-methyl-4H-2,3,4,5,10b-pentaazabenz[e]azulene,
4-(4-methoxybenzyl)-1-methyl-6-phenyl-4H-2,3,4,5,10b-pentaazabenz-[e]azulene,
4-(4-methoxybenzyl)-1,9-dimethyl-6-phenyl-4H-2,3,4,5,10b-pentaazabenz[e]azulene,
8-chloro-4-(4-methoxybenzyl)-1-methyl-6-phenyl-4H-2,3,4,5,10b-pentaazabenz[e]azulene,
4-(4-methoxybenzyl)-1-methyl-8-nitro-6-phenyl-4H-2,3,4,5,10b-pentaazabenz[e]azulene,
4-(4-methoxybenzyl)-1-methyl-6-(4-methylphenyl)-4H-2,3,4,5,10b-pentaazabenz[e]azulene,
8-chloro-6-(2-chlorophenyl)-4-(4-methoxybenzyl)-1-methyl-4H-2,3,4,5,10b-pentaazabenz[e]azulene,
4-(4-chlorophenyl)-6-(4-methoxybenzyl)-2,3,9-trimethyl-6H-5,6,7,8,9a-pentaazathien[2,3-e]azulene,
4-(4-chlorophenyl)-2-ethyl-6-(4-methoxybenzyl)-9-methyl-6H-5,6,7,8,9a-pentaazathien[2,3-e]azulene,
6-(4-methoxybenzyl)-2,9-dimethyl-4-phenyl-6H-5,6,7,8,9a-pentaazathien[2,3-e]azulene,
6-(4-methoxybenzyl)-2,3,9-trimethyl-4-phenyl-6H-5,6,7,8,9a-pentaazathien[2,3-e]azulene,
2-ethyl-6-(4-methoxybenzyl)-9-methyl-4-phenyl-6H-5,6,7,8,9a-pentaazathien[2,3-e]azulene,
6-(4-methoxybenzyl)-4-(4-methoxyphenyl)-2,3,9-trimethyl-6H-5,6,7,8,9a-pentaazathien[2,3-e]azulene,
6-(4-chlorophenyl)-1methyl-4-(pyridin-3-methyl)-4H-2,3,4,5,10b-pentaazabenz[e]azulene,
4-(2-chlorophenyl)-2,3,9-trimethyl-6-(pyridin-4-ylmethyl)-6H-5,6,7,8,9a-pentaazathien[2,3-e]azulene,
6-(4-chlorophenyl)-4-(3-fluorobenzyl)-1-methyl-4H-2,3,4,5,10b-pentaazabenz[e]azulene,
6-(4-chlorophenyl)-4-(2-fluorobenzyl)-1-methyl-4H-2,3,4,5,10b-pentaazabenz[e]azulene,
6-(4-chlorophenyl)-4-(3-fluorobenzyl)-1-methyl-4H-2,3,4,5,10b-pentaazabenz[e]azulene,
6-(4-chlorophenyl)-4-(4-fluorobenzyl)-1-methyl-4H-2,3,4,5,10b-pentaazabenz[e]azulene,
6-(4-chlorophenyl)-4-(2,4-difluorobenzyl)-1-methyl-4H-2,3,4,5,10b-pentaazabenz[e]azulene,
6-(4-chlorophenyl)-4-(2,5-difluorobenzyl)-1-methyl-4H-2,3,4,5,10b-pentaazabenz[e]azulene,
6-(4-chlorophenyl)-4-(3,5-difluorobenzyl)-1-methyl-4H-2,3,4,5,10b-pentaazabenz[e]azulene,
6-(4-chlorophenyl)-4-(3,4-difluorobenzyl)-1-methyl-4H-2,3,4,5,10b-pentaazabenz[e]azulene,
6-(4-chlorophenyl)-1-methyl-4-(2-trifluoromethylbenzyl)-4H-2,3,4,5,10b-pentaazabenz[e]azulene,
6-(4-chlorophenyl)-1-methyl-4-(4-trifluoromethylbenzyl)-4H-2,3,4,5,10b-pentaazabenz[e]azulene,
6-(4-chlorophenyl)-1-methyl-4-(3-trifluoromethylbenzyl)-4H-2,3,4,5,10b-pentaazabenz[e]azulene,
6-(4-chlorophenyl)-1-methyl-4-(4-trifluoromethoxybenzyl)-4H-2,3,4,5,10b-pentaazabenz[e]azulene,
6-(4chlorophenyl)-1-methyl-4-(3-nitrobenzyl)-4H-2,3,4,5,10b-pentaazabenz[e]azulene,
4-(2-chlorobenzyl)-6-(4-chlorophenyl)-1-methyl-4H-2,3,4,5,10b-pentaazabenz[e]azulene,
4-(3-chlorobenzyl)-6-(4-chlorophenyl)-1-methyl-4H-2,3,4,5,10b-pentaazabenz[e]azulene,
4-(4-chlorobenzyl)-6-(4-chlorophenyl)-1-methyl-4H-2,3,4,5,10b-pentaazabenz[e]azulene,
6-(4-chlorophenyl)-4-(2-cyanobenzyl)-1-methyl-4H-2,3,4,5,10b-pentaazabenz[e]azulene,
6-(4-chlorophenyl)-4-(4cyanobenzyl)-1-methyl-4H-2,3,4,5,10b-pentaazabenz[e]azulene,
6-(4-chlorophenyl)-4-(2-methoxybenzyl)-1-methyl-4H-2,3,4,5,10b-pentaazabenz[e]azulene,
6—(4-chlorophenyl)-4-(3-methoxybenzyl)-1-methyl-4H-2,3,4,5,10b-pentaazabenz[e]azulene,
6-(4-chlorophenyl)-4-(4-methoxybenzyl)-1-methyl-4H-2,3,4,5,10b-pentaazabenz[e]azulene,
6-(4-chlorophenyl)-4-(2,5-dimethoxybenzyl)-1-methyl-4H-2,3,4,5,10b-pentaazabenz[e]azulene,
6-(4-chlorophenyl)-1-methyl-4-(3,4,5-trimethoxybenzyl)-4H-2,3,4,5,10b-pentaazabenz[e]azulene,
4-(5-acetyl-2-methoxybenzyl)-6-(4-chlorophenyl)-1-methyl-4H-2,3,4,5,10b-pentaazabenz[e]azulene,
6-(4-chlorophenyl)-1-methyl-4-(3,4-methylenedioxybenzyl)-4H-2,3,4,5,10b-pentaazabenz[e]azulene,
4-(2-chloro-4,5-methylenedioxybenzyl)-6-(4-chlorophenyl)-1-methyl-4H-2,3,4,5,10b-pentaazabenz[e]azulene,
6-(4-chlorophenyl)-4-(2-methoxy-5-nitrobenzyl)-1-methyl-4H-2,3,4,5,10b-pentaazabenz[e]azulene,
6-(4-chlorophenyl)-4-(4-methoxy-3-nitrobenzyl)-1-methyl-4H-2,3,4,5,10b-pentaazabenz[e]azulene,
4-(3-chloro-4-methoxybenzyl)-6-(4-chlorophenyl)-1-methyl-4H-2,3,4,5,10b-pentaazabenz[e]azulene,
6-(4-chlorophenyl)-4-(3,5-dichloro-4-methoxybenzyl)-1-methyl-4H-2,3,4,5,10b-pentaazabenz[e]azulene,
6-(4-chlorophenyl)-1-methyl-4-(2-methylbenzyl)-4H-2,3,4,5,10b-pentaazabenz[e]azulene,
6-(4-chlorophenyl)-1-methyl-4-(3-methylbenzyl)-4H-2,3,4,5,10b-pentaazabenz[e]azulene,
6-(4-chlorophenyl)-1-methyl-4-(4-methylbenzyl)-4H-2,3,4,5,10b-pentaazabenz[e]azulene,
4-(4-tert-butylbenzyl)-6-(4-chlorophenyl)-1-methyl-4H-2,3,4,5,10b-pentaazabenz[e]azulene,
6-(4-chlorophenyl)-1-methyl-4-(naphthalen-1-ylmethyl)-4H-2,3,4,5,10b-pentaazabenz[e]azulene,
6-(4-chlorophenyl)-1-methyl-4-(naphthalen-2-ylmethyl)-4H-2,3,4,5,10b-pentaazabenz[e]azulene,
4-(4-benzyloxybenzyl)-6-(4-chlorophenyl)-1-methyl-4H-2,3,4,5,10b-pentaazabenz[e]azulene,
4-benzyl-6-(4-chlorophenyl)-1-methyl-4H-2,3,4,5,10b-pentaazabenz[e]azulene,
6-(4-chlorophenyl)-1-methyl-4-(4-phenylbenzyl)-4H-2,3,4,5,10b-pentaazabenz[e]azulene,
4-(4-chlorophenoxymethyl)-6-(4-chlorophenyl)-1-methyl-4H-2,3,4,5,10b-pentaazabenz[e]azulene,
6-(4-chlorophenyl)-1-methyl-4-(pyridin-2-ylmethyl)-4H-2,3,4,5,10b-pentaazabenz[e]azulene,
6-(4-chlorophenyl)-1-methyl-4-(pyridin-3-ylmethyl)-4H-2,3,4,5,10b-pentaazabenz[e]azulene,
6-(4-chlorophenyl)-4-[2-(indol-3-yl)ethyl]-1-methyl-4H-2,3,4,5,10b-pentaazabenz[e]azulene,
6-(4-chlorophenyl)-4-(2-methyl-1,3-thiazol-4-ylmethyl)-1-methyl-4H-2,3,4,5,10b-pentaazabenz[e]azulene,
6-(4-chlorophenyl)-4-(5-chlorothiophen-2-ylmethyl)-1-methyl-4H-2,3,4,5,10b-pentaazabenz[e]azulene,
6-(4-chlorophenyl)-1-methyl-4-(3,5-dimethylisoxazol-4-ylmethyl)-4H-2,3,4,5,10b-pentaazabenz[e]azulene,
6-(4-chlorophenyl)-1-methyl-4-phenethyl-4H-2,3,4,5,10b-pentaazabenz[e]azulene,
6-(4-chlorophenyl)-1-methyl-4-(3-phenylpropyl)-4H-2,3,4,5,10b-pentaazabenz[e]azulene,
6-(4-chlorophenyl)-4-(3,3-diphenylpropyl)-1-methyl-4H-2,3,4,5,10b-pentaazabenz[e]azulene,
6-(4chlorophenyl)-4-cyclopropylmethyl-1-methyl-4H-2,3,4,5,10b-pentaazabenz[e]azulene,
6-(4chlorophenyl)-4-cyclohexylmethyl-1-methyl-4H-2,3,4,5,10b-pentaazabenz[e]azulene, 6-(4-chlorophenyl)-4-(2-cyclohexylethyl)-1-methyl-4H-2,3,
4,5,10b-pentaazabenz[e]azulene,
6-(4-chlorophenyl)-1-methyl-4-(3-phenyl-2-propenyl)-4H-
2,3,4,5,10b-pentaazabenz[e]azulene,
4-allyl-6-(4-chlorophenyl)-1-methyl-4H-2,3,4,5,10b-
pentaazabenz[e]azulene,
6-(4-chlorophenyl)-1-methyl-4-(2-methyl-2-propenyl)-4H-
2,3,4,5,10b-pentaazabenz[e]azulene,
6-(4-chlorophenyl)-4-(2-chloro-2-propenyl)-1-methyl-4H-
2,3,4,5,10b-pentaazabenz[e]azulene,
4-(2-bromo-2-propenyl)-6-(4-chlorophenyl)-1-methyl-4H-
2,3,4,5,10b-pentaazabenz[e]azulene,
6-(4-chlorophenyl)-4-(2,3-dichloro-2-propenyl)-1-methyl-
4H-2,3,4,5,10b-pentaazabenz[e]azulene,
6-(4-chlorophenyl)-4-(3,4-dibenzyloxybenzyl)-11-methyl-
4H-2,3,4,5,10b-pentaazabenz[e]azulene,
4-benzyloxymethyl-6-(4-chlorophenyl)-1-methyl-4H-2,3,4,
5,10b-pentaazabenz[e]azulene,
6-(4-chlorophenyl)-1-methyl-4-(3-phenoxypropyl)-4H-2,3,
4,5,10b-pentaazabenz[e]azulene,
6-(4-chlorophenyl)-4-(3,3-dichloro-2-propenyl)-1-methyl-
4H-2,3,4,5,10b-pentaazabenz[e]azulene,
6-(4-chlorophenyl)-4-(4-methoxy-3-methylbenzyl)-1-
methyl-4H-2,3,4,5,10b-pentaazabenz[e]azulene,
6-(4-chlorophenyl)-1-methyl-4-(pyridin-4-ylmethyl)-4H-2,
3,4,5,10b-pentaazabenz[e]azulene,
6-(4-chlorophenyl)-1-methyl-4-(4-methylsulfonylbenzyl)-
4H-2,3,4,5,10b-pentaazabenz[e]azulene,
6-(4-chlorophenyl)-1-methyl-4-(4-nitrobenzyl)-4H-2,3,4,5,
10b-pentaazabenz[e]azulene,
6-(4chlorophenyl)-4-(2,6-dichloropyridin-4-ylmethyl)-1-
methyl-4H-2,3,4,5,10b-pentaazabenz[e]azulene,
6-(4-chlorophenyl).-4-(2,2,2-trifluoroethyl)-1-methyl-4H-2,
3,4,5,10b-pentaazabenz[e]azulene,
6-(4-chlorophenyl)-4-(3,5-dinitrobenzyl)-1-methyl-4H-2,3,
4,5,10b-pentaazabenz[e]azulene,
8-chloro-1-methyl-6-phenyl-4-(pyridin-4-ylmethyl)-4H-2,
3,4,5,10b-pentaazabenz[e]azulene,
8-chloro-1-methyl-6-phenyl-4-(pyridin-3-ylmethyl)-4H-2,
3,4,5,10b-pentaazabenz[e]azulene,
1-methyl-6-phenyl-4-(pyridin-3-ylmethyl)-4H-2,3,4,5,10b-
pentaazabenz[e]azulene,
1-methyl-6-phenyl-4-(pyridin-4-ylmethyl)-4H-2,3,4,5,10b-
pentaazabenz[e]azulene,
1,9-dimethyl-6-phenyl-4-(pyridin-3-ylmethyl)-4H-2,3,4,5,
10b-pentaazabenz[e]azulene,
1,9-dimethyl-6-phenyl-4-(pyridin-4-ylmethyl)-4H-2,3,4,5,
10b-pentaazabenz[e]azulene,
4-(3-cyanobenzyl)-1,9-dimethyl-6-phenyl-4H-2,3,4,5,10b-
pentaazabenz[e]azulene,
1-methyl-8-nitro-6-phenyl-4-(pyridin-3-ylmethyl)-4H-2,3,
4,5,10b-pentaazabenz[e]azulene,
1-methyl-8-nitro-6-phenyl-4-(pyridin-4-ylmethyl)-4H-2,3,
4,5,10b-pentaazabenz[e]azulene,
1-methyl-6-(4-methylphenyl)-4-(pyridin-4-ylmethyl)-4H-2,
3,4,5,10b-pentaazabenz[e]azulene,
4-(3cyanobenzyl)-1-methyl-6-(4-methylphenyl)-4H-2,3,4,
5,10b-pentaazabenz[e]azulene,
8-chloro--(2chlorophenyl)-1-methyl-4-(pyridin-3-ylmethyl)
-4H- 2,3,4,5,10b-pentaazabenz[e]azulene,
8-chloro-6-(2-chlorophenyl)-1-methyl-4-(pyridin-4-
ylmethyl)-4H-2,3,4,5,10b-pentaazabenz[e]azulene,
4-(4-chlorophenyl)-2,3,9-trimethyl-6-(pyridin-3-ylmethyl)-
6H-5,6,7,8,9a-pentaazathien[2,3-e]azulene,
4-(4-chlorophenyl)-2,3,9-trimethyl-6-(pyridin-4-ylmethyl)-
6H-5,6,7,8,9a-pentaazathien[2,3-e]azulene,
4-(4-chlorophenyl)-2-ethyl-9-methyl-6-(pyridin-3-
ylmethyl)-6H-5,6,7,8,9a-pentaazathien[2,3-e]azulene, 4-(4-chlorophenyl)-2-ethyl-9-methyl-6-(pyridin-4-
ylmethyl)-6H-5,6,7,8,9a-pentaazathien[2,3-e]azulene,
2,9-dimethyl-4-phenyl-6-(pyridin-3-ylmethyl)-6H-5,6,7,8,
9a-pentaazathien[2,3-e]azulene,
2,9-dimethyl-4-phenyl-6-(pyridin-4-ylmethyl)-6H-5,6,7,8,
9a-pentaazathien[2,3-e]azulene,
2,3,9-trimethyl-4-phenyl-6-(pyridin-3-ylmethyl)-6H-5,6,7,
8,9a-pentaazathien[2,3-e]azulene,
2,3,9-trimethyl-4-phenyl-6-(pyridin-4-ylmethyl)-6H-5,6,7,
8,9a-pentaazathien[2,3-e]azulene,
2-ethyl-9-methyl-4-phenyl-6-(pyridin-3-ylmethyl)-6H-5,6,
7,8,9a-pentaazathien[2,3-e]azulene,
2-ethyl-9-methyl-4-phenyl-6-(pyridin-4-ylmethyl)-6H-5,6,
7,8,9a-pentaazathien[2,3-e]azulene,
4-(4-methoxyphenyl)-2,3,9-trimethyl-6-(pyridin-3-
ylmethyl)-6H-5,6,7,8,9a-pentaazathien[2,3-e]azulene,
4-(4-methoxyphenyl)-2,3,9-trimethyl-6-(pyridin-4-
ylmethyl)-6H-5,6,7,8,9a-pentaazathien[2,3-e]azulene,
6-(4-chlorophenyl)-1-methyl-4-(2-nitrobenzyl)-4H-2,3,4,5,
10b-pentaazabenz[e]azulene,
6-(4-chlorophenyl)-4-ethoxycarbonylmethyl-1-methyl-4H-
2,3,4,5,10b-pentaazabenz[e]azulene,
[6-(4-chlorophenyl)-1-methyl-4H-2,3,4,5,10b-pentaazabenz
[e]azulene-4-yl]acetic acid,
6-(4-chlorophenyl)-1-methyl-4-phenylcarbamoylmethyl-
4H-2,3,4,5,10b-pentaazabenz[e]azulene,
6-(4-chlorophenyl)-1-methyl-4-(4-
methylphenylcarbamoylmethyl)-4H-2,3,4,5,10b-
pentaazabenz[e]azulene,
6-(4-chlorophenyl)-4-(2-methoxyphenylcarbamoylmethyl)-
1-methyl-4H-2,3,4,5,10b-pentaazabenz[e]azulene,
6-(4-chlorophenyl)-4-(2,5-
dimethoxyphenylcarbamoylmethyl)-1-methyl-4H-2,3,4,
5,10b-pentaazabenz[e]azulene,
4-(4-chloro-2,5-dimethoxyphenylcarbamoylmethyl)-6-(4-
chlorophenyl)-1-methyl-4H-2,3,4,5,10b-pentaazabenz[e]
azulene,
6-(4-chlorophenyl)-1-methyl-4-(naphthalen-1-
ylcarbamoylmethyl)-4H-2,3,4,5,10b-pentaazabenz[e]
azulene,
6-(4-chlorophenyl)-1-methyl-4-(pyridin-3-
ylcarbamoylmethyl)-4H-2,3,4,5,10b-pentaazabenz[e]
azulene,
6-(4-chlorophenyl)-4-(cyclohexylcarbamoylmethyl)-1-
methyl-4H-2,3,4,5,10b-pentaazabenz[e]azulene,
6-(4-chlorophenyl)-1-methyl-4-n-propylcarbamoylmethyl-
4H-2,3,4,5,10b-pentaazabenz[e]azulene,
4-bromoacetyl-6-(4-chlorophenyl)-1-methyl-4H-2,3,4,5,
10b-pentaazabenz[e]azulene,
6-(4-chlorophenyl)-4-(2-methoxyphenylaminoacetyl)-11-
methyl-4H-2,3,4,5,10b-pentaazabenz[e]azulene,
6-(4-chlorophenyl)-1-methyl-4-phenylaminoacetyl-4H-2,3,
4,5,10b-pentaazabenz[e]azulene,
6-(4-chlorophenyl)-1-methyl-4-(4-
methylphenylaminoacetyl)-4H-2,3,4,5,10b-pentaazabenz
[e]azulene,
6-(4-chlorophenyl)-4-(3-fluorophenylaminoacetyl)-1-
methyl-4H-2,3,4,5,10b-pentaazabenz[e]azulene,
6-(4-chlorophenyl)-4-(2,5-dimethoxyphenylaminoacetyl)-
1-methyl-4H-2,3,4,5,10b-pentaazabenz[e]azulene,
6-(4-chlorophenyl)-1-methyl-4-phenylthioacetyl-4H-2,3,4,
5,10b-pentaazabenz[e]azulene,
6-(4-chlorophenyl)-1-methyl-4-phenylacetyl-4H-2,3,4,5,
10b-pentaazabenz[e]azulene,
6-(4-chlorophenyl)-1-methyl-4-phenyloxalyl-4H-2,3,4,5,
10b-pentaazabenz[e]azulene,
6-(4-chlorophenyl)-4-ethoxymethyl-1-methyl-4H-2,3,4,5,
10b-pentaazabenz[e]azulene,

[6-(4-chlorophenyl)-1-methyl-4H-2,3,4,5,10b-pentaazabenz[e]azulene-4-ylmethyl]-phenylamine,
4-benzylcarbamoyl-6-(4-chlorophenyl)-1-methyl-4H-2,3,4,5,10b-pentaazabenz[e]azulene,
6-(4-chlorophenyl)-1-methyl-4-(3-methylphenylcarbamoyl)-4H-2,3,4,5,10b-pentaazabenz[e]azulene,
6-(4-chlorophenyl)-4-(4-hydroxybenzyl)-1-methyl-4H-2,3,4,5,10b-pentaazabenz[e]azulene,
6-(4-chlorophenyl)-4-(3,4-dihydroxybenzyl)-1-methyl-4H-2,3,4,5,10b-pentaazabenz[e]azulene,
6-(4-chlorophenyl)-4-(4-ethoxybenzyl)-1-methyl-4H-2,3,4,5,10b-pentaazabenz[e]azulene,
6-(4-chlorophenyl)-1-methyl-4-(4-methylsulfonylphenyl)hydroxymethyl-4H-2,3,4,5,10b-pentaazabenz[e]azulene,
4-(4-aminobenzyl)-6-(4-chlorophenyl)-1-methyl-4H-2,3,4,5,10b-pentaazabenz[e]azulene,
6-(4-chlorophenyl)-4-(4-formylaminobenzyl)-1-methyl-4H-2,3,4,5,10b-pentaazabenz[e]azulene,
4-(4-acetylaminobenzyl)-6-(4-chlorophenyl)-1-methyl-4H-2,3,4,5,10b-pentaazabenz[e]azulene,
6-(4-chlorophenyl)-4-(4-methylsulfonylaminobenzyl)-1-methyl-4H-2,3,4,5,10b-pentaazabenz[e]azulene,
4-[4-bis(methylsulfonyl)aminobenzyl]-6-(4-chlorophenyl)-4H-2,3,4,5,10b-pentaazabenz[e]azulene,
6-(4-chlorophenyl)-4-(4-dimethylaminobenzyl)-11-methyl-4H-2,3,4,5,10b-pentaazabenz[e]azulene,
6-(4-chlorophenyl)-4-(2-hydroxy-2-phenylethyl)-1-methyl-4H-2,3,4,5,10b-pentaazabenz[e]azulene,
6-(4-chlorophenyl)-4-(2-oxo-2-phenylethyl)-1-methyl-4H-2,3,4,5,10b-pentaazabenz[e]azulene,
6-(4-chlorophenyl)-1-methyl-4-[3-phenyl-2-(tetrahydropyran-2-yloxy)-propyl]-4H-2,3,4,5,10b-pentaazabenz[e]azulene,
6-(4-chlorophenyl)-4-[2-(2-methoxyphenyl)-2-(tetrahydropyran-2-yloxy)-ethyl]-1-methyl-4H-2,3,4,5,10b-pentaazabenz[e]azulene,
6-(4-chlorophenyl)-4-(2-hydroxy-3-phenylpropyl)-1-methyl-4H-2,3,4,5,10b-pentaazabenz[e]azulene,
6-(4-chlorophenyl)-4-(2-oxo-3-phenylpropyl)-1-methyl-4H-2,3,4,5,10b-pentaazabenz[e]azulene,
6-(4-chlorophenyl)-4-[2-(4-chlorophenyl)-2-oxoethyl]-1-methyl-4H-2,3,4,5,10b-pentaazabenz[e]azulene,
6-(4-chlorophenyl)-1-methyl-4-[2-(4-methylphenyl)-2-oxoethyl]-4H-2,3,4,5,10b-pentaazabenz[e]azulene,
6-(4-chlorophenyl)-4-[2-(2-methoxyphenyl)-2-oxoethyl]-1-methyl-4H-2,3,4,5,10b-pentaazabenz[e]azulene,
6-(4-chlorophenyl)-4-[2-(2,5-dimethoxyphenyl)-2-oxoethyl)-1-methyl-4H-2,3,4,5,10b-pentaazabenz[e]azulene,
6-(4-chlorophenyl)-4-[3-(2-methoxyphenyl)-2-oxopropyl]-1-methyl-4H-2,3,4,5,10b-pentaazabenz[e]azulene,
6-(4-chlorophenyl)-4-[3-(2,5-dimethoxyphenyl)-2-oxopropyl]-1-methyl-4H-2,3,4,5,10b-pentaazabenz[e]azulene,
4-benzyl-6-(4-chlorophenyl)-1-methyl-4H-2,3,4,5,10b-pentaazabenz[e]azulene, and
6-(4-chlorophenyl)-4-(4-methoxybenzyl)-4H-3,4,5,10b-tetraazabenz[e]azulene.

or a pharmaceutically acceptable salt thereof.

(8) Triazepine compounds of the formula [I']

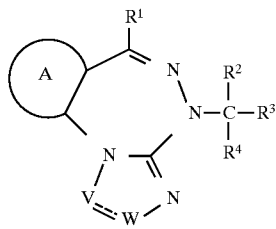

wherein
$R^1$ is an optionally substituted aryl or an optionally substituted heteroaryl;
$R^2$ is a hydrogen atom, a hydroxy or a halogen atom;
$R^4$ is a hydrogen atom or a halogen atom, or $R^2$ and $R^4$ form carbonyl combinedly together with the carbon atom to which they are bonded;
$R^3$ is a lower alkoxy, a cycloalkyl, an optionally substituted aryl, an optionally substituted heteroaryl, —$CR^5$=$CR^6R^7$ wherein $R^5$, $R^6$ and $R^7$ are the same or different and each is hydrogen atom, halogen atom, lower alkyl or optionally substituted aryl, a group of the formula

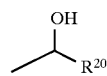

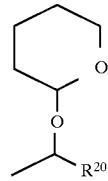

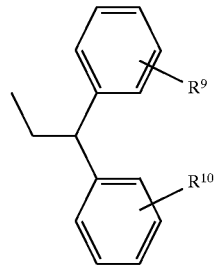

or

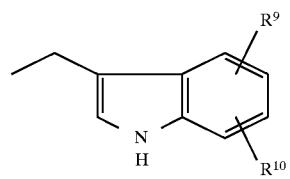

wherein $R^8$ is hydrogen atom, lower alkyl, cycloalkyl, optionally substituted aryl, aralkyl or optionally substituted heteroaryl, $R^9$ and $R^{10}$ are the same or different and each is hydrogen atom, lower alkyl, lower alkoxy, hydroxy, halogen atom, nitro or amino, $R^{20}$ is optionally substituted aryl, aralkyl or optionally substituted heteroaryl, —X—Y wherein X is —$(CH_2)_m$— wherein m is an integer of 1 to 4, —CO—, —COCH$_2$—, —NH—, —NHCH$_2$—, —CH$_2$NHCO—, —OCH$_2$—, —$(CH_2)_m$O— wherein n is an integer of 1 to 4 or —CH$_2$S—, and Y is halogen atom, cycloalkyl, optionally substituted aryl or optionally substituted heteroaryl, or —OR$^{18}$ wherein R$^{18}$ is optionally substituted aryl;

ring A is a ring selected from the following rings

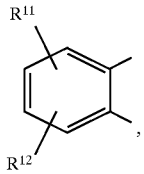

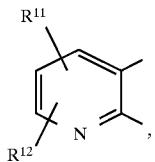

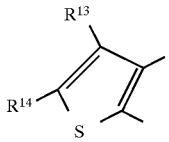

and

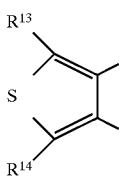

wherein R$^{11}$ and R$^{12}$ are the same or different and each is hydrogen atom, halogen atom, lower alkyl (said lower alkyl is optionally substituted halogen atom, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl), lower alkenyl, aralkyl, aralkyl substituted by alkyl, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl, R$^{13}$ and R$^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and

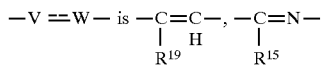

wherein R$^{15}$ is lower alkyl and R$^{19}$ is hydrogen atom or lower alkyl, and pharmaceutically acceptable salts thereof.

(9) Triazepine compounds of the above (8), wherein the ring A is

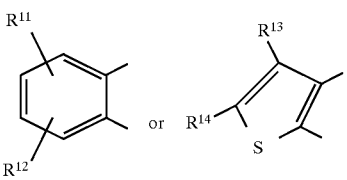

wherein R$^{11}$, R$^{12}$, R$^{13}$ and R$^{14}$ are as defined in (8), and pharmaceutically acceptable salts thereof.

(10) Triazepine compounds of the above (9), wherein $$-V=W- \text{ is } -\underset{\underset{R^{15}}{|}}{C}=N-$$

wherein R$^{15}$ is lower alkyl, and pharmaceutically acceptable salts thereof.

(11) Triazepine compounds of the above (10), wherein R$^{1}$ is an optionally substituted aryl, and pharmaceutically acceptable salts thereof.

(12) Triazepine compounds of the above (11), wherein R$^{1}$ is an optionally substituted phenyl, and pharmaceutically acceptable salts thereof.

(13) Triazepine compounds of the above (12), wherein R$^{2}$ and R$^{4}$ are both hydrogen atom, and pharmaceutically acceptable salts thereof.

(14) Triazepine compounds of the above (13), wherein R$^{3}$ is pyridyl or an optionally substituted phenyl, and pharmaceutically acceptable salts thereof.

(15) Triazepine compounds selected from the group of the compounds of the above (7), and pharmaceutically acceptable salts thereof.

(16) Pharmaceutical compositions comprising a triazepine compound of the formula [I']

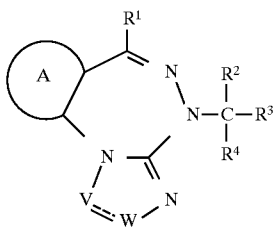

[I']

wherein R$^{1}$, R$^{2}$, R$^{3}$, R$^{4}$, ring A and —V---W— are as defined in (8), or a pharmaceutically acceptable salt thereof, and a pharmaceutically acceptable carrier.

(17) Pharmaceutical compositions of (16), wherein, in the formula [I'], the ring A is

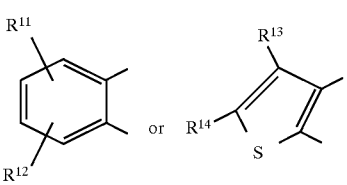

wherein R$^{11}$, R$^{12}$, R$^{13}$ and R$^{14}$ are as defined in (8).

(18) Pharmaceutical compositions of (17), wherein, in the formula [I'],

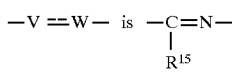

wherein $R^{15}$ is a lower alkyl.

(19) Pharmaceutical compositions of (18), wherein, in the formula [I'], $R^1$ is an optionally substituted aryl.

(20) Pharmaceutical compositions of (19), wherein, in the formula [I'], $R^1$ is an optionally substituted phenyl.

(21) Pharmaceutical compositions of (20), wherein, in the formula [I'], $R^2$ and $R^4$ are both hydrogen atom.

(22) Pharmaceutical compositions of (21), wherein, in the formula [I'], $R^3$ is pyridyl or an optionally-substituted phenyl.

(23) Pharmaceutical compositions comprising a triazepine compound selected from the group of the compounds of (7), or a pharmaceutically acceptable salts thereof, and a pharmaceutically acceptable carrier.

(24) Triazepine compounds of the formula [II']

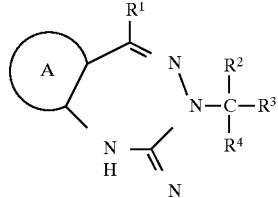

wherein $R^1$, $R^2$, $R^3$, $R^4$ and ring A are as defined in (8), and salts thereof.

(25) Triazepinethione compounds of the above (24), wherein the ring A is

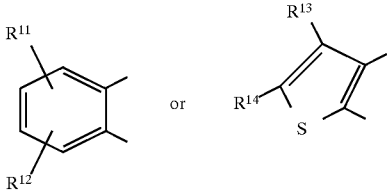

wherein $R^{11}$, $R^{12}$, $R^{13}$ and $R^{14}$ are as defined in (8), $R^1$ is an optionally substituted phenyl, and $R^2$ and $R^4$ are both hydrogen atom, and salts thereof.

(26) Triazepinethione compounds of the above (25), which are selected from the group of
5-(4-chlorophenyl)-3-(3,4-dimethoxybenzyl)-1,3-dihydrobenzo[e]-[1,2,4]triazepine-2-thione,
3-(4-methoxybenzyl)-5-phenyl-1,3-dihydrobenzo[e][1,2,4]triazepine-2-thione,
5-(4-chlorophenyl)-3-(4-methoxybenzyl)-1,3-dihydrobenzo[e][1,2,4]-triazepine-2-thione.
7-chloro-3-(4-methoxybenzyl)-5-phenyl-1,3-dihydrobenzo[e][1,2,4]-triazepine-2-thione,
3-(4-methoxybenzyl)-7-nitro-5-phenyl-1,3-dihydrobenzo[e][1,2,4]-triazepine-2-thione,
3-(4-methoxybenzyl)-5-(4-methylphenyl)-1,3-dihydrobenzo[e][1,2,4]-triazepine-2-thione,
7-chloro-5-(2-chlorophenyl),-3-(4-methoxybenzyl)-1,3-dihydrobenzo-[e][1,2,4]triazepine-2-thione,
5-(4-chlorophenyl)-3-(pyridin-3-ylmethyl)-1,3-dihydrobenzo[e][1,2,4]triazepine-2-thione,
4-(4-chlorophenyl)-6-(4-methoxybenzyl)-2,3-dimethyl-6,8-dihydro-1-thia-5,6,8-triazaazulene-7-thione,
4-(4-chlorophenyl)-2-ethyl-6-(4-methoxybenzyl)-6,8-dihydro-1-thia-5,6,8-triazaazulene-7-thione,
6-(4-methoxybenzyl)-2-methyl-4-phenyl-6,8-dihydro-1-thia-5,6,8-triazaazulene-7-thione,
6-(4-methoxybenzyl)-2,3-dimethyl-4-phenyl-6,8-dihydro-1-thia-5,6,8-triazaazulene-7-thione,
2-ethyl-6-(4-methoxybenzyl)-4-phenyl-6,8-dihydro-1-thia-5,6,8-triazaazulene-7-thione,
6-(4-methoxybenzyl)-4-(4-methoxyphenyl)-2,3-dimethyl-6,8-dihydro-1-thia-5,6,8-triazaazulene-7-thione,
4-(2-chlorophenyl)-2,3-dimethyl-6-(pyridin-4-ylmethyl)-6,8-dihydro-1-thia-5,6,8-triazaazulene-7-thione,
3-(4-methoxybenzyl)-8-methyl-5-phenyl-1,3-dihydrobenzo[e][1,2,4]-triazepine-2-thione, and
3-benzyl-5-(4-chlorophenyl)-1,3-dihydrobenzo[e][1,2,4]triazepine-2-thione, and salts thereof.

(27) Alkylthiotriazepine compounds of the formula [III']

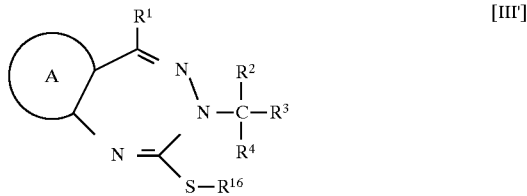

wherein $R^1$, $R^2$, $R^3$, $R^4$ and ring A are as defined in (8), and $R^{16}$ is a lower alkyl, and salts thereof.

(28) Alkylthiotriazepine compounds of the above (27), wherein the ring A is

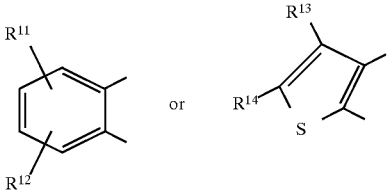

wherein $R^{11}$, $R^{12}$, $R^{13}$ and $R^{14}$ are as defined in (8), $R^1$ is an optionally substituted phenyl, and $R^2$ and $R^4$ are both hydrogen atom, and salts thereof.

(29) Alkylthiotriazepine compounds of the above (28), which are selected from the group of
5-(4-chlorophenyl)-3-(3,4-dimethoxybenzyl)-2-methylthio-3H-benzo[e][1,2,4]triazepine,
3-(4-methoxybenzyl)-2-methylthio-5-phenyl-3H-benzo[e][1,2,4]-triazepine,
7-chloro-3-(4-methoxybenzyl)-2-methylthio-5-phenyl-3H-benzo[e][1,2,4]triazepine,
3-(4-methoxybenzyl)-8-methyl-2-methylthio-5-phenyl-3H-benzo[e]-[1,2,4]triazepine,
3-(4-methoxybenzyl)-7-nitro-2-methylthio-5-phenyl-3H-benzo[e][1,2,4]triazepine,
3-(4-methoxybenzyl)-5-(4-methylphenyl)-2-methylthio-3H-benzo[e][1,2,4]triazepine,
7-chloro-5-(2-chlorophenyl)-3-(4-methoxybenzyl)-2-methylthio-3H-benzo[e][1,2,4]triazepine,
5-(4-chlorophenyl)-2-methylthio-3-(pyridin-3-ylmethyl)-3H-benzo[e][1,2,4]triazepine,
4-(4-chlorophenyl)-6-(4-methoxybenzyl)-2,3-dimethyl-7-methylthio-6H-1-thia-5,6,8-triazaazulene,
4-(4-chlorophenyl)-2-ethyl-6-(4-methoxybenzyl)-7-methylthio-6H-1-thia-5,6,8-triazaazulene,
6-(4-methoxybenzyl)-2-methyl-7-methylthio-4-phenyl-6H-1-thia-5,6,8-triazaazulene,
6-(4-methoxybenzyl)-2,3-dimethyl-7-methylthio-4-phenyl-6H-1-thia-5,6,8-triazaazulene,
2-ethyl-6-(4-methoxybenzyl)-7-methylthio-4-phenyl-6H-1-thia-5,6,8-triazaazulene, 6-(4-methoxybenzyl)-4-(4-methoxyphenyl)-2,3-dimethyl-7-methylthio-6H-1-thia-5,6,8-triazaazulene,
4-(2-chlorophenyl)-2,3-dimethyl-7-methylthio-6-(pyridin-4-ylmethyl)-6H-1-thia-5,6,8-triazaazulene, and
5-(4-chlorophenyl)-3-(4-methoxybenzyl)-2-methylthio-3H-benzo[e][1,2,4]triazepine, and salts thereof.

(30) Acylhydrazotriazepine compounds of the formula [IV']

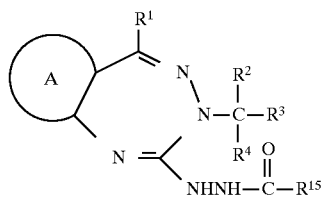

wherein $R^1$, $R^2$, $R^3$, $R^4$, $R^{15}$ and ring A are as defined in (8), and salts thereof.

(31) Acylhydrazotriazepine compounds of the above (30), wherein the ring A is

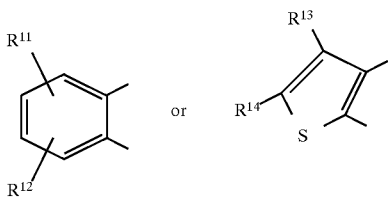

wherein $R^{11}$, $R^{12}$, $R^{13}$ and $R^{14}$ are as defined in (8), $R^1$ is an optionally substituted phenyl, and $R^2$ and $R^4$ are both hydrogen atom, and salts thereof.

(32) Acylhydrazotriazepine compounds of the above (31), which are selected from the group of
acetic acid N'-[5-(4-chlorophenyl)-3-(3,4-dimethoxybenzyl)-3H-benzo[e][1,2,4]triazepin-2-yl] hydrazide,
acetic acid N'-(3-(4-methoxybenzyl)-5-phenyl-3H-benzo[e][1,2,4]-triazepin-2-yl]hydrazide, and
acetic acid N'-[3-(4-methoxybenzyl)-8-methyl-5-phenyl-3H-benzo[e]-[1,2,4]triazepin-2-yl]hydrazide, and salts thereof.

(33) A method for treating osteoporosis, comprising administering a triazepine compound of the formula [I] of the above (1) or a pharmaceutically acceptable salt thereof.

(34) Use of a triazepine compound of the formula [I] of the above (1) or a pharmaceutically acceptable salt thereof for producing a therapeutic agent for osteoporosis.

The definitions of the respective substituents to be used in the present specification are as follows.

Optionally substituted aryl means phenyl, naphthyl or biphenylyl which may have 1 to 3 substituents on the ring. Examples of the substituent include halogen atom (e.g., chlorine, bromine, fluorine and iodine), lower alkyl (e.g., alkyl having 1 to 6 carbon atoms, such as methyl, ethyl, propyl, isopropyl, butyl, tert-butyl, isobutyl, pentyl, isopentyl and hexyl), lower alkoxy (e.g., alkoxy having 1 to 6 carbon atoms, such as methoxy, ethoxy, propoxy, isopropoxy, butoxy, tert-butoxy and hexyloxy), aralkyloxy (e.g., benzyloxy), methylenedioxy, haloalkyl (e.g. haloalkyl wherein alkyl moiety has 1 to 4 carbon atoms, such as chloromethyl, bromomethyl, fluoromethyl, trifluoromethyl, trifluoroethyl, pentafluoropropyl and chlorobutyl), haloalkyloxy (e.g., trifluoromethoxy and trifluoroethoxy), haloalkylsulfonylamino (e.g., trifluoromethanesulfonylamino), hydroxy, nitro, amino, mono- or di-substituted amino such as alkylamino (e.g., methylamino and dimethylamino), acylamino (e.g., acetylamino and formylamino), alkylsulfonylamino (e.g., methanesulfonylamino) and bisalkylsulfonylamino (e.g., bismethanesulfonylamino), cyano, alkylsulfonyl (e.g., methanesulfonyl), acyl (e.g., acetyl, propionyl, butyryl and pivaloyl), acyloxy wherein acyl moiety is alkanoyl having 2 to 5 carbon atoms (e.g., acetyl, propionyl, butyryl and pivaloyl) or aroyl such as benzoyl optionally having, on the ring, 1 to 3 substituents selected from halogen atom (same as above), lower alkyl (same as above), lower alkoxy (same as above), haloalkyl (same as above) and hydroxy, which is exemplified by benzoyl, chlorobenzoyl, methylbenzoyl and methoxybenzoyl, and aralkyl such as benzyl, 2-phenylethyl and 3-phenylpropyl wherein alkyl moiety has 1 to 6 carbon atoms and which may have, on the ring, 1 to 3 substituents selected from halogen atom (same as above), lower alkyl (same as above), lower alkoxy (same as above) and hydroxy. Preferred are phenyl, biphenylyl, naphthyl and phenyl having, as substituent, halogen atom (same as above), lower alkyl (same as above), lower alkoxy (same as above), aralkyloxy (same as above), haloalkyl (same as above), haloalkyloxy (same as above), haloalkylsulfonylamino (same as above), nitro, amino, mono- or di-substituted amino (same as above), alkylsulfonylamino (same as above), bisalkylsulfonylamino (same as above), alkylsulfonyl (same as above), acyloxy (same as above), cyano or hydroxy. Particularly preferred are phenyl, 2-methylphenyl, 3-methylphenyl, 4-methylphenyl, 2-methoxyphenyl, 3-methoxyphenyl, 4-methoxyphenyl, 2,5-dimethoxyphenyl, 3,4-dimethoxyphenyl, 3,4,5-trimethoxyphenyl, 5-acetyl-2-methoxyphenyl, 4-ethoxyphenyl, 3,4-methylenedioxyphenyl, 2-chloro-4,5-methylenedioxyphenyl, 2-fluorophenyl, 3-fluorophenyl, 4-fluorophenyl, 2,4-difluorophenyl, 2,5-difluorophenyl, 3,4-difluorophenyl, 3,5-difluorophenyl, 2-chlorophenyl, 3-chlorophenyl, 4-chlorophenyl, 3-chloro-4-methoxyphenyl, 3,5-dichloro-4-methoxyphenyl, 4-chloro-2,5-dimethoxyphenyl, 2-trifluoromethylphenyl, 3-trifluoromethylphenyl, 4-trifluoromethylphenyl, 4-trifluoromethoxyphenyl, 2-nitrophenyl, 3-nitrophenyl, 4-nitrophenyl, 2-methoxy-5-nitrophenyl, 4-methoxy-3-nitrophenyl, 2-cyanophenyl, 3-cyanophenyl, 4-cyanophenyl, 4-aminophenyl, 4-formylaminophenyl, 4-acetylaminophenyl, 4-dimethylaminophenyl, 4-methanesulfonylaminophenyl, 4-bismethanesulfonylaminophenyl, 4-trifluoromethanesulfonylaminophenyl, 4-methylsulfonylphenyl, 4-hydroxyphenyl, 3,4-dihydroxyphenyl, 4-benzyloxyphenyl, 3,4-dibenzyloxyphenyl, 3-benzyloxy-4-methoxyphenyl, 4-hydroxy-3-methoxyphenyl, 4-benzyloxy-3-hydroxyphenyl, 3-benzyloxy-4-hydroxyphenyl, 4-benzyloxy-3-methoxyphenyl, biphenylyl, 1-naphthyl and 2-naphthyl.

Optionally substituted heteroaryl means, for example, pyridyl, thienyl, thiazolyl or isoxazolyl which may have, on the ring, 1 to 3 substituents. Examples of the substituent include halogen atom (e.g., chlorine, bromine, fluorine and iodine), lower allyl (e.g., alkyl having 1 to 6 carbon atoms, such as methyl, ethyl, propyl, isopropyl, butyl, tert-butyl, isobutyl, pentyl, isopentyl and hexyl), lower alkoxy (e.g., alkoxy having 1 to 6 carbon atoms, such as methoxy, ethoxy, propoxy, isopropoxy, butoxy, tert-butoxy and hexyloxy), aralkyloxy (e.g., benzyloxy), methylenedioxy, haloalkyl (e.g., haloalkyl wherein alkyl moiety has 1 to 4 carbon atoms, such as chloromethyl, bromomethyl, fluoromethyl, trifluoromethyl, trifluoroethyl, pentafluoropropyl and chlorobutyl), haloalkyloxy (e.g., trifluoromethoxy and trifluoroethoxy), haloalkylsulfonylamino (e.g., trifluoromethanesulfonylamino), hydroxy, nitro, amino, mono- or di-substituted amino such as alkylamino (e.g., methylamino and dimethylamino), acylamino (e.g., acetylamino and formylamino), alkylsulfonylamino (e.g., methanesulfonylamino) and bisalkylsulfonylamino (e.g., bismethanesulfonylamino), cyano, alkylsulfonyl (e.g., methanesulfonyl), acyl (e.g., acetyl, propionyl, butyryl and pivaloyl), acyloxy wherein acyl moiety is alkanoyl having 2 to 5 carbon atoms (e.g., acetyl, propionyl, butyryl and pivaloyl) or aroyl such as benzoyl optionally having, on the ring, 1 to 3 substituents selected from halogen atom (same as above), lower alkyl (same as above), lower alkoxy (same as above), haloalkyl (same as above) and hydroxy, which is exemplified by benzoyl, chlorobenzoyl, methylbenzoyl and methoxybenzoyl, and aralkyl such as benzyl, 2-phenylethyl and 3-phenylpropyl wherein alkyl moiety has 1 to 6 carbon atoms and optionally having, on the ring, 1 to 3 substituents selected from halogen atom (same as above), lower alkyl (same as above), lower alkoxy (same as above) and hydroxy. Preferred are pyridyl, thienyl, thiazolyl and isoxazolyl, and these heteroaryl groups may have 1 to 3 substituents selected from halogen atom (same as above), lower alkyl (same as above), lower alkoxy (same as above), aralkyloxy (same as above), haloalkyl (same as above), haloalkyloxy (same as above), haloalkylsulfonylamino (same as above), nitro, amino, mono- or di-substituted amino (same as above), alkylsulfonylamino (same as above), bisalkylsulfonylamino (same as above), alkylsulfonyl (same as above), acyloxy (same as above), cyano and hydroxy. More preferred are pyridyl, 2-methylpyridyl, 3-methylpyridyl, 4-methylpyridyl, 2,5-dimethylpyridyl, 2,6-dimethylpyridyl, 3,5-dimethylpyridyl, 2-methoxypyridyl, 3-methoxypyridyl, 4-methoxypyridyl, 2,5-dimethoxypyridyl, 2,6-dimethoxypyridyl, 3,5-dimethoxypyridyl, 2-fluoropyridyl, 3-fluoropyridyl, 4-fluoropyridyl, 2,5-difluoropyridyl, 2,6-difluoropyridyl, 3,5-difluoropyridyl, 2-chloropyridyl, 3-chloropyridyl, 4-chloropyridyl, 2,5-dichloropyridyl, 2,6-dichloropyridyl, 3,5-dichloropyridyl, 4-trifluoromethylpyridyl, 4-trifluoromethoxypyridyl, 2-nitropyridyl, 3-nitropyridyl, 4-nitropyridyl, 2-cyanopyridyl, 3-cyanopyridyl, 4-cyanopyridyl, 4-aminopyridyl, 4-formylaminopyridyl, 4-acetylaminopyridyl, 4-dimethylaminopyridyl, 4-methanesulfonylaminopyridyl, 4-bismethanesulfonylaminopyridyl, 4-trifluoromethanesulfonylaminopyridyl, 2-hydroxypyridyl, 3-hydroxypyridyl, 4-hydroxypyridyl, 2-benzyloxypyridyl, 3-benzyloxypyridyl, 4-benzyloxypyridyl, thienyl, 2-methylthienyl, 3-methylthienyl, 2,3-dimethylthienyl, 3,4-dimethylthienyl, 2-methoxythienyl, 3-methoxythienyl, 2-fluorothienyl, 3-fluorothienyl, 2,3-difluorothienyl, 3,4-difluorothienyl, 2-chlorothienyl, 3-chlorothienyl, 2,3-dichlorothienyl, 3,4-dichlorothienyl, 2-trifluoromethylthienyl, 3-trifluoromethylthienyl, 2-trifluoromethoxythienyl, 3-trifluoromethoxythienyl, 2-nitrothienyl, 3-nitrothienyl, 2-cyanothienyl, 3-cyanothienyl, 2-aminothienyl, 3-aminothienyl, 2-formylaminothienyl, 3-formylaminothienyl, 2-acetylaminothienyl, 3-acetylaminothienyl, 2-dimethylaminothienyl, 3-dimethylaminothienyl, 2-methanesulfonylaminothienyl, 3-methanesulfonylaminothienyl, 2-bismethanesulfonylaminothienyl, 3-bismethanesulfonylaminothienyl, 2-trifluoromethanesulfonylaminothienyl, 3-trifluoromethanesulfonylaminothienyl, 2-hydroxythienyl, 3-hydroxythienyl, 2-benzyloxythienyl, 3-benzyloxythienyl, isoxazolyl, 3-methylisoxazolyl, 4-methylisoxazolyl, 5-methylisoxazolyl, 3,4-dimethylisoxazolyl, 3,5-dimethylisoxazolyl, 4,5-dimethylisoxazolyl, 3-chloroisoxazolyl, 4-chloroisoxazolyl, 5-chloroisoxazolyl, 3,4-dichloroisoxazolyl, 3,5-dichloroisoxazolyl, 4,5-dichloroisooxazolyl, thiazolyl, 2-methylthiazolyl, 4-methylthiazolyl, 5-methylthiazolyl, 2,4-dimethylthiazolyl, 2,5-dimethylthiazolyl, 4,5-dimethylthiazolyl, 2-chlorothiazolyl, 4-chlorothiazolyl, 5-chlorothiazolyl, 2,4-dichlorothiazolyl, 2,5-dichlorothiazolyl and 4,5-dichlorothiazolyl.

Lower alkyl means linear or branched alkyl having 1 to 6 carbon atoms, such as methyl, ethyl, propyl, isopropyl, butyl, isobutyl, tert-butyl, pentyl, tert-pentyl and hexyl, with preference given to alkyl having 1 to 4 carbon atoms, such as methyl, ethyl, propyl, isopropyl, butyl, isobutyl and tert-butyl.

Halogen atom is chlorine, bromine, fluorine or iodine, with preference given to chlorine.

Aralkyl is arylalkyl wherein aryl is phenyl and alkyl moiety has 1 to 6 carbon atoms, which is exemplified by benzyl, phenylethyl, phenylpropyl, phenylbutyl and phenylhexyl. It may have, on the phenyl ring, 1 to 3 substituents selected from, for example, halogen atom (e.g., chlorine, bromine and fluorine), alkyl (e.g., alkyl having 1 to 6 carbon atoms, such as methyl, ethyl, propyl, isopropyl, butyl, tert-butyl, isobutyl, pentyl, isopentyl and hexyl), alkoxy (e.g., alkoxy having 1 to 6 carbon atoms, such as methoxy, ethoxy, propoxy, isopropoxy, butoxy, tert-butoxy and hexyloxy), haloalkyl (e.g., haloalkyl wherein alkyl moiety has 1 to 4 carbon atoms, such as chloromethyl, bromomethyl, fluoromethyl, trifluoromethyl, trifluoroethyl, pentafluoropropyl and chlorobutyl), hydroxy, nitro, amino, cyano, acyloxy wherein acyl moiety is alkanoyl having 2 to 5 carbon atoms (e.g., acetyl, propionyl, butyryl and pivaloyl) or aroyl such as benzoyl optionally having, on the ring, 1 to 3 substituents selected from halogen atom (same as above), alkyl (same as above), alkoxy (same as above), haloalkyl (same as above) and hydroxy, which is exemplified by benzoyl, chlorobenzoyl, methylbenzoyl and methoxybenzoyl. Preferred is aralkyl which has phenyl or phenyl having substituent selected from halogen atom (same as above), alkyl (same as above), alkoxy (same as above), haloalkyl (same as above), hydroxy, nitro, amino and cyano, and alkyl moiety having 1 to 4 carbon atoms. Particularly preferred is aralkyl which has phenyl or phenyl having substituent selected from halogen atom (same as above), alkyl (same as above) and alkoxy (same as above), and alkyl moiety having 1 to 4 carbon atoms.

Lower alkoxy means linear or branched alkoxy having 1 to 6 carbon atoms, such as methoxy, ethoxy, propoxy, isopropoxy, butoxy, tert-butoxy, pentyloxy, tert-pentyloxy and hexyloxy, with preference given to alkoxy having 1 to 4 carbon atoms, such as methoxy, ethoxy, propoxy, isopropoxy, butoxy and tert-butoxy, and particular preference given to methoxy, ethoxy, propoxy and butoxy.

Cycloalkyl has 3 to 10 carbon atoms, and is exemplified by cyclopropyl, 2,3-dimethylcyclopropyl, cyclobutyl, 3-methylcyclobutyl, cyclopentyl, 3,4-dimethylcyclopentyl, cyclohexyl, 4-methylcyclohexyl, cycloheptyl, cyclooctyl, norbornyl, adamantyl, bicyclo[3.3.0]octan-1-yl and bicyclo[3.3.1]nonan-9-yl. Preferred are, for example, cyclopropyl, cyclobutyl, cyclopentyl, cyclohexyl and cycloheptyl, and particularly preferred are, for example, cyclopropyl, cyclobutyl, cyclopentyl and cyclohexyl.

Amino substituted by lower alkyl is alkylamino mono- or di-substituted by alkyl having 1 to 5 carbon atoms, and is exemplified by methylamino, dimethylamino, ethylamino, diethylamino, propylamino and dipropylamino. Preferred are methylamino, dimethylamino, ethylamino and diethylamino.

Cyclic amino is exemplified by pyrrolidinyl, piperidino, and morpholino, thiomorpholino and piperazinyl having, as a hetero atom, oxygen, sulfur or nitrogen atom, wherein lower alkyl or aralkyl may substitute the 4-position nitrogen atom of piperazinyl.

Acyl means, for example, alkanoyl having 2 to 5 carbon atoms such as acetyl, propionyl, butyryl and pivaloyl, or benzoyl. Preferred are formyl, acetyl, propionyl and benzoyl.

Acyloxy is, for example, alkanoyloxy having 2 to 5 carbon atoms such as acetyloxy, propionyloxy, butyryloxy and pivaloyloxy, or benzoyloxy. Preferred are acetyloxy, propionyloxy and benzoyloxy.

Carbamoyl substituted by lower alkyl means alkylcarbamoyl mono- or di-substituted by alkyl having 1 to 5 carbon atoms such as methylcarbamoyl, dimethylcarbamoyl, ethylcarbaoyl, diethylcarbamoyl, propylcarbamoyl and dipropylcarbamoyl. Preferred are methylcarbamoyl, dimethylcarbamoyl, ethylcarbamoyl and diethylcarbamoyl.

Cyclic aminocarbonyl means that having the above-mentioned cyclic amino moiety and is exemplified by pyrrolidinylcarbonyl, piperidinocarbonyl, morpholinocarbonyl, thiomorpholinocarbonyl, piperazinylcarbonyl and 4-methyl-1-piperazinylcarbonyl. Preferred are pyrrolidinylcarbonyl, piperidinocarbonyl, morpholinocarbonyl and piperazinylcarbonyl.

Lower alkoxycarbonyl is alkoxycarbonyl wherein alkoxy moiety has 1 to 5 carbon atoms and is exemplified by methoxycarbonyl, ethoxycarbonyl, propoxycarbonyl, isopropoxycarbonyl, butoxycarbonyl, isobutoxycarbonyl and tert-butoxycarbonyl. Preferred are methoxycarbonyl, ethoxycarbonyl and propoxycarbonyl.

Aralkyloxycarbonyl is phenylalkoxycarbonyl wherein alkoxy moiety has 1 to 5 carbon atoms, such as benzyloxycarbonyl, 2-phenylethoxycarbonyl and 3-phenylpropoxycarbonyl which may have, as substituent, halogen atom, nitro, alkyl, alkoxy and trifluoromethyl.

Lower alkenyl means alkenyl having 2 to 6 carbon atoms, such as ethenyl, 1-propenyl, 1-butenyl, 2-butenyl, 3-butenyl, 2-methyl-1-propenyl, 1-pentenyl, 2-pentenyl, 3-pentenyl, 2-methyl-1-butenyl, 3-methyl-1-butenyl, 1-hexenyl, 2-hexenyl, 3-hexenyl, 4-hexenyl, 5-hexenyl, 2-methyl-1-pentenyl, 3-methyl-1-pentenyl, 4methyl-1-pentenyl, 2,3-dimethyl-1-butenyl and 3,3-dimethyl-1-butenyl, with preference given to alkenyl having 2 to 4 carbon atoms, such as ethenyl, 1-propenyl, 1-butenyl, 2-butenyl, 3-butenyl and 2-methyl-1-propenyl.

Aralkyl substituted by lower alkyl is that wherein the above-mentioned aralkyl is substituted by alkyl having 1 to 6 carbon atoms, and is exemplified by 4-methylbenzyl, 4-ethylbenzyl, 4-propylbenzyl, 4-isopropylbenzyl, 4-methylphenylethyl, 4-ethylphenylethyl and 4-propylphenylethyl. Preferred are 4-methylbenzyl, 4-ethylbenzyl and 4-isopropylbenzyl.

Lower alkynyl means alkynyl having 2 to 6 carbon atoms, such as ethynyl, 1-propynyl, 1-butynyl, .2-butynyl, 3-butynyl, 1-pentynyl, 2-pentynyl, 3-pentynyl, 3-methyl-1-butynyl, 1-hexynyl, 2-hexynyl, 3-hexynyl, 4-hexynyl, 5-hexynyl, 3-methyl-1-pentynyl, 4-methyl-1-pentynyl and 3,3-dimethyl-1-butynyl, with preference given to alkynyl having 2 to 4 carbon atoms, such as ethynyl, 1-propynyl, 1-butynyl, 2-butynyl and 3-butynyl.

Haloalkyl is that wherein alkyl moiety has 1 to 4 carbon atoms, such as chloromethyl, bromomethyl, fluoromethyl, trifluoromethyl, trichloromethyl, trifluoroethyl, trichloroethyl, pentafluoropropyl and chlorobutyl, with preference given to chloromethyl, bromomethyl, fluoromethyl, trifluoromethyl and trichloromethyl.

Lower alkylcarbonyl is alkylcarbonyl wherein alkyl moiety has 1 to 5 carbon atoms, and is exemplified by acetyl, propionyl, butyryl, isobutyryl and pivaloyl.

Examples of pharmaceutically acceptable salt include, but not limited to, addition salts with various inorganic acids, such as hydrochloride, hydrobromide, sulfate, phosphate and nitrate; addition salts with various organic acids, such as acetate, propionate, succinate, glycolate, lactate, malate, oxalate, tartrate, citrate, maleate, fumarate, methanesulfonate, benzenesulfonate, p-toluenesulfonate and ascorbate, and salts with various amino acids, such as aspartate and glutamate. It may be a hydrate where necessary.

Examples of salt of compound [II], compound [III'] and compound [IV'] include, but not limited to, addition salts with inorganic acid addition salts, organic acid addition salts and salts with amino acids as exemplified for the above-mentioned pharmaceutically acceptable salt. It may be a hydrate where necessary.

Now, various substituents are described in more detail in the following.

$R^1$ means optionally substituted aryl or optionally substituted heteroaryl, wherein preferred are phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-trifluoromethylphenyl, 3-trifluoromethylphenyl, 4-trifluoromethylphenyl, 2-nitrophenyl, 3-nitrophenyl, 4-nitrophenyl, 2-hydroxyphenyl, 3-hydroxyphenyl, 4-hydroxyphenyl, 2-benzyloxyphenyl, 3-benzyloxyphenyl, 4-benzyloxyphenyl, 2-cyanophenyl, 3-cyanophenyl, 4-cyanophenyl, 2-aminophenyl, 3-aminophenyl, 4-aminophenyl, 2-dimethylaminophenyl, 3-dimethylaminophenyl, 4-dimethylaminophenyl, pyridyl, 2-methylpyridyl, 3-methylpyridyl, 4-methylpyridyl, 2-methoxypyridyl, 3-methoxypyridyl, 4-methoxypyridyl, 2-fluoropyridyl, 3-fluoropyridyl, 4-fluoropyridyl, 2-chloropyridyl, 3-chloropyridyl, 4-chloropyridyl, 2-trifluoromethylpyridyl, 3-trifluoromethylpyridyl, 4-trifluoromethylpyridyl, 2-nitropyridyl, 3-nitropyridyl, 4-nitropyridyl, 2-hydroxypyridyl, 3-hydroxypyridyl, 4-hydroxypyridyl, 2-benzyloxypyridyl, 3-benzyloxypyridyl, 4-benzyloxypyridyl, 2-cyanopyridyl, 3-cyanopyridyl, 4-cyanopyridyl, 2-aminopyridyl, 3-aminopyridyl, 4-aminopyridyl, 2-dimethylaminopyridyl, 3-dimethylaminopyridyl and 4-dimethylaminopyridyl; more preferred are phenyl, 2-methylphenyl, 3-methylphenyl, 4-methylphenyl, 2-methoxyphenyl, 3-methoxyphenyl, 4-methoxyphenyl, 2-fluorophenyl, 3-fluorophenyl, 4-fluorophenyl, 2-chlorophenyl, 3-chlorophenyl, 4-chlorophenyl, 2-trifluoromethylphenyl, 3-trifluoromethylphenyl, 4-trifluoromethylphenyl, 2-nitrophenyl, 3-nitrophenyl, 4-nitrophenyl, 2-hydroxyphenyl, 3-hydroxyphenyl, 4-hydroxyphenyl, 2-aminophenyl, 3-aminophenyl and 4-aminophenyl, and particularly preferred are phenyl, 2-methylphenyl, 3-methylphenyl, 4-methylphenyl, 2-chlorophenyl, 3-chlorophenyl, 4-chlorophenyl, 2-methoxyphenyl, 3-methoxyphenyl and 4-methoxyphenyl.

R² means hydrogen atom, hydroxy, halogen atom or lower alkyl, or R² and R⁴ combinedly together form carbonyl with the carbon atom to which they are bonded. R² is preferably hydrogen atom or hydroxy, or R² and R⁴ combinedly together form carbonyl with the carbon atom to which they are bonded. R² is more preferably hydrogen atom or R² and R⁴ combinedly together form carbonyl with the carbon atom to which they are bonded, and particularly preferably, R² is hydrogen atom.

R³ is hydrogen atom, lower alkyl, lower alkoxy, cycloalkyl, optionally substituted aryl, optionally substituted heteroaryl, —CR⁵=CR⁶R⁷ wherein R⁵, R⁶ and R⁷ are the same or different and each is hydrogen atom, halogen atom, lower alkyl or optionally substituted aryl, a group of the formula

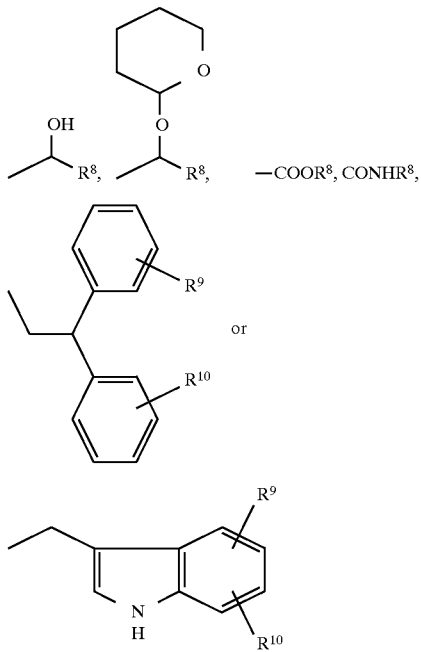

wherein R⁸ is hydrogen atom, lower alkyl, cycloalkyl, optionally substituted aryl, aralkyl or optionally substituted heteroaryl, and R⁹ and R¹⁰ are the same or different and each is hydrogen atom, lower alkyl, lower alkoxy, hydroxy, halogen atom, nitro or amino, —X—Y wherein X is —(CH₂)ₘ— wherein m is an integer of 1 to 4, —CO—, —COCH₂—, —NH—, —NHCH₂—, —CH₂NHCO—, —OCH₂—, —(CH₂)ₙO—wherein n is an integer of 1 to 4, or —CH₂S—, and Y is halogen atom, cycloalkyl, optionally substituted aryl or optionally substituted heteroaryl, or —OR¹⁸ wherein R¹⁸ is optionally substituted aryl, with preference given to phenyl, 2-methylphenyl, 3-methylphenyl, 4-methylphenyl, 2-ethylphenyl, 3-ethylphenyl, 4-ethylphenyl, 2-tert-butylphenyl, 3-tert-butylphenyl, 4-tert-butylphenyl, 2-methoxyphenyl, 3-methoxyphenyl, 4-methoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-ethoxyphenyl, 3-ethoxyphenyl, 4-ethoxyphenyl, 2-hydroxyphenyl, 3-hydroxyphenyl, 4-hydroxyphenyl, 2,4-dihydroxyphenyl, 2,5-dihydroxyphenyl, 3,4-dihydroxyphenyl, 3,5-dihydroxyphenyl, 2-fluorophenyl, 3-fluorophenyl, 4-fluorophenyl, 2,4-difluorophenyl, 2,5-difluorophenyl, 3,4-difluorophenyl, 3,5-difluorophenyl, 2-chlorophenyl, 3-chlorophenyl, 4-chlorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-aminophenyl, 3-aminophenyl, 4-aminophenyl, 2-methylaminophenyl, 3-methylaminophenyl, 4-methylaminophenyl, 2-dimethylaminophenyl, 3-dimethylaminophenyl, 4-dimethylaminophenyl, 2-cyanophenyl, 3-cyanophenyl, 4-cyanophenyl, 2-nitrophenyl, 3-nitrophenyl, 4-nitrophenyl, 3-chloro-4-methoxyphenyl, 3-chloro-5-methoxyphenyl, 4-chloro-5-methoxyphenyl, 3,5-dichloro-4-methoxyphenyl, 4-chloro-2,5-dimethoxyphenyl, 2-methoxy-3-nitrophenyl, 2-methoxy-4-nitrophenyl, 2-methoxy-5-nitrophenyl, 3-methoxy-4-nitrophenyl, 3-methoxy-5-nitrophenyl, 4-methoxy-2-nitrophenyl, 4-methoxy-3-nitrophenyl, 2-acetyl-3-methoxyphenyl, 2-acetyl-4-methoxyphenyl, 5-acetyl-2-methoxyphenyl, 3-acetyl-4-methoxyphenyl, 3-acetyl-5-methoxyphenyl, 3,4-methylenedioxyphenyl, 2-chloro-4,5-methylenedioxyphenyl, 3-chloro-4,5-methylenedioxyphenyl, 2-benzyloxyphenyl, 3-benzyloxyphenyl, 4-benzyloxyphenyl, 3,4-dibenzyloxyphenyl, 3,5-dibenzyloxyphenyl, 2-formylaminophenyl, 3-formylaminophenyl, 4-formylaminophenyl, 2-acetylaminophenyl, 3-acetylaminophenyl, 4-acetylaminophenyl, 2-methylsulfonylphenyl, 3-methylsulfonylphenyl, 4-methylsulfonylphenyl, 2-methylsulfonylaminophenyl, 3-methylsulfonylaminophenyl, 4-methylsulfonylaminophenyl, 2-bis(methylsulfonyl)aminophenyl, 3-bis(methylsulfonyl)aminophenyl, 4-bis(methylsulfonyl)aminophenyl, 2-phenylphenyl, 3-phenylphenyl, 4-phenylphenyl, 1-naphthyl, 2-naphthyl, 2-pyridyl, 3-pyridyl, 4-pyridyl, 2-methylpyridyl, 3-methylpyridyl, 4-methylpyridyl, 2-methoxypyridyl, 3-methoxypyridyl, 4-methoxypyridyl, 2-hydroxypyridyl, 3-hydroxypyridyl, 4-hydroxypyridyl, 2-fluoropyridyl, 3-fluoropyridyl, 4-fluoropyridyl, 2-chloropyridyl, 3-chloropyridyl, 4-chloropyridyl, 2,5-dichloropyridyl, 2,6-dichloropyridyl, 3,5-dichloropyridyl, 4-trifluoromethylpyridyl, 4-trifluoromethoxypyridyl, 2-nitropyridyl, 3-nitropyridyl, 4-nitropyridyl, 2-cyanopyridyl, 3-cyanopyridyl, 4-cyanopyridyl, 4-aminopyridyl, 4-dimethylaminopyridyl, 4-formylaminopyridyl, 4-acetylaminopyridyl, 4-methanesulfonylaminopyridyl, 4-bismethanesulfonylaminopyridyl, thienyl, 2-methylthienyl, 3-methylthienyl, 2,3-dimethylthienyl, 3,4-dimethylthienyl, 2-chlorothienyl, 3-chlorothienyl, 2,3-dichlorothienyl, 3,4-dichlorothienyl, isoxazolyl, 3-methylisoxazolyl, 4-methylisoxazolyl, 5-methylisoxazolyl, 3,4-dimethylisoxazolyl, 3,5-dimethylisoxazolyl, 4,5-dimethylisoxazolyl, 3-chloroisoxazolyl, 4-chloroisoxazolyl, 5-chloroisoxazolyl, 3,4-dichloroisoxazolyl, 3,5-dichloroisoxazolyl, 4,5-dichloroisoxazolyl, thiazolyl, 2-methylthiazolyl, 4-methylthiazolyl, 5-methylthiazolyl, 2,4-dimethylthiazolyl, 2,5-dimethylthiazolyl, 4,5-dimethylthiazolyl, 2-chlorothiazolyl, 4-chlorothiazolyl, 5-chlorothiazolyl, 2,4-dichlorothiazolyl, 2,5-dichlorothiazolyl, 4,5-dichlorothiazolyl, ethenyl, 1-methylethenyl, propenyl, 2-phenylethenyl, 1-chloroethenyl, 2-chloroethenyl, 1,2-dichloroethenyl, 2,2-dichloroethenyl, 1,2,2-trichloroethenyl, 1-bromoethenyl, 2-bromoethenyl, phenylhydroxymethyl, 2-phenyl-1-hydroxyethyl, 2-(2-methoxyphenyl)-1-hydroxyethyl, 2-(3-methoxyphenyl)-1-hydroxyethyl, 2-(4-methoxyphenyl)-1-hydroxyethyl, benzoyl, 2-methylbenzoyl, 3-methylbenzoyl, 4-methylbenzoyl, 2-methoxybenzoyl, 3-methoxybenzoyl, 4-methoxybenzoyl, 2,3-dimethoxybenzoyl, 2,4-dimethoxybenzoyl, 2,5-dimethoxybenzoyl, 3,5-dimethoxybenzoyl, 2-fluorobenzoyl, 3-fluorobenzoyl, 4-fluorobenzoyl, 2-chlorobenzoyl, 3-chlorobenzoyl, 4-chlorobenzoyl, 2-phenyl-1-oxoethyl, 2-(2-methoxyphenyl)-1-oxoethyl, 2-(3-methoxyphenyl)-1-oxoethyl, 2-(4-methoxyphenyl)-1-oxoethyl, 2-(2,3-dimethoxyphenyl)-1-oxoethyl, 2-(2,4-dimethoxyphenyl)-1-oxoethyl, 2-(2,5-dimethoxyphenyl)-1-oxoethyl, 2-(3,5-dimethoxyphenyl)-1-oxoethyl, (2-methoxyphenyl)(2-tetrahydropyranyloxy)methyl, (3-methoxyphenyl)(2-tetrahydropyranyloxy)methyl, (4-methoxyphenyl)(2-tetrahydropyranyloxy)methyl, 2-phenyl-1-(2-tetrahydropyranyloxy)ethyl, 2,2-diphenylethyl, 2,2-bis(2-methylphenyl)ethyl, 2,2-bis(3-methylphenyl)ethyl, 2,2-bis(4-methylphenyl)ethyl, 2,2-bis(2-methoxyphenyl)ethyl, 2,2-bis(3-methoxyphenyl)ethyl, 2,2-bis(4-methoxyphenyl)ethyl, 3-indolylmethyl, 4-methoxyindol-3-ylmethyl, 5-methoxyindol-3-ylmethyl, 6-methoxyindol-3-ylmethyl, cyclopropyl, cyclobutyl, cyclopentyl, cyclohexyl, cyclopropylmethyl, cyclobutylmethyl, cyclopentylmethyl, cyclohexylmethyl, benzyl, phenethyl, methoxy, ethoxy, propoxy, butoxy, tert-butoxy, 2-chlorophenoxy, 3-chlorophenoxy, 4-chlorophenoxy, benzyloxy, fluoromethyl, chloromethyl, bromomethyl, carboxy, methoxycarbonyl, ethoxycarbonyl, propoxycarbonyl, butoxycarbonyl, tert-butoxycarbonyl, phenylaminocarbonyl, 2-methylphenylaminocarbonyl, 3-methylphenylaminocarbonyl, 4-methylphenylaminocarbonyl, 2-methoxyphenylaminocarbonyl, 3-methoxyphenylaminocarbonyl, 4-methoxyphenylaminocarbonyl, 2,3-dimethoxyphenylaminocarbonyl, 2,4-dimethoxyphenylaminocarbonyl, 2,5-dimethoxyphenylaminocarbonyl, 3,4,5-trimethoxyphenylaminocarbonyl, 1-naphthylaminocarbonyl, 2-naphthylaminocarbonyl, 2-pyridylaminocarbonyl, 3-pyridylaminocarbonyl, 4-pyridylaminocarbonyl, cyclopropylaminocarbonyl, cyclobutylaminocarbonyl, cyclopentylaminocarbonyl, cyclohexylaminocarbonyl, methylaminocarbonyl, ethylaminocarbonyl, propylaminocarbonyl, butylaminocarbonyl, tert-butylaminocarbonyl, phenylamino, benzylamino, phenylaminomethyl, 2-methylphenylaminomethyl, 3-methylphenylaminomethyl, 4-methylphenylaminomethyl, 2-methoxyphenylaminomethyl, 3-methoxyphenylaminomethyl, 4-methoxyphenylaminomethyl, 2,3-dimethoxyphenylaminomethyl, 2,4-dimethoxyphenylaminomethyl, 2,5-dimethoxyphenylaminomethyl, 2-fluorophenylaminomethyl, 3-fluorophenylaminomethyl, 4-fluorophenylaminomethyl, 2-chlorophenylaminomethyl, 3-chlorophenylaminomethyl, 4-chlorophenylaminomethyl, 2-bromophenylaminomethyl, 3-bromophenylaminomethyl, 4-bromophenylaminomethyl, 2-phenoxyethyl, 3-phenoxyethyl, 4-phenoxyethyl and phenylthiomethyl, with more preference given to phenyl, 2-methylphenyl, 3-methylphenyl, 4-methylphenyl, 4-tert-butylphenyl, 4-methoxyphenyl, 2,4-dimethoxyphenyl, 2,5-dimethoxyphenyl, 3,4-dimethoxyphenyl, 3,4,5-trimethoxyphenyl, 4-ethoxyphenyl, 4-hydroxyphenyl, 3,4-dihydroxyphenyl, 2-fluorophenyl, 3-fluorophenyl, 4-fluorophenyl, 2,4-difluorophenyl, 2,5-difluorophenyl, 3,4-difluorophenyl, 3,5-difluorophenyl, 2-chlorophenyl, 3-chlorophenyl, 4-chlorophenyl, 2-trifluoromethylphenyl, 3-trifluoromethylphenyl, 4-trifluoromethylphenyl, 4-trifluoromethoxyphenyl, 4-aminophenyl, 4-dimethylaminophenyl, 2-cyanophenyl, 3-cyanophenyl, 4-cyanophenyl, 2-nitrophenyl, 3-nitrophenyl, 4-nitrophenyl, 3-chloro-4-methoxyphenyl, 3,5-dichloro-4-methoxyphenyl, 2-methoxy-5-nitrophenyl, 4-methoxy-3-nitrophenyl, 5-acetyl-2-methoxyphenyl, 3,4-methylenedioxyphenyl, 2-chloro-4,5-methylenedioxyphenyl, 4-benzyloxyphenyl, 3,4-dibenzyloxyphenyl, 4-formylaminophenyl, 4-acetylaminophenyl, 4-methylsulfonylphenyl, 4-methylsulfonylaminophenyl, 4-bis(methylsulfonyl)aminophenyl, 4-phenylphenyl, 1-naphthyl, 2-naphthyl, 2-pyridyl, 3-pyridyl, 4-pyridyl, 2,6-dichloropyridin-4-yl, 3,5-dimethylisoxazolin-3-yl, 2-methyl-1,3-thiazolin-3-yl, 2-chloro-4-thienyl, ethenyl, 1-methylethenyl, 2-phenylethenyl, 1-chloroethenyl, 1,2-dichloroethenyl, 2,2-dichloroethenyl, 1-bromoethenyl, phenylhydroxymethyl, 2-phenyl-1-hydroxyethyl, 2-(2-methoxyphenyl)-1-hydroxyethyl, benzoyl, 2-methoxybenzoyl, 4-methoxybenzoyl, 4-methylbenzoyl, 2,5-dimethoxybenzoyl, 4-chlorobenzoyl, 2-phenyl-1-oxoethyl, 2-(2-methoxyphenyl)-1-oxoethyl, 2-(2,5-dimethoxyphenyl)-1-oxoethyl, (2-methoxyphenyl) (2-tetrahydropyranyloxy)methyl, 2-phenyl-1-(2-tetrahydropyranyloxy)ethyl, 2,2-diphenylethyl, 3-indolylmethyl, cyclopropyl, cyclohexyl, cyclohexylmethyl, benzyl, phenethyl, ethoxy, 4-chlorophenoxy, benzyloxy, bromomethyl, carboxy, ethoxycarbonyl, phenylaminocarbonyl, 4-methylphenylaminocarbonyl, 2-methoxyphenylaminocarbonyl, 2,5-dimethoxyphenylaminocarbonyl, 3,4,5-trimethoxyphenylaminocarbonyl, 1-naphthylaminocarbonyl, 3-pyridylaminocarbonyl, cyclohexylaminocarbonyl, propylaminocarbonyl, phenylamino, benzylamino, phenylaminomethyl, 4-methylphenylaminomethyl, 2-methoxyphenylaminomethyl, 2,5-dimethoxyphenylaminomethyl, 3-fluorophenylaminomethyl, 2-phenoxyethyl and phenylthiomethyl, and particular preference given to phenyl, 4-methoxyphenyl, 2,4-dimethoxyphenyl, 3,4-dimethoxyphenyl, 3,4,5-trimethoxyphenyl, 4-ethoxyphenyl, 4-hydroxyphenyl, 3,4-dihydroxyphenyl, 2-fluorophenyl, 3-fluorophenyl, 4-fluorophenyl, 2,4-difluorophenyl, 2,5-difluorophenyl, 3,4-difluorophenyl, 3,5-difluorophenyl, 2-chlorophenyl, 3-chlorophenyl, 4-chlorophenyl, 4-aminophenyl, 4-dimethylaminophenyl, 2-cyanophenyl, 3-cyanophenyl, 4-cyanophenyl, 2-nitrophenyl, 3-nitrophenyl, 4-nitrophenyl, 4-formylaminophenyl, 4-acetylaminophenyl, 4-methylsulfonylphenyl, 4-methylsulfonylaminophenyl, 4-bis(methylsulfonyl)aminophenyl, 2-pyridyl, 3-pyridyl, 4-pyridyl, 2,6-dichloropyridin-4-yl, ethenyl, 1-methylethenyl, 2-phenylethenyl, 1-chloroethenyl, 1-bromoethenyl, 1,2-dichloroethenyl, 2,2-dichloroethenyl, phenylhydroxymethyl, 2-phenyl-1-hydroxyethyl, 2-(2-methoxyphenyl)-1-hydroxyethyl, benzoyl, 2-methoxybenzoyl, 4-methoxybenzoyl, 2,5-dimethoxybenzoyl, 4-chlorobenzoyl, 2-phenyl-1-oxoethyl, 2-(2-methoxyphenyl)-1-oxoethyl, 2-(2,5-dimethoxyphenyl)-1-oxoethyl, 2,2-diphenylethyl, 3-indolylmethyl, cyclopropyl, cyclohexyl, cyclohexylmethyl, benzyl, phenethyl, ethoxy, 4-chlorophenoxy, benzyloxy, bromomethyl, carboxy, ethoxycarbonyl, phenylaminocarbonyl, 4-methylphenylaminocarbonyl, 2-methoxyphenylaminocarbonyl, 2,5-dimethoxyphenylaminocarbonyl, 3,4,5-trimethoxyphenylaminocarbonyl, phenylamino, benzylamino, phenylaminomethyl, 2-methoxyphenylaminomethyl, 2,5-dimethoxyphenylaminomethyl, 3-fluorophenylaminomethyl and phenylthiomethyl.

$R^4$ means hydrogen atom or halogen atom, with preference given to hydrogen atom.

Ring A is selected from the following:

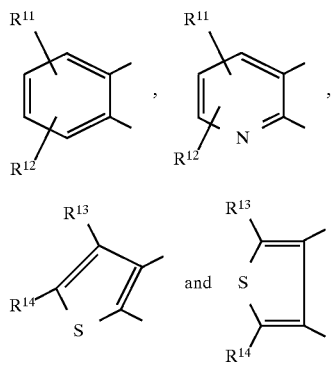

wherein $R^{11}$ and $R^{12}$ are the same or different and each is hydrogen atom, halogen atom, lower alkyl (said lower alkyl may be substituted by halogen atom, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl), lower alkenyl, aralkyl, aralkyl substituted by lower alkyl, lower alkoxy, nitro, amino, amino substituted by lower allyl, cyclic amino, hydroxy, acyloxy, cyano, carbamoyl, carbamoyl substituted by lower alkyl, cyclic aminocarbonyl, carboxy, lower alkoxycarbonyl or aralkyloxycarbonyl, $R^{13}$ and $R^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl, with preference given to the following:

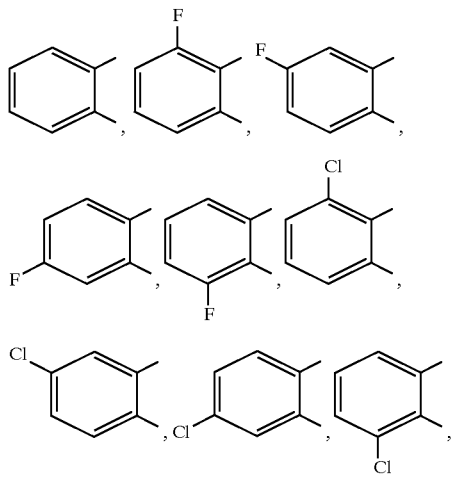

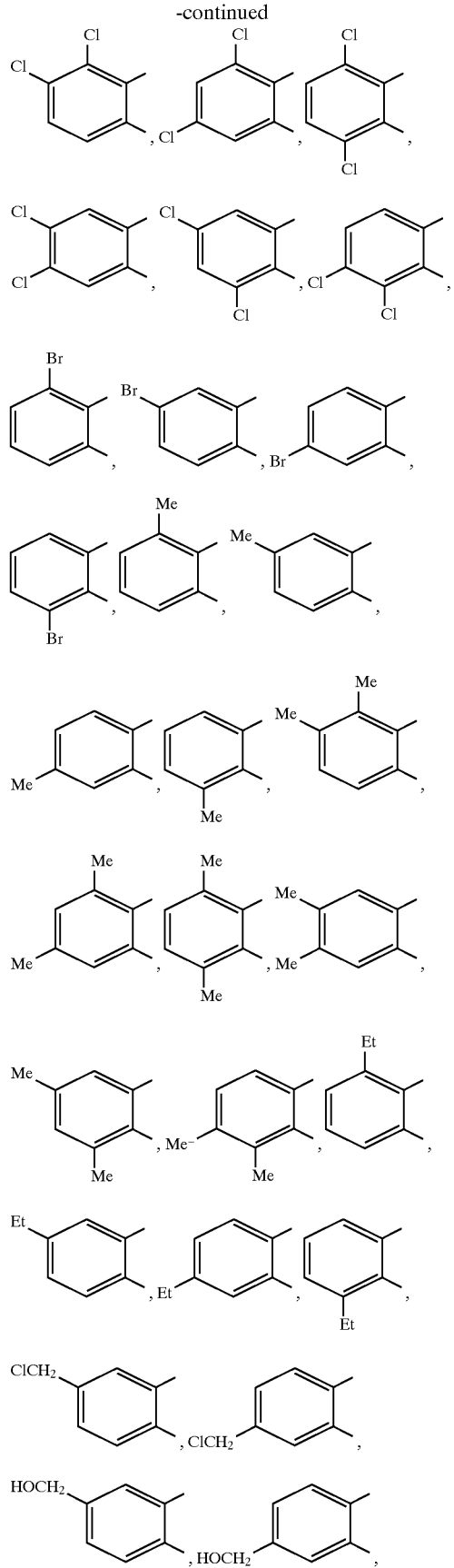

-continued
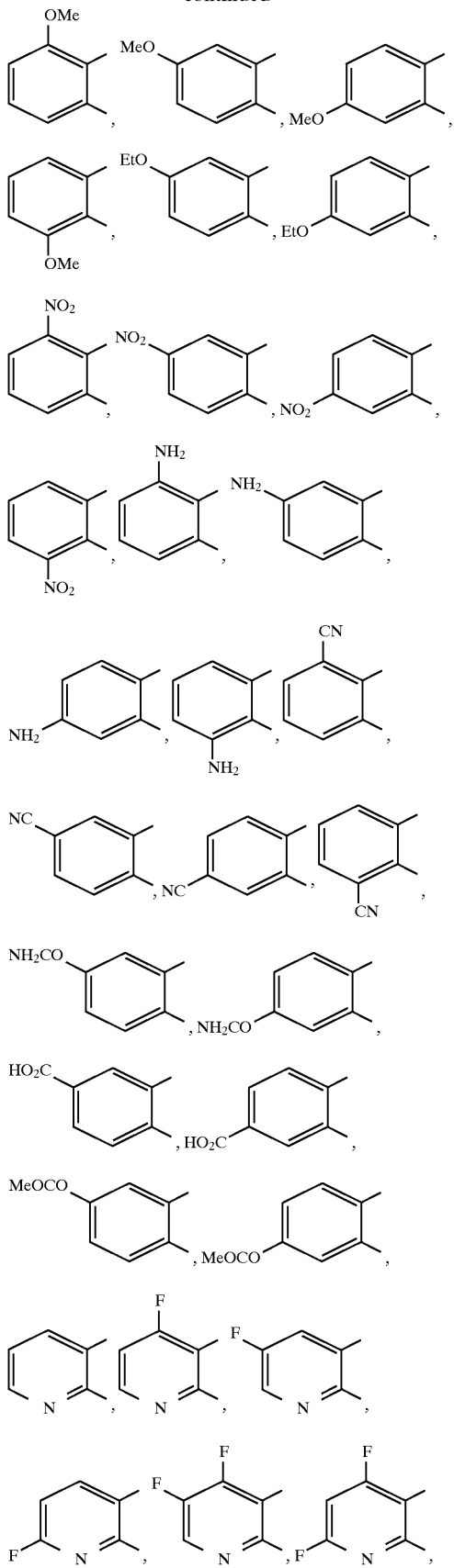
-continued
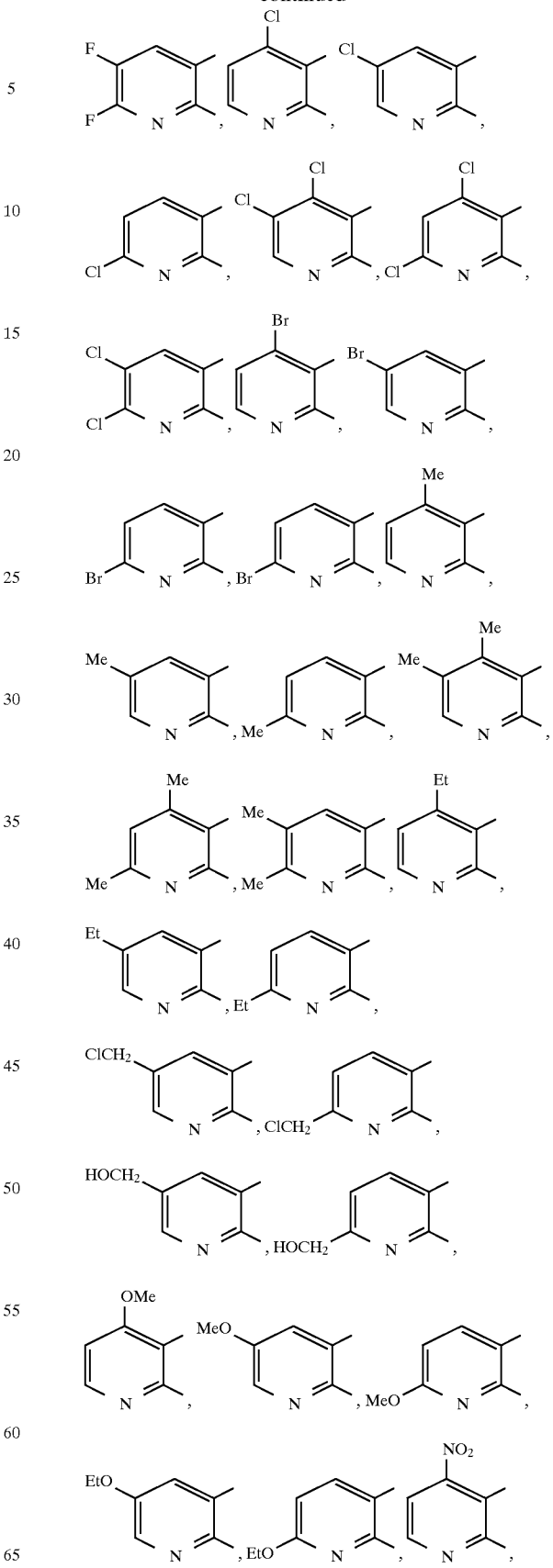

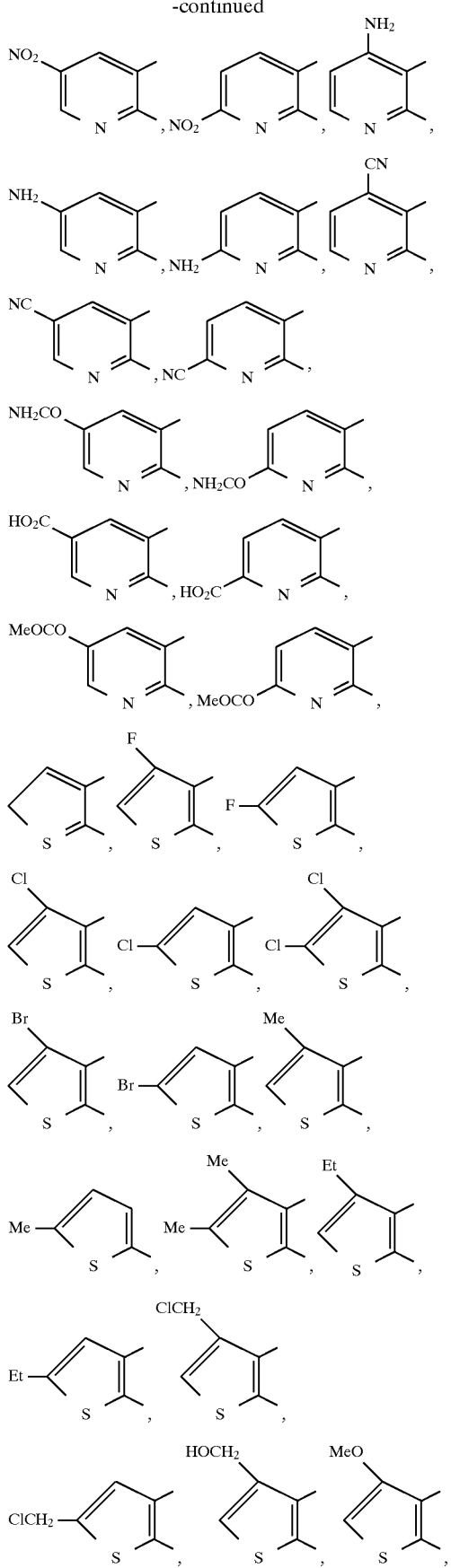
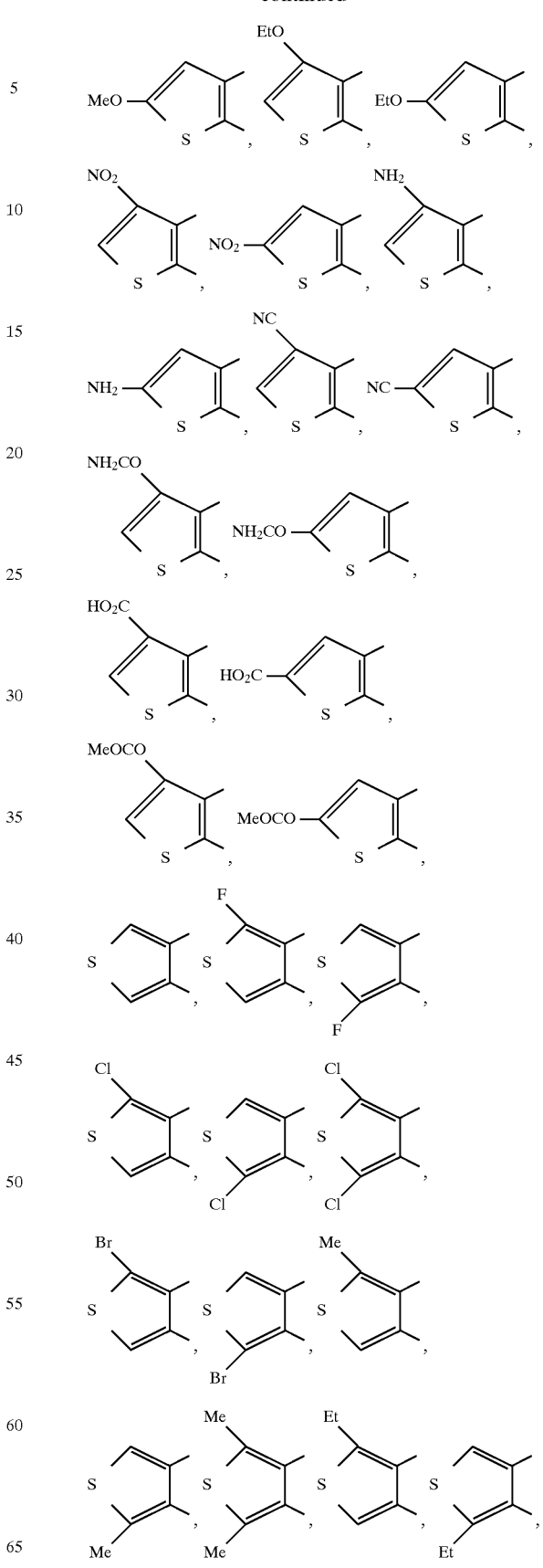

-continued
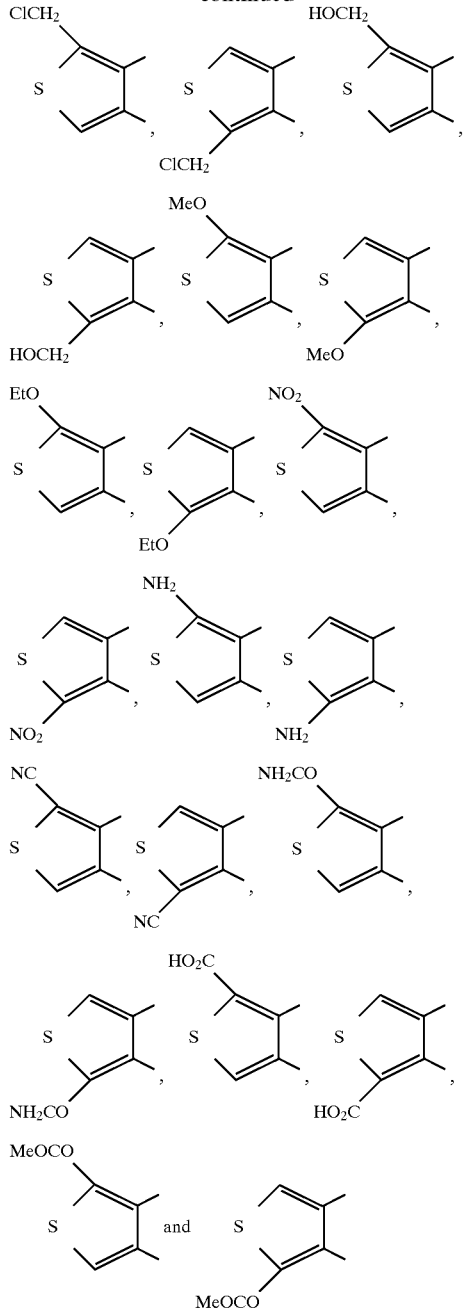
and with more preference given to the following:
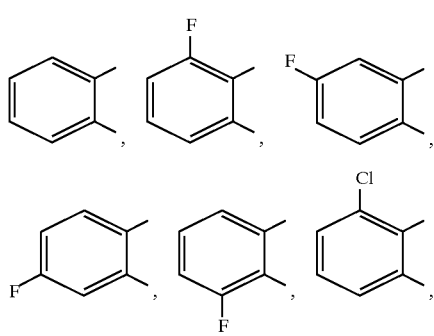
-continued
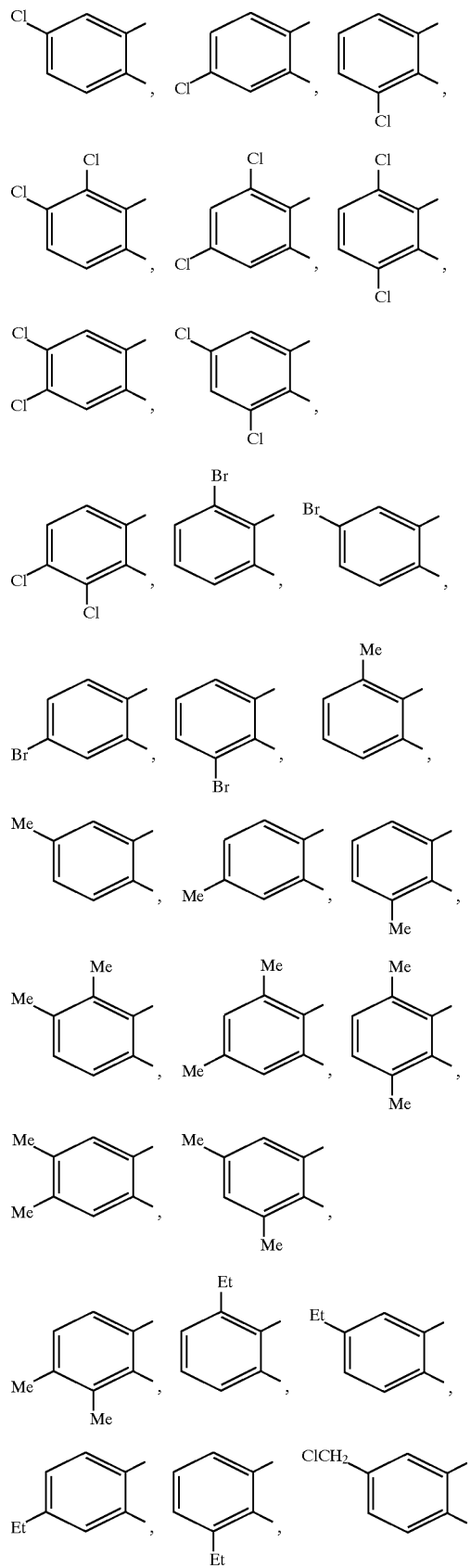

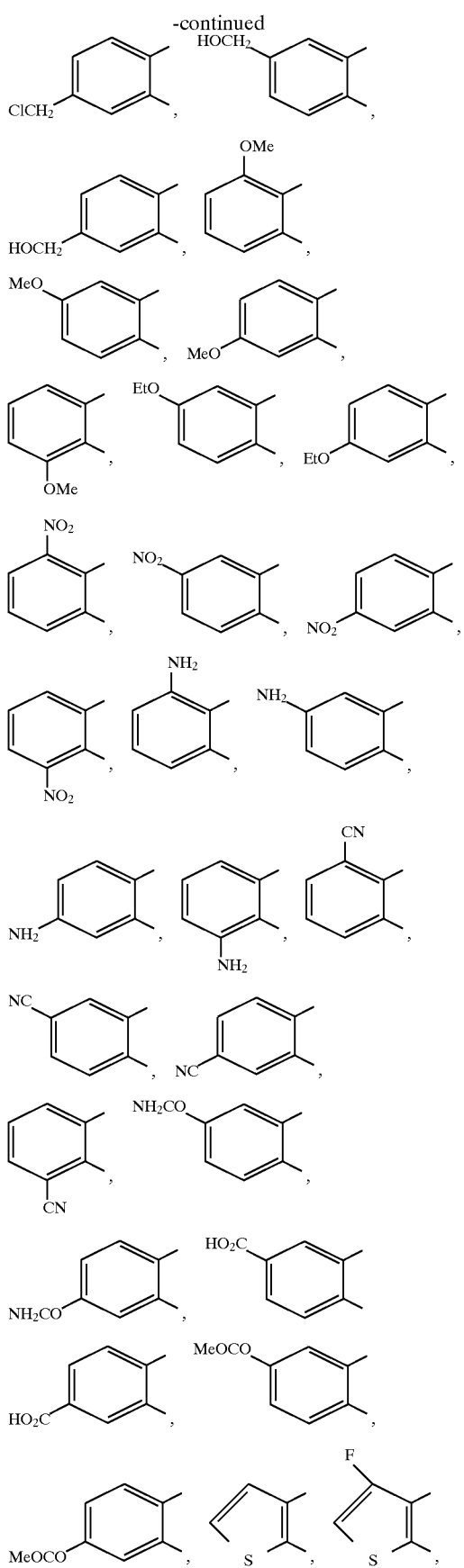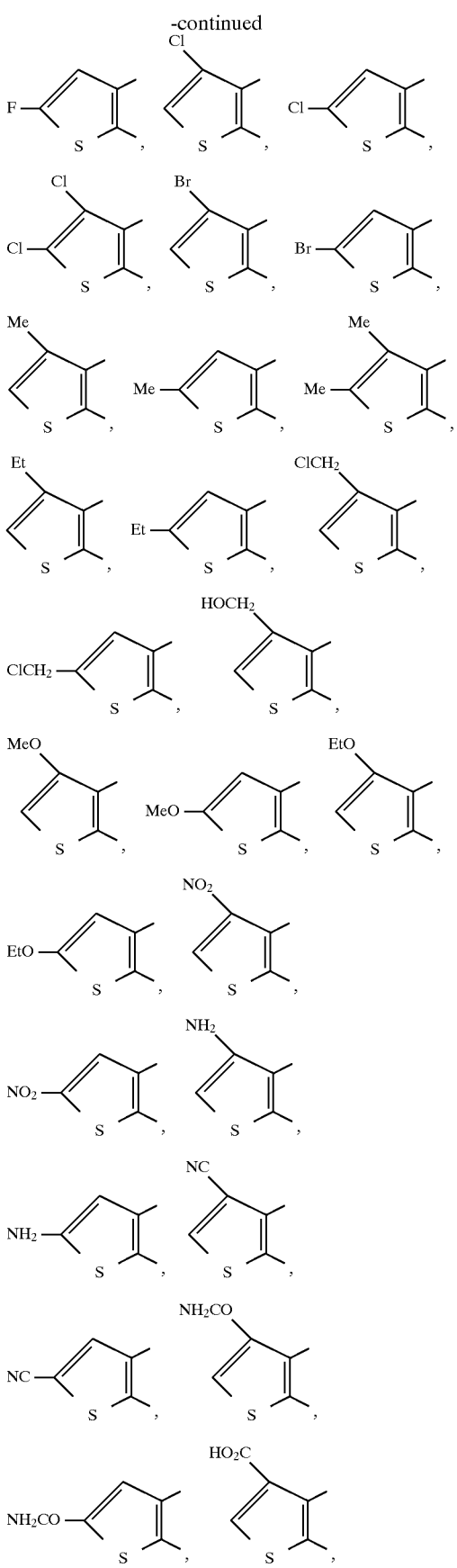

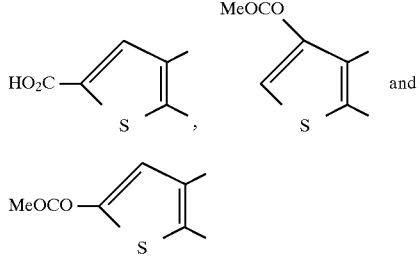
Particularly preferred are the following:
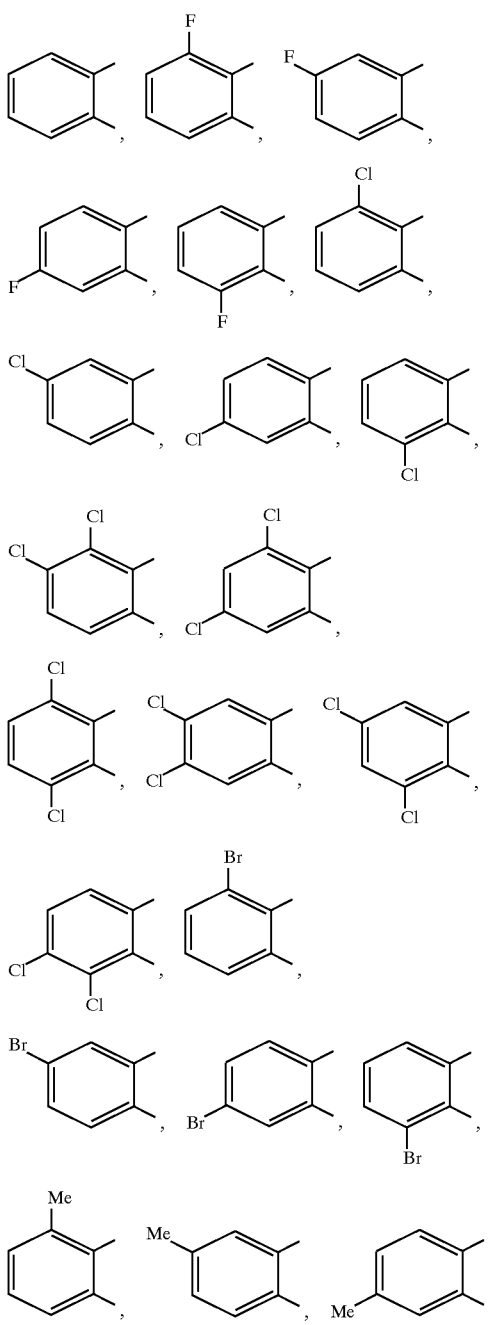
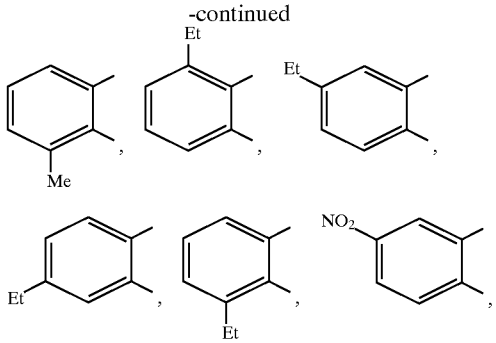
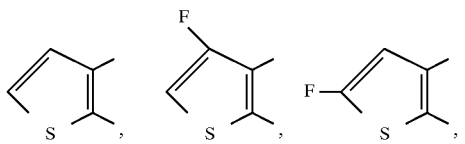
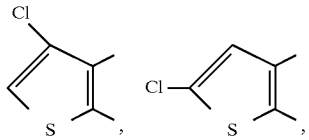
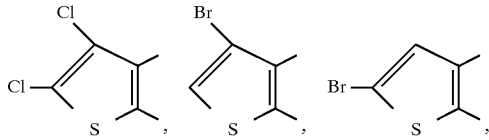
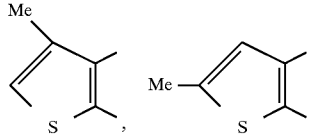
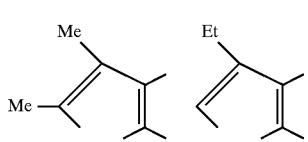
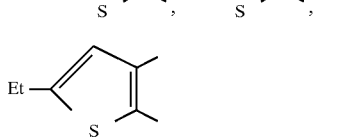
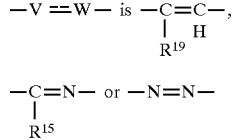
—V═W— is —C═C—,
               |  |
               $R^{19}$  H
—C═N— or —N═N—
 |
 $R^{15}$
wherein $R^{15}$ is lower alkyl and $R^{19}$ is hydrogen atom or lower alkyl. Preferred are
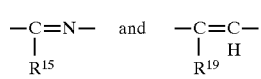
wherein $R^{15}$ and $R^{19}$ are as defined above, and particularly preferred is

wherein $R^{15}$ is as defined above.
The method for producing the compounds of the present invention is explained in the following.
Production 1
The method for producing, of the compounds of the formula [I], the objective compound [I-1] wherein
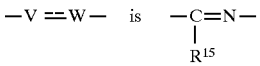
wherein $R^{15}$ is as defined above, and $R^2$ and $R^4$ are both hydrogen atom, is shown below.
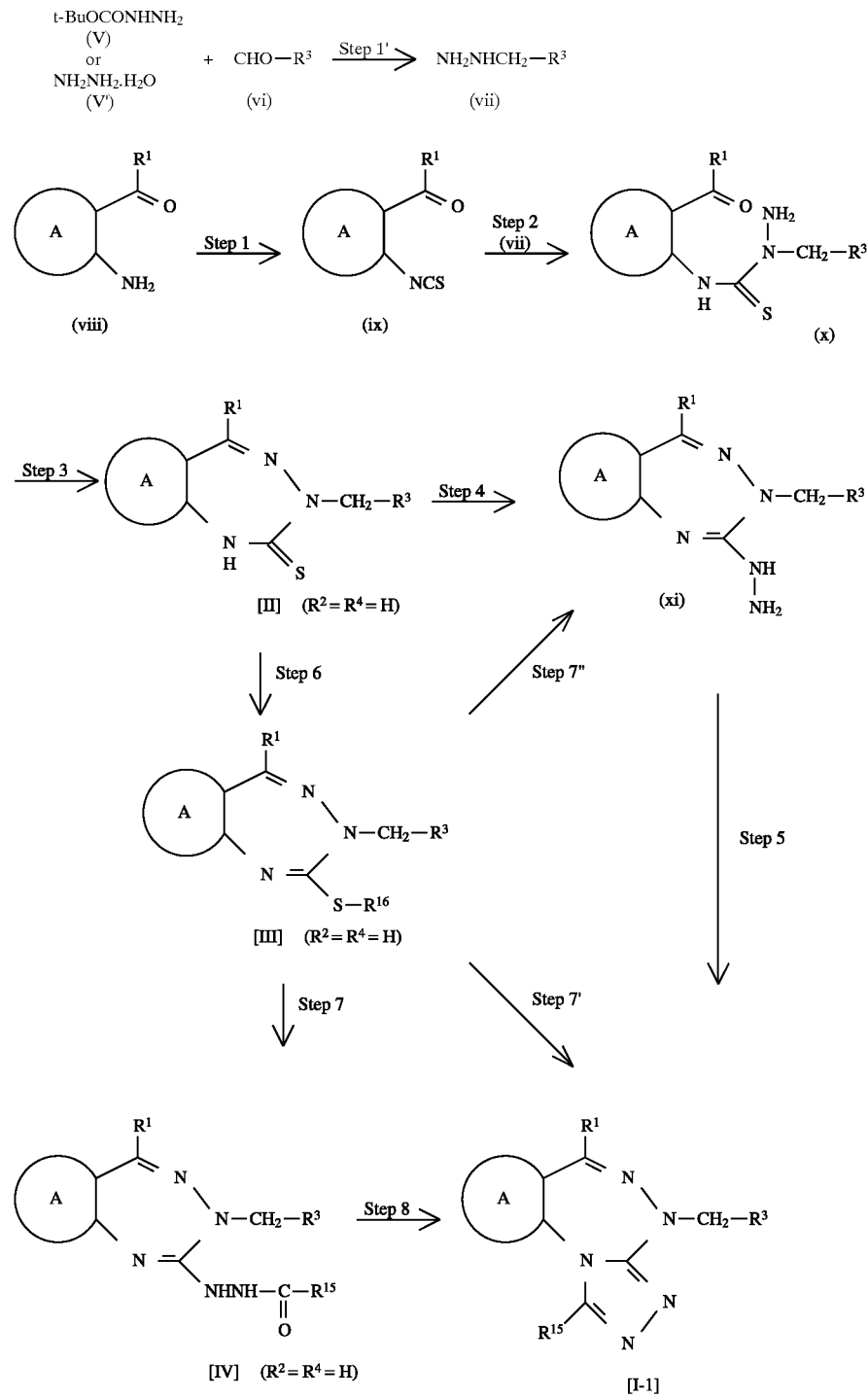

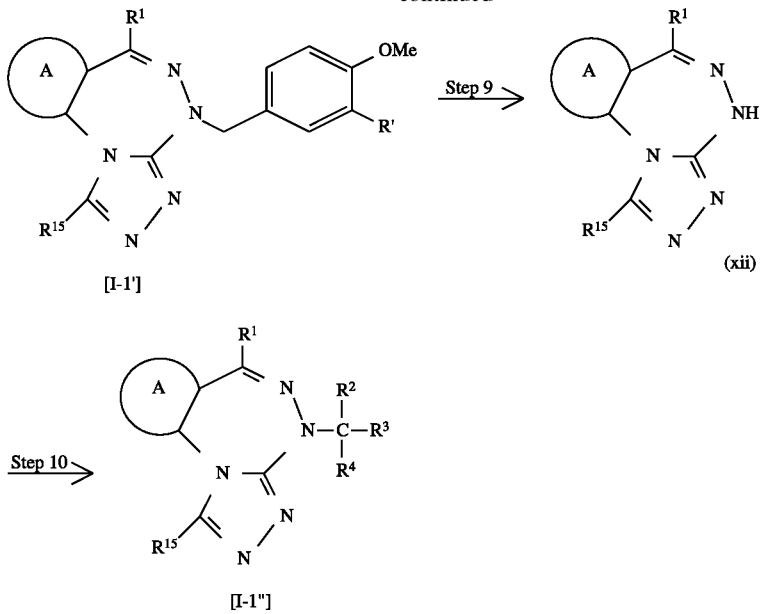

Step 1

A ketone compound (viii) wherein $R^1$ and A are respectively as defined above, which is obtained by the method known or described in Japanese Patent Unexamined Publication No. 2-256681 is reacted with thiophosgene thiocarbonyldiimidazole, di-2-pyridylthiocarbonate, diethylthiocarbamyl chloride or carbon disulfide in a solvent-such as dichloromethane, chloroform, tetrahydrofuran, 1,4-dioxane, methanol, ethanol, n-propanol, isopropanol, ethyl acetate, acetone, acetonitrile, toluene and water, or a mixed solvent thereof to give alternatively, the corresponding urea compound may be synthesized with the use of phosgene or carbonyldiimidazole and converted to thione using diphosphorus pentasulfide or Lawesson's [2,4-bis(4-methoxyphenyl)-1,3-dithia-2,4-diphosphetane-2,4-disulfide] to give compound (ix).

Step 1'

This steps is directed to the preparation of hydrazine compound (vii) to be used in Step 2.

A Schiff's base prepared by reacting tert-butyl carbazate (tert-butoxycarbonyl hydrazine) (v) and aldehyde compound (vi) wherein $R^3$ is as defined above, is subjected to catalytic reduction using a catalyst such as palladium-carbon, palladium black, palladium hydroxide-carbon and Raney nickel. Then, tert-butoxycarbonyl is deprotected using an acid such as hydrochloric acid to give desired hydrazine compound (vii) wherein $R^3$ is as defined above, or its salt. The solvent to be used for these reactions may be any as long as it does not participate in the reaction, and is exemplified by methanol, ethanol, n-propanol, isopropanol, water, acetic acid and a mixed solvent thereof. The protecting-group may be any, besides tert-butoxycarbonyl, as long as it can be conventionally used as a protecting group for amino, and the method for deprotection may be one conventionally used for deprotecting said protecting group. In addition, hydrazine monohydrate (v') may be used instead of protected hydrazine such as tert-butoxycarbonyl hydrazine. In this case, deprotection is not necessary.

Step 2

The compound (ix) obtained in Step 1 is reacted with hydrazine compound (vii) obtained in Step 1' or its salt in a solvent such as dichloromethane, chloroform, methanol, ethanol, n-propanol, isopropanol, tetrahydrofuran, 1,4-dioxane, acetone, ethyl acetate and water, or a mixed solvent thereof, under ice-cooling to under hating, preferably under ice-cooling to room temperature to give compound (x) wherein $R^1$, $R^3$ and A are respectively as defined above. When a salt of hydrazine compound is used, an organic base such as triethylamine and N,N-diisopropylethylamine or an inorganic base such as sodium hydrogencarbonate is preferably added.

Step 3

The compound (x) obtained in Step 2 is heated in a solvent such as methanol, ethanol, n-propanol, isopropanol, tetrahydrofuran, 1,4-dioxane, benzene and toluene, or a mixed solvent thereof in the presence of an inorganic acid such as hydrochloric acid, sulfuric acid and hydrobromic acid or an organic acid such as p-toluenesulfonic acid and trifluoroacetic acid-to give compound [II] wherein $R^1$, $R^3$ and A are as defined above, or its salt.

Step 4

The compound [II] obtained in Step 3 is reacted with hydrazine or its hydrate in a solvent such as tetrahydrofuran, N,N-dimethylformamide, methanol, ethanol, n-propanol and isopropanol, or a mixed solvent thereof at room temperature to under heating to give compound (xi) wherein $R^1$, $R^3$ and A are respectively as defined above.

Step 5

The compound (xi) obtained in Step 4 is reacted with orthoester of the formula: $R^{15}$—$C(OEt)_3$ wherein $R^{15}$ is as defined above, in a solvent such as benzene, toluene and N,N-dimethylformamide, or a mixed solvent thereof under heating, preferably with reflux under heating to give objective compound [I-1] wherein $R^1$, $R^3$, $R^{15}$ and A are respectively as defined above. In this reaction, addition of an acid such as acetic acid and p-toluenesulfonic acid or silica gel is sometimes preferable.

Step 6

This step and the next step are directed to the preparation of objective compound [I-1] from compound [II] via a different route.

The compound [II] obtained in Step 3 is dissolved or suspended in a solvent such as. N,N-dimethylformamide and tetrahydrofuran and sodium hydride is added. Then, the mixture is reacted with alkyl halide of the formula: $R^{16}$-Hal wherein $R^{16}$ is lower alkyl and Hal is halogen atom, to give compound [III] wherein $R^1$, $R^3$, $R^{16}$ and A are respectively as defined above. Alternatively, the compound [II] is reacted with $R^{16}$-Hal or

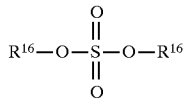

wherein $R^{16}$ and Hal are respectively as defined above, in a solvent such as acetone, methyl ethyl ketone and toluene, or in a solvent such as methanol and ethanol or a mixture of methanol or ethanol and water, in the presence of a base such as an aqueous solution of sodium carbonate, potassium carbonate, sodium hydroxide.

Step 7

The compound [III] obtained in Step 6 is dissolved or suspended in a solvent such as ethanol, n-propanol, isopropanol, n-butanol and toluene, or a mixed solvent thereof and added with

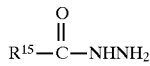

wherein $R^{15}$ is as defined above. The mixture is heated, preferably refluxed under heating to give compound [IV] wherein $R^1$, $R^3$, $R^{15}$ and A are respectively as defined above. In this case, addition of an acid such as acetic acid, p-toluenesulfonic acid and trifluoroacetic acid is sometimes preferable.

Step 7'

The compound [III] obtained in Step 6 is dissolved or suspended in a solvent such as ethanol, n-propanol, isopropanol, n-butanol and toluene, and added with

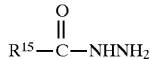

wherein $R^{15}$ is as defined above, which is followed by heat-reacting at preferably 90° C.–110° C. or at a temperature higher than that to give objective compound [I-1] wherein $R^1$, $R^3$, $R^{15}$ and A are respectively as defined above. In this case again, addition of an acid such as acetic acid, p-toluenesulfonic acid and trifluoroacetic acid is sometimes preferable. When these acids are added in not less than one equivalent relative to compound [III], a salt of compound [I-1] can be directly obtained.

Step 7"

This step is directed to the preparation of compound (xi) by a different method.

The compound [III] is reacted with hydrazine instead of

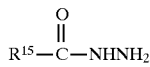

shown in Step 7, in a solvent such as methanol, ethanol, n-propanol, isopropanol and n-butanol, or a mixed solvent thereof to give compound (xi).

Step 8

The compound [IV] obtained in Step 7 is heated or preferably refluxed under heating in a solvent such as benzene and toluene to give objective compound [I-1]. In this reaction, addition of an acid such as acetic acid, p-toluenesulfonic acid and hydrochloric acid is sometimes preferable.

Step 9

This step and the next step are directed to the substitution of a moiety

of a compound wherein $R^2$ and $R^4$ are hydrogen atom and $R^3$ is 4-methoxyphenyl or 3,4-dimethoxyphenyl.

Of the compounds [I-1], a compound [I-1'] (in the reaction flow, R' is hydrogen atom or methoxy, and $R^1$, $R^{15}$ and A are as defined above) wherein $R^2$ and $R^4$ are hydrogen atom and $R^3$ is 4-methoxyphenyl or 3,4-dimethoxyphenyl is reacted in a solvent such as chloroform, 1,4-dioxane, acetic acid and trifluoroacetic acid, or a mixed solvent thereof, in the presence of a strong acid such as sulfuric acid, hydrochloric acid and hydrobromic acid to give compound (xii) wherein $R^1$, $R^{15}$ and A are as defined above. In this reaction, addition of a benzyl cation trapping agent such as phenol, anisole and thioanisole is sometimes preferable.

Step 10-1

Compound (xii) obtained in Step 9 is reacted with

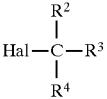

wherein Hal is halogen atom, and $R^2$, $R^3$ and $R^4$ are respectively as defined above, in a solvent such as N,N-dimethylformamide, dimethyl sulfoxide, tetrahydrofuran, acetone, methyl ethyl ketone, dichloromethane, chloroform and water, or a mixed solvent thereof, in the presence of a base such as sodium hydride, potassium hydride, sodium hydroxide, potassium hydroxide, sodium carbonate, potassium carbonate, triethylamine, N,N-diisopropylethylamine, pyridine and N,N-dimethylaminopyridine under ice-cooling to under heating, preferably under ice-cooling to room temperature to give objective compound [I-1"] wherein $R^1$, $R^2$, $R^3$, $R^4$, $R^{15}$ and A are respectively as defined above. In this reaction, the base to be used is appropriately selected depending on the reactivity and stability of the compound

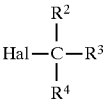

to be reacted. These bases may be used in an appropriate combination as the case demands.

Step 10-2

When a reaction is carried out using a compound

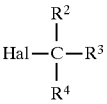

as shown in Step 10-1 wherein $R^2$ and $R^4$ are hydrogen atom, the use of the same solvent and the same base as in Step 10-1 in the presence of the air (oxygen) may result in the production of objective compound [I-1"] wherein $R^2$ is hydroxy and $R^4$ is hydrogen atom.

Step 10-3

According to the method of Edward et al [*Tetrahedron Lett.*, 31, 3417 (1990)], compound (xii) is reacted with an alcohol compound of the formula: $R^3R^4CHOH$ wherein $R^3$ and $R^4$ are respectively as defined above, and triphenylphosphine in a solvent such as tetrahydrofuran, diethyl ether, 1,4-dioxane and N,N-dimethylformamide. Then, dialkyl azodicarboxylate is added to the reaction system and the mixture is reacted under ice cooling to 40° C., preferably at room temperature or 25° C. to give objective compound [I-1"] wherein $R^2$ is hydrogen atom.

Step 10-4

The compound (xii) is reacted in a solvent such as methanol, ethanol, n-propanol and isopropanol using an aqueous solution of formaldehyde and the solvent used ($R^{31}CH_2OH$ wherein $R^{31}$ is lower alkyl) as reagents, or with an aqueous solution of formaldehyde and $Y'NH_2$ wherein $Y'$ is an optionally substituted aryl or an optionally substituted heteroaryl, at room temperature to heat-refluxing temperature to give objective compound [I-1"] wherein $R^2$ and $R^4$ are both a hydrogen atom and $R^3$ is a lower alkoxy or —NHY' wherein Y' is as defined above.

Step 10-5

The compound (xii) is reacted with an isocyanate compound of the formula: Y'NCO wherein Y' is as defined above, in a solvent such as dichloromethane, chloroform, N,N-dimethylformamide, tetrahydrofuran and anhydrous acetonitrile in the presence of, where necessary, an inorganic base such as sodium hydroxide and potassium hydroxide or organic base such as triethylamine and N,N-diisopropylethylamine to give objective compound [I-1"] wherein $R^2$ and $R^4$ form carbonyl together with the carbon atom to which $R^2$ and $R^4$ bind and $R^3$ is -NHY' wherein Y' is as defined above.

Step 10-6

The compound (xii) is reacted with an oxirane compound of the formula

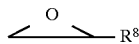

wherein $R^8$ is as defined above, in a solvent such as N,N-dimethylformamide, dimethyl sulfoxide and tetrahydrofuran, in the presence of a base such as sodium hydride and potassium hydride to give objective compound [I-1"] wherein both $R^2$ and $R^4$ are hydrogen atoms and $R^3$ is of the formula

wherein $R^8$ is as defined above.

Step 10-7

Of the compounds obtained in Step 10-1, a compound wherein $R^3$ is expressed by the formula

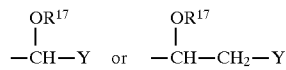

wherein $R^{17}$ is a protecting group for hydroxy and Y is as defined above, is deprotected to give objective compound [I-1"] wherein $R^3$ is

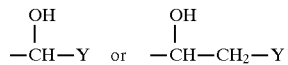

wherein Y is as defined above. The protecting group for hydroxy may be any as long as it is conventionally used for this end, and when tetrahydropyranyl is used, for example, the solvent may be any as long as it does not participate in the reaction, such as methanol, ethanol, n-propanol, isopropanol, tetrahydrofuran, 1,4-dioxane, dichloromethane and chloroform, and the reagent may be an organic acid such as p-toluenesulfonic acid and trifluoroacetic acid, or an inorganic acid such as hydrochloric acid, sulfuric acid and: hydrobromic acid.

Step 10-8

The compound obtained in Step 10-6 or 7 wherein $R^3$ is

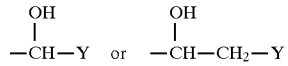

is subjected to an oxidation with an oxidizing agent such as chromium trioxide, pyridinium chlorochromate, pyridinium chromate, Jones reagent (mixture of chromium trioxide and sulfuric acid) and an oxidizing agent prepared from dimethyl sulfoxide and oxalyl chloride in a solvent such as acetic acid, pyridine, dichloromethane and water, or a mixed solvent thereof to give objective compound [I-1]" wherein $R^3$ is

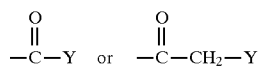

wherein Y is as defined above.

Step 10-9

Of the compounds obtained in Step 10-1, a compound wherein $R^3$ is —$CO_2Et$ is reacted with a base such as sodium hydroxide and potassium hydroxide, in a solvent such as methanol, ethanol, n-propanol, isopropanol, tetrahydrofuran, 1,4-dioxane and water, or a mixed solvent thereof to give objective compound [I-1" wherein $R^3$ is —$CO_2H$.

Step 10-10

The compound obtained in Step 10-9 wherein $R^3$ is —$CO_2H$ is reacted with alkyl halocarbonate such as ethyl chlorocarbonate and isobutyl chlorocarbonate, and $R^8NH_2$ wherein $R^8$ is as defined above, in a solvent such as N,N-dimethylformamide, dimethyl sulfoxide, tetrahydrofuran, acetone and dichloromethane, or a mixed solvent thereof, in the presence of a base such as triethylamine and N,N-diisopropylethylamine to give objective compound [I-1"] wherein $R^3$ is —$CONHR^8$ wherein $R^8$ is as defined above. Alternatively, conventional peptide linkage formation is followed to give objective compound [I-1"] wherein $R^3$ is —$CONHR^8$ [Nobuo Izumiya, Pepuchido Gosei no Kiso to Jikken, Maruzen (1985)].

Step 10-11

Of the compounds obtained in Step 10-1, a compound wherein $R^3$ is —$CH_2$-Hal wherein Hal is halogen atom, is reacted with $Y'NH_2$ wherein Y' is as defined above, or Y'SH wherein Y' is as defined above, in a solvent such as ethanol, dichloromethane, N,N-dimethylformamide, dimethyl sulfoxide, tetrahydrofuran and water, or a mixed solvent thereof, in the presence of a base such as sodium hydride, potassium hydride, sodium hydroxide, potassium hydroxide, potassium carbonate, triethylamine and N,N-diisopropylethylamine to give objective compound [I-1"]

wherein R³ is —CH₂NHY' wherein Y' is as defined above or —CH₂SY' wherein Y' is as defined above.

Step 10-12

Of the compounds obtained in Step 10-1, a compound wherein R³ is substituted aryl or substituted heteroaryl and the substituent is nitro is subjected to catalytic reduction using hydrogen, in the presence of a catalyst such as palladium-carbon, palladium hydroxide-carbon, palladium black and Raney nickel, or catalytic reduction using formic acid, ammonium formate, cyclohexene or cyclohexadiene in the presence of the above-mentioned catalyst, in a solvent such as methanol, ethanol, n-propanol, isopropanol, 1,4-dioxane, acetic acid and water, or a mixed solvent thereof. Alternatively, reduction using a reducing agent such as sodium borohydride and lithium borohydride in the above-mentioned solvent gives objective compound [I-1"] wherein R³ is substituted aryl or substituted heteroaryl and the substituent is amino, or objective compound [I-1"] wherein R³ is substituted aryl or substituted heteroaryl and the substituent is formylamino. A mixture thereof may be obtained, which is separated by a conventional method.

Step 10-13

The compound obtained in Step 10-12 wherein R³ is substituted aryl or substituted heteroaryl and the substituent is amino is reacted with an acylating agent such as acetic anhydride, or acetic anhydride and formic acid, or acetyl chloride, or alkylsulfonyl halide such as methanesulfonyl chloride, in a solvent such as dichloromethane, chloroform, pyridine, ethanol, acetone and tetrahydrofuran to give objective compound [I-1"] wherein R³ is substituted aryl or substituted heteroaryl and the substituent is acylamino, alkylsulfonylamino, or bis(alkylsulfonyl)amino or halogenoalkylsulfonylamino. Addition of a base such as triethylamine and N,N-diisopropylethylamine may be preferable as the case demands.

Step 10-14

The compound obtained in Step 10-12 wherein R³ is substituted aryl or substituted heteroaryl and the substituent is amino is subjected to reduction under a hydrogen atmosphere using a catalyst such as palladium-carbon, palladium hydroxide-carbon and palladium black, in a solvent such as methanol, ethanol, n-propanol, isopropanol and water, or a mixed solvent thereof in the presence of an aqueous solution of formaldehyde to give objective compound [I-1"] wherein R³ is substituted aryl or substituted heteroaryl and the substituent is methylamino or dimethylamino. A mixture thereof may be obtained, which is separated by a conventional method.

Step 10-15

Of the compounds obtained in Step 10-1, a compound wherein R³ is substituted aryl or substituted heteroaryl and the substituent is benzyloxy is subjected to reduction under a hydrogen atmosphere using a catalyst such as palladium-carbon, palladium hydroxide-carbon and palladium black, or catalytic reduction using formic acid, ammonium formate, cyclohexene or cyclohexadiene in the presence of a catalyst such as palladium-carbon, palladium hydroxide-carbon, palladium black and Raney nickel, in a solvent such as methanol, ethanol, n-propanol, isopropanol, 1,4-dioxane and acetic acid, or a mixed solvent thereof to give objective compound [I-1"] wherein R³ is substituted aryl or substituted heteroaryl and the substituent is hydroxy. When the substituent is dibenzyloxy, a corresponding catechol compound is obtained by the above reaction.

Step 10-16

The compound obtained in Step 10-15 wherein R³ is substituted aryl or substituted heteroaryl and the substituent is hydroxy is reacted with diazoalkane such as diazomethane and diazoethane, in a solvent such as tetrahydrofuran, diethyl ether and 1,4-dioxane to give objective compound [I-1"] wherein R³ is substituted aryl or substituted heteroaryl and the substituent is lower alkoxy.

Production 2

In this section, a method for producing objective compound [I-2] by a production method different from Production 1 is shown.

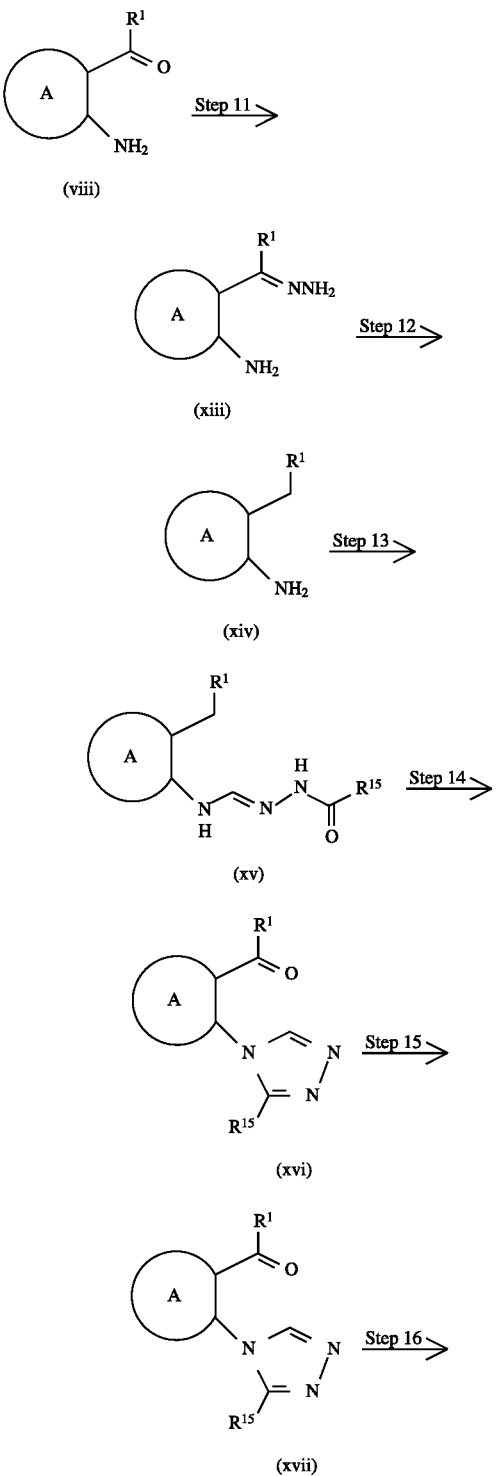

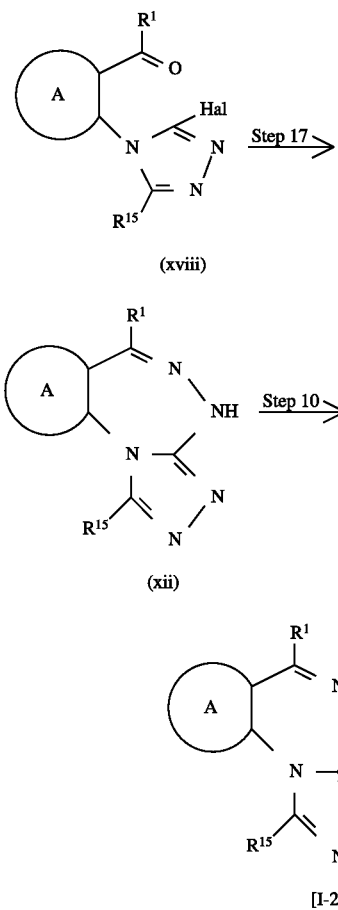

Step 11

The compound (viii) is reacted with hydrazine in a solvent such as diethylene glycol, ethylene glycol monomethyl ether, dimethyl sulfoxide and N,N-dimethylformamide under heating, preferably at a temperature not less than 150° C. to give compound (xiii) wherein $R^1$ and A are respectively as defined above.

Step 12

The compound (xiii) obtained in Step 11 is reacted in a solvent such as diethylene glycol, ethylene glycol monomethyl ether, dimethyl sulfoxide and N,N-dimethylformamide in the presence of a base such as sodium hydroxide, potassium hydroxide and lithium hydroxide under heating, preferably from 80° C. to 150° C., to give compound (xiv) wherein $R^1$ and A are respectively as defined above.

Step 13

The compound (xiv) obtained in Step 12 and tri-(lower) alkyl orthoformate such as triethyl orthoformate are reacted under heating, preferably from 100° C. to 150° C. Then, the mixture is reacted with an acyl hydrazide compound of the formula: $R^{15}CONHNH2$ wherein $R_{15}$ is as defined above, in a solvent such as methanol, ethanol, n-propanol and isopropanol, preferably at room temperature to give compound (xv) wherein $R^1$, $R^{15}$ and A are respectively as defined above.

Step 14

The compound (xv) obtained in Step 13 is reacted in a solvent such as diethylene glycol dimethyl ether, ethylene glycol monomethyl ether, dimethyl sulfoxide, N,N-dimethylformamide, pyridine and water, or a mixed solvent thereof under heating, preferably with reflux under heating to give compound (xvi) wherein $R^1$, $R^{15}$ and A are respectively as defined above.

Step 15

The compound (xvi) obtained in Step 14 is subjected to oxidation with an oxidizing agent such as chromium trioxide, pyridinium chlorochromate and Jones reagent in a solvent such as acetic acid, pyridine, dichloromethane and water, or a mixed solvent thereof to give compound (xvii) wherein $R^1$, $R^{15}$ and A are respectively as defined above.

Step 16

The compound (xvii) is halogenated with a halogenating agent such as N-bromosuccinimide, N-chlorosuccinimide, N-iodosuccinimide and carbon tetrabromide in a solvent such as carbon tetrachloride, chloroform, dichloromethane and 1,2-dichloroethane under heating, preferably with reflux under heating to give compound (xviii) wherein $R^1$, $R^{15}$ and A are respectively as defined above, and Hal means halogen atom.

Step 17

The compound (xviii) is reacted with hydrazine sulfate in a solvent such as methanol, ethanol, n-propanol and isopropanol, or a mixed solvent thereof in the presence of a weak base such as sodium acetate, potassium acetate and lithium acetate under heating, preferably with reflux under heating to give compound (xii) wherein $R^1$, $R^{15}$ and A are respectively as defined above. This compound can be introduced into the objective compound [I-2] wherein $R^1$, $R^2$, $R^3$, $R^4$, $R^{15}$ and A are respectively as defined above, by the method shown in Step 10.

Production 3

A novel method for producing the objective compound [I-3] by a production method different from the production method shown in Production 1 and Production 2 is shown in the following.

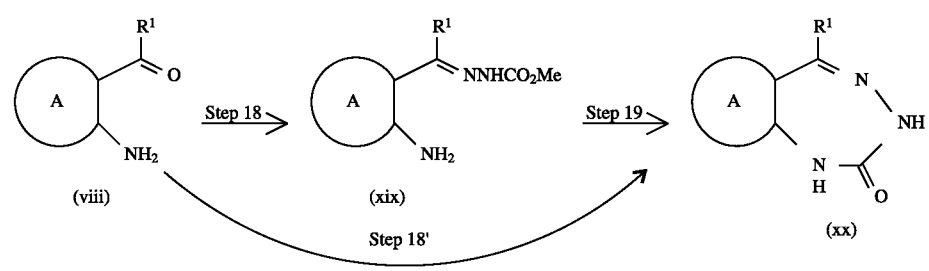

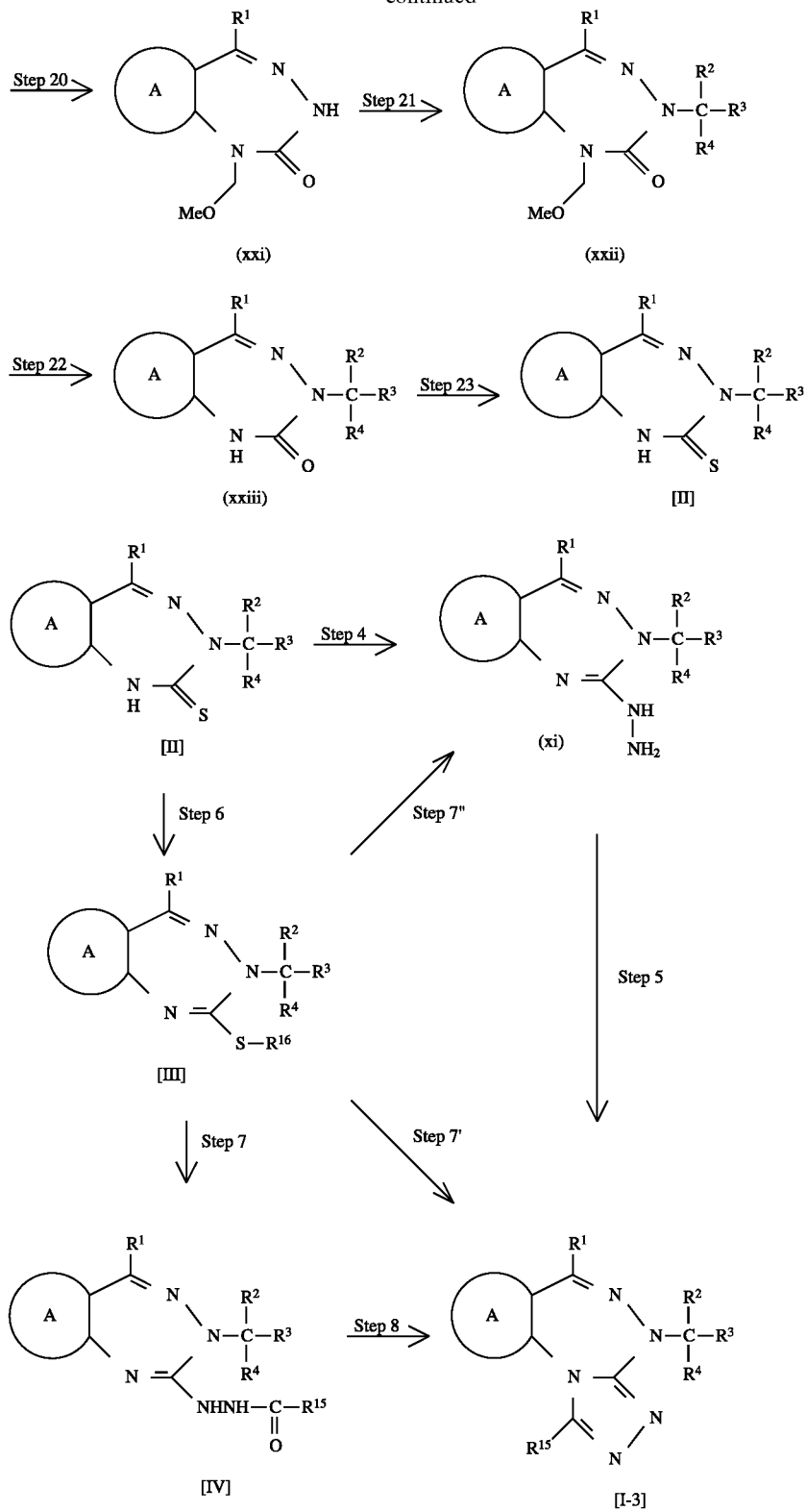

Step 18

The compound (viii) is reacted with methyl carbazate in a solvent such as methanol, ethanol, n-propanol and isopropanol, or a mixed solvent thereof, in the presence of p-toluenesulfonic acid, under heating, preferably with reflux under heating to give compound (xix) wherein $R^1$ and A are respectively as defined above.

Step 19

The compound (xix) obtained in Step 18 is reacted in a solvent such as dimethyl sulfoxide and N,N- dimethylformamide, under heating, preferably with reflux under heating to give compound (xx) wherein $R^1$ and A are respectively as defined above.

Step 18'

This step is for performing Step 18 and Step 19 in a single step.

The compound (viii) is reacted with methyl carbazate in a solvent such as dimethyl sulfoxide and N,N-dimethylformamide, under heating, preferably with reflux under heating to give compound (xx).

Step 20

This step is for selective protection of the 1-position nitrogen atom of triazepine ring of compound (xx) wherein the protecting group may be any as long as it can selectively protect, and is exemplified by methoxymethyl, which is explained in the following.

The compound (xx) obtained in Step 19 or Step 18' is reacted with chloromethyl methyl ether in a solvent such as N,N-dimethylformamide and tetrahydrofuran in the presence of a base such as sodium hydroxide, potassium hydroxide, lithium hydroxide, sodium carbonate and potassium carbonate to give compound (xxi) wherein $R^1$ and A are respectively as defined above.

Step 21

The compound (xxi) obtained in Step 20 is reacted with

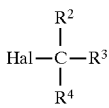

wherein $R^2$, $R^3$, $R^4$ and Hal are respectively as defined above, according to the method of Step 10-1 to give compound (xxii) wherein $R^1$, $R^2$, $R^3$, $R^4$ and A are respectively as defined above.

Step 22

This step is directed to removing the protecting group of the 1-position nitrogen atom of the triazepine ring of compound (xxii), which is carried out by a conventional method used for removing said protecting group. Examples thereof include deprotection of methoxymethyl, which is described in the following.

The compound (xxii) obtained in Step 21 is reacted in the presence of an acid such as hydrochloric acid, sulfuric acid, hydrobromic acid, trifluoroacetic acid and trifluoromethanesulfonic acid in a solvent such as methanol, ethanol, n-propanol, isopropanol, tetrahydrofuran, 1,4-dioxane and water, or a mixed solvent thereof to give compound (xxiii) wherein $R^1$, $R^2$, $R^3$, $R^4$ and A are respectively as defined above.

Step 23

The compound (xxiii) obtained in Step 22 is reacted with an agent for converting the compound to thione, such as diphosphorus pentasulfide and Lawesson's reagent, in a solvent such as diethylene glycol, diethylene glycol dimethyl ether, ethylene glycol monomethyl ether, dimethyl sulfoxide and N,N-dimethylformamide, in the presence or absence of sodium carbonate and potassium hydrogencarbonate to give compound [II] wherein $R^1$, $R^2$, $R^3$, $R^4$, $R^{15}$ and A are respectively as defined above. This compound [II] can be introduced into the objective compound [I-3] wherein $R^1$, $R^2$, $R^3$, $R^4$, $R^{15}$ and A are respectively as defined above, according to the method of Step 4 and Step 5, or Step 6, Step 7 and Step 8, and where necessary, Step 9 and Step 10.

Production 4

A production method of, of the compounds of the formula [I], the objective compound [I-4] wherein

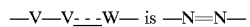

is shown in the following.

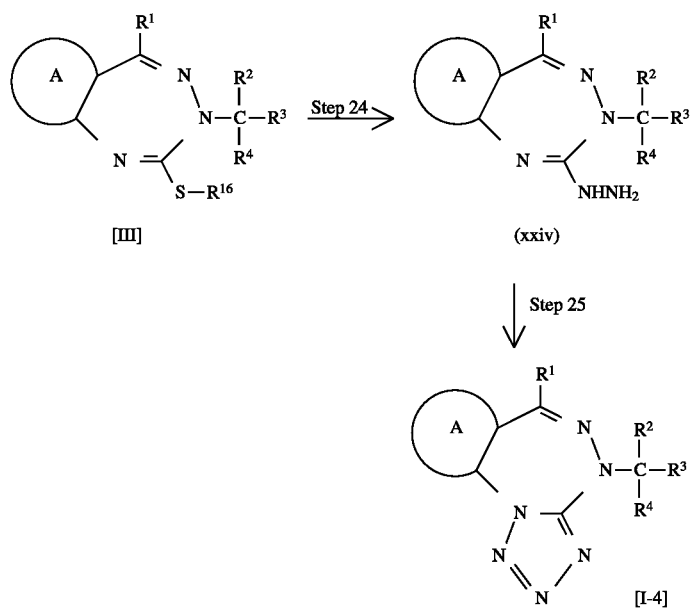

Step 24

The compound [III] obtained in Step 6 or a salt thereof is reacted with hydrazine or a hydrate thereof in a solvent such as methanol, ethanol, n-propanol and isopropanol from room temperature to under heat-refluxing to give compound (xxiv) wherein $R^1$, $R^2$, $R^3$, $R^4$ and A are respectively as defined above.

Step 25

The compound (xxiv) obtained in Step 24 or a salt thereof is reacted with sodium nitrite in a solvent such as water in the presence of an acid such as hydrochloric acid or acetic acid under ice-cooling to room temperature, preferably from 0° C. to 10° C. to give the objective compound [I-4] wherein $R^1$, $R^2$, $R^3$, $R^4$ and A are respectively as defined above.

Production 5

A production method of, of the compounds of the formula [I], the objective compound [I-5] wherein

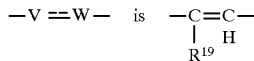

wherein $R^{19}$ is as defined above, is shown in the following.

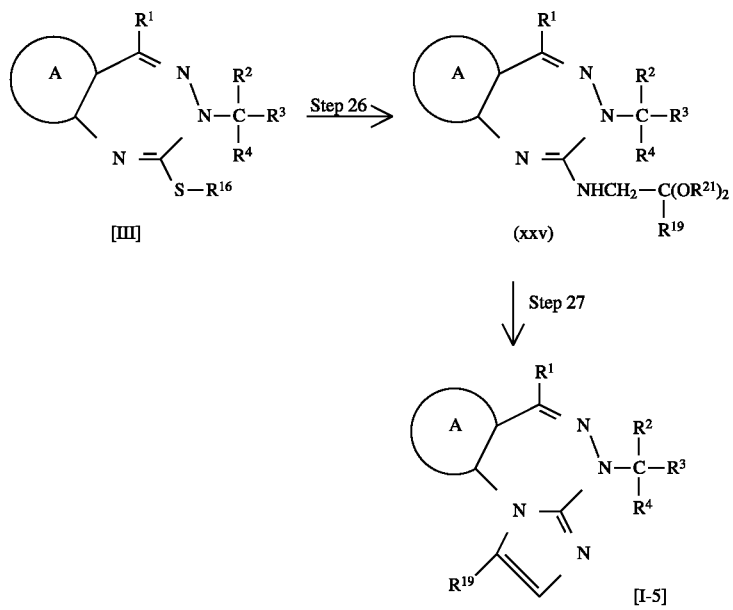

Step 26

A compound [III] obtained in Step 6 or a salt thereof is reacted with aminoketone dialkyl acetal such as aminoacetaldehyde dimethyl acetal in a solvent such as diethylene glycol, ethylene glycol monomethyl ether and 2-ethoxyethanol under heating, preferably with reflux under heating to give compound (xxv) wherein $R^{21}$ is lower alkyl and $R^1$, $R^2$, $R^3$, $R^4$, $R^{19}$ and A are respectively as defined above. In this reaction, addition of an acid such as acetic acid, p-toluenesulfonic acid and trifluoroacetic acid is sometimes preferable.

Step 27

The compound (xxv) obtained in Step 26 or a salt thereof is reacted with a strong acid such as hydrochloric acid, sulfuric acid and hydrobromic acid in a solvent such as 1,4-dioxane, acetic acid and water, or a mixed solvent thereof, under heating, preferably with reflux under heating to give the objective compound (I-5] wherein $R^1$, $R^2$, $R^3$, $R^4$, $R^{19}$ and A are respectively as defined above.

The compound of the present invention thus obtained, which is shown by the formula [I] has pharmacological actions such as bone resorption-inhibitory action and osteogenesis-promoting action, and is useful as a therapeutic agent for osteoporosis and rheumatoid arthritis. When the compound of the present invention is used as a therapeutic agent for osteoporosis or rheumatoid arthritis, it is generally administered systemically or topically by oral or parenteral administration.

While the dose varies depending on the age, body weight, symptom, therapeutic effect, administration route, treatment time and the like, it is generally from 0.01 mg to 100 mg for an adult, which is orally or parenterally administered once to several doses per day.

When the compound of the present invention is formulated into solid compositions for oral administration, it can be prepared into a dosage form such as tablet, pill, powder, granule and the like. In such solid compositions, one or more active substances are admixed with at least one inert diluent, dispersing agent or adsorbent, such as lactose, mannitol, glucose, hydroxypropylcellulose, microcrystalline cellulose, starch, polyvinylpyrrolidone, magnesium aluminometasilicate and anhydrous silicate powder. Moreover, the compositions may comprise other additives other than the diluent by a conventional method.

When the compound is formulated into tablet or pill, a gastric coating or an enteric coating of, for example, sucrose, gelatin, hydroxypropylcellulose or hydroxymethylcellulose phthalate may be applied, or two or more layers may be formed. Moreover, a capsule made from a substance such as gelatin and ethylcellulose may be used.

When a liquid composition for oral administration is desired, the compound can be formulated into a dosage form such as pharmaceutically acceptable emulsion, solution, suspension, syrup, elixir and the like. Examples of the diluent to be used include purified water, ethanol, vegetable oil and emulsifier. This composition may also comprise, besides the diluent, auxiliary agents such as wetting agent, suspending agent, sweetener, flavor, aromatic and preservative.

When the compound is prepared into an injection for parenteral administration, a sterile aqueous or nonaqueous solvent, solubilizer, suspending agent or emulsifier is used. Examples of the aqueous solvent, solubilizer and suspending agent include distilled water for injection, physiological saline, cyclodextrin and its derivatives, organic amines such as triethanolamine, diethanolamine, monoethanolamine and triethylamine, and inorganic alkaline solution. Examples of nonaqueous solvent include propylene glycol, polyethylene glycol and vegetable oils such as olive oil, and alcohols such as ethanol. As the solubilizer, for example, polyoxyethylene hydrogenated castor oil, surfactants such as sucrose fatty acid ester (forming mixed micelle), lecithin and hydrogenated lecithin (forming liposome) may be used. In addition, an emulsion preparation comprising a nonaqueous solvent such as vegetable oil, and lecithin, polyoxyethylene hydrogenated castor oil or polyoxyethylene polyoxypropylene glycol may be produced.

As other compositions for parenteral administration, an external liquid, liniment such as ointment, suppository or pessary comprising one or more active ingredients, which can be formulated by a method known per se may be employed.

The compounds of the above-mentioned formulas [II], [III] and [IV] are useful as intermediate compounds for producing the triazepine compounds of the formula [I]. Using these intermediate compounds and following the above-mentioned production methods, the objective compound [I] can be produced. In particular, of the intermediate compounds of the formulas [II], [III] and [IV], the compounds of the formulas [II'], [III'] and [IV'] are novel compounds and are useful as intermediate compounds for producing the triazepine compound of the formula [I].

EXAMPLES

The compounds of the present invention which are expressed by the formula [I] and methods for producing same are explained in detail by illustrative examples. It is needless to say that the present invention is not limited to these examples.

Preparative Example 1 (Step 1')

3,4-Dimethoxybenzylhydrazine hydrochloride

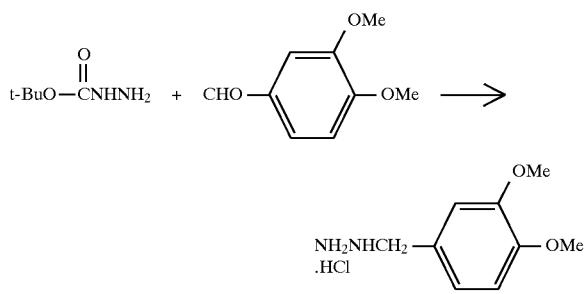

tert-Butyl carbazate (59.65 g) and 3,4-dimethoxybenzaldehyde (75 g) were dissolved in ethanol (1.3 L). To the solution were added acetic acid (77 ml) and 10% palladium-carbon (1.5 g), and the mixture was subjected to catalytic reduction under a hydrogen atmosphere at 1 atm for 2 days with vigorous stirring. The catalyst was removed by filtration, and the filtrate was concentrated under reduced pressure to give an oil. Anisole (54 ml) and 1,4-dioxane (100 ml) were added to the oil. The mixture was cooled in an ice bath, and a 4N hydrogen chloride-dioxane solution (360 ml) was added. The mixture was stirred under ice-cooling for one hour and at room temperature for 4 hours. After the completion of the reaction, diethyl ether (800 ml) was gradually added to the mixture, and the precipitated viscous solid was collected by filtration. The solid was dissolved in methanol (1.5 L) heated to 50° C., and the solution was concentrated to about a half volume to precipitate crystals. The crystals were collected by filtration, successively washed with cold methanol and diethyl ether, and dried to give 57.8 g of the title compound as colorless needles.

Melting point: 178°–180° C.

Preparative Example 2 (Step 1')

3-Pyridylmethylhydrazine dihydrochloride

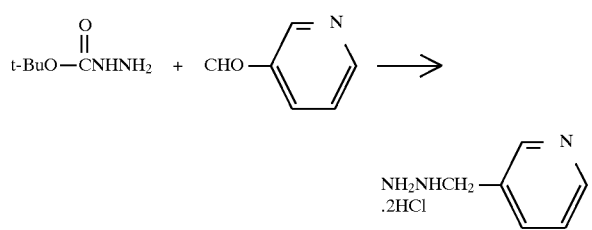

tert-Butyl carbazate (13.22 g), 3-pyridinecarboxaldehyde (9.44 ml) and acetic acid (11.5 ml) were dissolved in methanol (230 ml) under ice-ling, and the solution was stirred at room temperature for one hour. The air in the reactor was replaced with an argon gas, and 10% palladium-carbon (1.0 g) suspended in an adequate amount of methanol was added under an argon atmosphere. The air inside the reactor was replaced with hydrogen, and the mixture was subjected to catalytic reduction for 2 days with vigorous stirring. The catalyst was removed by filtration, the filtrate (1.7 L) (about 0.93 mol inclusive) and anisole (101 ml, 0.93 mol) were mixed, and the mixture was cooled with ice. A 4N hydrochloric acid/dioxane solution (0.93 L) was added to the mixture with stirring under ice-cooling, and the mixture was stirred at 50° C. for one hour and at 60° C. for 3 hours. The reaction mixture was cooled to room temperature. The precipitated crystals were collected by filtration, washed with ethanol, and dried under reduced pressure to give 8.68 g of the title compound as pale-yellow needles.

Melting point: 189°–191° C.

$^1$H NMR(300 MHz, δ ppm, DMSO-d$_6$) 4.27(2H,s), 8.03 (1H,dd,J=7.8 and 5.7 Hz), 8.55(1H,d,J=7.8 Hz), 8.86(1H,d, J=5.7 Hz), 8.91(1H,s)

Preparative Examples 3 and 4 (Step 1')

In the same manner as in Preparative Example 1, the compound of Preparative Example 3 was obtained from tert-butyl carbazate and 4-methoxybenzaldehyde, and in the same manner as in Preparative Example 2, the compound of Preparative Example 4 was obtained from tert-butyl carbazate and 4-pyridinecarboxaldehyde. The compounds are shown in Table 1.

| Preparative Ex. | Structural formula | Melting point (°C.) |
|---|---|---|
| 3 | NH$_2$NHCH$_2$—⟨C$_6$H$_4$⟩—OMe .HCl | 184–185 |
| 4 | NH$_2$NHCH$_2$—⟨pyridyl⟩ .2HCl | 156–158 |

Preparative Example 5 (Step 1)
2-(4-Chlorobenzoyl)phenyl isothiocyanate

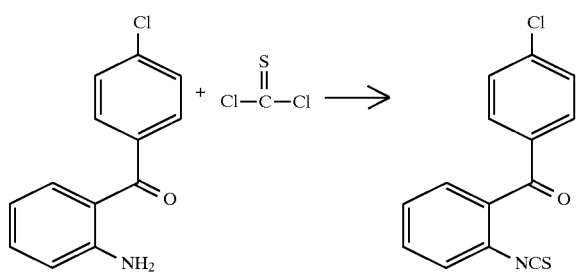

According to the method described in U.S. Pat. No. 4,144,233, the title compound (74.1 g) was obtained as yellow crystals from thiophosgene (22.6 ml) and 2-aminophenyl 4-chlorophenyl ketone (62.6 g) (Tokyo Kasei Kogyo).

Melting point: 80°–82° C.

Mass spectrum (low resolution): 274.1

Preparative Examples 6–11 (Step 1)

In the same manner as in Preparative Example 5, the compound of Preparative Example 6 was obtained from 2-aminophenyl phenyl ketone, the compound of Preparative Example 7 was obtained from 2-amino-5-chlorophenyl phenyl ketone, the compound of Preparative Example 8 was obtained from 2-amino-4-methylphenyl phenyl ketone, the compound of Preparative Example 9 was obtained from 2-amino-5-nitrophenyl phenyl ketone, the compound of Preparative Example 10 was obtained from 2-aminophenyl 4-methylphenyl ketone, and the compound of Preparative Example 11 was obtained from 2-amino-5-chlorophenyl 2-chlorophenyl ketone. The compounds are shown in Table 2.

TABLE 2

| Prep. Ex. | Structural formula | Mass spectrum (low resolution) | $^1$H NMR (300 MHz, δ ppm, CDCl$_3$) | Melting point, °C. |
|---|---|---|---|---|
| 6 | | 239.0 | 7.34–7.39(2H, m), 7.47–7.55(4H, m), 7.59–7.65(1H, m), 7.80–7.83(2H, m). | Oily substance |
| 7 | | 274.0 | | 44–46 |
| 8 | | 254.1 | | 45–48 |
| 9 | | 285.0 | | 82–85 |

TABLE 2-continued

| Prep. Ex. | Structural formula | Mass spectrum (low resolution) | $^1$H NMR (300 MHz, δ ppm, CDCl$_3$) | Melting point, °C. |
|---|---|---|---|---|
| 10 | ![structure with Me, NCS] | 254.1 | | Oily substance |
| 11 | ![structure with Cl, Cl, NCS] | 307.9 | 7.25–7.28(2H, m), 7.38–7.52(4H, m), 7.57 (1H, d, J=2.3Hz). | |

Preparative Example 12 (Step 1)

3-(4-Chlorobenzoyl)-4,5-dimethylthiophene-2-isothiocyanate 3-(4-Chlorobenzoyl)-4,5-dimethylthiophene-2-isothiocyanate

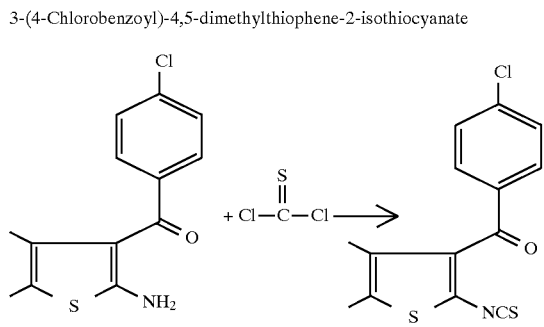

In the same manner as in Preparative Example 5, the title compound (1.16 g) was obtained as a crude oil from 2-amino-3-(4-chlorobenzoyl)-4,5-dimethylthiophene (1 g) obtained by the method described in Japanese Patent Unexamined Publication No. 256681/1990 and thiophosgene (316 μl).

Preparative Examples 13–18

In the same manner as in Preparative Example 12, the compound of Preparative Example 13 was obtained from 2-amino-3-(4-chlorobenzoyl)-5-ethylthiophene, the compound of Preparative Example 14 was obtained from 2-amino-3-benzoyl-5-methylthiophene, the compound of Preparative Example 15 was obtained from 2-amino-3-benzoyl-4,5-dimethylthiophene, the compound of Preparative Example 16 was obtained from 2-amino-3-benzoyl-5-ethylthiophene, the compound of Preparative Example 17 was obtained from 2-amino-3-(4-methoxybenzoyl)-4,5-dimethylthiophene, and the compound of Preparative Example 18 was obtained from 2-amino-3-(2-chlorobenzoyl)-4,5-dimethylthiophene. The compounds are shown in Table 3.

TABLE 3-(1)

| Prep. Ex. | Structural formula | Mass spectrum (low resolution) | $^1$H NMR (300 MHz, δ ppm, CDCl$_3$) | Melting point, °C. |
|---|---|---|---|---|
| 13 | ![structure with Cl, NCS, ethyl-thiophene] | 308.0 | 1.31(3H, t, J=7.6Hz), 2.77(2H, q, J=7.6Hz), 6.80(1H, s), 7.47(2H, d, J=8.5Hz), 7.75(2H, d, J=8.5Hz). | |

TABLE 3-(1)-continued

| Prep. Ex. | Structural formula | Mass spectrum (low resolution) | $^1$H NMR (300 MHz, δ ppm, CDCl$_3$) | Melting point, °C. |
|---|---|---|---|---|
| 14 | 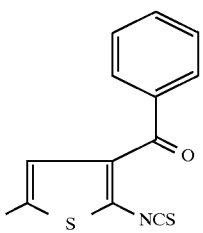 | 260.0 | 2.44(3H, d, J=1.5Hz), 6.79(1H, q, J=1.5Hz), 7.46–7.52(2H, m), 7.56–7.61(1H, m), 7.79–7.82(2H, m). | |
| 15 | 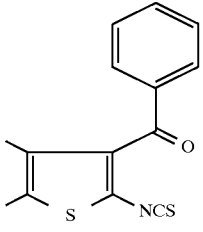 | 307.9 | 2.05(3H, s), 2.33(3H, s), 7.48–7.62(3H, m), 7.82–7.86(2H, m). | |

TABLE 3-(2)

| Prep. Ex. | Structural formula | Mass spectrum (low resolution) | $^1$H NMR (300 MHz, δ ppm, CDCl$_3$) | Melting point, °C. |
|---|---|---|---|---|
| 16 | 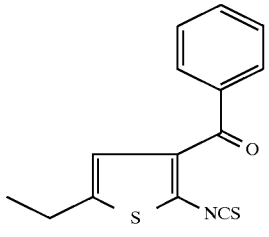 | 274.0 | 1.31(3H, t, J=6Hz), 2.78(2H, m), 6.82(1H, t, J=1.0Hz), 7.47–7.62(3H, m), 7.79–7.83(2H, m). | |
| 17 | 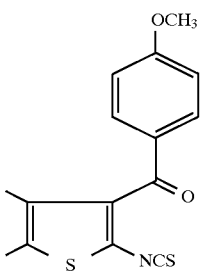 | 304.0 | | |
| 18 | 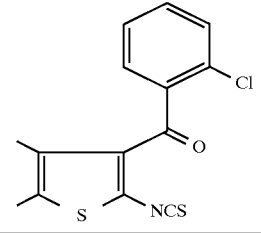 | | | 76~79 |

Preparative Example 19 (Step 2)

N-[2-(4-Chlorobenzoyl)phenyl]-1-(3,4-dimethoxybenzyl)hydrazinecarbothioamide

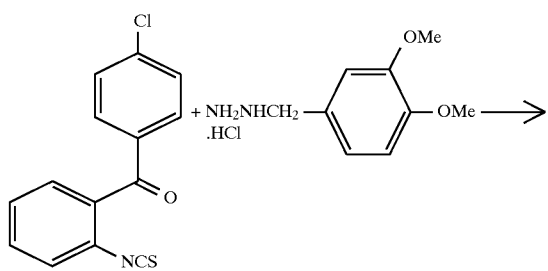

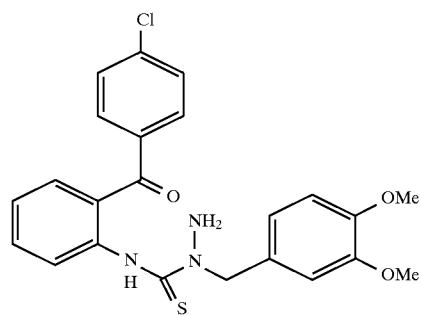

3,4-Dimethoxybenzylhydrazine hydrochloride (22.99 g) obtained in Preparative Example 1 was dissolved in methanol (460 ml), the solution was cooled with ice, and triethylamine (14.8 ml) was dropwise added over 5 minutes. A solution of 2-(4-chlorobenzoyl)phenyl isothiocyanate (24.2 g) obtained in Preparative Example 5 in tetrahydrofuran (240 ml) was added to the reaction mixture under ice-cooling. The mixture was stirred under ice-cooling for 15 minutes and at room temperature for 40 minutes. After the completion of the reaction, the solvent was distilled away under reduced pressure. The residue was dissolved in dichloromethane (500 ml) and washed twice with water. The organic layer was dried over anhydrous sodium sulfate, filtrated, and concentrated under reduced pressure. The residue was crystallized from diethyl ether to give 34.7 g of the title compound as pale-yellow needles.

Melting point: 162°–166° C.

Preparative Examples 20–25 (Step 2)

In the same manner as in Preparative Example 19, the compound of Preparative Example 20 was obtained from the compounds of Preparative Examples 3 and 6, the compound of Preparative Example 21 was obtained from the compounds of Preparative Examples 3 and 5, the compound of Preparative Example 22 was obtained from the compounds of Preparative Examples 3 and 7, the compound of Preparative Example 23 was obtained from the compounds of Preparative Examples 3 and 9, the compound of Preparative Example 24 was obtained from the compounds of Preparative Examples 3 and 10, and the compound of Preparative Example 25 was obtained from the compounds of Preparative Examples 3 and 11. The compounds are shown in Table 4.

TABLE 4-(1)

| Prep. Ex. | Structural formula | $^1$H NMR (300 MHz), δ ppm, CDCl$_3$ | Melting point, °C. |
|---|---|---|---|
| 20 | | 3.72(2H, s), 3.79(3H, s), 5.38(2H, s), 6.86(2H, s), 7.17(1H, m), 7.30(2H, m), 7.44–7.61(5H, m), 7.80(2H, m), 8.78(1H, d, J=10.1Hz), 11.77(1H, s). | Oily substance |
| 21 | | | 180 |

TABLE 4-(1)-continued
| Prep. Ex. | Structural formula | $^1$H NMR (300 MHz), δ ppm, CDCl$_3$ | Melting point, °C. |
|---|---|---|---|
| 22 | 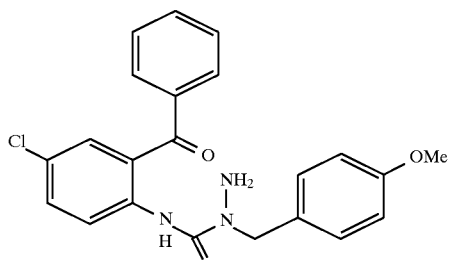 | | 132~134 (decomposition) |
TABLE 4-(2)
| Prep. Ex. | Structural formula | $^1$H NMR (300 MHz), δ ppm, CDCl$_3$ | Melting point, °C. |
|---|---|---|---|
| 23 | 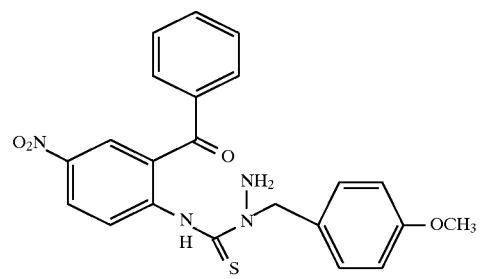 | | 142~144 |
| 24 | 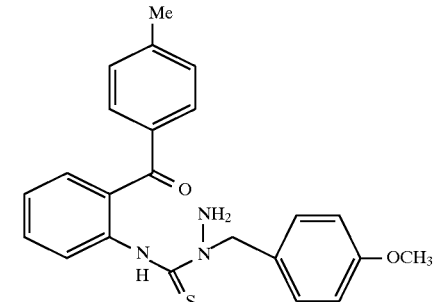 | | 170~172 |
| 25 | 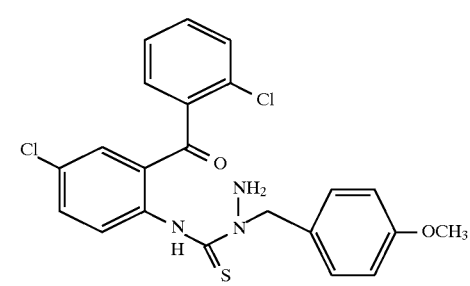 | | 135~138 |
Preparative Example 26
N-[2-(4-Chlorobenzoyl)phenyl]-1-(pyridin-3-ylmethyl)hydrazinecarbothioamide

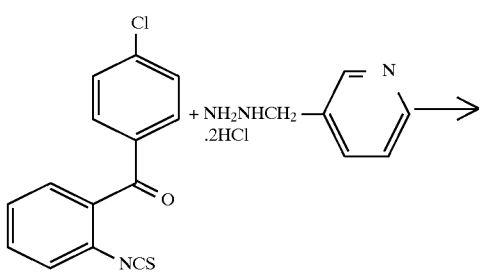

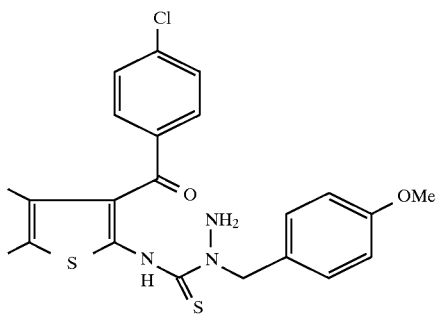

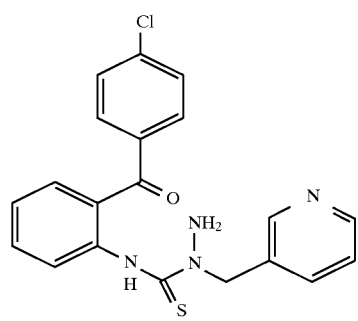

3-Pyridylmethylhydrazine dihydrochloride (11.8 g) obtained in Preparative Example 2 was dissolved in water (25 ml), and sodium hydrogencarbonate (10.08 g) was added. The solution was cooled with ice. A solution of 2-(4-chlorobenzoyl)phenyl isothiocyanate (16.4 g) obtained in Preparative Example 5 in tetrahydrofuran (30 ml) was cooled with ice and added to the solution previously prepared. The mixture was stirred under ice-cooling for 30 minutes. The temperature of the reaction mixture was raised to room temperature, and ethanol (30 ml) was added. The precipitated crystals were collected by filtration, washed with a mixed solvent of ethanol:water (80:20), and dried under reduced pressure to give 19.9 g of the title compound as colorless crystals.

Melting point: 165°–166° C.

Preparative Example 27

N-[3-(4-chlorobenzoyl)-4,5-dimethylthiophen-2-yl]-1-(4-methoxybenzyl)hydrazinecarbothioamide

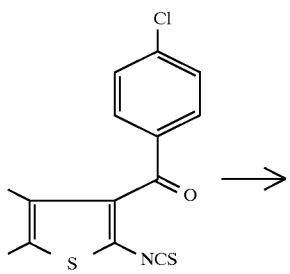

4-Methoxybenzylhydrazine hydrochloride (745 mg) obtained in Preparative Example 3 was dissolved in methanol (10 ml). The solution was cooled with ice, and triethylamine (550 µl) was dropwise added. A solution of 3-(4-chlorobenzoyl)-4,5-dimethylthiophene-2-isothiocyanate (1.16 g) obtained in Preparative Example 12 in tetrahydrofuran (10 ml) was cooled with ice, and added to the reaction mixture previously prepared. The mixture was stirred under ice-cooling for 30 minutes and at room temperature for 30 minutes. After the completion of the reaction, the solvent was distilled away under reduced pressure, and the residue was subjected to silica gel column chromatography. A product obtained from the fractions eluted with hexane:ethyl acetate=3:1 was crystallized from diethyl ether to give 830 mg of the title compound as yellow crystals.

Melting point: 157°–160° C.

Preparative Examples 28–33 (Step 2)

In the same manner as in Preparative Example 27, the compound of Preparative Example 28 was obtained from the compounds of Preparative Examples 3 and 13, the compound of Preparative Example 29 was obtained from the compounds of Preparative Examples 3 and 14, the compound of Preparative Example 30 was obtained from the compounds of Preparative Examples 3 and 15, the compound of Preparative Example 31 was obtained from the compounds of Preparative Examples 3 and 16, the compound of Preparative Example 32 was obtained from the compounds of Preparative Examples 3 and 17, and the compound of Preparative Example 33 was obtained from the compounds of Preparative Examples 3 and 18. The compounds are shown in Table 5.

TABLE 5-(1)

| Example | Structural formula | $^1$H NMR (300 MHz, δ ppm, CDCl$_3$) | Melting point, °C. |
|---|---|---|---|
| 28 | (structure: 5-ethyl-thiophene with 3-(4-chlorobenzoyl) and 2-NH-C(=S)-N(NH$_2$)-CH$_2$-C$_6$H$_4$-OCH$_3$) | 1.29(3H, t, J=9.0Hz), 2.73(2H, q, J=9.0Hz), 3.81(3H, s), 3.90(2H, s), 5.36(2H, s), 6.71(1H, m), 6.90(2H, d, J=8.8Hz), 7.33(2H, d, J=8.8Hz), 7.44(2H, d, J=8.8Hz), 7.64(2H, d, J=8.8Hz). | |
| 29 | (structure: 5-methyl-thiophene with 3-benzoyl and 2-NH-C(=S)-N(NH$_2$)-CH$_2$-C$_6$H$_4$-OCH$_3$) | 2.36(3H, s), 3.80(3H, s), 3.92(2H, s), 5.35(2H, s), 6.75(1H, d, J=1.2Hz), 6.89(2H, d, J=8.4Hz), 7.32(2H, d, J=9.0Hz), 7.42–7.55(3H, m), 7.67–7.70(2H, m), 14.03(1H, s). | 166~169 |
| 30 | (structure: 4,5-dimethyl-thiophene with 3-benzoyl and 2-NH-C(=S)-N(NH$_2$)-CH$_2$-C$_6$H$_4$-OCH$_3$) | | 140~143 |

TABLE 5-(2)

| Prep. Ex. | Structural formula | $^1$H NMR (300 MHz, δ ppm, CDCl$_3$) | Melting point, °C.) |
|---|---|---|---|
| 31 | (structure: 5-ethyl-thiophene with 3-benzoyl and 2-NH-C(=S)-N(NH$_2$)-CH$_2$-C$_6$H$_4$-OCH$_3$) | | 131~132 |

TABLE 5-(2)-continued

| Prep. Ex. | Structural formula | $^1$H NMR (300 MHz, δ ppm, CDCl$_3$) | Melting point, °C.) |
|---|---|---|---|
| 32 | (structure: thiophene with 4-methoxybenzoyl and thiourea-N-(4-methoxybenzyl)) | | 133~134 |
| 33 | (structure: thiophene with 2-chlorobenzoyl and thiourea-N-(pyridin-2-ylmethyl)) | | 154~157 |

Example 1 (Step 3)

5-(4-Chlorophenyl)-3-(3,4-dimethoxybenzyl)-1,3-dihydrobenzo[e]triazepine-2-thione

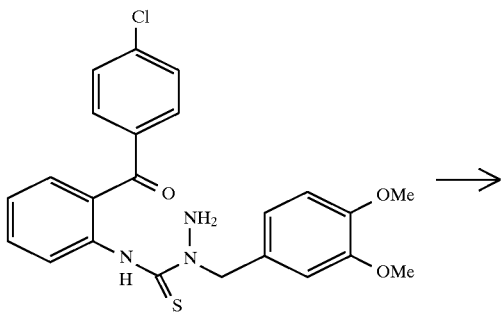

N-[2-(4-Chlorobenzoyl)phenyl]-1-(3,4-dimethoxybenzyl)hydrazinecarbothioamide (35.75 g) obtained in Preparative Example 19 was suspended in ethanol (360 ml). p-Toluenesulfonic acid monohydrate (0.45 g) was added, and the mixture was refluxed under heating for one hour. After the completion of the reaction, the reaction mixture was concentrated under reduced pressure. The residue was dissolved in diethyl ether (500 ml), and successively washed with water, a saturated aqueous sodium hydrogencarbonate solution and water. The organic layer was dried, filtrated and concentrated, and the precipitated crystals were collected by filtration to give 28.6 g of the title compound as yellow crystals.

Melting point: 136°–137° C.

Example 2 (Step 3)

3-(4-Methoxybenzyl)-5-phenyl-1,3-dihydrobenzo[e][1,2,4]triazepine-2-thione

Example 3 (Step 3)

5-(4-Clorophenyl)-3-(4-methoxybenzyl)-1,3-dihydrobenzo[e][1,2,4]triazepine-2-thione

Example 4 (Step 3)

7-Cloro-3-(4-methoxybenzyl)-5-phenyl-1,3-dihydrobenzo[e][1,2,4]triazepine-2-thione

Example 5 (Step 3)

3-(4-Methoxybenzyl)-7-nitro-5-phenyl-1,3-dihydrobenzo[e][1,2,4]triazepine-2-thione

Example 6 (Step 3)

3-(4-Methoxybenzyl)-5-(4-methylphenyl)-1,3-dihydrobenzo[e][1,2,4]triazepine-2-thione

Example 7 (Step 3)

7-Chloro-5-(2-chlorophenyl)-3-(4-methoxybenzyl)-1,3-dihydrobenzo[e][1,2,4]triazepine-2-thione In the same manner as in Example 1, the compounds of Examples 2, 3, 4, 5, 6 and 7 were obtained from the compounds of Preparative Examples 20, 21, 22, 23, 24 and 25, respectively. The compounds are shown in Table 6.

TABLE 6-(1)
| Example | Structural formula | ¹H NMR (300 MHz, δ ppm, CDCl₃) | Melting point, °C. |
|---|---|---|---|
| 2 | | | 137~141 |
| 3 | | | 152 |
| 4 | | | 159~163 |
TABLE 6-(2)
| Example | Structural formula | ¹H NMR (300 MHz, δ ppm, CDCl₃) | Melting point, °C. |
|---|---|---|---|
| 5 | 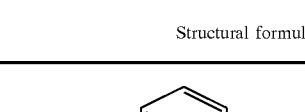 | 3.79(3H, s), 5.30(2H, s), 6.86(2H, d, J=8.7Hz), 7.07(1H, d, J=8.8Hz), 7.21–7.51(7H, m), 7.75(1H, s), 7.86(1H, d, J=2.5Hz), 8.29(1H, dd, J=8.8 and 2.6Hz). | Oily substance |

TABLE 6-(2)-continued

| Example | Structural formula | ¹H NMR (300 MHz, δ ppm, CDCl₃) | Melting point, °C. |
|---|---|---|---|
| 6 | | | 135~136 |
| 7 | | | 155~157 |

Example 8 (Step 3)

5-(4-Chlorophenyl)-3-(pyridin-3-ylmethyl)-1,3-dihydrobenzo[e][1,2,4]triazepine-2-thione hydrochloride

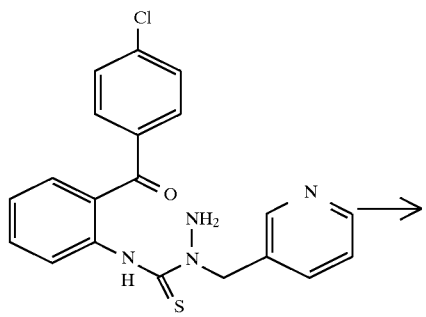

N-[2-(4-Chlorobenzoyl)phenyl]-1-(pyridin-3-ylmethyl)hydrazinecarbothioamide (1.0 g) obtained in Preparative Example 26 was suspended in 2-propanol, 4N hydrochloric acid/1,4-dioxane (0.63 ml) was added, and the mixture was stirred at 60° C. for one hour. The reaction mixture was cooled to room temperature, added with diethyl ether (20 ml), and allowed to stand for 2 hours. The resulting crystals were collected by filtration, and washed with diethyl ether to give 985 mg of the title compound as yellow crystals.

Melting point: 136°–137° C.

Example 9 (Step 3)

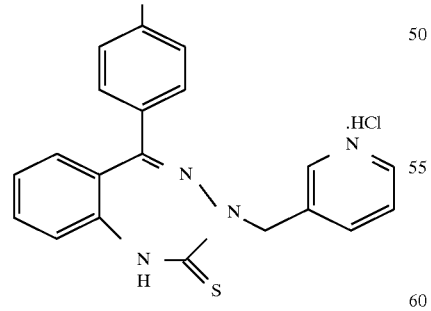

5-(4-Chlorophenyl)-3-(pyridin-3-ylmethyl)-1,3-dihydrobenzo[e][1,2,4]triazepine-2-thione p-toluenesulfonate In the same manner as in Example 8, the title compound was obtained. The compound is shown in Table 7

TABLE 7

| Example | Structural formula | Melting point (°C.) |
|---|---|---|
| 9 | | 199~202 |

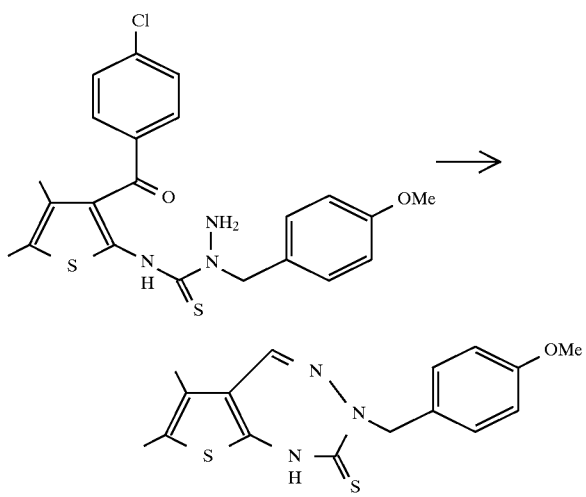

Example 10 (Step 3)

4-(4-Chlorophenyl)-6-(4-methoxybenzyl)-2,3-dimethyl-6,8-dihydro-1-thia-5,6,8-triazaazulene-7-thione N-[3-(4-Chlorobenzoyl)-4,5-dimethylthiophen-2-yl]-1-(4-methoxybenzyl)hydrazinecarbothioamide (750 mg) obtained in Preparative Example 27 was suspended in ethanol (15 ml), and p-toluenesulfonic acid monohydrate was added. The mixture was refluxed under heating for one hour. After the completion of the reaction, the reaction mixture was concentrated under reduced pressure. The residue was dissolved in chloroform, and successively washed with water, a saturated aqueous sodium hydrogencarbonate solution and water. The organic layer was dried over anhydrous sodium sulfate, filtrated, and concentrated under reduced pressure. The residue was purified by silica gel column chromatography (hexane:ethyl acetate=3:1) to give 530 mg of the title compound as yellow crystals.

Melting point: 108°–110° C.

Example 11 (Step 3)

4-(4-Chlorophenyl)-2-ethyl-6-(4-methoxybenzyl)-6,8-dihydro-1-thia-5,6,8-triazaazulene-7-thione

Example 12 (Step 3)

6-(4-Methoxybenzyl)-2-methyl-4-phenyl-6,8-dihydro-1-thia-5,6,8-triazaazulene-7-thione

Example 13 (Step 3)

6-(4-Methoxybenzyl)-2,3-dimethyl-4-phenyl-6,8-dihydro-1-thia-5,6,8-triazaazulene-7-thione

Example 14 (Step 3)

2-Ethyl-6-(4-methoxybenzyl)-4-phenyl-6,8-dihydro-1-thia-5,6,8-triazaazulene-7-thione

Example 15 (Step 3)

6-(4-Methoxybenzyl)-4-(4-methoxyphenyl)-2,3-dimethyl-6,8-dihydro-1-thia-5,6,8-triazaazulene-7-thione

Example 16 (Step 3)

4-(2-Chlorophenyl)-2,3-dimethyl-6-(pyridin-4-ylmethyl)-6,8-dihydro-1-thia-5,6,8-triazaazulene-7-thione In the same manner as in Example 10, the compounds of Examples 11, 12, 13, 14, 15 and 16 were obtained from the compounds of Preparative Examples 28, 29, 30, 31, 32 and 33, respectively. The compounds are shown in Table 8.

TABLE 8-(1)

| Example | Structural formula | $^1$H NMR (300 MHz, δ ppm, CDCl$_3$) | Melting point, °C. |
|---|---|---|---|
| 11 | | 1.26(3H, t, J=7.5Hz), 2.71(2H, q, J=7.5Hz), 3.79(3H, s), 5.22(2H, s), 6.20(1H, s), 6.85(2H, d, J=8.7Hz), 7.19(2H, d, J=8.7Hz), 7.27–7.32(4H, m), 7.77(1H, m). | 135 |
| 12 | | | 179~181 |
| 13 | | 1.39(3H, s), 2.23(3H, s), 3.78(3H, s), 5.17(2H, bs), 6.83(2H, d, J=8.7Hz), 7.11–7.15(2H, m), 7.24–7.42(4H, m), 7.59(1H, m). | 157~160 |

TABLE 8-(2)

| Example | Structural formula | $^1$H NMR (300 MHz, δ ppm, CDCl$_3$) | Melting point, °C. |
|---|---|---|---|
| 14 | | | 198~200 |

TABLE 8-(2)-continued

| Example | Structural formula | ¹H NMR (300 MHz, δ ppm, CDCl₃) | Melting point, °C. |
|---|---|---|---|
| 15 | | | 148~150 |
| 16 | | | 196~199 |

Example 17 (Step 2, Step3)

3-(4-Methoxybenzyl)-8methyl-5-phenyl-1,3-dihydrobenzo[e][1,2,4]triazepine-2-thione In the same manner as in Preparative Example 19, 2-benzoyl-5-methylphenyl isothiocyanate (4.2 g) obtained in Preparative Example 8, 4-methoxybenzylhydrazine hydrochloride (3.3 g) obtained in Preparative Example 3 and triethylamine (2.44 ml) were reacted. The reaction solvent was distilled away, and the oily residue was heated at 50° C. for 2 hours. The mixture was extracted in the same manner as in Example 1, and crystallized from chloroform-diethyl ether to give 1.78 g of the title compound as yellow crystals.

Melting point: 190°–191° C.

Example 18 (Step 4)

5-(4-Chlorophenyl)-3-(4-methoxybenzyl)-3H-benzo[e][1,2,4]-triazepin-2-ylhydrazine

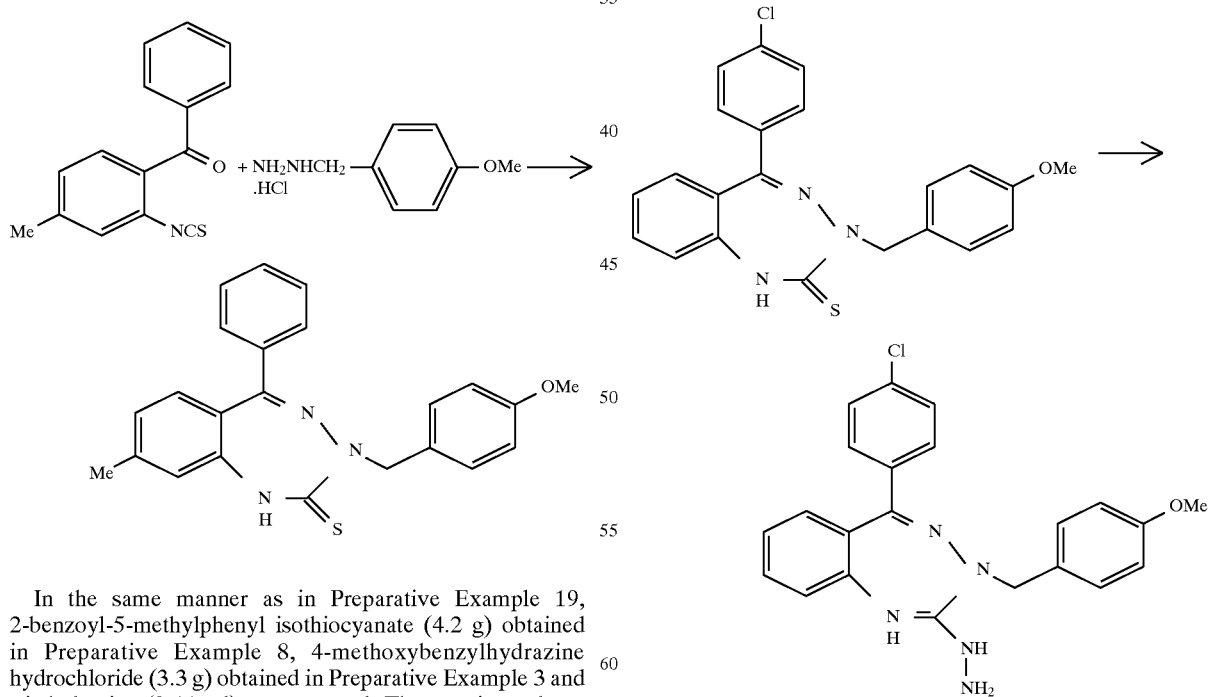

5-(4-Chlorophenyl)-3-(4-methoxybenzyl)-1,3-dihydrobenzo[e][1,2,4]triazepine-2-thione (41 mg) obtained in Example 3 was dissolved in tetrahydrofuran (0.4 ml), and hydrazine monohydrate (49 μl) was added. The mixture was stirred at room temperature for 18 hours. After the completion of the reaction, the reaction mixture was concentrated under reduced pressure. The residue was dissolved in ethyl acetate, and washed three times with water. The organic layer was dried, filtrated, and concentrated under reduced pressure. The residue was purified by preparative thin-layer chromatography (chloroform:methanol= 20:1) to give 27 mg of the title compound as a pale-yellow powder.

$^1$H NMR(300 Hz, δ ppm, CDCl$_3$) 3.78(3H,s), 4.71(2H,s), 6.82(2H,d,J=8.8 Hz), 7.00(3H,m), 7.15–7.28(6H,m), 7.41( (1H,m)

Example 19 (Step6)

5-(4-Chlorophenyl)-3-(3,4-dimethoxybenzyl)-2-methylthio-3H-benzo[e][1,2,4]triazepine

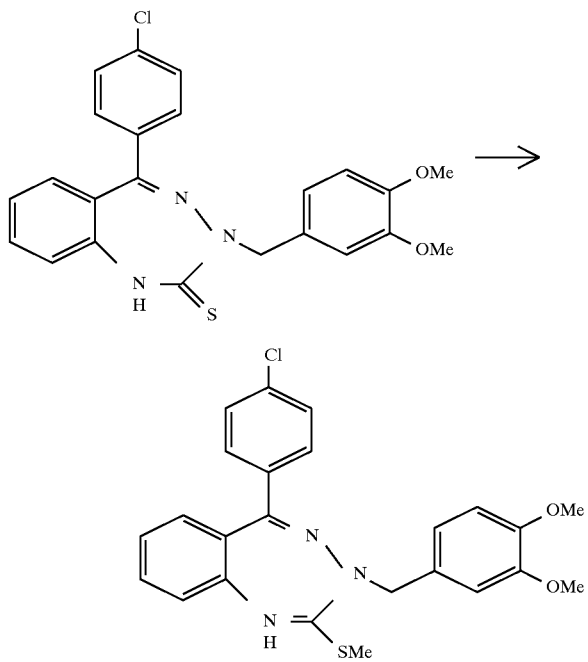

5-(4-Chlorophenyl)-3-(3,4-dimethoxybenzyl)-1,3-dihydrobenzo[e][1,2,4]triazepine-2-thione (41 g) obtained in Example 1 was dissolved in anhydrous N,N-dimethylformamide (200 ml), and sodium hydride (60% in oil, 3.51 g) was added. The mixture was stirred at room temperature for 30 minutes under an argon atmosphere, and cooled with ice. Methyl iodide (5.47 ml) was added, and the mixture was stirred under ice-cooling for 30 minutes and at room temperature for 1 hour. After the completion of the reaction, the reaction mixture was cooled with ice, added with acetic acid (1.67 ml), and concentrated under reduced pressure. The resulting residue was dissolved in ethyl acetate, and successively washed with a 5% aqueous citric acid solution, a saturated aqueous sodium hydrogencarbonate solution and water. The ethyl acetate layer was dried, filtrated, and concentrated under reduced pressure. The resulting oil was crystallized from diethyl ether-n-hexane to give 30.43 g of the title compound as pale-yellow crystals.

Melting point: 136°–137° C.

Example 20 (Step 6)

3-(4-Methoxybenzyl)-2-methylthio-5-phenyl-3H-benzo[e][1,2,4]-triazepine

Example 21 (Step 6)

7-Chloro-3-(4-methoxybenzyl)-2-methylthio-5-phenyl-3H-benzo[e][1,2,4]triazepine

Example 22 (Step 6)

3-(4-Methoxybenzyl)-8-methyl-2-methylthio-5-phenyl-3H-benzo[e][1,2,4]triazepine

Example 23 (Step 6)

3-(4-Methoxybenzyl)-2-methylthio-7-nitro-5-phenyl-3H-benzo[e][1,2,4]triazepine

Example 24 (Step 6)

3-(4-Methoxybenzyl)-5-(4-methylphenyl)-2-methylthio-3H-benzo[e][1,2,4]triazepine

Example 25 (Step 6)

7-Chloro-5-(2-chlorophenyl)-3-(4-methoxybenzyl)-2-methylthio-3H-benzo[e][1,2,4]triazepine In the same manner as in Example 19, the compounds of Examples 20, 21, 22, 23, 24 and 25 were obtained from the compounds of Examples 2, 4, 17, 5, 6 and 7, respectively. The compounds are shown in Table 9.

TABLE 9-(1)

| Example | Structural formula | $^1$H NMR(300MHz, δppm, CDCl$_3$) | Melting point, °C. |
|---|---|---|---|
| 20 | | 2.35(3H, s), 3.79(3H, s), 4.71(2H, s), 6.83 (2H, d, J=8.8Hz), 6.97 (2H, d, J=3.9Hz), 7.15 (1H, d, J=8.0Hz), 7.24–7.43(8H, m). | |

TABLE 9-(1)-continued

| Example | Structural formula | ¹H NMR(300MHz, δppm, CDCl₃) | Melting point, °C. |
|---|---|---|---|
| 21 | (structure) | 2.52(3H, s), 3.79(3H, s), 4.70(2H, s), 6.84(2H, m), 6.93 (1H, d, J=2.4Hz), 7.07 (1H, d, J=8.5Hz), 7.22–7.42(8H, m). | |
| 22 | (structure) | 2.39(3H, s), 2.57 (3H, broad s), 3.79(3H, s), 4.73(2H, s), 6.79–6.87(4H, m), 7.03(1H, m), 7.24–7.38(7H, m). | |

TABLE 9-(2)

| Example | Structural formula | ¹H NMR(300MHz, δppm, CDCl₃) | Melting point, °C. |
|---|---|---|---|
| 23 | (structure) | 2.56(3H, s), 3.80(3H, s), 4.71(2H, s), 6.85 (2H, d, J=9.0Hz), 7.20–7.46(8H, m), 7.86 (1H, d, J=3.0Hz), 8.23 (1H, dd, J=7.2 and 2.6Hz). | 148~151 |
| 24 | (structure) | 2.34(3H, s), 2.53(3H, s), 3.78(3H, s), 4.70(2H, s), 6.82 (2H, d, J=8.4Hz), 6.96–6.98(2H, m), 7.08–7.23(7H, m), 7.32–7.42(1H, m). | Amorphous solid |

TABLE 9-(2)-continued

| Example | Structural formula | ¹H NMR(300MHz, δppm, CDCl₃) | Melting point, °C. |
|---|---|---|---|
| 25 | | | 139~140 |

Example 26 (Step 6)

5-(4-Chlorophenyl)-2-methylthio-3-(pyridin-3-ylmethyl)-3H-benzo[e][1,2,4]triazepine

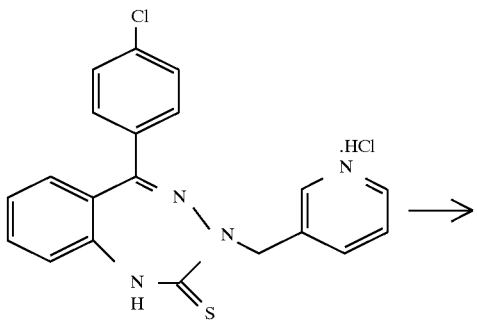

5-(4-Chlorophenyl)-3-(pyridin-3-ylmethyl)-1,3-dihydrobenzo[e][1,2,4]triazepine-2-thione hydrochloride (1.97 g) obtained in Example 8 was dissolved in anhydrous N,N-dimethylformamide (20 ml), and sodium hydride (380 mg) was added under ice-cooling with stirring. The mixture was heated to room temperature, and stirred for 30 minutes. The mixture was cooled with ice, and methyl iodide (296 μl) was added to the mixture. The mixture was heated to room temperature, and stirred for 30 minutes. The reaction mixture was poured into water (50 ml), and neutralized with citric acid. The reaction mixture was extracted with ethyl acetate (50 ml), washed with water five times, dried over anhydrous sodium sulfate, and filtrated. The filtrate was concentrated under reduced pressure to give 1.79 g of the title compound as a yellow oil.

¹H NMR(300 MHz, δ ppm, CDCl₃ ) 2.56(3H,s), 4.77(2H, s), 6.92–7.02(2H,m), 7.15–7.32(6H,m), 7.43(1H,m), 7.61 (1H,m), 8.50(1H,dd,J=4.8 and 1.7 Hz), 8.59(1H,d,J=1.7 Hz)

Example 27 (Step 6)

5-(4-Chlorophenyl)-2-methylthio-3-(pyridin-3-ylmethyl)-3H-benzo[e][1,2,4]triazepine

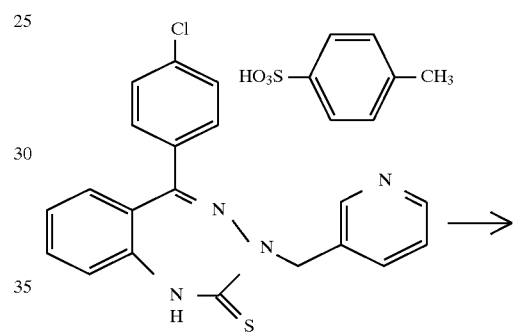

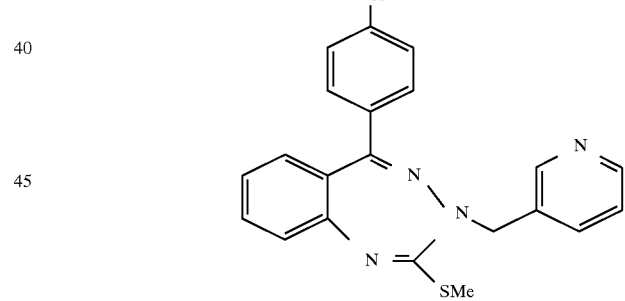

In the same manner as in Example 26, the title compound was obtained as an amorphous compound from 5-(4-chlorophenyl)-3-(pyridin-3-ylmethyl)-1,3-dihydrobenzo[e][1,2,4]triazepine-2-thione p-toluenesulfonate obtained in Example 9. The NMR data of the compound is consistent with that of Example 26.

Example 28 (Step 6)

4-(4Chlorophenyl)-6-(4-methoxybenzyl)-2,3-dimethyl-7-methylthio-6H-1-thia-5,6,8-triazaazulene

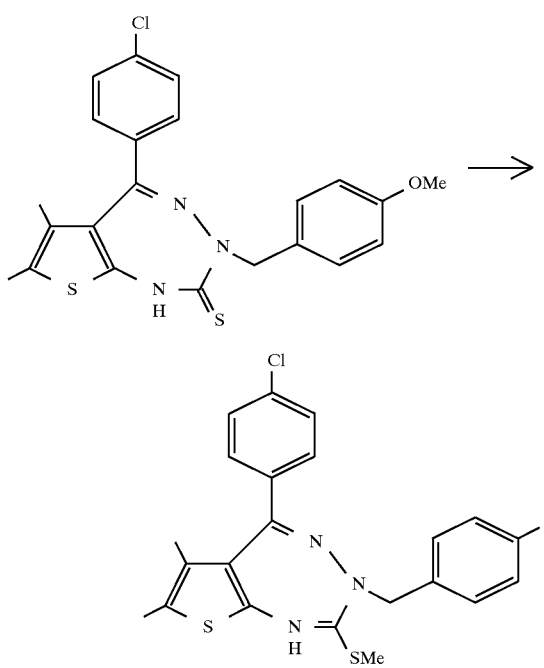

4-(4-Chlorophenyl)-6-(4-methoxybenzyl)-2,3-dimethyl-6,8-dihydro-1-thia-5,6,8-triazaazulene-7-thione (442 mg) obtained in Example 10 was dissolved in acetone (5 ml), and anhydrous potassium carbonate (1.38 g) and methyl iodide (74.7 μl) were added. The mixture was stirred at room temperature for one hour. Potassium carbonate was removed by filtration, and the filtrate was concentrated under reduced pressure. The residue was purified by silica gel column chromatography (hexane:ethyl acetate=4:1) to give 430 mg of the title compound as an amorphous compound.

Example 29 (Step 6)

4-(4-Chlorophenyl)-2-ethyl-6-(4-methoxybenzyl)-7-methylthio-6H-1-thia-5,6,8-triazaazulene

Example 30 (Step 6)

6-(4-Methoxybenzyl)-2-methyl-7-methylthio-4-phenyl-6H-1-thia-5,6,8-triazaazulene

Example 31 (Step 6)

6-(4-Methoxybenzyl)-2,3-dimethyl-7-methylthio-4-phenyl-6H-1-thia-5,6,8-triazaazulene

Example 32 (Step 6)

2-Ethyl-6-(4-methoxybenzyl)-7-methylthio-4-phenyl-6H-1-thia-5,6,8-triazaazulene

Example 33 (Step 6)

6-(4-Methoxybenzyl)-4-(4-methoxyphenyl)-2,3-dimethyl-7-methylthio-6H-1-thia-5,6,8-triazaazulene

Example 34 (Step 6)

4-(2-Chlorophenyl)-2,3-dimethyl-7-methylthio-6-(pyridin-4-ylmethyl)-6H-1-thia-5,6,8-triazaazulene In the same manner as in Example 28, the compounds of Examples 29, 30, 31, 32, 33 and 34 were obtained from the compounds of Examples 11, 12, 13, 14, 15 and 16, respectively. The compounds are shown in Table 10.

TABLE 10-(1)

| Example | Structural formula | $^1$H NMR(300MHz, δppm, CDCl$_3$) | Melting point, °C. |
|---|---|---|---|
| 29 | | 1.26 (3H, t, J=7.5Hz), 2.51(3H, s), 2.72(2H, m), 3.80(3H, s), 4.72(2H, s), 6.26(1H, s), 6.86 (2H, d, J=8.7Hz), 7.20–7.36(6H, m). | |
| 30 | | 2.36 (3H, d, J=1.1Hz), 2.51(3H, s), 3.80(3H, s), 4.73(2H, s), 6.26 (1H, q, J=1.1Hz), 6.84–6.88(2H, m), 7.28–7.42(7H, m). | Amorphous solid |

TABLE 10-(1)-continued

| Example | Structural formula | $^1$H NMR(300MHz, δppm, CDCl$_3$) | Melting point, °C. |
|---|---|---|---|
| 31 | | | 127~128 |

TABLE 10-(2)

| Example | Structural formula | $^1$H NMR(300MHz, δppm, CDCl$_3$) | Melting point, °C. |
|---|---|---|---|
| 32 | | 1.26 (3H, t, J=7.5Hz), 2.51(3H, s), 2.72(2H, m), 3.80(3H, s), 4.74(2H, s), 6.29 (1H, t, J=1.0Hz), 6.87 (2H, d, J=8.7Hz), 7.28–7.38(7H, m). | Amorphous solid |
| 33 | | 1.45(3H, s), 2.25(3H, s), 2.49(3H, s), 3.79(3H, s), 3.80(3H, s), 4.71(2H, broad), 6.79 (2H, d, J=8.9Hz), 6.85 (2H, d, J=8.7Hz), 7.14 (2H, d, J=8.8Hz), 7.32 (2H, d, J=8.6Hz). | Amorphous solid |
| 34 | | | 156~159 |

Example 35 (Step 6)

5-(4-Chlorophenyl)-3-(4-methoxybenzyl)-2-methylthio-3H-benzo-[e][1,2,4]triazepine

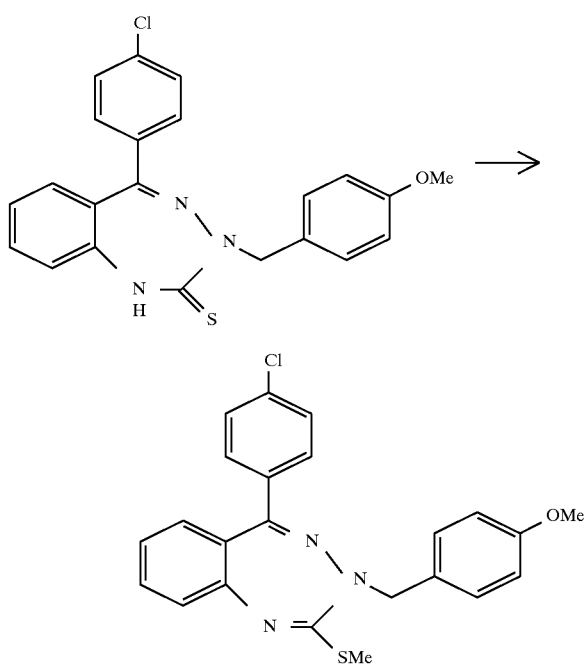

5-(4-Clorophenyl)-3-(4-methoxybenzyl)-1,3-dihydrobenzo[e][1,2,4]triazepine-2-thione (100 mg) obtained in Example 3 was dissolved in acetone (1 ml), and anhydrous potassium carbonate (339 mg) and methyl iodide (18 μl) were added. The mixture was stirred at room temperature for 2 hours. Potassium carbonate was removed by filtration, and the filtrate was concentrated under reduced pressure. The residue was dissolved in diethyl ether, and successively washed with water, a 5% aqueous citric acid solution and water. The organic layer was dried, filtrated, and concentrated under reduced pressure. The residue was purified by preparative thin-layer chromatography (n-hexane:ethyl acetate=3:1) to give 97 mg of the title compound.

$^1$H NMR(300 MHz, δ ppm, CDCl$_3$) 2.53(3H,s), 3.78(3H, s), 4.70(2H,s), 6.82(2H,d,J=8.7 Hz), 6.96(2H,m), 7.15(1H, d,J=7.9 Hz), 7.21–7.28(6H,m), 7.40(1H,m)

Example 36 (Step 7")

5-(4-Chlorophenyl)-3-(4-methoxybenzyl)-3H-benzo[e][1,2,4]-triazepin-2-ylhydrazine

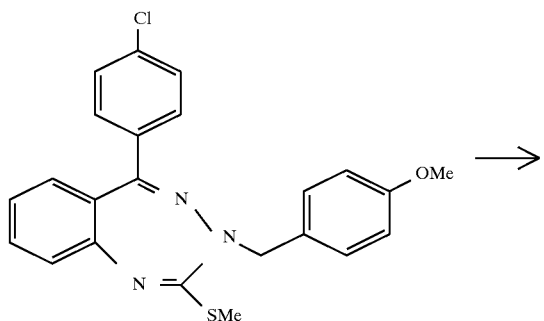

-continued

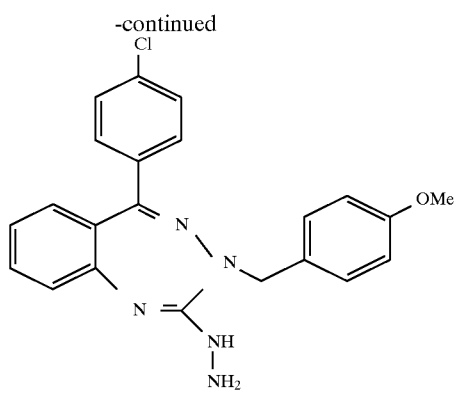

5-(4-Chlorophenyl)-3-(4-methoxybenzyl)-2-methylthio-3H-benzo[e][1,2,4]triazepine (42.2 mg) obtained in Example 35 and hydrazine monohydrate (10 μl) were dissolved in ethanol (0.4 ml), and the solution was stirred under heating at 70° C. for 24 hours. After the completion of the reaction, the mixture was concentrated under reduced pressure. The resulting residue was dissolved in ethyl acetate, and washed three times with water. The organic layer was dried, filtrated, and concentrated under reduced pressure. The residue was purified by preparative thin-layer chromatography (chloroform:methanol=20:1) to give 10.8 mg of the title compound. The spectrum data of the compound was consistent with that of Example 18.

Example 37 (Step 7)

Acetic acid N'-[5-(4-chlorophenyl)-3-(3,4-dimethoxybenzyl)-3H-benzo[e][1,2,4]triazepin-2-yl] hydrazide

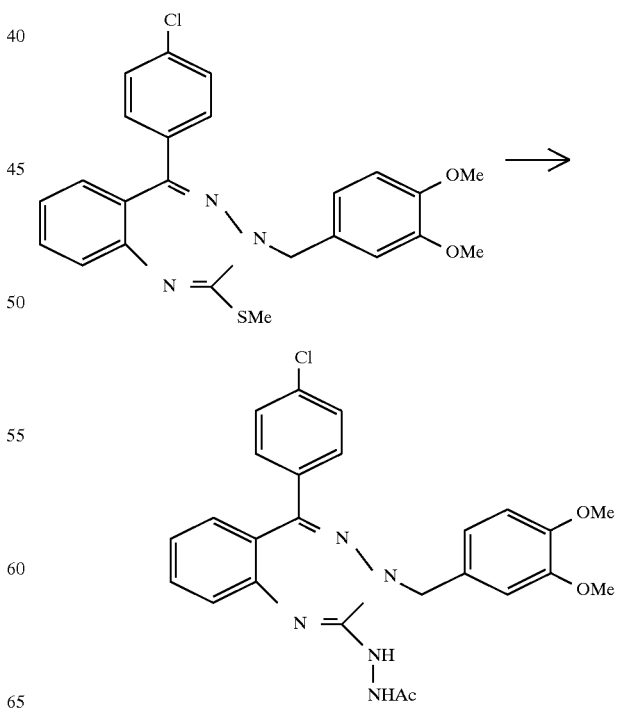

5-(4-Chlorophenyl)-3-(3,4-dimethoxybenzyl)-2-methylthio-3H-benzo[e][1,2,4]triazepine (51.5 g) obtained in Example 19 was dissolved in n-butanol (110 ml), and acetylhydrazine (16.89 g) was added. The mixture was stirred at 110° C. for 3 hours. The reaction mixture was cooled and the precipitated solid was collected by filtration, and successively washed with diethyl ether and water. The solid was dissolved in dichloromethane (1 L), and dried over anhydrous sodium sulfate. The drying agent was removed by filtration, and the filtrate was concentrated. Diethyl ether was added to the concentrated filtrate to give 48.1 g of the title compound as crystals.

Melting point: 145°–146° C.

Example 38 (Step 7)

Acetic acid N'-[3-(4-methoxybenzyl)-5-phenyl-3H-benzo[e][1,2,4]-triazepin-2-yl]hydrazide

Example 39 (Step 7)

Acetic acid N'-[3-(4-methoxybenzyl)-8-methyl-5-phenyl-3H-benzo[e][1,2,4]triazepin-2-yl]hydrazide In the same manner as in Example 37, the compounds of Examples 38 and 39 were obtained from the compounds of Examples 20 and 22, respectively. The compounds are shown in Table 11.

Example 40 (Step 5)

6-(4-Chlorophenyl)-4-(4-methoxybenzyl)-1-methyl-4H-2,3,4,5,10b-pentaazabenz[e]azulene

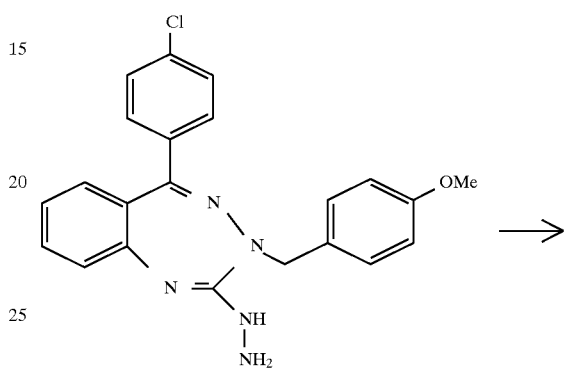

TABLE 11

| Example | Structural formula | Melting point, °C. |
|---------|-------------------|--------------------|
| 38 | | 213~216 |
| 39 | | 235~238 |

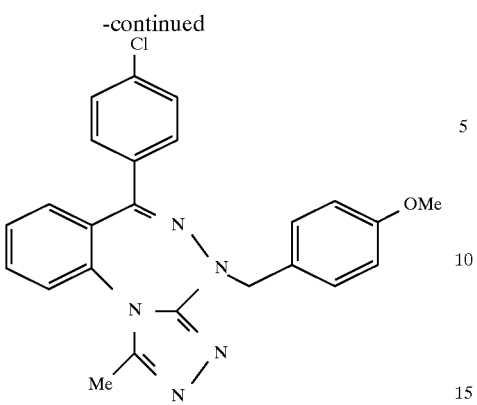

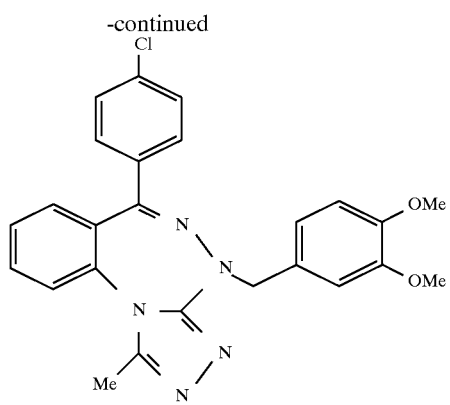

5-(4-Chlorophenyl)-3-(4-methoxybenzyl)-3H-benzo[e][1,2,4]-triazepin-2-ylhydrazine (23 mg) obtained in Example 18 or Example 36, triethyl orthoacetate (15 μl) and p-toluenesulfonic acid monohydrate (2.4 mg) were suspended in toluene (0.5 ml). The suspension was refluxed under heating for 3 hours and cooled. Ethyl acetate was added, and the organic layer was successively washed with an aqueous sodium hydrogencarbonate solution and water. The organic layer was dried, filtrated, and concentrated under reduced pressure. The residue was crystallized from ethyl acetate-diethyl ether to give 16 mg of the title compound as colorless needles.

Melting point: 192°–193° C.

$^1$H NMR(300 MHz, δ ppm, CDCl$_3$) 2.60(3H,s), 3.79(3H, s), 4.89–5.04(2H,m), 6.83–6.85(2H,m), 6.96(2H,m), 7.18–7.37(9H,m), 7.59–7.64(1H,m)

Example 41 (Step 8)

6-(4-Chlorophenyl)-4-(3,4-dimethoxybenzyl)-1-methyl-4H-2,3,4,5,10b-pentaazabenz[e]azulene

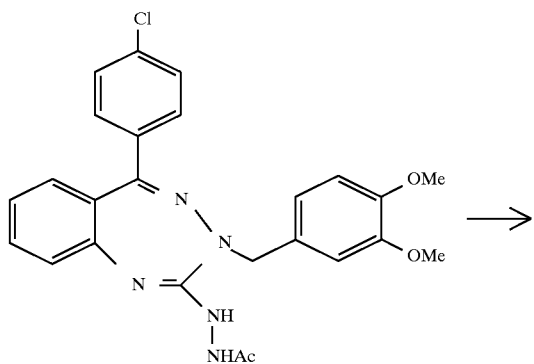

Acetic acid N'-[5-(4-chlorophenyl)-3-(3,4-dimethoxybenzyl)-3H-benzo[e][1,2,4]triazepin-2-yl] hydrazide (48 g) obtained in Example 37 and p-toluenesulfonic acid monohydrate (2.1 g) were suspended in toluene, and the suspension was stirred under heating at 110° C. for 30 minutes. After the completion of the reaction, the solvent was distilled away under reduced pressure. The residue was dissolved in dichloromethane, and successively washed with a saturated aqueous sodium hydrogencarbonate and water. The dichloromethane layer was dried, filtrated, and concentrated. The residue was crystallized from diethyl ether to give 42.4 g of the title compound as colorless crystals.

Melting point: 235°–237° C.

Example 42 (Step 8)

4-(4-Methoxybenzyl)-1-methyl-6-phenyl-4H-2,3,4,5,10b-pentaazabenz[e]azulene

Example 43 (Step 8)

4-(4-Methoxybenzyl)-1,9-dimethyl-6-phenyl-4H-2,3,4,5,10b-pentaazabenz[e]azulene

In the same manner as in Example 41, the compounds of Examples 42 and 43 were obtained from the compounds of Examples 38 and 39, respectively. The compounds are shown in Table 12.

TABLE 12

| Example | Structural formula | Melting point, °C. |
|---|---|---|
| 42 | | 139~140 |
| 43 | | 101~105 |

Example 44 (Step 7')

8Chloro-4-(4-methoxybenzyl)-1-methyl-6-phenyl-4H-2,3,4,5,10b-pentaazabenz[e]azulene

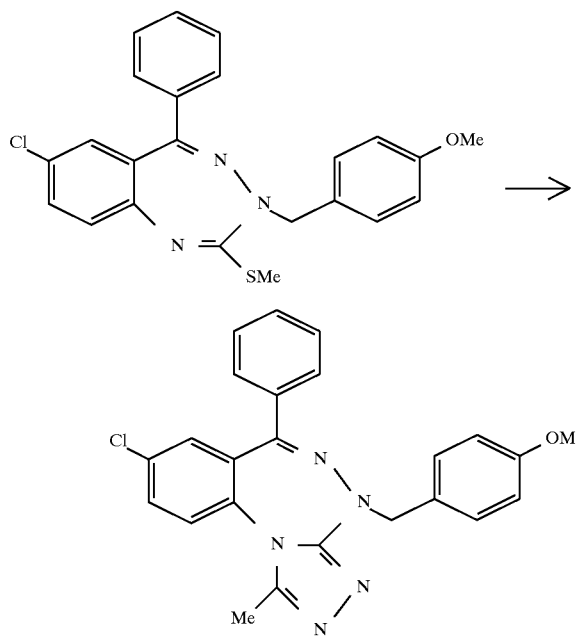

7-Chloro-3-(4-methoxybenzyl)-2-methylthio-5-phenyl-3H-benzo[e][1,2,4]triazepine (600 mg) obtained in Example 21, acetylhydrazine (220 mg) and p-toluenesulfonic acid monohydrate (80 mg) were dissolved in n-butanol (6 ml), and the solution was stirred under heating at 90° C. for 2 hours and 110° C. for 1.5 hours. After the completion of the reaction, the solvent was distilled away under reduced pressure, and the residue was dissolved in ethyl acetate, and successively washed with water, a saturated aqueous sodium hydrogencarbonate solution and water. The organic layer was dried, filtrated, and concentrated under reduced pressure. The residue was applied to silica gel column chromatography (chloroform:acetone=5:1), and a product obtained from the fraction was crystallized from diethyl ether to give 100.7 mg of the title compound as crystals.

Melting point: 116°–118° C.

Example 45 (Step 7')

4-(4-Methoxybenzyl)-1-methyl-8-nitro-6-phenyl-4H-2,3,4,5,10b-pentaazabenz[e]azulene

Example 46 (Step 7')

4-(4-Methoxybenzyl)-1-methyl-6-(4-methylphenyl)-4H-2,3,4,5,10b-pentaazabenz[e]azulene

Example 47 (Step 7')

8-Chloro-6-(2-chlorophenyl)-4-(4-methoxybenzyl)-1-methyl-4H-2,3,4,5,10b-pentaazabenz[e]azulene In the same manner as in Example 44, the compounds of Examples 45, 46 and 47 were obtained from the compounds of Examples 23, 24 and 25, respectively. The compounds are shown in Table 13.

TABLE 13
| Example | Structural formula | ¹H NMR (300 MHz, δ ppm, CDCl₃) | Melting point, °C. |
|---|---|---|---|
| 45 | | 2.67(3H, s), 3.79(3H, s), 4.97(2H, broad), 6.85(2H, d, J=8.8Hz), 7.32(2H, d, J=8.7Hz), 7.37–7.51(6H, m), 8.09(1H, d, J=2.5Hz), 8.45(1H, dd, J=8.6 and 2.6Hz). | 189 (decomposition) |
| 46 | | | 194~196 |
| 47 | | | 188~191 |
Example 48 (Step 7')
4-(4-Chlorophenyl)-6-(4-methoxybenzyl)-2,3,9-trimethyl-6H-5,6,7,8,9a-pentaazathien[2,3-e]azulene
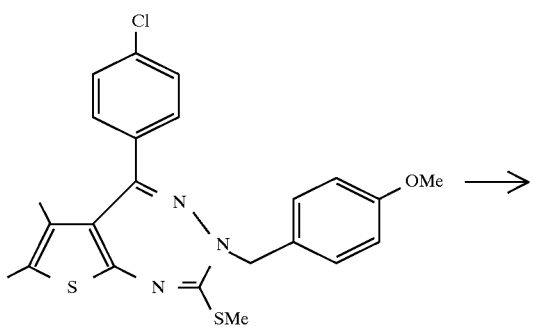
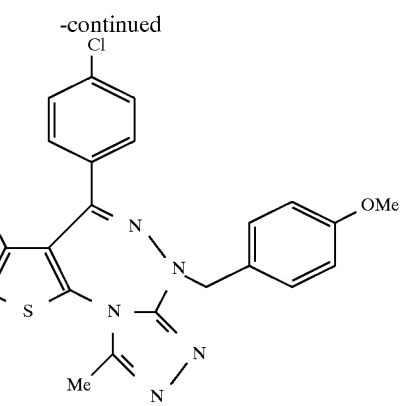
4-(4-Chlorophenyl)-6-(4-methoxybenzyl)-2,3-dimethyl-7-methylthio-6H-1-thia-5,6,8-triazaazulene (350 mg) obtained in Example 28, acetylhydrazine (114 mg) and p-toluenesulfonic acid monohydrate (14.6 mg) were dissolved in n-butanol (13.5 ml), and the solution was stirred under heating at 110° C. for 12 hours. After the completion of the reaction, the solvent was distilled away under reduced pressure. The residue was dissolved in ethyl acetate, and successively washed with water, a saturated aqueous sodium hydrogencarbonate solution and water. The organic layer was dried, filtrated, and concentrated under reduced pressure. The residue was applied to silica gel column chromatography (chloroform:methanol=5:1), and a product obtained from the fraction was crystallized from a mixed solvent of ethyl acetate and diethyl ether (1:3) to give 160 mg of the title compound as colorless crystals.

Melting point: 214°–216° C.

$^1$H NMR(300 MHz, δ ppm, CDCl$_3$) 1.26(3H,s), 2.36(3H, s), 2.65(3H,s), 3.81 (3H,s), 4.95(2H,m), 6.86(2H,d,J=8.7 Hz), 7.23–7.31 (4H,m), 7.35(2H,d,J=8.7 Hz)

Example 49 (Step 7')

4-(4-Chlorophenyl)-2-ethyl-6-(4-methoxybenzyl)-9-methyl-6H-5,6,7,8,9a-pentaazathien[2,3-e]azulene

Example 50 (Step 7')

6-(4-Methoxybenzyl)-2,9-dimethyl-4-phenyl-6H-5,6,7,8,9a-pentaazathien[2,3-e]azulene

Example 51 (Step 7')

6-(4-Methoxybenzyl)-2,3,9-trimethyl-4-phenyl-6H-5,6,7,8,9a-pentaazathien[2,3-e]azulene

Example 52 (Step 7')

2-Ethyl -6-(4-methoxybenzyl)-9-methyl-4-phenyl-6H-5,6,7,8,9a-pentaazathien[2,3-e]azulene

Example 53 (Step 7')

6-(4-Methoxybenzyl)-4-(4-methoxyphenyl)-2,3,9-trimethyl-6H-5,6,7,8,9a-pentaazathien[2,3-e]azulene In the same manner as in Example 48, the compounds of Examples 49, 50, 51, 52 and 53 were obtained from the compounds of Examples 29, 30, 31, 32 and 33, respectively. The compounds are shown in Table 14.

TABLE 14-(1)

| Example | Structural formula | $^1$H NMR(300MHz, δppm, CDCl$_3$) | Melting point, °C. |
|---|---|---|---|
| 49 | (structure shown) | | 141~143 |
| 50 | (structure shown) | 2.47 (3H, d, J=1.1Hz), 2.61(3H, s), 3.81(3H, s), 4.97(2H, s), 6.42 (1H, q, J=1.1Hz), 6.85–6.90(2H, m), 7.32–7.40(7H, m). | Amorphous solid |

TABLE 14-(1)-continued

| Example | Structural formula | ¹H NMR(300MHz, δppm, CDCl₃) | Melting point, °C. |
|---|---|---|---|
| 51 | | | 169~171 |

TABLE 14-(2)

| Example | Structural formula | ¹H NMR(300MHz, δppm, CDCl₃) | Melting point, °C. |
|---|---|---|---|
| 52 | | | 118~119 |
| 53 | | | 221~225 |

Example 54 (Step 7')

6-(4-Chlorophenyl)-1-methyl-4-(pyridin-3-ylmethyl)-4H-2,3,4,5,10b-pentaazabenz[e]azulene

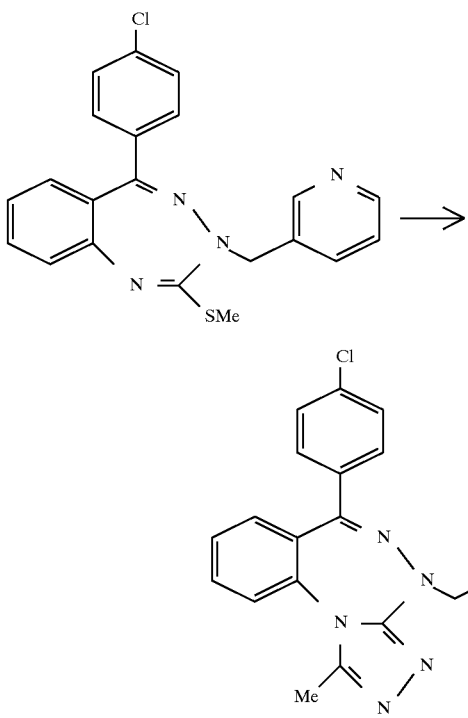

5(4-Chlorophenyl)-2-methylthio-3-(pyridin-3-ylmethyl)-3H-benzo[e][1,2,4]triazepine (800 mg) obtained in Example 26 was dissolved in 1-butanol (4 ml), and acetohydrazine (151 mg,) and p-toluenesulfonic acid monohydrate (19.4 mg,) were added. The mixture was stirred at 100° C. for 3 hours in a water bath. The reaction was cooled to room temperature, gradually added with diethyl ether 10 ml), and allowed to stand for one hour. The precipitated crystals were collected by filtration, and washed with diethyl ether to give 488 mg of the title compound as colorless crystals.

Melting point: 240°–243° C.

$^1$HNMR(300 MHz,δ ppm, CDCl$_3$) 2.62(3H,s), 4.98(1H, m), 5.11(1H,m), 7.18–7.40(8H,m), 7.64(1H,dt,J=7.8 and 1.4 Hz), 7.72(1H,dt,J=7.8 and 1.9 Hz), 8.51(1H,dd,J=4.8 and 1.6 Hz), 8.65(1H,d,J=1.6 Hz)

The title compound can be also prepared according to a method similar to that in Example 56 (see Example 98).

Example 55 (Step 7')

4-(2-Chlorophenyl)-2,3,9-trimethyl-6(pyridin-4-ylmethyl)-6H-5,6,7,8,9a-pentaazathien[2,3-e]azulene In the same manner as in Example 54, the title compound was obtained from the compound of Example 34. The compound is shown in Table 15.

TABLE 15

| Example | Structural formula | Melting point, °C. |
|---|---|---|
| 55 | 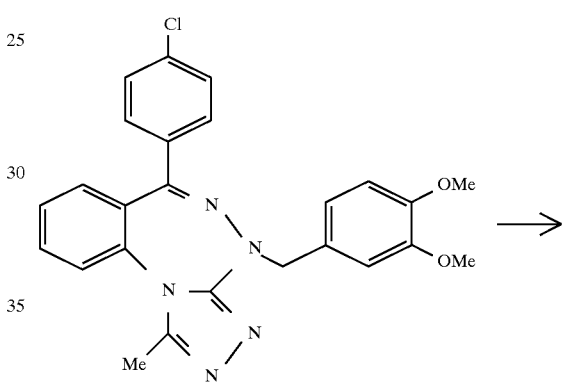 | 199–202 |

Preparative Example 34 (Step 9)
6-(4-Chlorophenyl)-1-methyl-4H-2,3,4,5,10b-pentaazabenz[e]azulene

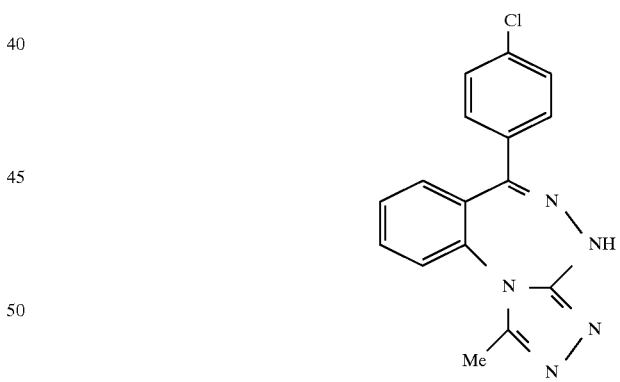

6-(4-Chlorophenyl)-4-(3,4-dimethoxybenzyl)-methyl-4H- 2,3,4,5,10b-pentaazabenz[e]azulene (2.02 g) obtained in Example 41 and anisole (1.4 ml) were dissolved in trifluoroacetic acid (8 ml), and concentrated sulfuric acid (1.3 ml) was added. The mixture was stirred for 10 minutes. Concentrated sulfuric acid (3.9 ml) was added, and the mixture was stirred for 45 minutes. The mixture was added with concentrated sulfuric acid (1.3 ml), and stirred for 1.5 hours. The reaction mixture was poured into ice-water (300 ml), and extracted with ethyl acetate. The organic layer was successively washed with an aqueous sodium hydrogencarbonate solution and water, dried, filtrated, and concentrated. The residue was crystallized from diethyl ether to give 748 mg of the title compound as colorless crystals.

Melting point: 231°–233° C.

Preparative Example 35 (Step 9)

1-Methyl-6-(4-methylphenyl)-4H-2,3,4,5,10b-pentaazabenz[e]azulene

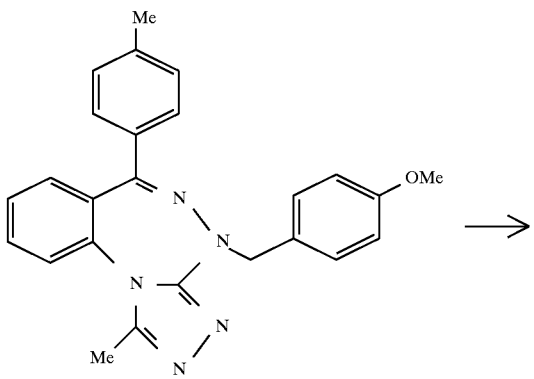

4-(4-Methoxybenzyl)-1-methyl-6-(4-methylphenyl)-4H-2, 3,4,5,10b-pentaazabenz[e]azulene (800 mg) obtained in Example 46 was dissolved in a 25% hydrobromic acid/ acetic acid solution (8 ml), and anisole (0.22 ml) was added. The mixture was stirred under heating at 40° C. for 3 hours. Diisopropyl ether (200 ml) was added to the reaction mixture, and the resulting crystals were collected by filtration. The crystals were dissolved in water (10 ml), and sodium hydrogencarbonate was added to neutralize the solution. The precipitated crystals were collected by filtration, dissolved in methylene chloride (30 ml), washed with water, and dried over anhydrous sodium sulfate. After filtration, the filtrate was concentrated, and the residue was crystallized from ethyl acetate to give 345 mg of the title compound.

Melting point: 259°–261° C.

Preparative Example 36 (Step 9)

7-Nitro-1-methyl-6-phenyl-4H-2,3,4,5,10b-pentaazabenz[e]azulene

Preparative Example 37 (Step 9)

8-Chloro-6-(2-chlorophenyl)-1-methyl-4H-2,3,4,5,10b-pentaazabenz[e]azulene

In the same manner as in Preparative Example 34, the compounds of Preparative Example 36 and 37 were obtained from the compounds of Example 45 and 47, respectively. The compounds are shown in Table 16.

TABLE 16

| Example | Structural formula | Melting point, °C. |
|---------|-------------------|-------------------|
| 36 | 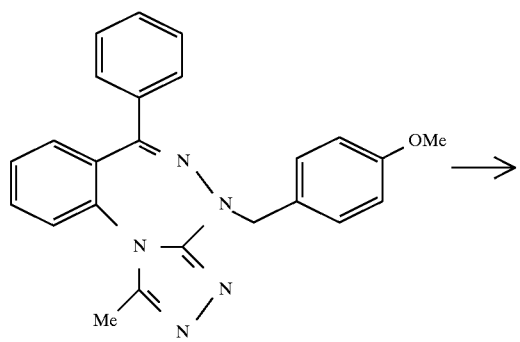 | 258~260 |
| 37 | 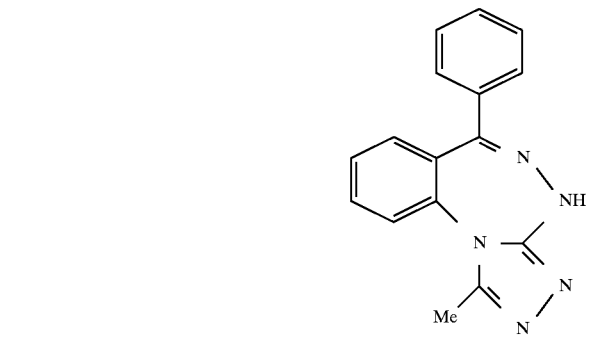 | 282~284 |

Preparative Example 38 (Step 9)

1-Methyl-6-phenyl-4H-2,3,4,5,10b-pentaazabenz[e]azulene

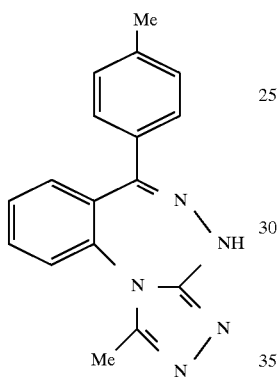

4-(4-Methoxybenzyl)-1-methyl-6-phenyl-4H-2,3,4,5,10b-pentaazabenz[e]azulene (94 mg) obtained in Example 42 and anisole (20 μl) were dissolved in a 25% hydrobromic acid/acetic acid solution (6.9 ml), and the solution was stirred at room temperature for 32 hours. The reaction mixture was concentrated under reduced pressure, and ethyl acetate and a saturated aqueous sodium hydrogencarbonate solution were added to the residue. The organic layer was saparated. The organic layer was washed with water, dried, filtrated, and concentrated under reduced pressure. The residue was purified by preparative thin-layer chromatography (chloroform:methanol=20:1), and crystallized from diethyl ether to give 48.5 mg of the title compound as colorless needles.

Melting point: 227°–230° C.

Preparative Example 39 (Step 9)

1,9-Dimethyl-6-phenyl-4H-2,3,4,5,10b-pentaazabenz[e]azulene.

In the same manner as in Preparative Example 38, the compound of Preparative Example 39 was obtained from the compound of Example 43. The compound is shown in Table 17.

TABLE 17

| Preparative Ex. | Structural formula | Melting point, °C. |
|---|---|---|
| 39 | 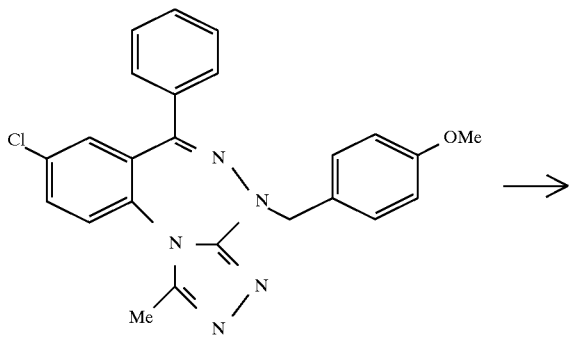 | 248~251 |

Preparative Example 40 (Step 9)

8-Chloro-1-methyl-6-phenyl-4H-2,3,4,5,10b-pentaazabenz[e]azulene hydrobromide

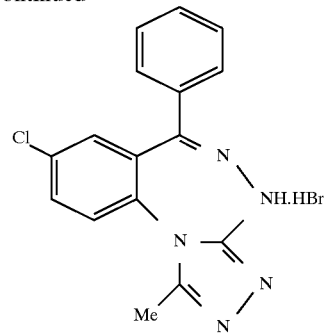

8-Chloro-4-(4-methoxybenzyl)-1-methyl-6-phenyl-4H-2,3,4,5,10b-pentaazabenz[e]azulene (105 mg) obtained in Example 44 was reacted according to a method similar to that in Preparative Example 38, and the solvent was distilled away under reduced pressure to give crystals. The crystals were washed with diethyl ether and dried to give 108.2 mg of the title compound.

Melting point: 191°–192° C. (dec.)

Preparative Example 41 (Step 9)

8-Chloro-1-methyl-6-phenyl-4H-2,3,4,5,10b-pentaazabenz[e]azulene

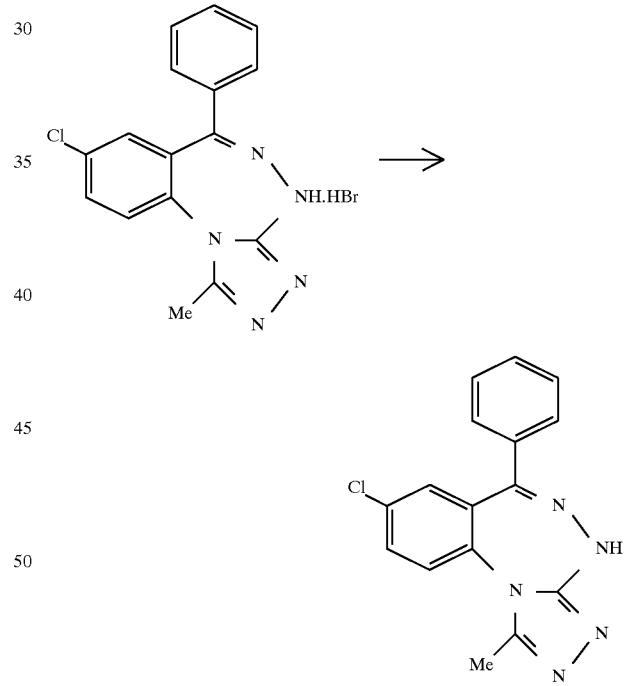

8-Chloro-1-methyl-6-phenyl-4H-2,3,4,5,10b-pentaazabenz[e]azulene hydrobromide (102 mg) obtained in Preparative Example 40 was extracted according to the method described in Preparative Example 34, and the extract was crystallized from diethyl ether to give the title compound as crystals.

Melting point: 140°–142° C.

Preparative Example 42 (Step 9)

4-(4-Chlorophenyl)-2,3,9-trimethyl-6H-5,6,7,8,9a-pentaazathien[2,3-e]azulene

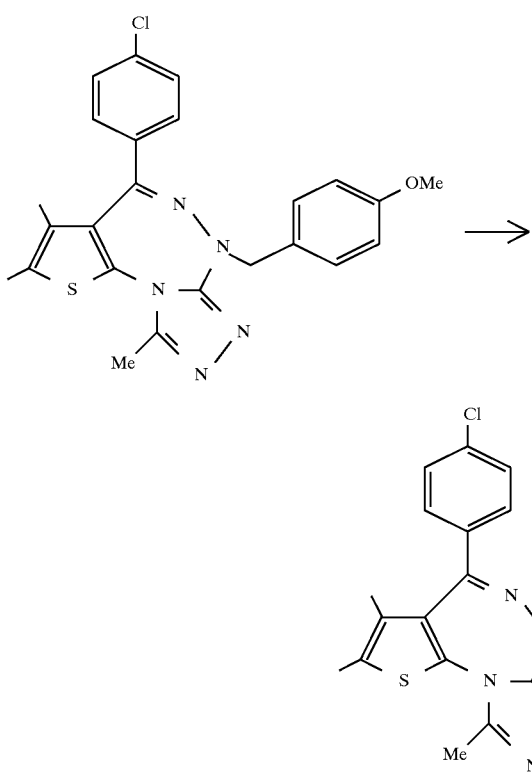

4-(4-Chlorophenyl)-6-(4-methoxybenzyl)-2,3,9-trimethyl-6H-5,6,7,8,9a-pentaazathien[2,3-e]azulene (100 mg) obtained in Example 48 and anisole (24 μl) were dissolved in a 25% hydrobromic acid/acetic acid solution (1 ml), and the solution was stirred at 40° C. for 5 hours. The reaction mixture was cooled to room temperature, and diisopropyl ether (30 ml) was added. The precipitated oil on the reactor wall was separated from the organic solvent. The oil was dissolved in chloroform, successively washed with water, a saturated aqueous sodium hydrogencarbonate solution and water, and dried over anhydrous sodium sulfate. After filtration, the filtrate was concentrated under reduced pressure, and the residue was crystallized from diethyl ether to give 68 mg of the title compound as yellow crystals.

Melting point: 247° C.

$^1$H NMR(300 MHz, δ ppm, CDCl$_3$) 1.58(3H,s), 2.36(3H,s), 2.62(3H,s), 7.35(2H,d,J=8.9 Hz), 7.43(2H,d,J=8.9 Hz), 7.83(1H,s)

Preparative Example 43 (Step 9)

4-(4-Chlorophenyl)-2-ethyl-9-methyl-6H-5,6,7,8,9a-pentaazathien[2,3-e]azulene

Preparative Example 44 (Step 9)

2,9-Dimethyl-4-phenyl-6H-5,6,7,8,9a-pentaazathien[2,3-e]azulene

Preparative Example 45 (Step 9)

2,3,9-Trimethyl-4-phenyl-6H-5,6,7,8,9a-pentaazathien[2,3-e]azulene

Preparative Example 46 (Step 9)

2-Ethyl-9-methyl-4-phenyl-6H-5,6,7,8,9a-pentaazathien[2,3-e]azulene

Preparative Example 47 (Step 9)

4-(4-Methoxyphenyl)-2,3,9-trimethyl-6H-5,6,7,8,9a-pentaazathien[2,3-e]azulene

In the same manner as in Preparative Example 42, the compounds of Preparative Examples 43, 44, 45, 46 and 47 were obtained from the compounds of Examples 49, 50, 51, 52 and 53, respectively. The compounds are shown in Table 18.

TABLE 18-(1)

| Prep. Ex. | Structural formula | $^1$H NMR(300MHz, δppm, CDCl$_3$) | Melting point, °C. |
|---|---|---|---|
| 43 | | 1.32(3H, t, J=7.5Hz), 2.62(3H, s), 2.82(2H, t, J=7.5Hz), 6.43(1H, s), 7.37(2H, d, J=8.4Hz), 7.49(2H, d, J=8.4Hz), 7.63(1H, m). | |

TABLE 18-(1)-continued

| Prep. Ex. | Structural formula | ¹H NMR(300MHz, δppm, CDCl₃) | Melting point, °C. |
|---|---|---|---|
| 44 | | 2.47(3H, d, J=1.5Hz), 2.61(3H, s), 6.44(1H, q, J=1.5Hz), 7.36–7.45(3H, m), 7.52–7.55(2H, m), 7.68(1H, brs). | 226~232 |
| 45 | | 1.63(3H, s), 2.36(3H, s), 2.62(3H, s), 7.34–7.48(5H, m), 7.62(1H, brs). | |

TABLE 18-(2)

| Example | Structural formula | ¹H NMR (300MHz, δ ppm, CDCl₃) | Melting point, °C. |
|---|---|---|---|
| 46 | | | 183~184 |
| 47 | (OCH₃) | | 254~257 |

Example 56 (Step 10-1)

6-(4-Chlorophenyl)-4-(3-cyanobenzyl)-1-methyl-4H-2,3,4,5,10b-pentaazabenz[e]azulene

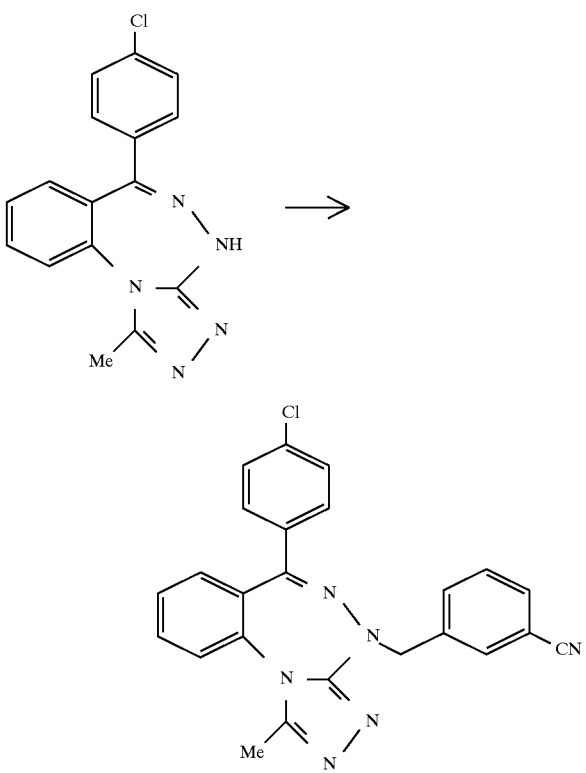

6-(4-Chlorophenyl)-1-methyl-4H-2,3,4,5,10b-pentaazabenz[e]azulene (20 mg) obtained in Preparative Example 34 was dissolved in anhydrous N,N-dimethylformamide (0.4 ml) under an argon atmosphere, and the solution was ice-cooled. Potassium hydroxide (13 mg) pulverized in a mortar was added all at once. 3-(Chloromethyl)benzonitrile (15.2 mg) was added, and the mixture was stirred under ice-cooling for 10 minutes and at room temperature for one hour. After the completion of the reaction, the reaction mixture was cooled with ice, and added with a 5% aqueous citric acid solution and ethyl acetate. The organic layer was separated, and successively washed with a saturated aqueous sodium hydrogencarbonate solution and water. The organic layer was dried, filtrated, and concentrated under reduced pressure. The resulting residue was crystallized from diethyl ether to give 8.4 mg of the title compound.

Melting point: 140°–141° C.

$^1$H NMR(300 MHz, δ ppm, CDCl$_3$) 2.62(3H,s), 4.92–5.16(2H,m), 7.24–7.69(12H,m)

Example 57–119 (Step 10-1)

In the same manner as in Example 56, the following compounds of Examples 57–119 were obtained from the compound of Preparative Example 34. The compounds are shown in Tables 19–23.

Example 57

6-(4-Chlorophenyl)-4-(2-fluorobenzyl)-1-methyl-4H-2,3,4,5,10b-pentaazabenz[e]azulene Example 58

6-(4-Chlorophenyl)-4-(3-fluorobenzyl)-1-methyl-4H-2,3,4,5,10b-pentaazabenz[e]azulene Example 59

6-(4-Chlorophenyl)-4-(4-fluorobenzyl)-1-methyl-4H-2,3,4,5,10b-pentaazabenz[e]azulene Example 60

6-(4-Chlorophenyl)-4-(2,4-difluorobenzyl)-1-methyl-4H-2,3,4,5,10b-pentaazabenz[e]azulene Example 61

6-(4-Chlorophenyl)-4-(2,5-difluorobenzyl)-1-methyl-4H-2,3,4,5,10b-pentaazabenz[e]azulene Example 62

6-(4-Chlorophenyl)-4-(3,5-difluorobenzyl)-1-methyl-4H-2,3,4,5,10b-pentaazbenz[e]azulene Example 63

6-(4-Chlorophenyl)-4-(3,4-difluorobenzyl)-1-methyl-4H-2,3,4,5,10b-pentaazabenz[e]azulene Example 64

6-(4-Chlorophenyl)-1-methyl-4-(2-trifluoromethylbenzyl)-4H-2,3,4,5,10b-pentaazabenz[e]azulene Example 65

6-(4-Chlorophenyl)-1-methyl-4-(4-trifluoromethylbenzyl)-4H-2,3,4,5,10b-pentaazabenz[e]azulene Example 66

6-(4-Chlorophenyl)-1-methyl-4-(3-trifluoromethylbenzyl)-4H-2,3,4,5,10b-pentaazabenz[e]azulene Example 67

6-(4-Chlorophenyl)-1-methyl-4-(4-trifluoromethoxybenzyl)-4H-2,3,4,5,10b-pentaazabenz[e]azulene Example 68

6-(4-Chlorophenyl)-1-methyl-4-(3-nitrobenzyl)-4H-2,3,4,5,10b-pentaazabenz[e]azulene Example 69

4-(2-Chlorobenzyl)-6-(4-chlorophenyl)-1-methyl-4H-2,3,4,5,10b-pentaazabenz[e]azulene Example 70

4-(3-Chlorobenzyl)-6-(4-chlorophenyl)-1-methyl-4H-2,3,4,5,10b-pentaazabenz[e]azulene Example 71

4-(4-Chlorobenzyl)-6-(4-chlorophenyl)-1-methyl-4H-2,3,4,5,10b-pentaazabenz[e]azulene Example 72

6-(4-Chlorophenyl)-4-(2-cyanobenzyl)-1-methyl-4H-2,3,4,5,10b-pentaazabenz[e]azulene Example 73

6-(4-Chlorophenyl)-4-(3-cyanobenzyl)-1-methyl-4H-2,3,4,5,10b-pentaazabenz[e]azulene

Example 74

6-(4-Chlorophenyl)-4-(4-cyanobenzyl)-1-methyl-4H-2,3,4,5,10b-pentaazabenz[e]azulene

Example 75

6-(4-Chlorophenyl)-4-(2-methoxybenzyl)-1-methyl-4H-2,3,4,5,10b-pentaazabenz[e]azulene

Example 76

6-(4-Chlorophenyl)-4-(3-methoxybenzyl)-1-methyl-4H-2,3,4,5,10b-pentaazabenz[e]azulene

Example 77

6-(4-Chlorophenyl)-4-(4-methoxybenzyl)-1-methyl-4H-2,3,4,5,10b-pentaazabenz[e]azulene

Example 78

6-(4-Chlorophenyl)-4-(2,5-dimethoxybenzyl)-1-methyl-4H-2,3,4,5,10b-pentaazabenz[e]azulene

Example 79

6-(4-Chlorophenyl)-1-methyl-4-(3,4,5-trimethoxybenzyl)-4H-2,3,4,5,10b-pentaazabenz[e]azulene

Example 80

4-(5-Acetyl-2-methoxybenzyl)-6-(4-chlorophenyl)-1-methyl-4H-2,3,4,5,10b-pentaazabenz[e]azulene

Example 81

6-(4-Chlorophenyl)-1-methyl-4-(3,4-methylenedioxybenzyl)-4H-2,3,4,5,10b-pentaazabenz[e]azulene

Example 82

4-(2-Chloro-4,5-methylenedioxybenzyl)-6-(4-chlorophenyl)-1-methyl-4H-2,3,4,5,10b-pentaazabenz[e]azulene

Example 83

6-(4-Chlorophenyl)-4-(2-methoxy-5-nitrobenzyl)-1-methyl-4H-2,3,4,5,10b-pentaazabenz[e]azulene

Example 84

6-(4-Chlorophenyl)-4-(4-methoxy-3-nitrobenzyl)-1-methyl-4H-2,3,4,5,10b-pentaazabenz[e]azulene

Example 85

4-(3-Chloro-4-methoxybenzyl)-6-(4-chlorophenyl)-1-methyl-4H-2,3,4,5,10b-pentaazabenz[e]azulene

Example 86

6-(4-Chlorophenyl)-4-(3,5-dichloro-4-methoxybenzyl)-1-methyl-4H-2,3,4,5,10b-pentaazabenz[e]azulene

Example 87

6-(4-Chlorophenyl)-1-methyl-4-(2-methylbenzyl)-4H-2,3,4,5,10b-pentaazabenz[e]azulene

Example 88

6-(4-Chlorophenyl)-1-methyl-4-(3-methylbenzyl)-4H-2,3,4,5,10b-pentaazabenz[e]azulene

Example 89

6-(4-Chlorophenyl)-1-methyl-4-(4-methylbenzyl)-4H-2,3,4,5,10b-pentaazabenz[e]azulene

Example 90

4-(4-tert-Butylbenzyl)-6-(4-chlorophenyl)-1-methyl-4H-2,3,4,5,10b-pentaazabenz[e]azulene

Example 91

6-(4-Chlorophenyl)-1-methyl-4-(naphthalen-1-ylmethyl)-4H-2,3,4,5,10b-pentaazabenz[e]azulene

Example 92

6-(4-Chlorophenyl)-1-methyl-4-(naphthalen-2-ylmethyl)-4H-2,3,4,5,10b-pentaazabenz[e]azulene

Example 93

4-(4-Benzyloxybenzyl)-6-(4-chlorophenyl)-1-methyl-4H-2,3,4,5,10b-pentaazabenz[e]azulene

Example 94

4-Benzyl-6-(4-chlorophenyl)-1-methyl-4H-2,3,4,5,10b-pentaazabenz[e]azulene

Example 95

6-(4-Chlorophenyl)-1-methyl-4-(4-phenylbenzyl)-4H-2,3,4,5,10b-pentaazabenz[e]azulene

Example 96

4-(4-Chlorophenoxymethyl)-6-(4-chlorophenyl)-1-methyl-4H-2,3,4,5,10b-pentaazabenz[e]azulene

Example 97

6-(4-Chlorophenyl)-1-methyl-4-(pyridin-2-ylmethyl)-4H-2,3,4,5,10b-pentaazabenz[e]azulene

Example 98

6-(4-Chlorophenyl)-1-methyl-4-(pyridin-3-ylmethyl)-4H-2,3,4,5,10b-pentaazabenz[e]azulene

Example 99

6-(4-Chlorophenyl)-4-[2-(indol-3-yl)ethyl]-1-methyl-4H-2,3,4,5,10b-pentaazabenz[e]azulene

Example 100

6-(4-Chlorophenyl)-4-(2-methyl-1,3-thiazol-4-ylmethyl)-1-methyl-4H-2,3,4,5,10b-pentaazabenz[e]azulene

Example 101

6-(4-Chlorophenyl)-4-(5-chlorothiophen-2-ylmethyl)-1-methyl-4H-2,3,4,5,10b-pentaazabenz[e]azulene

Example 102

6-(4-Chlorophenyl)-1-methyl-4-(3,5-dimethylisoxazol-4-ylmethyl)-4H-2,3,4,5,10b-pentaazabenz[e]azulene

Example 103

6-(4-Chlorophenyl)-1-methyl-4-phenethyl-4H-2,3,4,5,10b-pentaazabenz[e]azulene

Example 104

6-(4-Chlorophenyl)-1-methyl-4-(3-phenylpropyl)-4H-2,3,4,5,10b-pentaazabenz[e]azulene

Example 105

6-(4-Chlorophenyl)-4-(3,3-diphenylpropyl)-1-methyl-4H-2,3,4,5,10b-pentaazabenz[e]azulene

Example 106

6-(4-Chlorophenyl)-4-cyclopropylmethyl-1-methyl-4H-2,3,4,5,10b-pentaazabenz[e]azulene

Example 107

6-(4-Chlorophenyl)-4-cyclohexylmethyl-1-methyl-4H-2,3,4,5,10b-pentaazabenz[e]azulene

Example 108

6-(4-Chlorophenyl)-4-(2-cyclohexylethyl)-1-methyl-4H-2,3,4,5,10b-pentaazabenz[e]azulene

Example 109

6-(4-Chlorophenyl)-1-methyl-4-(3-phenyl-2-propenyl)-4H-2,3,4,5,10b-pentaazabenz[e]azulene

Example 110

4-Allyl-6-(4-chlorophenyl)-1-methyl-4H-2,3,4,5,10b-pentaazabenz[e]azulene

Example 111

6-(4-Chlorophenyl)-1-methyl-4-(2-methyl-2-propenyl)-4H-2,3,4,5,10b-pentaazabenz[e]azulene

Example 112

6-(4-Chlorophenyl)-4-(2-chloro-2-propenyl)-1l-methyl-4H-2,3,4,5,10b-pentaazabenz[e]azulene

Example 113

4-(2-Bromo-2-propenyl)-6-(4-chlorophenyl)-1l-methyl-4H-2,3,4,5,10b-pentaazabenz[e]azulene

Example 114

6-(4-Chlorophenyl)-4-(2,3-dichloro-2-propenyl)-1-methyl-4H-2,3,4,5,10b-pentaazabenz[e]azulene

Example 115

6-(4-Chlorophenyl)-4-(3,4-dibenzyloxybenzyl)-1-methyl-4H-2,3,4,5,10b-pentaazabenz[e]azulene

Example 116

4-Benzyloxymethyl-6-(4-chlorophenyl)-1-methyl-4H-2,3,4,5,10b-pentaazabenz[e]azulene

Example 117

6-(4-Chlorophenyl)-1-methyl-4-(3-phenoxypropyl)-4H-2,3,4,5,10b-pentaazabenz[e]azulene

Example 118

6-(4-Chlorophenyl)-4-(3,3-dichloro-2-propenyl)-1-methyl-4H-2,3,4,5,10b-pentaazabenz[e]azulene

Example 119

6-(4-Chlorophenyl)-4-(4-methoxy-3-methylbenzyl)-1-methyl-4H-2,3,4,5,10b-pentaazabenz[e]azulene

TABLE 19

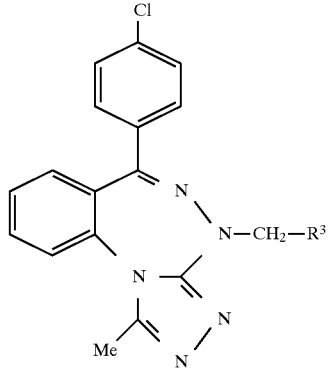

| Example | $R^3$ | melting point, °C. | Example | $R^3$ | melting point, °C. |
|---|---|---|---|---|---|
| 57 | 2-F-C6H4 | 228~229 | 65 | 4-CF3-C6H4 | 205~209 |

TABLE 19-continued
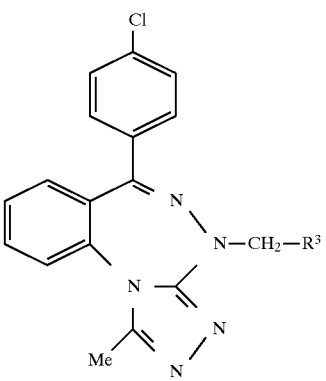
| Example | R³ | melting point, °C. | Example | R³ | melting point, °C. |
|---|---|---|---|---|---|
| 58 | 3-F-C₆H₄ | 193~196 | 66 | 3-CF₃-C₆H₄ | 147~148 |
| 59 | 4-F-C₆H₄ | 256~257 | 67 | 4-OCF₃-C₆H₄ | 122 |
| 60 | 2,4-diF-C₆H₃ | 209~210 | 68 | 3-NO₂-C₆H₄ | 172~175 |
| 61 | 2,5-diF-C₆H₃ | 205 | 69 | 2-Cl-C₆H₄ | 234~235 |
| 62 | 3,5-diF-C₆H₃ | 206~211 | 70 | 3-Cl-C₆H₄ | 194~195 |
| 63 | 3,4-diF-C₆H₃ | 195~196 | 71 | 4-Cl-C₆H₄ | 252~253 |
| 64 | 2-CF₃-C₆H₄ | 170~171 | 72 | 2-CN-C₆H₄ | 223~224 |

TABLE 20

[Structure: 4-chlorophenyl(2-methylphenyl)methylene hydrazine linked to a triazole ring with Me substituent, with N-CH2-R3 group]

| Example | R³ | melting point, °C. | Example | R³ | melting point, °C. |
|---|---|---|---|---|---|
| 73 | 3-CN-phenyl | 140~141 | 81 | 3,4-methylenedioxyphenyl | 206~208 |
| 74 | 4-CN-phenyl | 287~289 (decomposition) | 82 | 5-chloro-3,4-methylenedioxyphenyl | 273~274 |
| 75 | 2-MeO-phenyl | 85~89 | 83 | 4-MeO-3-NO₂-phenyl | 246 |
| 76 | 3-OMe-phenyl | 202~204 | 84 | 3-NO₂-4-OMe-phenyl | 218~221 (decomposition) |
| 77 | 4-OMe-phenyl | 191~193 | 85 | 3-Cl-4-OMe-phenyl | 191~193 |
| 78 | 2-MeO-4-OMe-phenyl | 163~165 | 86 | 3,5-diCl-4-OMe-phenyl | 189 |
| 79 | 2,3,4-triOMe-phenyl | 182~183 | 87 | 2-Me-phenyl | 248~249 |

TABLE 20-continued

[Structure: 4-chlorophenyl and 2-methylphenyl groups attached via C=N to a triazole ring system with N-CH₂-R³ substituent and Me group]

| Example | R³ | melting point, °C. | Example | R³ | melting point, °C. |
|---|---|---|---|---|---|
| 80 | 3-MeO, 4-COMe-phenyl | 144~148 | 88 | 3-methylphenyl (Me) | 207~208 |

TABLE 21

[Structure: 4-chlorophenyl and 2-methylphenyl groups attached via C=N to a triazole ring system with N-CH₂-R³ substituent and Me group]

| Example | R³ | melting point, °C. | Example | R³ | melting point, °C. |
|---|---|---|---|---|---|
| 89 | 4-Me-phenyl | 194~197 | 97 | 2-pyridyl | 187~188 |
| 90 | 4-t-Bu-phenyl | 154~156 | 98 | 3-pyridyl | 233~239 |
| 91 | 1-naphthyl | 129~134 | 99 | 3-ethyl-1H-indol-yl | 198~202 |

TABLE 21-continued
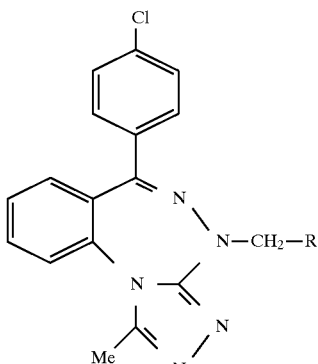
| Example | R³ | melting point, °C. | Example | R³ | melting point, °C. |
|---|---|---|---|---|---|
| 92 | 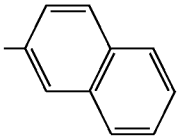 | 220~223 | 100 | 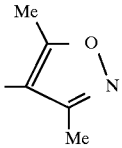 | 223~226 |
| 93 | 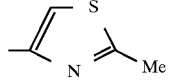 | 175~176 | 101 | 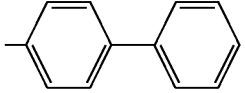 | 203~205 |
| 94 | 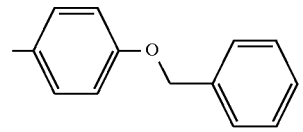 | 235~238 | 102 | 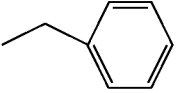 | 115~118 |
| 95 | 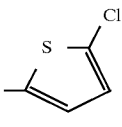 | 171 | 103 | 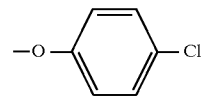 | 202 |
| 96 | 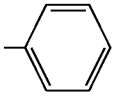 | 180~181 | 104 | 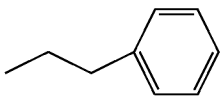 | 156~157 |

TABLE 22
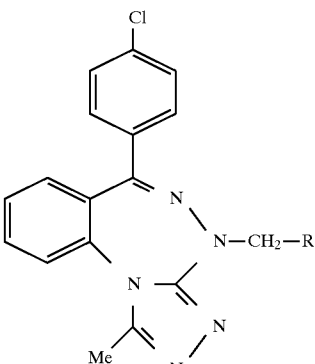
| Example | R³ | melting point, °C. | Example | R³ | melting point, °C. |
|---|---|---|---|---|---|
| 105 | 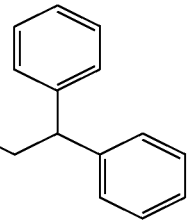 | 202~203 | 110 | 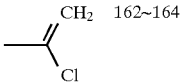 | 170~171 |
| 106 | 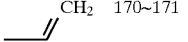 | 177~178 | 111 | 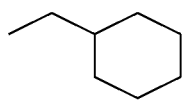 | 153~154 |
| 107 |  | 179~181 | 112 | 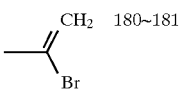 | 162~164 |
| 108 | 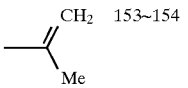 | 249~251 | 113 | 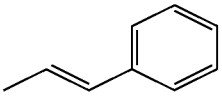 | 180~181 |
| 109 | 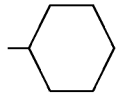 | 204~205 | 114 | 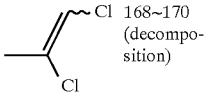 | 168~170 (decomposition) |

TABLE 23

[Structure: 4-chlorophenyl group attached to core with N=N, N—CH₂—R³, Me, and triazole ring system]

| Example | R³ | ¹H NMR(300MHz, δppm, CDCl₃) | melting point, °C. |
|---|---|---|---|
| 115 | [2-benzyloxy-3-benzyloxy-phenyl-methyl group] | 2.60(3H, s), 4.81–4.85(1H, m), 5.02–5.05(1H, m), 5.06(2H, s), 5.13(2H, s), 6.72–7.00(3H, m), 7.17–7.44(17H, m), 7.60–7.66(1H, m). | |
| 116 | [—O—CH₂—phenyl] | 2.60(3H, s), 4.65(2H, s), 5.38(1H, m), 5.49(1H, m), 7.18–7.41(10H, m), 7.52(2H, d, J=8.6Hz), 7.63(1H, dt, J=7.6 and 1.4Hz). | |
| 117 | [propyl—O—phenyl] | 2.28(2H, m), 2.59(3H, s), 4.04(4H, m), 6.81–6.93(3H, m), 7.19–7.64(10H, m). | 138~142 |
| 118 | [CH₃—CH=CCl₂] | 2.60(3H, s), 4.54(2H, d, J=6.6Hz), 6.27(1H, t, J=6.6Hz), 7.25–7.41(5H, m), 7.47–7.52(2H, m), 7.60–7.67(1H, m). | |
| 119 | [2-methyl-4-methyl-OMe phenyl] | | 187~188 |

Example 120 (Step 10-1)

6(4-Chlorophenyl)-1-methyl-4-(pyridin-4-ylmethyl)-4H-2,3,4,5,10b-pentaazabenz[e]azulene

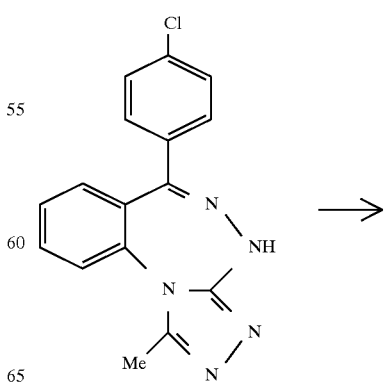

→

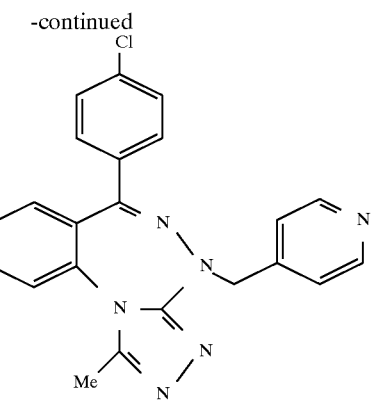

6-(4-Chlorophenyl)-1-methyl-4H-2,3,4,5,10b-pentaazabenz[e]azulene (783 mg) obtained in Preparative Example 34 was dissolved in anhydrous N,N-dimethylformamide (8 ml) under an argon gas atmosphere and cooled in an ice-bath. Sodium hydride (60% in oil, 120 mg) was added thereto and the mixture was stirred under ice-cooling for 5 minutes and at room temperature for 10 minutes. The reaction mixture was cooled in an ice-bath again and 4-picolyl chloride hydrochloride (415 mg) was added in a solid state to the reaction mixture. The mixture was stirred under ice-cooling for 25 minutes. After the completion of the reaction, ice-water (50 ml) and ethyl acetate (40 ml) were added and the organic layer was separated. The organic layer was washed with water three times, dried over anhydrous sodium sulfate and filtered. The filtrate was concentrated under reduced pressure and the residue was crystallized from diethyl ether to give 760 mg of the title compound.

Melting point: 223°–225° C.

$^1$H NMR(300 MHz, δ ppm, CDCl$_3$) 2.63(3H,s), 4.98–5.14(2H,m), 7.25–7.70(10H,m), 8.54(2H,dd,J=4.5 and 3.0 Hz)

Examples 121 to 138 (Step 10-1)

In the same manner as in Example 120, the compounds of Examples 121 to 125 were obtained from the compound of Preparative Example 34, the compounds of Examples 126 and 127 were obtained from the compound of Preparative Example 41, the compounds of Examples 128 and 129 were obtained from the compound of Preparative Example 38, the compounds of Examples 130, 131 and 132 were obtained from the compound of Preparative Example 39, the compounds of Examples 133 and 134 were obtained from the compound of Preparative Example 36, the compounds of Examples 135 and 136 were obtained from the compound of Preparative Example 35, and the compounds of Examples 137 and 138 were obtained from the compound of Preparative Example 37. These compounds are shown in Tables 24 and 25.

Example 121

6-(4-Chlorophenyl)-1-methyl-4-(4-methylsulfonylbenzyl)-4H-2,3,4,5,10b-pentaazabenz[e]azulene Example 122

6-(4-Chlorophenyl)-1-methyl-4-(4-nitrobenzyl)-4H-2,3,4,5,10b-pentaazabenz[e]azulene Example 123

6-(4-Chlorophenyl)-4-(2,6-dichloropyridin-4-ylmethyl)-1-methyl-4H-2,3,4,5,10b-pentaazabenz[e]azulene Example 124

6-(4-Chlorophenyl)-4-(2,2,2-trifluoroethyl)-1-methyl-4H-2,3,4,5,10b-pentaazabenz[e]azulene Example 125

6-(4-Chlorophenyl)-4-(3,5-dinitrobenzyl)-1-methyl-4H-2,3,4,5,10b-pentaazabenz[e]azulene Example 126

8-Chloro-1-methyl-6-phenyl-4-(pyridin-4-ylmethyl)-4H-2,3,4,5,10b-pentaazabenz[e]azulene Example 127

8-Chloro-1-methyl-6-phenyl-4-(pyridin-3-ylmethyl)-4H-2,3,4,5,10b-pentaazabenz[e]azulene Example 128

1-Methyl-6-phenyl-4-(pyridin-3-ylmethyl)-4H-2,3,4,5,10b-pentaazabenz[e]azulene

Example 129

1-Methyl-6-phenyl-4-(pyridin-4-ylmethyl)-4H-2,3,4,5,10b-pentaazabenz[e]azulene

Example 130

1,9-Dimethyl-6-phenyl-4-(pyridin-3-ylmethyl)-4H-2,3,4,5,10b-pentaazabenz[e]azulene Example 131

1,9-Dimethyl-6-phenyl-4-(pyridin-4-ylmethyl)-4H-2,3,4,5,10b-pentaazabenz[e]azulene Example 132

4-(3-Cyanobenzyl)-1,9-dimethyl-6-phenyl-4H-2,3,4,5,10b-pentaazabenz[e]azulene

Example 133

1-Methyl-8-nitro-6-phenyl-4-(pyridin-3-ylmethyl)-4H-2,3,4,5,10b-pentaazabenz[e]azulene Example 134

1-Methyl-8-nitro-6-phenyl-4-(pyridin-4-ylmethyl)-4H-2,3,4,5,10b-pentaazabenz[e]azulene Example 135

1-Methyl-6-(4-methylphenyl)-4-(pyridin-4-ylmethyl)-4H-2,3,4,5,10b-pentaazabenz[e]azulene Example 136

4-(3-Cyanobenzyl)-1-methyl-6-(4-methylphenyl)-4H-2,3,4,5,10b-pentaazabenz [e]azulene Example 137

8-Chloro-6-(2-chlorophenyl)-1-methyl-4-(pyridin-3-ylmethyl)-4H-2,3,4,5,10b-pentaazabenz[e]azulene Example 138

8-Chloro-6-(2-chlorophenyl)-1-methyl-4-(pyridin-4-ylmethyl)-4H-2,3,4,5,10b-pentaazabenz[e]azulene

TABLE 24-(1)

| Ex. | A | R¹ | R³ | ¹H NMR(300MHz, δppm, CDCl₃) | melting point, °C. |
|---|---|---|---|---|---|
| 121 | o-C₆H₄(Me) | 4-Cl-C₆H₄ | 4-SO₂Me-C₆H₄ | 2,62(3H, s), 3.03(3H, s), 5.03(1H, m), 5.19(1H, m), 7.23–7.43(7H, m), 7.56–7.69(3H, m), 7.87 (2H, d, J=8.4Hz). | |
| 122 | o-C₆H₄(Me) | 4-Cl-C₆H₄ | 4-NO₂-C₆H₄ | 2.62(3H, s), 5.03(1H, m), 5.11(1H, m), 7.24–7.43(7H, m), 7.54 (2H, d, J=8.8Hz), 7.68(1H, m), 8.17 (2H, d, J=8.8Hz). | |
| 123 | o-C₆H₄(Me) | 4-Cl-C₆H₄ | 2,6-di-Cl-pyridin-4-yl | 2,63(3H, s), 4.92(1H, m), 5.09(1H, m), 7.26–7.47(9H, m), 7.70 (1H, dt, J=7.8 and 1.6Hz). | |
| 124 | o-C₆H₄(Me) | 4-Cl-C₆H₄ | —CF₃ | | 177~180 (decomposition) |

TABLE 24-(2)

| Ex. | A | R¹ | R³ | ¹H NMR(300MHz, δppm, CDCl₃) | melting point, °C. |
|---|---|---|---|---|---|
| 125 | o-C₆H₄(Me) | 4-Cl-C₆H₄ | 3,5-di-NO₂-C₆H₃ | 2.63(3H, s), 5.15(1H, m), 5.28(1H, m), 7.20–7.47(6H, m), 7.68(1H, m), 8.63 (1H, d, J=2.2Hz), 8.95 (1H, t, J=2.2Hz). | Amorphous solid |

TABLE 24-(2)-continued
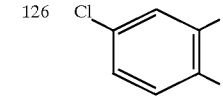
| Ex. | A | R¹ | R³ | ¹H NMR(300MHz, δppm, CDCl₃) | melting point, °C. |
|---|---|---|---|---|---|
| 126 | 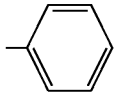 | 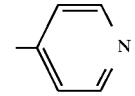 | 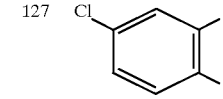 | 2.60(3H, s), 4.98(1H, m), 5.12(1H, m), 7.26–7.47(9H, m), 7.62 (1H, dd, J=8.8 and 2.4Hz), 8.55(1H, m), 8.56(1H, m). | Amorphous solid |
| 127 | 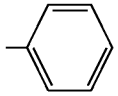 | 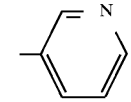 | 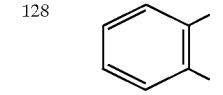 | 2.60(3H, s), 4.98(1H, m), 5.11(1H, m), 7.21(1H, d, J=2.4Hz), 7.25–7.31(2H, m), 7.35–7.38(3H, m), 7.42–7.48(1H, m), 7.59(1H, dd, J=8.7 and 2.4Hz), 7.74(1H, dt, J=8.0 and 1.8Hz), 8.53(1H, dd, J=4.8 and 1.6Hz), 8.67(1H, d, J=1.8Hz). | Amorphous solid |
TABLE 25-(1)
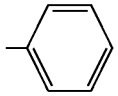
| Ex. | A | R¹ | R³ | ¹H NMR(300MHz, δppm, CDCl₃) | Melting point, °C. |
|---|---|---|---|---|---|
| 128 | 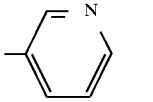 | 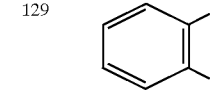 | 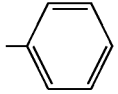 | | 179~181 |
| 129 | 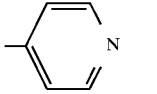 | 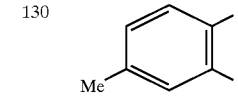 | 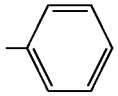 | | 193~194 |
| 130 | 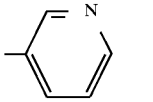 | | | | 196~197 |

TABLE 25-(1)-continued

| Ex. | A | R¹ | R³ | ¹H NMR(300MHz, δppm, CDCl₃) | Melting point, °C. |
|---|---|---|---|---|---|
| 131 | 3,4-(Me)C₆H₃ | C₆H₅ | 4-pyridyl | | 240~241 |
| 132 | 3,4-(Me)C₆H₃ | C₆H₅ | 3-CN-C₆H₄ | | 165~166 |
| 133 | 3-NO₂-C₆H₃ | C₆H₅ | 3-pyridyl | | 212~213 |
| 134 | 3-NO₂-C₆H₃ | C₆H₅ | 4-pyridyl | | 202~203 |

TABLE 25-(2)

| Ex. | A | R¹ | R³ | ¹H NMR(300MHz, δppm, CDCl₃) | Melting point, °C. |
|---|---|---|---|---|---|
| 135 | C₆H₄ | 4-CH₃-C₆H₄ | 4-pyridyl | | 205~207 |
| 136 | C₆H₄ | 4-CH₃-C₆H₄ | 3-CN-C₆H₄ | 2.36(3H, s) 2.62(3H, s), 5.07(2H, m), 7.16 (2H, d, J=9Hz), 7.25–7.68 (10H, m). | Amorphous solid |
| 137 | 4-Cl-C₆H₃ | 2-Cl-C₆H₄ | 3-pyridyl | | 162~165 |

TABLE 25-(2)-continued

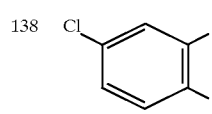

| Ex. | A | R¹ | R³ | ¹H NMR(300MHz, δppm, CDCl₃) | Melting point, °C. |
|---|---|---|---|---|---|
| 138 | 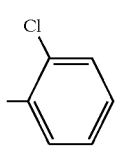 | 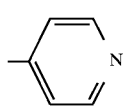 | 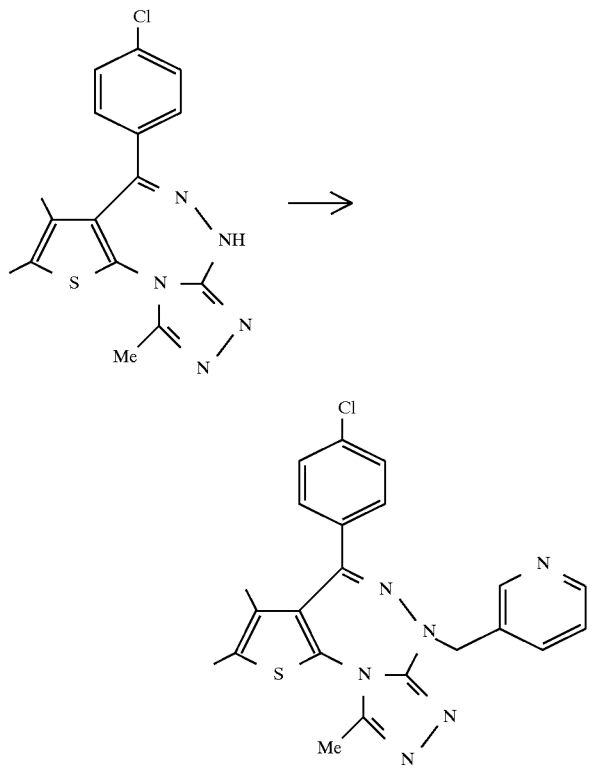 | 2.61(3H, s), 4.98(1H, m), 5.15(1H, m), 7.27–7.46(9H, m), 7.63 (1H, dd, J=8.9 and 4.0Hz), 8.55 (2H, dd, J=4.5 and 2.0Hz). | Amorphous solid |

Example 139 (Step 10-1)

4-(4-Chlorophenyl)-2,3,9-trimethyl-6-(pyridin-3-ylmethyl)-6H-5,6,7,8,9a -pentaazathien[2,3-e]azulene 4-(4-Chlorophenyl)-2,3,9-trimethyl-6H-5,6,7,8,9a-pentaazathien[2,3-e]azulene (1 g) obtained in Preparative Example 42 was dissolved in anhydrous N,N-dimethylformamide (10 ml) under an argon gas atmosphere and cooled in an ice-bath. Sodium hydride (60% in oil, 244 mg) was added thereto and the mixture was stirred under ice-cooling for 5 minutes and at room temperature for 30 minutes. The reaction mixture was cooled in an ice-bath again and 3-picolyl chloride hydrochloride (525 mg) was added to the reaction mixture. The mixture was stirred under ice-cooling for 4 hours. After completion of the reaction, a 1% aqueous solution of citric acid (50 ml) and ethyl acetate (50 ml) were added and the organic layer was separated. The organic layer was washed with water, dried over anhydrous sodium sulfate and filtered. The filtrate was concentrated under reduced pressure and the residue was subjected to silica gel column chromatography. The solid obtained by concentration of the fractions eluted with ethyl acetate-:methanol (95:5) was crystallized from ethyl acetate:diethyl ether (1:3) to give 936 mg of the title compound as colorless crystals.

Melting point: 195°–196° C.

¹H NMR(300 MHz, δ ppm, CDCl₃) 1.53(3H,s), 2.37(3H, s), 2.62(3H,s), 5.03(2H,s), 7.23–7.32(5H,m), 7.77(1H,m), 8.54(1H,dd,J=5.0 and 1.7 Hz), 8.70(1H,d,J=2.0 Hz)

Examples 140 to 150 (Step 10-1)

In the same manner as in Example 139, the compound of Example 140 was obtained from the compound of Preparative Example 42, the compounds of Examples 141 and 142 were obtained from the compound of Preparative Example 43, the compounds of Examples 143 and 144 were obtained from the compound of Preparative Example 44, the compounds of Examples 145 and 146 were obtained from the compound of Preparative Example 45, the compounds of Examples 147 and 148 were obtained from the compound of Preparative Example 46, and the compounds of Examples 149 and 150 were obtained from the compound of Preparative Example 47. These compounds are shown in Table 26.

Example 140

4-(4-Chlorophenyl)-2,3,9-trimethyl-6-(pyridin-4-ylmethyl)-6H-5,6,7,8,9a-pentaazathien[2,3-e]azulene Example 141

4-(4-Chlorophenyl)-2-ethyl-9-methyl-6-(pyridin-3-ylmethyl)-6H-5,6,7,8,9a-pentaazathien[2,3-e]azulene

Example 142

4-(4-Chlorophenyl)-2-ethyl-9-methyl-6-(pyridin-4-ylmethyl)-6H-5,6,7,8,9a-pentaazathien[2,3-e]azulene

Example 143

2,9-Dimethyl-4-phenyl-6-(pyridin-3-ylmethyl)-6H-5,6,7,8,9a-pentaazathien[2,3-e]azulene

Example 144

2,9-Dimethyl-4-phenyl-6-(pyridin-4-ylmethyl)-6H-5,6,7,8,9a-pentaazathien[2,3-e]azulene

Example 145

2,3,9-Trimethyl-4-phenyl-6-(pyridin-3-ylmethyl)-6H-5,6,7,8,9a-pentaazathien[2,3-e]azulene

Example 146

2,3,9-Trimethyl-4-phenyl-6-(pyridin-4-ylmethyl)-6H-5,6,7,8,9a-pentaazathien[2,3-e]azulene

Example 147

2-Ethyl-9-methyl-4-phenyl-6-(pyridin-3-ylmethyl)-6H-5,6,7,8,9a-pentaazathien[2,3-e]azulene

Example 148

2-Ethyl-9-methyl-4-phenyl-6-(pyridin-4-ylmethyl)-6H-5,6,7,8,9a-pentaazathien[2,3-e]azulene

Example 149

4-(4-Methoxyphenyl)-2,3,9-trimethyl-6-(pyridin-3-ylmethyl)-6H-5,6,7,8,9a-pentaazathien[2,3-e]azulene

Example 150

4-(4-Methoxyphenyl)-2,3,9-trimethyl-6-(pyridin-4-ylmethyl)-6H-5,6,7,8,9a-pentaazathien[2,3-e]azulene

TABLE 26-(1)

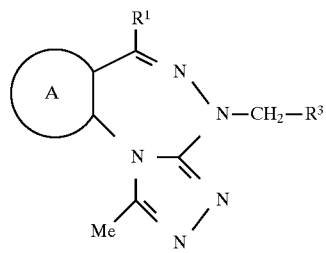

| Ex. | A | $R^1$ | $R^3$ | $^1$H NMR(300MHz, δppm, CDCl$_3$) | Melting point, °C |
|---|---|---|---|---|---|
| 140 | Me, Me—thiophene | —C$_6$H$_4$—Cl | —pyridin-4-yl | 1.58(3H, s), 2.40(3H, s), 2.63(3H, s), 5.04(2H, m), 7.21–7.33(6H, m), 8.55–8.57(2H, m). | 195~196 |
| 141 | Et—thiophene | —C$_6$H$_4$—Cl | —pyridin-3-yl | | 182~183 |
| 142 | Et—thiophene | —C$_6$H$_4$—Cl | —pyridin-4-yl | | 107~108 |
| 143 | Me—thiophene | —C$_6$H$_5$ | —pyridin-3-yl | 2.48 (3H, d, J=1.5Hz), 2.63(3H, s), 5.05(2H, s), 6.43 (1H, q, J=1.5Hz), 7.25–7.45(6H, m), 7.79 (1H, dt, J=7.5 and 2.0Hz), 8.53 (1H, dd, J=5.0 and 2.0Hz), 8.72 (1H, d, J=2.0Hz). | |

TABLE 26-(1)-continued

[Structure: ring A with R¹ substituent connected via C=N-N(CH₂-R³)-C(=N-N)-Me triazole system]

| Ex. | A | R¹ | R³ | ¹H NMR(300MHz, δppm, CDCl₃) | Melting point, °C. |
|---|---|---|---|---|---|
| 144 | 2,5-dimethylthiophene (Me-S-Me) | phenyl | 4-pyridyl | | 188~190 |

TABLE 26-(2)

[Structure: ring A with R¹ substituent connected via C=N-N(CH₂-R³)-C(=N-N)-Me triazole system]

| Ex. | A | R¹ | R³ | ¹H NMR(300MHz, δppm, CDCl₃) | Melting point, °C. |
|---|---|---|---|---|---|
| 145 | 3,4-dimethyl-2,5-dimethylthiophene | phenyl | 3-pyridyl | | 168~169 |
| 146 | 3,4-dimethyl-2,5-dimethylthiophene | phenyl | 4-pyridyl | | 182~183 |
| 147 | 2-ethyl-5-methylthiophene | phenyl | 3-pyridyl | | 147~148 |
| 148 | 2-ethyl-5-methylthiophene | phenyl | 4-pyridyl | | 187~189 |
| 149 | 3,4-dimethyl-2,5-dimethylthiophene | 4-methoxyphenyl | 3-pyridyl | | 191~192 |
| 150 | 3,4-dimethyl-2,5-dimethylthiophene | 4-methoxyphenyl | 4-pyridyl | | 154~156 |

Example 151

6-(4Chlorophenyl)-1-methyl-4-(pyridin-3-ylmethyl)-4H-2,3,4,5,10b-pentaazabenz[e]azulene monohydrochloride monohydrate

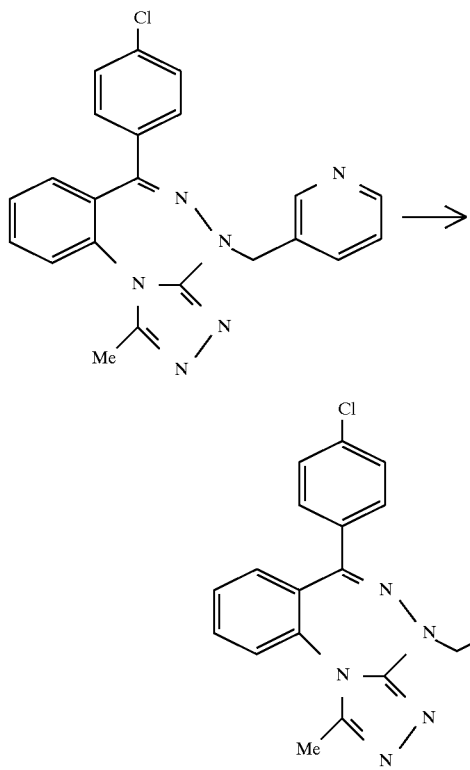

6-(4-Chlorophenyl)-1-methyl-4-(pyridin-3-ylmethyl)-4H-2,3,4,5,10b-pentaazabenz[e]azulene (501 mg) obtained in Example 54 or Example 98 was suspended in ethanol (10 ml) and a 4N hydrochloric acid/ethyl acetate solution (0.4 ml) was added thereto. The solution was concentrated to 3 ml and the precipitated crystals were collected by filtration. The crystals were suspended in ethanol (10 ml). The suspension was heated and allowed to stand at room temperature to give 395 mg of the title compound as colorless needles.

Melting point: 238°–240° C.

$^1$H NMR(300 MHz, δ ppm, DMSO-$d_6$) 2.49(3H,s), 4.98 (1H,m), 5.08(1H,m), 7.15(1H,d,J=7.2 Hz), 7.33–7.47(5H, m), 7.69(2H,m) 7.84(1H,dd,J=7.2 and 4.8 Hz), 8.38(1H,d, J=7.5 Hz), 8.72(1H,d,J=4.8 Hz), 8.87(1H,s)

Examples 152 to 156

In the same manner as in Example 151, the compound of Example 152 was obtained from the compound of Example 54 or Example 98 and p-toluenesulfonic acid monohydrate, the compound of Example 153 was obtained using methanesulfonic acid, the compound of Example 154 was obtained using benzenesulfonic acid, the compound of Example 155 was obtained from the compound of Example 126 and a 4N hydrochloric acid/ethyl acetate solution, and the compound of Example 156 was obtained from the compound of Example 143 and p-toluenesulfonic acid monohydrate. These compounds are shown in Table 27.

Example 152

6-(4-Chlorophenyl)-1-methyl-4-(pyridin-3-ylmethyl)-4H-2,3,4,5,10b-pentaazabenz[e]azulene p-toluenesulfonate

Example 153

6-(4-Chlorophenyl)-1-methyl-4-(pyridin-3-ylmethyl)-4H-2,3,4,5,10b-pentaazabenz[e]azulene 2 methanesulfonate

Example 154

6-(4-Chlorophenyl)-1-methyl-4-(pyridin-3-ylmethyl)-4H-2,3,4,5,10b-pentaazabenz[e]azulene 1.5 benzenesulfonate

Example 155

8-Chloro-1-methyl-6-phenyl-4-(pyridin-4-ylmethyl)-4H-2,3,4,5,10b-pentaazabenz[e]azulene hydrochloride

Example 156

2,9-dimethyl-4-phenyl-6-(pyridin-3-ylmethyl)-6H-5,6,7,8,9a-pentaazathien[2,3-e]azulene p-toluenesulfonate

Example 157

8-Chloro-1-methyl-6-phenyl-4-(pyridin-4-ylmethyl)-4H-2,3,4,5,10b-pentaazabenz[e]azulene p-toluenesulfonate TABLE 27-(1)
| Example | Structural formula | $^1$H NMR(300MHz, δppm, DMSO-d$_6$) | Melting point, °C. |
|---|---|---|---|
| 152 | 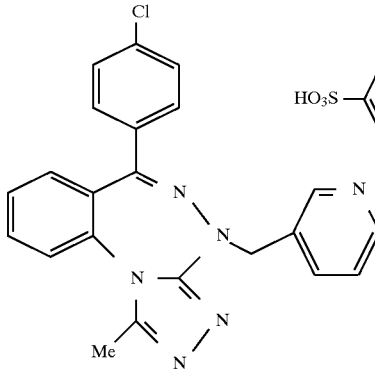 | 2.28(3H, s), 2.55(3H, s), 5.04(1H, m), 5.14(1H, m), 7.10 (2H, d, J=8.0Hz), 7.20 (1H, d, J=8.0Hz), 7.41–7.51(7H, m), 7.74(2H, m), 7.93 (1H, dd, J=8.3 and 5.6Hz). 8.48 (1H, d, J=8.3Hz), 8.78 (1H, d, J=5.6Hz), 8.94(1H, s). | 248~250 |
| 153 | 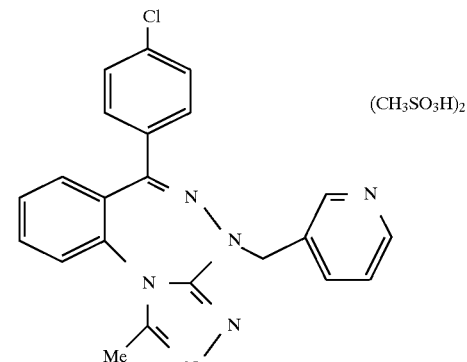 | | 213~215 |
| 154 | 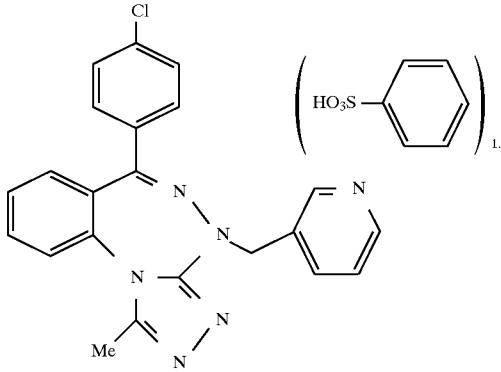 | | 247~250 |

TABLE 27-(2)

| Example | Structural formula | | $^1$H NMR(300MHz, δppm, DMSO-d$_6$) | Melting point, °C. |
|---|---|---|---|---|
| 155 | [structure with Cl, phenyl, pyridine, triazole, Me] | HCl | 2.57(3H, s), 5.12(1H, m), 5.28(1H, m), 7.22 (1H, d, J=2.0Hz), 7.38–7.54(5H, m), 7.80–7.89(2H, m), 7.94 (2H, d, J=6.5Hz), 8.82 (2H, d, J=5.6Hz). | |
| 156 | [structure with phenyl, thiophene, pyridine, triazole, Me] | HO$_3$S—C$_6$H$_4$—CH$_3$ | | 206~209 |
| 157 | [structure with Cl, phenyl, pyridine, triazole, Me] | HO$_3$S—C$_6$H$_4$—CH$_3$ | 2.27(3H, s), 2.55(3H, s), 5.15(1H, m), 5.30(1H, m), 7.10 (2H, d, J=8.0Hz), 7.21 (1H, d, J=2.5Hz), 7.38–7.52(7H, m), 7.79–7.88(2H, m), 7.95 (2H, d, J=6.5Hz), 8.82 (2H, d, J=6.5Hz). | |

Example 158

6-(4-Chlorophenyl)-1-methyl-4-(pyridin-3-ylmethyl)-4H-2,3,4,5,10b-pentaazabenz[e]azulene citrate

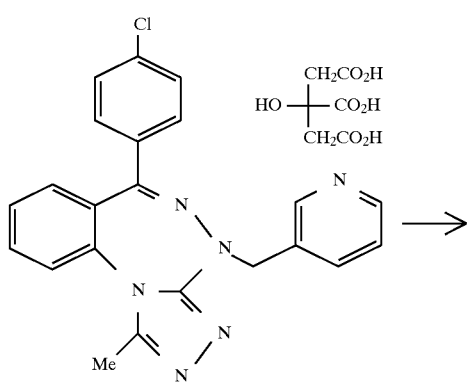

-continued

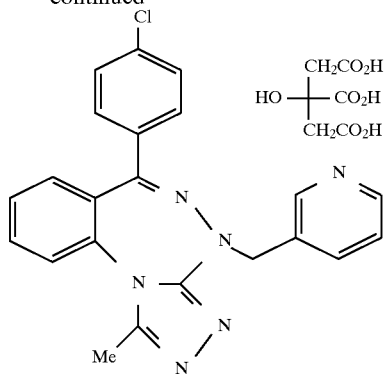

6-(4-Chlorophenyl)-1-methyl-4-(pyridin-3-ylmethyl)-4H-2,3,4,5,10b-pentaazabenz[e]azulene (401 mg) obtained in Example 54 or Example 98 was suspended in ethanol (20 ml). Anhydrous citric acid (192 mg) was added to the suspension and the mixture was heated. The resulting solution was concentrated to 10 ml and diethyl ether (7 ml) was added. The mixture was allowed to stand at room temperature and the precipitated crystals were collected by filtration. The crystals were suspended in ethanol (20 ml). The suspension was heated and allowed to stand at room temperature to give 395 mg of the title compound as colorless needles.

Melting point: 208°–209° C.

$^1$H NMR(300 MHz, δ ppm, DMSO-$d_6$) 2.53(3H,s), 2.66 (2H,d,J=15.3 Hz), 2.75(2H,d,J=15.3 Hz), 4.86(1H,m), 5.01 (1H,m), 7.20(1H,d,J=7.8 Hz), 7.35–7.53(6H,m), 7.69–7.81 (3H,m), 8.48(1H,dd,J=4.7 and 1.4 Hz), 8.60(1H,d,J=1.4 Hz)

Example 159 (Step 10-1)

6-(4-Chlorophenyl)-1-methyl-4-(2-nitrobenzyl)-4H-2,3, 4,5,10b-pentaazabenz[e]azulene

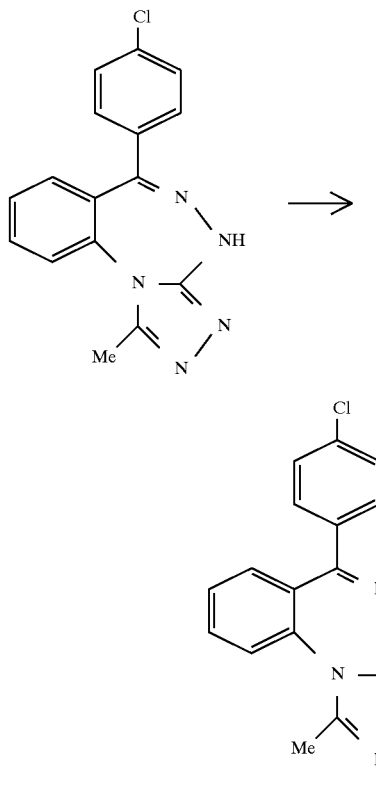

6-(4-Chlorophenyl)-1-methyl-4H-2,3,4,5,10b-pentaazabenz[e]azulene (217 mg) obtained in Preparative Example 34 was dissolved in anhydrous N,N-dimethylformamide (3 ml) under an argon gas atmosphere. 2-Nitrobenzyl bromide (756 mg) and potassium carbonate (967 mg) were added thereto and the mixture was stirred at room temperature for 3 hours. After completion of the reaction, the insoluble substance was filtered off. Ethyl acetate (50 ml) and water (40 ml) were added to the filtrate and organic layer was separated. The organic layer was successively washed with a 5% aqueous solution of citric acid, a saturated aqueous sodium hydrogencarbonate solution and water, dried, filtered and concentrated under reduced pressure. Then, the obtained residue was subjected to silica gel column chromatography. The residue obtained by concentration of the fractions eluted with chloroform:acetone (10:1) was crystallized from diethyl ether to give 46 mg of the title compound as yellow crystals.

Melting point: 204°–205° C.

Example 160 (Step 10-1)

6-(4-Chlorophenyl)-4-ethoxycarbonylmethyl-1-methyl-4H-2,3,4,5,10b-pentaazabenz[e]azulene In the same manner as in Example 159, the compound of Example 160 was obtained from the compound of Preparative Example 34. The compound is shown in Table 28.

TABLE 28

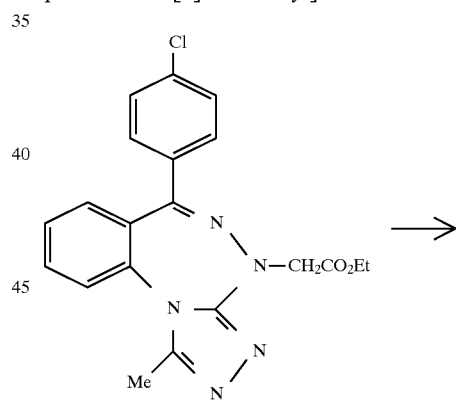

| Example | R³ | $^1$H NMR(300MHz, δppm, CDCl$_3$) | Melting point, °C. |
|---|---|---|---|
| 160 | —CO$_2$Et | | 111~112 |

Example 161 (Step 10-9)

[6-(4-Chlorophenyl)-1-methyl-4H-2,3,4,5,10b-pentaazabenz[e]azulen-4-yl]acetic acid

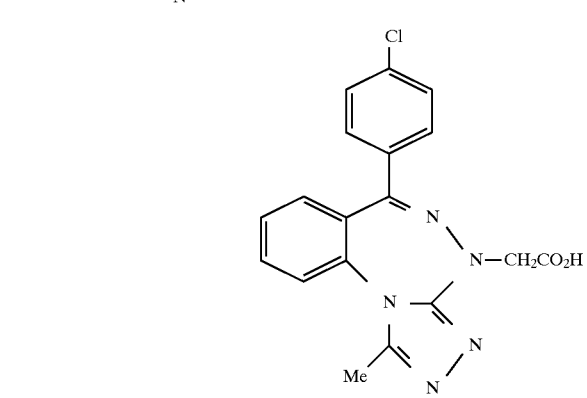

6-(4-Chlorophenyl)-4-ethoxycarbonylmethyl-1-methyl-4H -2,3,4,5,10b-pentaazabenz[e]azulene (151 mg)

obtained in Example 160 was dissolved in ethanol (1.5 ml) and cooled in an ice-bath. An aqueous solution of in sodium hydroxide (0.37 ml) was added thereto and the mixture was stirred under ice-cooling for 1 hour and at room temperature for 2 hours. The reaction mixture was cooled in an ice-bath again and 1N hydrochloric acid was added to the reaction mixture. The mixture was stirred for a while. Ethyl acetate (10 ml) and a saturated aqueous sodium chloride solution (5 ml) was added thereto and the organic layer was separated. The organic layer was further washed three times with a saturated aqueous sodium chloride solution, dried and filtered. The filtrate was concentrated under reduced pressure and the residue was crystallized from diethyl ether to give 129 mg of the title compound as crystals.

Melting point : 274°–275° C.

Example 162 (Step 10-10)

6-(4-Chlorophenyl)-1-methyl-4-phenylcarbamoylmethyl-4H-2,3,4,5,10b-pentaazabenz[e]azulene

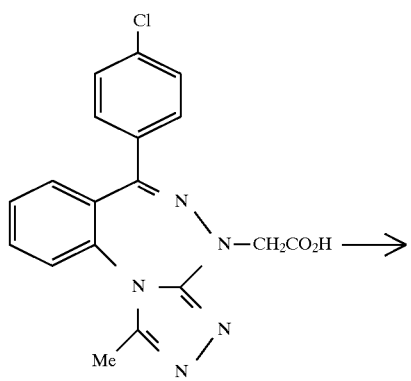

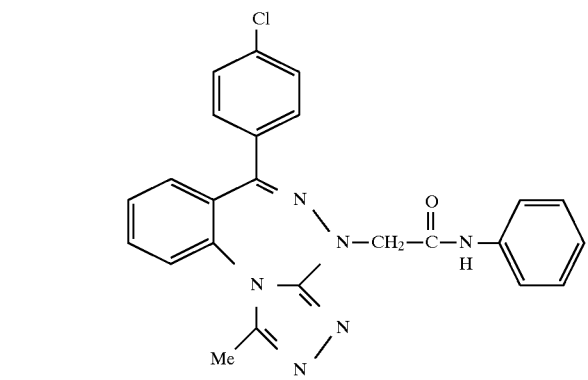

[6-(4-Chlorophenyl)-1-methyl-4H-2,3,4,5,10b-pentaazabenz[e]azulen-4-yl]acetic acid (114 mg) obtained in Example 161 was dissolved in anhydrous N,N-dimethylformamide (2.2 ml) and triethylamine (0.05 ml) was added. The mixture was cooled to −15° C. in a dry ice-acetone bath and isobutyl chlorocarbonate (0.4 ml) was added for 1 minute. The mixture was stirred for 40 minutes maintaining the internal temperature at −15° C. to −10° C. and then aniline (0.34 ml) was added. The internal temperature was raised to 0° C. for 30 minutes and the reaction mixture was stirred for another 30 minutes. Ethyl acetate (15 ml) and water (10 ml) were added to the reaction mixture and the organic layer was separated. The organic layer was washed with water, dried and filtered. The filtrate was concentrated under reduced pressure. The residue was dissolved in a small amount of chloroform and diethyl ether was added for crystallization to give 111 mg of the title compound as crystals.

Melting point: 249°–252° C.

Examples 163 to 170 (Step 10-10)

In the same manner as in Example 162, the compounds of Examples 163 to 170 were obtained from the compound of Example 161. These compounds are shown in Table 29.

Example 163

6-(4-Chlorophenyl)-1-methyl-4-(4-methylphenylcarbamoylmethyl)-4H-2,3,4,5,10b-pentaazabenz[e]azulene Example 164

6-(4-Chlorophenyl)-4-(2-methoxyphenylcarbamoylmethyl)-1-methyl-4H-2,3,4,5,10b-pentaazabenz[e]azulene Example 165

6-(4-Chlorophenyl)-4-(2,5-dimethoxyphenylcarbamoylmethyl)-1-methyl-4H-2,3,4,5,10b-pentaazabenz[e]azulene Example 166

4-(4-Chloro-2,5-dimethoxyphenylcarbamoylmethyl)-6-(4-chlorophenyl)-1-methyl-4H-2,3,4,5,10b-pentaazabenz[e]azulene Example 167

6-(4-Chlorophenyl)-1-methyl-4-(naphthalen-1-ylcarbamoylmethyl)-4H-2,3,4,5,10b-pentaazabenz[e]azulene Example 168

6-(4-Chlorophenyl)-1-methyl-4-(pyridin-3-ylcarbamoylmethyl)-4H-2,3,4,5,10b-pentaazabenz[e]azulene Example 169

6-(4-Chlorophenyl)-4-(cyclohexylcarbamoylmethyl)-1-methyl-4H-2,3,4,5,10b-pentaazabenz[e]azulene Example 170

6-(4-Chlorophenyl)-1-methyl-4-n-propylcarbamoylmethyl-4H-2,3,4,5,10b-pentaazabenz[e]azulene

TABLE 29

[Structure: core scaffold with 4-chlorophenyl group, showing N—CH₂—R³ substitution]

| Example | R³ | Melting point, °C. |
|---|---|---|
| 163 | —C(O)—NH—(4-methylphenyl) | 316~317 |
| 164 | —C(O)—NH—(2-methoxyphenyl) | 195~196 |
| 165 | —C(O)—NH—(2,5-dimethoxyphenyl) | 203~204 |
| 166 | —C(O)—NH—(4-chloro-2,5-dimethoxyphenyl) | 147~151 (decomposition) |
| 167 | —C(O)—NH—(1-naphthyl) | 257~258 |
| 168 | —C(O)—NH—(3-pyridyl) | 241~245 |
| 169 | —C(O)—NH—cyclohexyl | 242 |
| 170 | —C(O)—NH—propyl | 246~247 |

Example 171 (Step 10-1)

4-Bromoacetyl-6-(4-chlorophenyl)-1-methyl-4H-2,3,4,5,10b-pentaazabenz[e]azulene

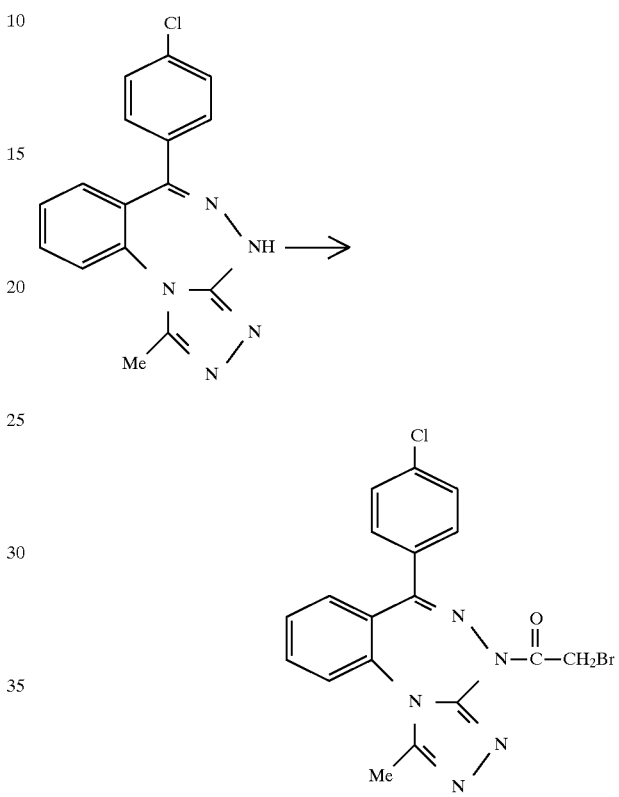

6-(4-Chlorophenyl)-1-methyl-4H-2,3,4,5,10b-pentaazabenz[e]azulene (100 mg) obtained in Preparative Example 34 was dissolved in anhydrous dichloromethane (1 ml) and anhydrous pyridine (52 μl) was added. The mixture was cooled in an ice-bath and bromoacetyl bromide (42 μl) was added. The mixture was stirred under ice-cooling for 30 minutes and at room temperature for 1.5 hours. Water was poured into the reaction mixture and the mixture was extracted with ethyl acetate. The organic layer was washed successively with a 5% aqueous citric acid solution and water, dried over anhydrous sodium sulfate and filtered. The filtrate was concentrated under reduced pressure and the residue was subjected to silica gel column chromatography to give the title compound (70 mg) as white crystals.

$^1$H NMR(300 MHz, δ ppm, CDCl$_3$) 2.70(3H,s), 4.23–4.42(2H,m), 7.36–7.52(5H,m), 7.62–7.65(2H,m), 7.72–7.78(1H,m)

Example 172 (Step 10-11)

6-(4-Chlorophenyl)-4-(2-methoxyphenylaminoacetyl)-1-methyl-4H-2,3,4,5,10b-pentaazabenz[e]azulene

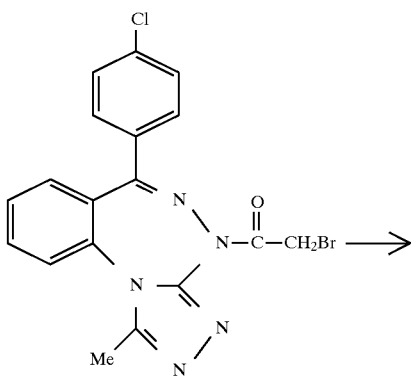

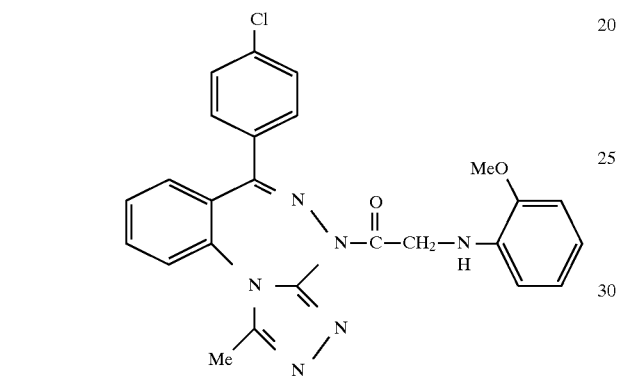

4-Bromoacetyl-6-(4-chlorophenyl)-1-methyl-4H-2,3,4,5,10b-pentaazabenz[e]azulene (8 mg) obtained in Example 171 was suspended in ethanol and 2-anisidine (12.5 μl) was added. The mixture was stirred at 80° C. for 3 hours. The reaction mixture was cooled to room temperature and concentrated under reduced pressure. Water (20 ml) was added to the residue and the mixture was extracted with ethyl acetate (20 ml). The organic layer was further washed with water, dried over anhydrous sodium sulfate and filtered. The filtrate was concentrated under reduced pressure and the residue was purified by preparative thin-layer chromatography to give 2.4 mg of the title compound as an oil.

$^1$H NMR(300 MHz, δ ppm, CDCl3) 2.67(3H,s), 3.82(3H, s), 4.35(2H,m), 6.37(1H,m), 6.60–6.72(3H,m), 7.29–7.43 (6H,m), 7.61–7.64(3H,m)

Examples 173 to 176 (Step 10-11)

In the same manner as in Example 172, the compounds of Examples 173 to 176 were obtained from the compound of Example 171. These compounds are shown in Table 30.

Example 173

6-(4-Chlorophenyl)-1-methyl-4-phenylaminoacetyl-4H-2,3,4,5,10b-pentaazabenz[e]azulene

Example 174

6-(4-Chlorophenyl)-1-methyl-4-(4-methylphenylaminoacetyl)-4H-2,3,4,5,10b-pentaazabenz[e]azulene

Example 175

6-(4-Chlorophenyl)-4-(3-fluorophenylaminoacetyl)-1-methyl-4H-2,3,4,5,10b-pentaazabenz[e]azulene

Example 176

6-(4-Chlorophenyl)-4-(2,5-dimethoxyphenylaminoacetyl)-1-methyl-4H-2,3,4,5,10b-pentaazabenz[e]azulene

TABLE 30

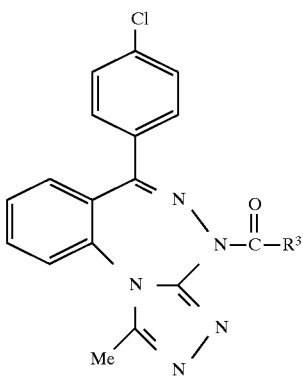

| Example | R³ | $^1$H NMR (300 MHz, δ ppm, CDCl₃) | Melting point, °C. |
|---|---|---|---|
| 173 | —CH₂—NH—C₆H₅ | | 130–133 |

TABLE 30-continued

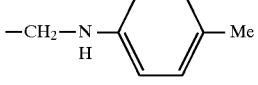

| Example | R³ | ¹H NMR (300 MHz, δ ppm, CDCl₃) | Melting point, °C. |
|---|---|---|---|
| 174 | —CH₂—NH—(C₆H₄)—Me | 2.19(3H, s), 2.67(3H, s), 4.25–4.39(2H, m), 6.42(2H, d, J=8.2Hz), 6.71(1H, s), 6.87(2H, d, J=8.2Hz), 7.31–7.44(5H, m), 7.61–7.66(3H, m). | |
| 175 | —CH₂—NH—(C₆H₄)—F | 2.68(3H, s), 4.25–4.40(2H, m), 6.16–6.20(1H, m), 6.28–6.37(2H, m), 6.97–7.05(1H, m), 7.32–7.47(5H, m), 7.61–7.70(3H, m). | |
| 176 | —CH₂—NH—(C₆H₃)(MeO)(OMe) | 2.67(3H, s), 3.63(3H, s), 3.77(3H, s), 4.31(2H, m), 5.98(1H, m), 6.07–6.11(1H, m), 6.60–6.62(1H, d, J=6.0Hz), 7.31–7.43(6H, m), 7.60–7.64(3h, m). | |

Example 177 (Step 10-11)

6-(4-Chlorophenyl)-1-methyl-4-phenylthioacetyl-4H-2,3,4,5,10b- pentaazabenz[e]azulene

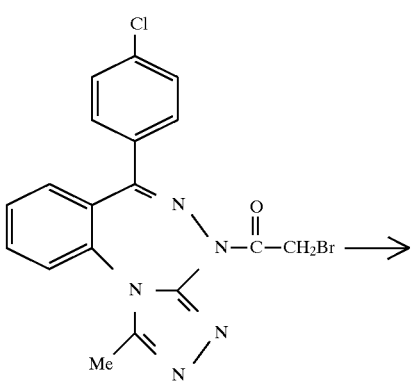 →

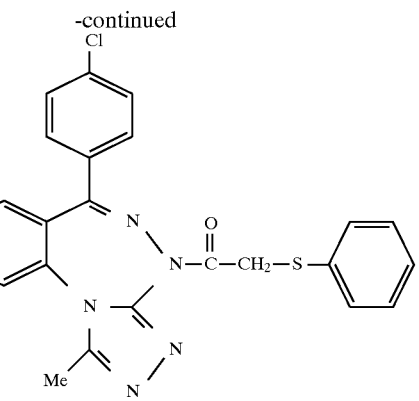

4-Bromoacetyl-6-(4-chlorophenyl)-1-methyl-4H-2,3,4,5,10b-pentaazabenz[e]azulene (8 mg) obtained in Example 171 was dissolved in anhydrous dichloromethane (0.8 ml), and thiophenol (2 μl) and triethylamine (2.8 μl) were added. The mixture was stirred at room temperature for 2 hours. After the completion of the reaction, water (20 ml) was added to the reaction mixture and the mixture was extracted with ethyl acetate (20 ml). The organic layer was washed successively with a 5% aqueous citric acid solution and water, dried over anhydrous sodium sulfate and filtered. The filtrate was concentrated under reduced pressure and the residue was purified by preparative thin-layer chromatography to give 2.1 mg of the title compound as an amorphous solid.

$^1$H NMR(300 MHz, δ ppm, CDCl$_3$) 2.69(3H,s), 3.96–4.12(2H,m), 7.03–7.76(13H,m)

Example 178 (Step 10-1)

6-(4-Chlorophenyl)-1-methyl-4-phenylacetyl-4H-2,3,4,5,10b-pentaazabenz[e]azulene

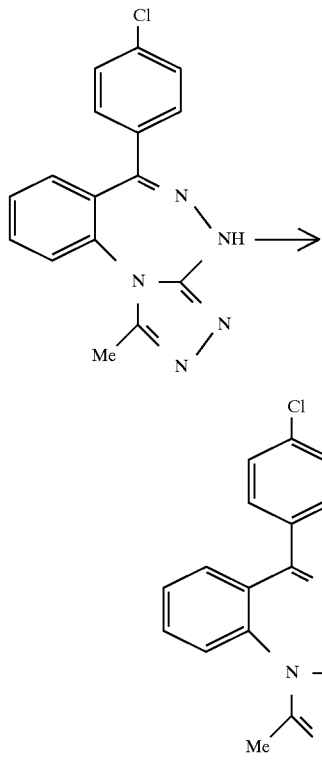

6-(4-Chlorophenyl)-1-methyl-4H-2,3,4,5,10b-pentaazabenz[e]azulene (20 mg) obtained in Preparative Example 34 was dissolved in anhydrous dichloromethane (0.2 ml). Pyridine (21 μl), 4-dimethylaminopyridine (1.5 mg) and phenylacetyl chloride (25.6 μl) were added and the mixture was stirred under ice-cooling for 30 minutes and at room temperature for 16 hours. After the completion of the reaction, water (30 ml) was added to the reaction mixture and the mixture was extracted with dichloromethane (30 ml). The organic layer was washed successively with a 5% aqueous citric acid solution and water, dried over anhydrous sodium sulfate and filtered. The filtrate was concentrated under reduced pressure and the residue was purified by preparative thin-layer chromatography and crystallized from diethyl ether to give 6 mg of the title compound as colorless crystals.

Melting point: 89°–90° C.

Example 179 (Step 10-1)

6-(4-Chlorophenyl)-1-methyl-4-phenyloxalyl-4H-2,3,4,5,10b-pentaazabenz[e]azulene In the same manner as in Example 178, the compound of Example 179 was obtained from the compound of Preparative Example 34. The compound is shown in Table 31.

TABLE 31

| Ex. | Structural formula | Melting point, °C. |
|---|---|---|
| 179 | 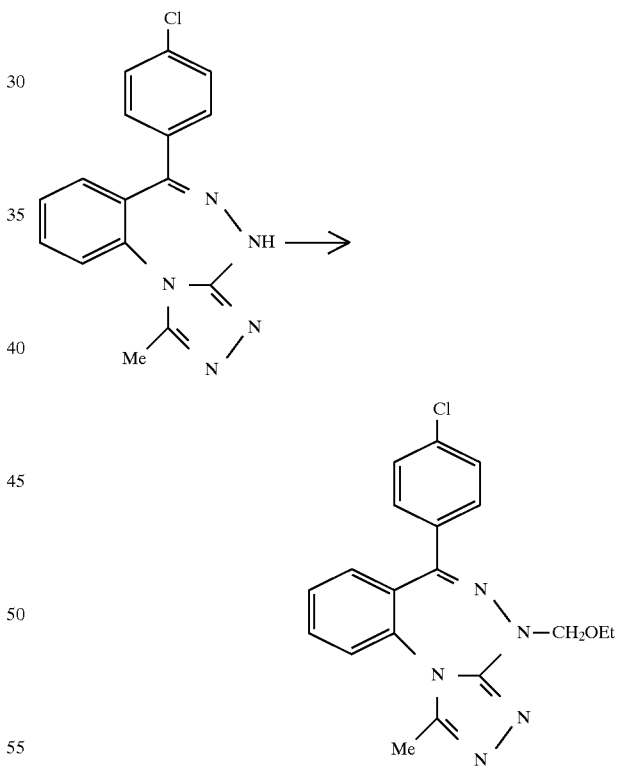 | 218–219 |

Example 180 (Step 10-4)

6-(4-Chlorophenyl)-4-ethoxymethyl-1-methyl-4H-2,3,4,5,10b-pentaazabenz[e]azulene 6-(4-Chlorophenyl)-1-methyl-4H-2,3,4,5,10b-pentaazabenz[e]azulene (84 mg) obtained in Preparative Example 34 was dissolved in ethanol (1 ml) and a 37% aqueous formaldehyde solution (0.12 ml) was added. The mixture was refluxed under heating for 3 days. The reaction solvent was distilled away under reduced pressure. The residue was purified by preparative thin-layer chromatography and crystallized from ethyl acetate/diethyl ether to give 70 mg of the title compound as colorless crystals.

Melting point: 98°–100° C.

Example 181 (Step 10-4)

[6-(4-Chlorophenyl)-1-methyl-4H-2,3,4,5,10b-pentaazabenz[e]azulen-4-ylmethyl]-phenylamine

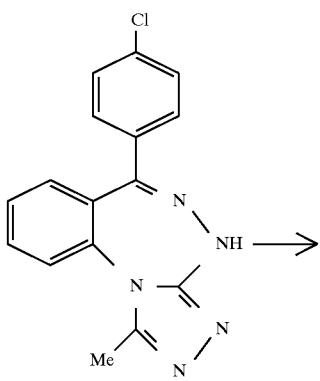

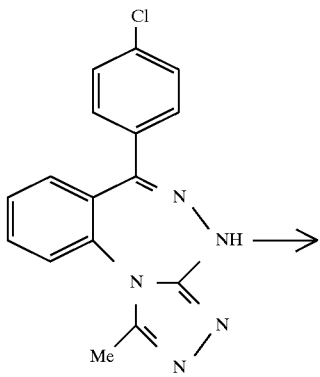

6-(4-Chlorophenyl)-1-methyl-4H-2,3,4,5,10b-pentaazabenz[e]azulene (20 mg) obtained in Preparative Example 34 was dissolved in ethanol (0.1 ml), and a 37% aqueous formaldehyde solution (6 μl) and aniline (7.6 μl) were added. The mixture was stirred under heating for 2 hours. The reaction mixture was cooled and the precipitated crystals were collected by filtration to give 13.8 mg of the title compound as colorless crystals.

Melting point: 223°–224° C.

Example 182 (Step 10-5)

4-Benzylcarbamoyl-6-(4-chlorophenyl)-1-methyl-4H-2,3,4,5,10b-pentaazabenz[e]azulene

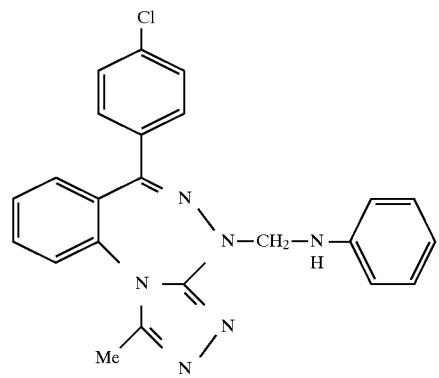

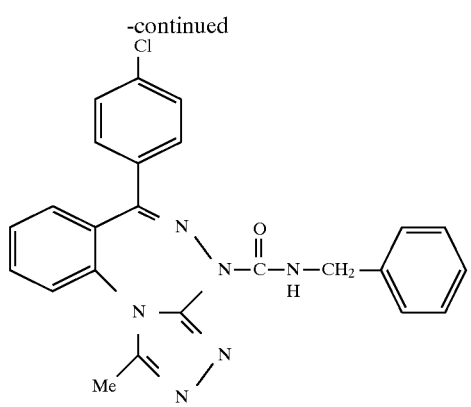

6-(4-Chlorophenyl)-1-methyl-4H-2,3,4,5,10b-pentaazabenz[e]azulene (206 mg) obtained in Preparative Example 34 was suspended in anhydrous acetonitrile. Sodium hydroxide (52 mg) pulverized in a mortar and benzyl isocyanate (100 μl) were added to the suspension and the mixture was stirred at room temperature for 2 hours and at 50° C. for 2 hours. After the completion of the reaction, the reaction mixture was concentrated under reduced pressure. Water (30 ml) was added to the residue and the mixture was extracted with ethyl acetate. The organic layer was dried over anhydrous magnesium sulfate and filtered. The filtrate was concentrated under reduced pressure. The residue was purified by silica gel column chromatography and crystallized from ethyl acetate-diethyl ether to give 80 mg of the title compound.

Melting point: 146°–149° C.

Example 183 (Step 10-5)

6-(4-Chlorophenyl)-1-methyl-4-(3-methylphenylcarbamoyl)-4H-2,3,4,5,10b-pentaazabenz[e]azulene In the same manner as in Example 182, the compound of Example 183 was obtained from the compound of Preparative Example 34. The compound is shown in Table 32.

TABLE 32

| Ex. | Structural formula | Melting point, °C. |
|---|---|---|
| 183 | ![structure] | 204~205 |

Example 184 (Step 10-15)

6-(4-Chlorophenyl)-4-(4-hydroxybenzyl)-1-methyl-4H-2,3,4,5,10b-pentaazabenz[e]azulene

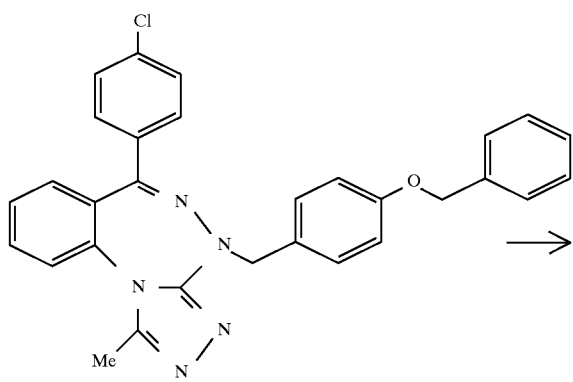

4-(4-Benzyloxybenzyl)-6-(4-chlorophenyl)-1-methyl-4H-2,3,4,5,10b-pentaazabenz[e]azulene (80 mg) obtained in Example 93 was dissolved in ethanol (1 ml). Palladium black (4 mg) was added and the mixture was stirred under a hydrogen atmosphere at 3 atm for 2 days. The catalyst was filtered off and the filtrate was concentrated under reduced pressure. The residue was purified by preparative thin-layer chromatography (chloroform: methanol=20:1) and crystallized from ethyl acetate-diethyl ether to give 29 mg of the title compound.

Melting point: 254°–257° C.

Example 185 (Step 10-15)

6-(4-Chlorophenyl)-4-(3,4-dihydroxybenzyl)-1-methyl-4H-2,3,4,5,10b-pentaazabenz[e]azulene In the same manner as in Example 184, the compound 185 was obtained from the compound of Example 115. The compound is shown in Table 33.

TABLE 33

| Ex. | Structural formula | $^1$H NMR (300 MHz, δ ppm, CDCl$_3$) |
|---|---|---|
| 185 | 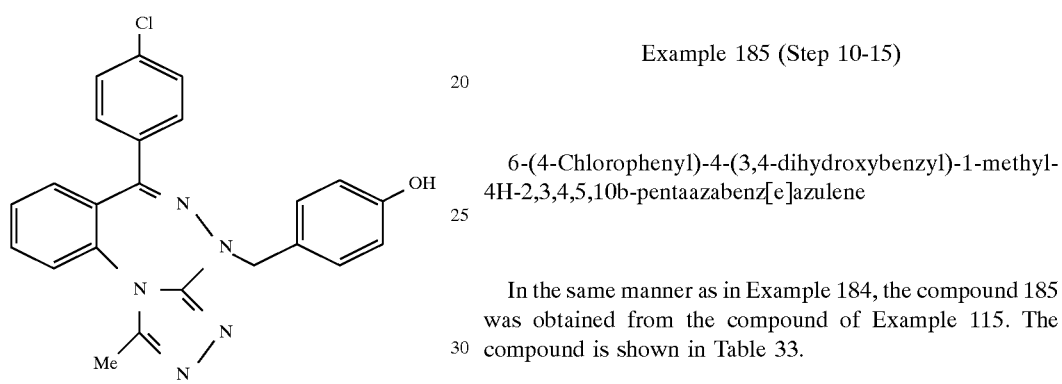 | 2.60(3H, s), 4.56–4.60(1H, m), 4.81–4.85(1H, m), 6.59–6.66(2H, m), 6.74–6.75(1H, m), 7.18–7.20 (1H, d, J=7.4Hz), 7.42–7.51(5H, m), 7.68–7.75(2H, m). |

Example 186 (Step 10-16)

6-(4-Chlorophenyl)-4-(4-ethoxybenzyl)-1-methyl-4H-2,3,4,5,10b-pentaazabenz[e]azulene

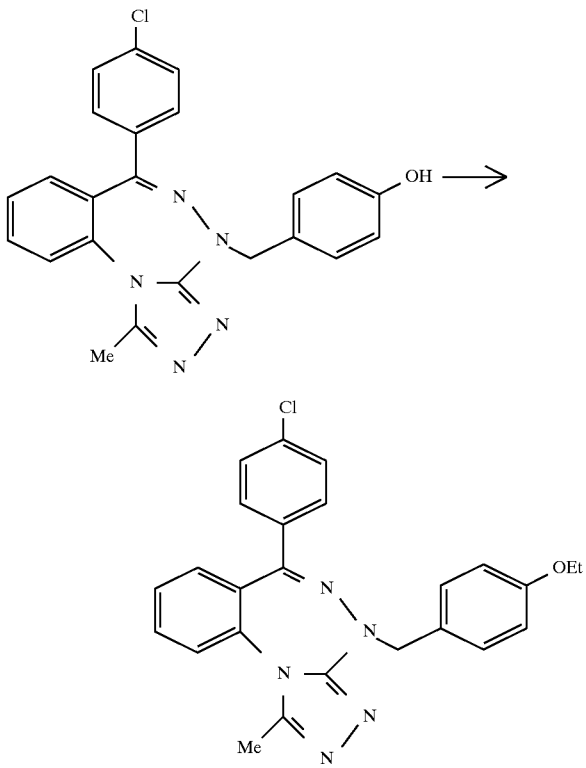

6-(4-Chlorophenyl)-4-(4-hydroxybenzyl)-1-methyl-4H-2,3,4,5,10b-pentaazabenz[e]azulene (15 mg) obtained in Example 184 was dissolved in tetrahydrofuran (2 ml) and the mixture was cooled in an ice-bath. A solution of diazoethane was added thereto and the mixture was stirred at 0° C. overnight. The reaction mixture was concentrated and the residue was purified by preparative thin-layer chromatography to give 12 mg of the title compound.

$^1$H NMR(300 MHz, δ ppm, CDCl$_3$) 1.40(3H,t,J=7.2 Hz), 2.60(3H,s), 4.02(2H,q,J=7.2 Hz), 4.88–5.03(2H,m), 6.83 (2H,d,J=9.0 Hz), 7.18–7.64(10H,m)

Example 187 (Step 10-2)

6-(4-Chlorophenyl)-1-methyl-4-(4-methylsulfonylphenyl)hydroxymethyl-4H-2,3,4,5,10b-pentaazabenz[e]azulene

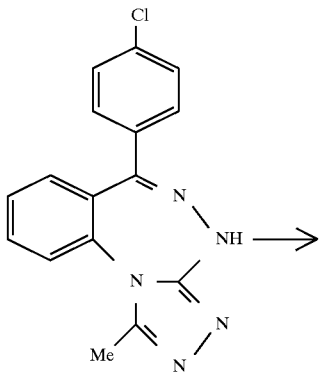

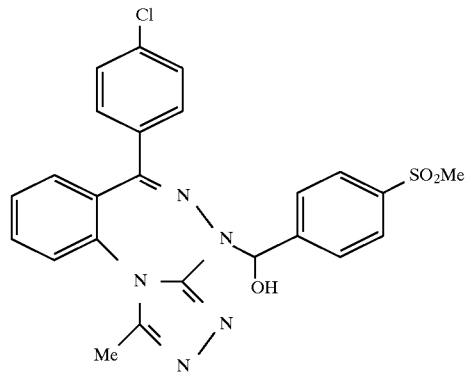

6-(4-Chlorophenyl)-1-methyl-4H-2,3,4,5,10b-pentaazabenz[e]azulene (93 mg) obtained in Preparative Example 34 was dissolved in N,N-dimethylfromamide (1 ml). Pulverized sodium hydroxide (100 mg) was added to the solution under dry air and the mixture was stirred at room temperature for 5 minutes. Then, p-methylsulfonylbenzyl chloride (68 mg) was added and the mixture was stirred at room temperature for 5 minutes. After the completion of the reaction, the reaction mixture was cooled in an ice-bath and a 5% aqueous citric acid solution and ethyl acetate were added. The organic layer was separated and successively washed with a saturated aqueous sodium hydrogencarbonate solution and water, dried and filtered. The filtrate was concentrated under reduced pressure. The residue was purified by preparative thin-layer chromatography and crystallized from ethyl acetate-diethyl ether to give 34 mg of the title compound.

Melting point: 142°–144° C.

Example 188 (Step 10-12)

4-(4-Aminobenzyl)-6-(4-chlorophenyl)-1-methyl-4H-2,3,4,5,10b-pentaazabenz[e]azulene and 6-(4-chlorophenyl)-4-(4-formylaminobenzyl)-1-methyl-4H-2,3,4,5,10b-pentaazabenz[e]azulene

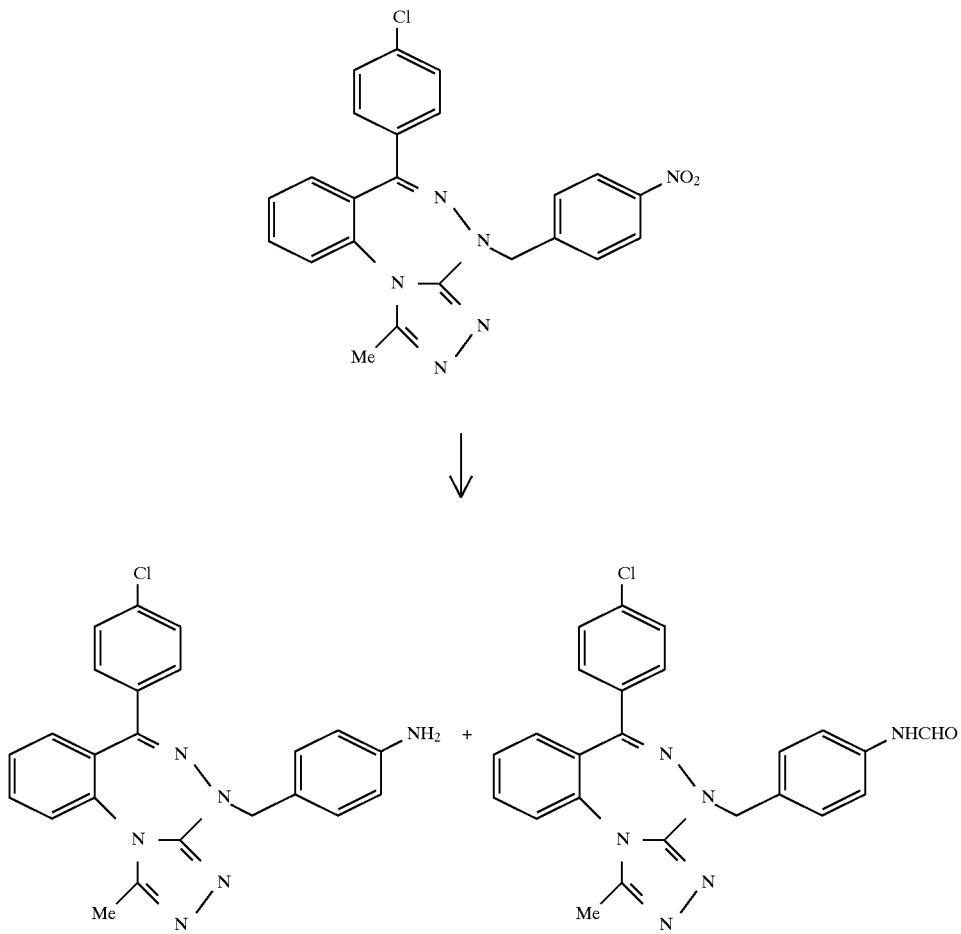

6-(4-Chlorophenyl)-1-methyl-4-(4-nitrobenzyl)-4H-2,3,4,5,10b-pentaabenz[e]azulene (680 mg) obtained in Example 122 was dissolved in methanol (20 ml) and formic acid (6 ml). Palladium black (68 mg) was added and the mixture was stirred at room temperature for 1 hour. The catalyst was filtered off and the filtrate was concentrated under reduced pressure. The residue was dissolved in ethyl acetate and water was added. The organic layer was separated and washed successively with a saturated aqueous sodium hydrogencarbonate solution and water, dried and filtered. The filtrate was concentrated under reduced pressure. The residue was purified by silica gel column chromatography and crystallized from diethyl ether to give 120 mg of 4-(4-aminobenzyl)-6-(4-chlorophenyl)-1-methyl-4H-2,3,4,5,10b-pentaazabenz[e]azulene (m.p. 234°–237° C.) and 340 mg of 6-(4-chlorophenyl)-4-(4-formylaminobenzyl)-1-methyl-4H-2,3,4,5,10b-pentaazabenz[e]azulene (m.p. 215°–216° C.).

Example 189 (Step 10-13)

4-(4-Acetylaminobenzyl)-6-(4-chlorophenyl)-1-methyl-4H- 2,3,4,5,10b-pentaazabenz[e]azulene

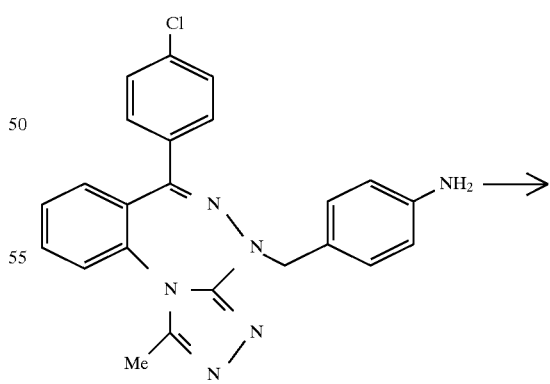

bis(methylsulfonyl)aminobenzyl]-6-(4-chlorophenyl)-4H-2,3,4,5,10b-pentaazabenz[e]azulene

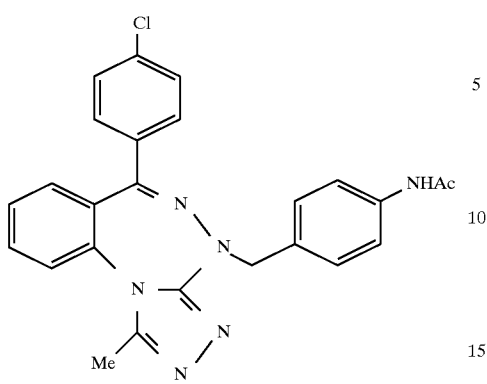

4-(4-Aminobenzyl)-6-(4-chlorophenyl)-1-methyl-4H-2,3,4,5,10b-pentaazabenz[e]azulene (12.4 mg) obtained in Example 188 was dissolved in dichloromethane (1 ml) and the mixture was ice-cooled. Acetyl chloride (2.4 μl) was added and the mixture was stirred at said temperature for 10 minutes and at room temperature for 20 minutes. After the completion of the reaction, dichloromethane was distilled away under reduced pressure. The residue obtained was crystallized from ethyl acetate-diethyl ether to give 11.1 mg of the title compound.

Melting point: 245°–249° C.

Example 190 (Step 10-13)

6-(4-Chlorophenyl)-4-(4-methylsulfonylaminobenzyl)-1-methyl-4H-2,3,4,5,10b-pentaazabenz[e]azulene and 4-[4-

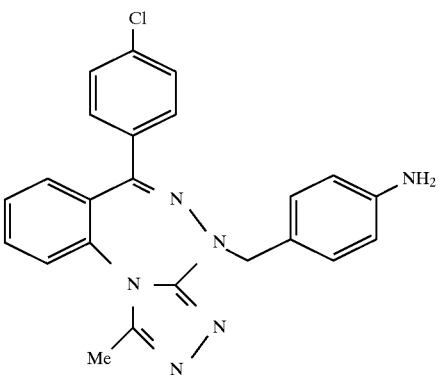

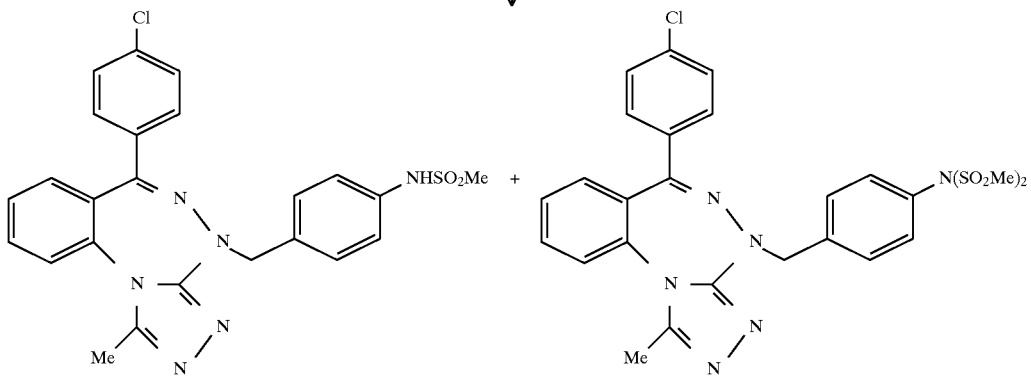

4-(4-Aminobenzyl)-6-(4-chlorophenyl)-1-methyl-4H-2,3,4,5,10b-pentaazabenz[e]azulene (24.8 mg) obtained in Example 188 was dissolved in dichloromethane (2 ml) and triethylamine (30 μl) was added. The mixture was ice-cooled and methanesulfonyl chloride (7 μl) was added. The mixture was stirred under ice-cooling for 10 minutes and at room temperature for 2 hours. The reaction mixture was concentrated under reduced pressure and a 5% aqueous citric acid solution and ethyl acetate were added. The organic layer, was separated, and successively washed with a saturated aqueous sodium hydrogencarbonate solution and water. The organic layer was dried, filtered and concentrated under reduced pressure. The residue obtained was separated and purified by preparative thin-layer chromatography. Both compounds were individually crystallized from ethyl acetate-diethyl ether to give 8 mg of 6-(4-chlorophenyl)-4-(4-methylsulfonylaminobenzyl)-1-methyl-4H-2,3,4,5,10b-pentaazabenz[e]azulene (m.p. 273°–275° C.) and 16 mg of 4-[4-bis(methylsulfonyl)aminobenzyl]-6-(4-chlorophenyl)-4H-2,3,4,5,10b-pentaazabenz[e]azulene (m.p. 220°–221° C.).

Example 191 (Step 10-14)

6-(4-Chlorophenyl)-4-(4-dimethylaminobenzyl)-1-methyl-4H-2,3,4,5,10b-pentaazabenz[e]azulene hydrochloride

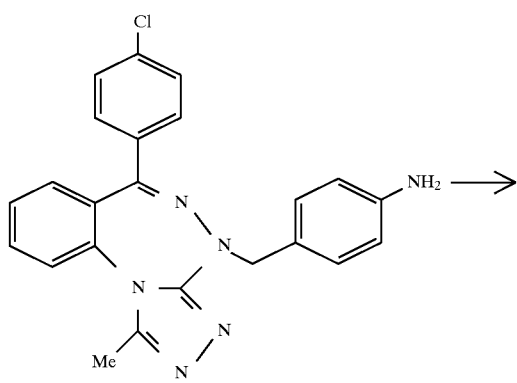

4-(4-Aminobenzyl)-6-(4-chlorophenyl)-1-methyl-4H-2,3,4,5,10b-pentaazabenz[e]azulene (124 mg) obtained in Example 188 was dissolved in ethanol (5 ml). A 25% aqueous formaldehyde solution (0.15 ml) and palladium black (10 mg) were added and the mixture was stirred under a hydrogen atmosphere for 2 days. The catalyst was filtered off and the filtrate was concentrated under reduced pressure. The residue obtained was purified by preparative thin-layer chromatography (chloroform:acetone=3:1) and the obtained solid was dissolved in diethyl ether. A solution (0.1 ml) of 1N hydrogen chloride-diethyl ether was added to allow precipitation of crystals. The crystals were collected by filtration and washed with diethyl ether to give 34 mg of the title compound.

Melting point: 169°–175° C.

Example 192 (Step 10-6)

6-(4-Chlorophenyl)-4-(2-hydroxy-2-phenylethyl)-1-methyl-4H-2,3,4,5,10b-pentaazabenz[e]azulene

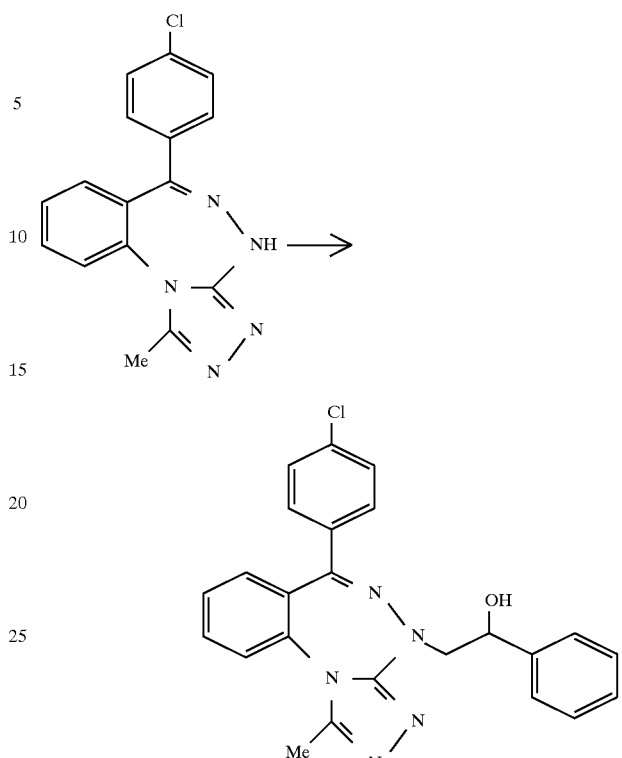

6-(4-Chlorophenyl)-1-methyl-4H-2,3,4,5,10b-pentaazabenz[e]azulene (103 mg) obtained in Preparative Example 34 was dissolved in N,N-dimethylformamide (10 ml) and the mixture was ice cooled. Sodium hydride (60% in oil, 15.9 mg) was added and the mixture was stirred under ice-cooling for 5 minutes and at room temperature for 10 minutes. Then, styrene oxide (46 µl) was added and the mixture was stirred at 50° C. for one hour. The reaction mixture was cooled to room temperature and water was added. The mixture was extracted with ethyl acetate, washed with water, dried over anhydrous magnesium sulfate and filtered. Purification by silica gel column chromatography gave 62 mg of the title compound as an amorphous solid.

$^1$H NMR(300 MHz, δ ppm, CDCl$_3$) 2.61(3H,s), 4.08(2H, m), 5.34(1H,m), 7.27–7.72(13H,m)

Example 193 (Step 10-8)

6-(4-Chlorophenyl)-4-(2-oxo-2-phenylethyl)-1-methyl-4H-2,3,4,5,10b-pentaazabenz[e]azulene

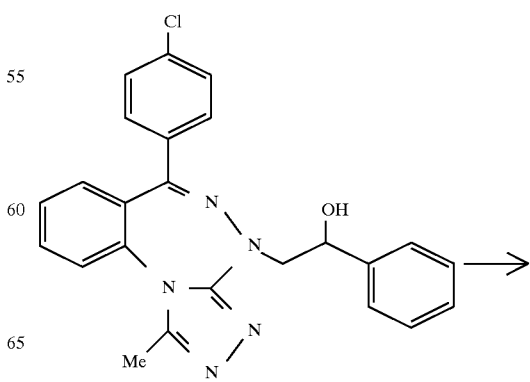

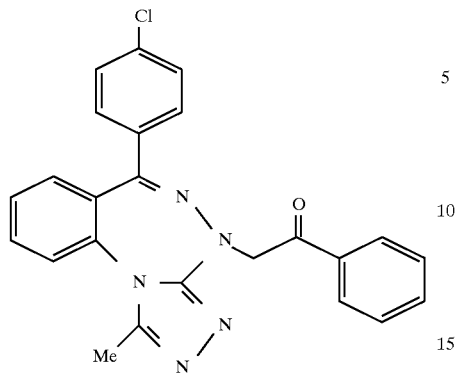

6-(4-Chlorophenyl)-4-(2-hydroxy-2-phenylethyl)-1-methyl-4H-2,3,4,5,10b-pentaazabenz[e]azulene (31 mg) obtained in Example 192 was dissolved in anhydrous dichloromethane (0.3 ml) and pyridinium dichromate (54.4 mg) was added, which was followed by stirring at room temperature. The reaction mixture was filtered through Celite, washed with water and dried over anhydrous sodium sulfate. The residue obtained by concentration under reduced pressure was purified by preparative thin-layer chromatography to give 2.0 mg of the title compound as an amorphous solid.

$^1$H NMR(300 MHz, δ ppm, CDCl$_3$) 2.63(3H,s), 5.40(2H, s), 7.28–7.67(11H,m), 8.03–8.07(2H,m)

Example 194 (Step 10-1)

6-(4-Chlorophenyl)-1-methyl-4-[3-phenyl-2-(tetrahydropyran-2-yloxy)propyl]-4H-2,3,4,5,10b-pentaazabenz[e]azulene

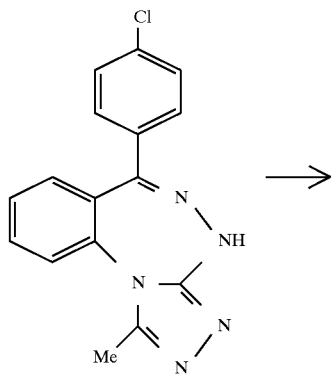

In the same manner as in Example 56, 156 mg of the title compound was obtained from 6-(4-chlorophenyl)-1-methyl-4H-2,3,4,5,10b-pentaazabenz[e]azulene (100 mg) obtained in Preparative Example 34. Note that 2-(1-benzyl-2-bromoethoxy)tetrahydropyran was used instead of 3-(chloromethyl)benzonitrile.

$^1$H NMR(300 MHz, δ ppm, CDCl$_3$) 0.96–1.66(7H,m), 2.57(3H,s), 2.88–3.47(3H,m), 3.95–4.78(4H,m), 7.13–7.65 (13H,m)

Example 195 (Step 10-1)

6-(4-Chlorophenyl)-4-[2-(2-methoxyphenyl)-2-(tetrahydropyran-2-yloxy)ethyl]-1-methyl-4H-2,3,4,5,10b-pentaazabenz[e]azulene In the same manner as in Example 194, the compound of Example 195 was obtained from the compound of Preparative Example 34. The compound is shown in Table 34.

TABLE 34

| Ex. | Structural formula | ¹H NMR (300 MHz, δ ppm, CDCl₃) |
|---|---|---|
| 195 | 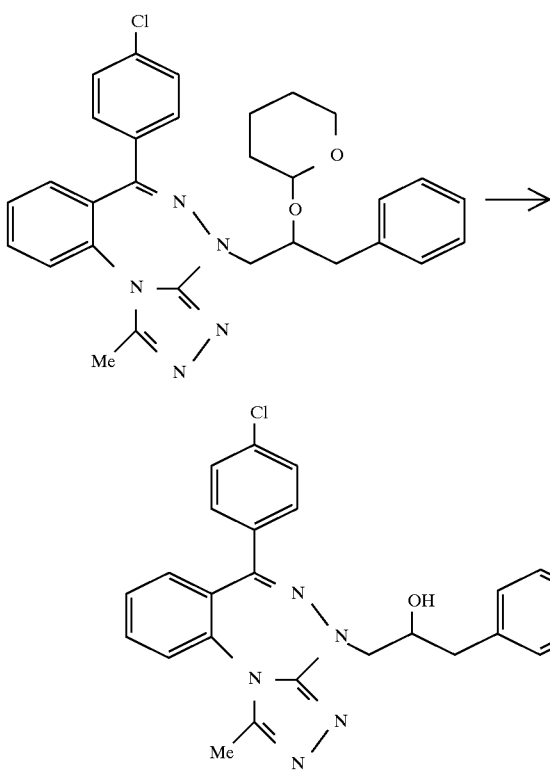 | 1.10–1.71(5H, m), 2.57(3H, s), 3.20(1H, m), 3.54(1H, m), 3.74–3.83(4H, m), 4.04–4.08(2H, m), 4.52–4.59(1H, m), 5.42(1H, m), 6.80–7.59(12H, m). |

Example 196 (Step 10-7)

6-(4-Chlorophenyl)-4-(2-hydroxy-3-phenylpropyl)-1-methyl-4H-2,3,4,5,10b-pentaazabenz[e]azulene

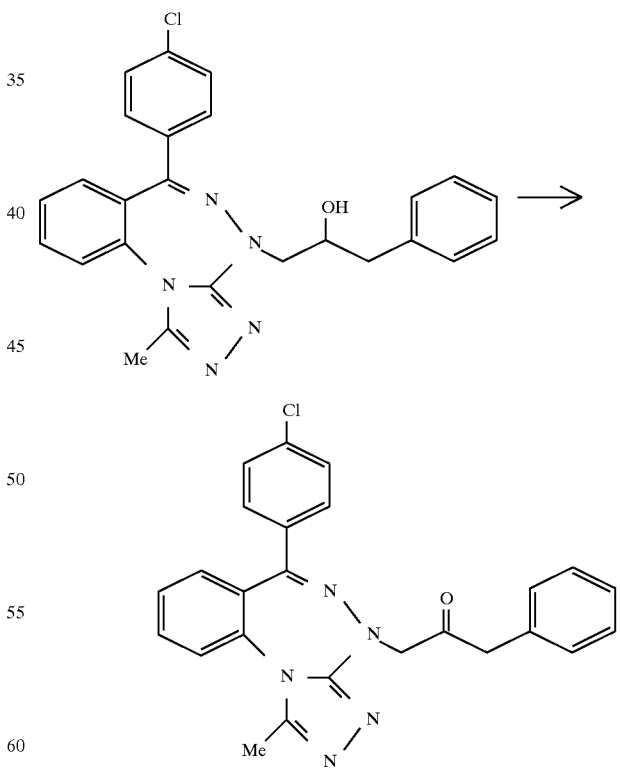

6-(4-Chlorophenyl)-1-methyl-4-[3-phenyl-2-(tetrahydropyran-2-yloxy)propyl]-4H-2,3,4,5,10b-pentaazabenz[e]azulene (146 mg) obtained in Example 194 was dissolved in ethanol (0.7 ml) and pyridinium-p-toluenesulfonic acid (218 mg) was added, which was followed by stirring for 18 hours at 55° C. The mixture was allowed to cool to room temperature, and water (30 ml) was added. The mixture was extracted with ethyl acetate (30 ml). The organic layer was washed with water, dried over anhydrous sodium sulfate and filtrated. The residue obtained by concentration under reduced pressure was purified by silica gel column chromatography to give 112 mg of the title compound as an amorphous solid.

¹H NMR(300 MHz, δ ppm, CDCl₃) 2.59(3H,s) 2.73–2.88 (2H,m), 3.81–3.98(2H,m), 4.44–4.61(1H,m), 7.22–7.44 (12H,m), 7.60–7.65(1H,t,J=7.5 Hz)

Example 197 (Step 10-8)

6-(4-Chlorophenyl)-4-(2-oxo-3-phenylpropyl)-1-methyl-4H-2,3,4,5,10b-pentaazabenz[e]azulene 6-(4-Chlorophenyl)-4-(2-hydroxy-3-phenylpropyl)-1-methyl-4H-2,3,4,5,10b-pentaazabenz[e]azulene (89 mg) obtained in Example 196 was dissolved in anhydrous dichloromethane (1 ml) and pyridinium chlorochromate (130 mg) was added, which was followed by stirring at room tem-

183 perature for 12 hours. After the completion of the reaction, the reaction mixture was purified by silica gel column chromatography and crystallized from diethyl ether to give 23 mg of the title compound as white crystals.

Melting point: 81°–84° C.

Example 198–203

In the same manner as in Examples 192–197, the compounds of Examples 198–203 were obtained from the compound of Preparative Example 34, which are shown in Table 35.

Example 198

6-(4-Chlorophenyl)-4-[2-(4-chlorophenyl)-2-oxoethyl]-1-methyl-4H-2,3,4,5,10b-pentaazabenz[e]azulene

Example 199

6-(4-Chlorophenyl)-1-methyl-4-[2-(4-methylphenyl)-2-oxoethyl]-4H-2,3,4,5,10b-pentaazabenz[e]azulene

184

Example 200

6-(4-Chlorophenyl)-4-[2-(2-methoxyphenyl)-2-oxoethyl]-1-methyl-4H-2,3,4,5,10b-pentaazabenz[e]azulene

Example 201

6-(4-Chlorophenyl)-4-[2-(2,5-dimethoxyphenyl)-2-oxoethyl]-1-methyl-4H-2,3,4,5,10b-pentaazabenz[e]azulene

Example 202

6-(4-Chlorophenyl)-4-[3-(2-methoxyphenyl)-2-oxopropyl]-1-methyl-4H-2,3,4,5,10b-pentaazabenz[e]azulene

Example 203

6-(4-Chlorophenyl)-4-[3-(2,5-dimethoxyphenyl)-2-oxopropyl]-1-methyl-4H-2,3,4,5,10b-pentaazabenz[e]azulene

TABLE 35

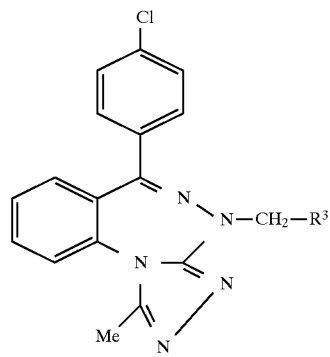

| Ex. | R³ | ¹H NMR (300 MHz, δ ppm, CDCl₃) | Melting point, °C. |
|---|---|---|---|
| 198 | (4-chlorobenzoyl-CH₂-) | 2.63(3H, s), 5.35(2H, s), 7.28–7.46(9H, m), 7.65(1H, t, J=7.5Hz), 7.98(2H, t, J=9.0Hz). | 222~223 |
| 199 | (4-methylbenzoyl-CH₂-) | 2.42(3H, s), 2.62(3H, s), 5.37(2H, s), 7.29–7.46(9H, m), 7.61–7.66(1H, m), 7.95(2H, d, J=6.0Hz). | 228~230 |
| 200 | (2-methoxybenzoyl-CH₂-) | | 224~225 |
| 201 | (2,5-dimethoxybenzoyl-CH₂-) | 2.61(3H, s), 3.77(3H, s), 3.89(3H, s), 5.34(2H, broad s), 6.88(1H, d, J=6.0Hz), 7.04(1H, dd, J=3.0 and 9.0Hz), 7.23–7.47(8H, m), 7.59–7.65(1H, m). | Amorphous solid |

TABLE 35-continued

[Structure: aryl compound with 4-chlorophenyl group, N—N—CH₂—R³, and triazole-like ring with Me substituent]

| Ex. | R³ | ¹H NMR (300 MHz, δ ppm, CDCl₃) | Melting point, °C. |
|---|---|---|---|
| 202 | [2-methoxyphenyl acetone group] | 2.60(3H, s), 3.74(2H, s), 3.83(3H, s), 3.85(2H, s), 6.71–6.80(3H, m), 7.25–7.41(7H, m), 7.60–7.66(1H, m). | Amorphous solid |
| 203 | [2,5-dimethoxyphenyl acetone group] | 2.60(3H, s), 3.72–3.74(8H, m), 4.78(2H, s), 6.71–6.77(3H, m), 7.24–7.64(8H, m). | Amorphous solid |

Preparative Example 48 (Step 11)

2-[(4-Chlorophenyl)hydrazonomethyl]phenylamine

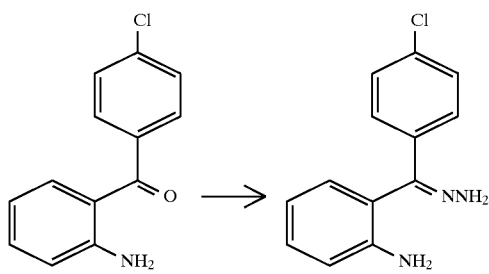

2-Aminophenyl 4-chlorophenyl ketone (27.2 g) was suspended in diethylene glycol (170 ml) and 100% hydrazine hydrate (23 ml) was added, which was followed by reflux under heating for 7 hours. The reaction mixture was allowed to cool to room temperature and water (400 ml) was added. The mixture was extracted with ethyl acetate. The organic layer was washed with water and dried over sodium sulfate. After filtration, the residue obtained by concentration under reduced pressure was subjected to silica gel column chromatography. The obtained solid was crystallized from petroleum ether-diethyl ether to give 20.25 g of the title compound.

Melting point: 85°–86° C.

Preparative Example 49 (Step 12)

2-(4-Chlorobenzyl)phenylamine

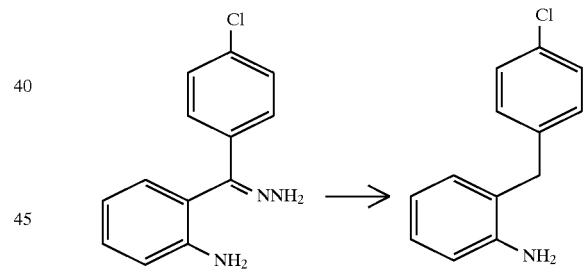

Potassium hydroxide (12.15 g) was dissolved in diethylene glycol (128 ml) and the volatile substance was distilled until the mixture reached 200° C. This solution was allowed to cool to room temperature and 2-[(4-chlorophenyl)hydrazonomethyl]phenylamine (20.25 g) obtained in Preparative Example 48 was added, which was followed by gradual heating to 150° C. The mixture was heated for 90 minutes at said temperature until generation of gases stopped. The solution was cooled to 120° C., poured into ice water and extracted with ethyl acetate. The organic layer was washed with water and dried over anhydrous magnesium sulfate. After filtration, the residue obtained by concentration under reduced pressure was subjected to silica gel column chromatography to give 17 g of the title compound as an oil.

¹H NMR(300 MHz, δ ppm, CDCl₃) 3.47(2H,s), 3.86(2H, s), 6.66–7.27(8H,m)

Preparative Example 50 (Step 13)

Acetic acid [2-(4-chlorobenzyl)phenylaminomethylene] hydrazide

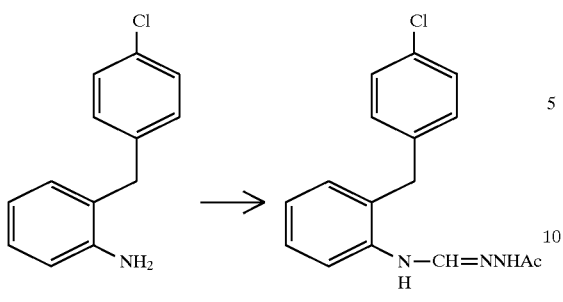

A mixture of 2-(4-chlorobenzyl)phenylamine (17 g) obtained in Preparative Example 49 and triethyl orthoformate (27.9 g) was refluxed under heating for 5 hours. The reaction mixture was allowed to cool to room temperature and absolute ethanol (160 ml) and acetohydrazide (11.6 g) were added, which was followed by stirring for 13 hours. The precipitated crystals were collected by filtration, washed with hexane-ethanol and dried to give 25 g of the title compound as colorless crystals.

Melting point: 163°–165° C.

Preparative Example 51 (Step 14)

4-[2-(4-Chlorobenzyl)phenyl]-3-methyl-4H-[1,2,4]triazole

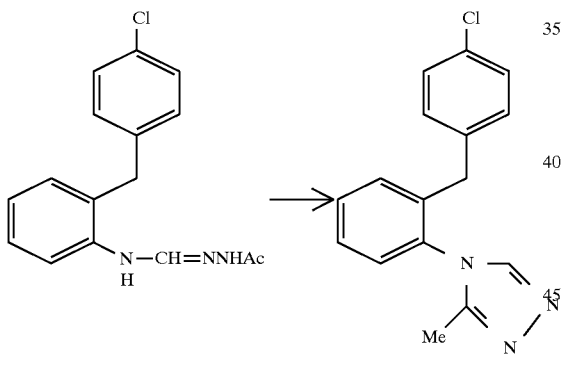

Acetic acid [2-(4-chlorobenzyl)phenylaminomethylene]hydrazide (11.6 g) obtained in Preparative Example 50 was dissolved in diethylene glycol dimethyl ether (250 ml) and the mixture was refluxed under heating for 14 hours. The mixture was cooled to room temperature and the solvent was distilled away under reduced pressure. The resulting crystals were collected by filtration, washed with diethyl ether and dried to give 6 g of the title compound as colorless crystals.

Melting point: 137°–139° C.

Preparative Example 52 (Step 15)

4-Chlorophenyl 2-(3-methyl-[1,2,4]triazol-4-yl)phenyl ketone

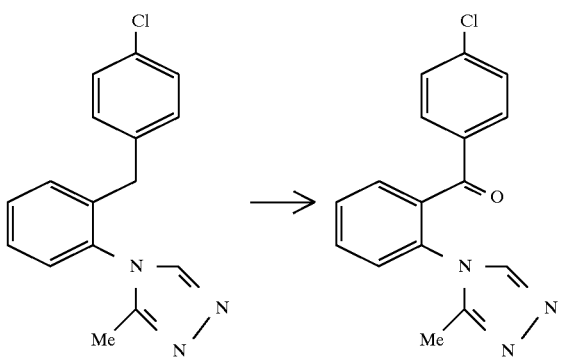

4-[2-(4-Chlorobenzyl)phenyl]-3-methyl-4H-[1,2,4]triazole (290 mg) obtained in Preparative Example 51 was dissolved in glacial acetic acid (1 ml) and Jones reagent (1.2 ml) was dropwise added under ice-cooling, which was followed by reflux under heating for 4 hours. The Jones reagent (0.2 ml) was further added and the mixture was refluxed under heating for 2 hours. After the completion of the reaction, it was poured into a 5% aqueous sodium hydroxide solution and extracted with chloroform. The organic layer was dried over anhydrous sodium sulfate. After filtration, the residue obtained by concentration under reduced pressure was subjected to silica gel column chromatography to give 185 mg of the title compound as crystals.

Melting point: 140°–141° C.

Preparative Example 53 (Step 16)

2-(3-Bromo-5-methyl-[1,2,4]triazol-4-yl)phenyl 4-chlorophenyl ketone

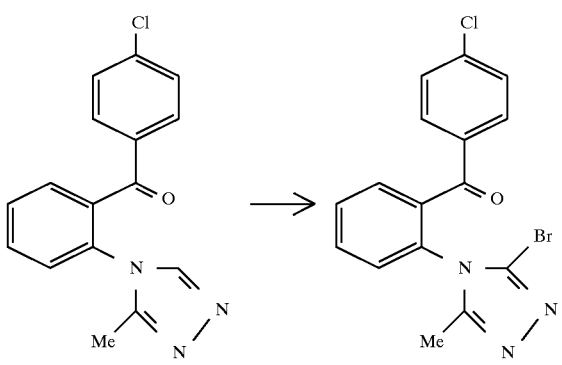

4-Chlorophenyl 2-(3-methyl-[1,2,4]triazol-4-yl)phenyl ketone (165 mg) obtained in Preparative Example 52 was dissolved in carbon tetrachloride and N-bromosuccinimide (110 mg) was added, which was followed by reflux under heating under a nitrogen atmosphere for 3 hours. After the completion of the reaction, the mixture was allowed to cool to room temperature and chloroform was added to dissolve the unsolved oil, followed by washing with water. The organic layer washed was dried over anhydrous magnesium sulfate. After filtration, the residue obtained by concentration under reduced pressure was subjected to silica gel column chromatography to give 65 mg of the title compound as crystals.

Melting point: 177°–179° C.

Preparative Example 54 (Step 17)

6-(4-Chlorophenyl)-1-methyl-4H-2,3,4,5,10b-pentaazabenz[e]azulene

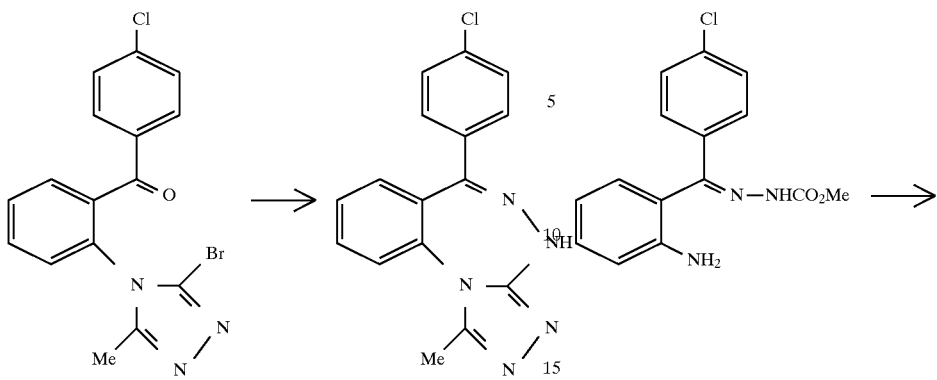

2-(3-Bromo-5-methyl-[1,2,4]triazol-4-yl)phenyl 4-chlorophenyl ketone (1.55 g) obtained in Preparative Example 53 was dissolved in absolute ethanol (30 ml) and hydrazine sulfate (1.95 g) and sodium acetate (2.87 g) were added, which was followed by reflux under heating under a nitrogen atmosphere for 1.60 hours. After the completion of the reaction, the reaction mixture was allowed to cool to room temperature and the residue was obtained by concentration under reduced pressure. Thereto was added a 5% aqueous sodium hydrogencarbonate solution and the mixture was extracted with ethyl acetate. The organic layer was washed with a saturated aqueous sodium chloride solution and dried over anhydrous magnesium sulfate. After filtration, the residue obtained by concentration under reduced pressure was subjected to silica gel column chromatography. The resulting product was crystallized from diethyl ether to give 670 mg of the title compound as needle crystals.

Melting point: 231°–233° C.

Preparative Example 55 (Step 18)

2-[(4-Chlorophenyl)carbomethoxyhydrazonomethyl]phenylamine

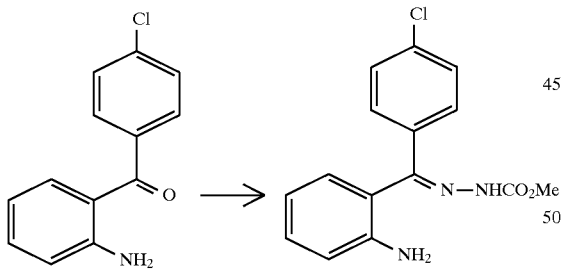

2-Aminophenyl 4-chlorophenyl ketone (25 g) was dissolved in ethanol (300 ml) and methyl carbazate (19.44 g) and p-toluenesulfonic acid monohydrate (6.16 g) were added, which was followed by reflux under heating for 12 hours. The reaction mixture was allowed to cool to room temperature, and the resulting crystals were collected by filtration and washed with ethanol to give 32 g of the title compound as white crystals.

Melting point: 217°–218° C.

Preparative Example 56 (Step 19)

5-(4-Chlorophenyl)-1,3-dihydrobenizo[e][1,2,4]triazepin-2-one

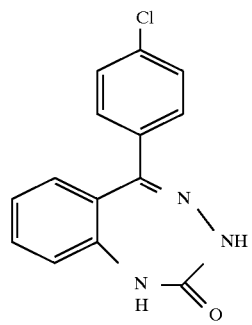

2-[(4-Chlorophenyl)carbomethoxyhydrazonomethyl]phenylamine (32 g) obtained in Preparative Example 55 was dissolved in dimethyl sulfoxide (100 ml) and the mixture was heated at 180° C. for 1.5 hours. The reaction mixture was cooled to room temperature and poured into water (1 L). The resulting crystals were collected by filtration and washed with water to give 26 g of the title compound as yellow crystals.

Melting point: 257°–259° C.

Preparative Example 57 (Step 18')

5-(4-Chlorophenyl)-1,3-dihydrobenzo[e][1,2,4]triazepin-2-one

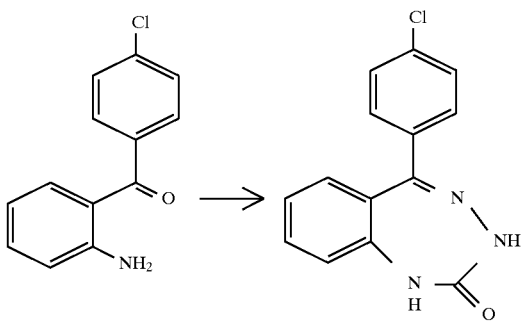

2-Aminophenyl 4-chlorophenyl ketone (25 g) was dissolved in dimethyl sulfoxide (100 ml) and methyl carbazate (22.4 g) was added, which was followed by heating with stirring at 180° C. for 18 hours. The reaction mixture was cooled to room temperature and poured into water (3 L). The resulting crystals were collected by filtration and washed with water to give 24 g of the title compound as yellow crystals.

The melting point of this compound was identical with that obtained in Preparative Example 56.

Preparative Example 58 (Step 20)

5-(4-Chlorophenyl)-1-methoxymethyl-1,3-dihydrobenzo[e][1,2,4]triazepin-2-one

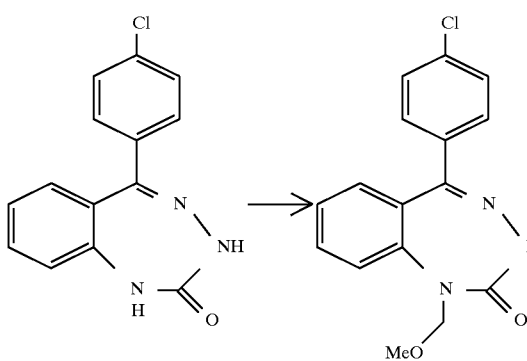

5-(4-Chlorophenyl)-1,3-dihydrobenzo[e][1,2,4]triazepin-2-one (1 g) obtained in Preparative Example 56 or Preparative Example 57 was suspended in N,N-dimethylformamide (20 ml) and potassium hydroxide (413 mg) was added, which was followed by stirring at room temperature for 15 minutes. Chloromethyl methyl ether (419 μl) was added to the reaction mixture and the mixture was stirred at room temperature for 30 minutes. The reaction mixture was poured into water (50 ml) and extracted with ethyl acetate. The organic layer washed with water and dried over anhydrous magnesium sulfate. After filtration, the residue obtained by concentration under reduced pressure was crystallized from ethyl acetate-diethyl ether to give 350 mg of the title compound as yellow crystals.

Melting point: 177°–180° C.

Preparative Example 59 (Step 21)

3-Benzyl-5-(4-chlorophenyl)-1-methoxymethyl-1,3-dihydrobenzo[e][1,2,4]triazepin-2-one

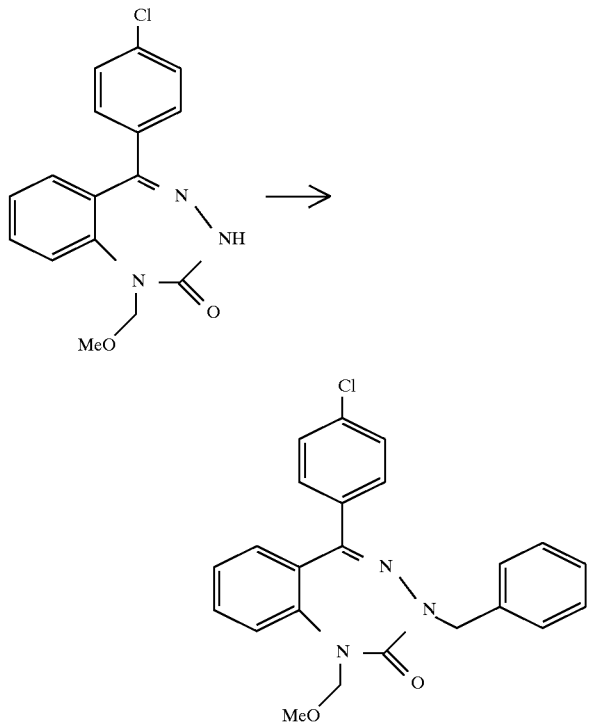

5-(4-Chlorophenyl)-1-methoxymethyl-1,3-dihydrobenzo[e][1,2,4]triazepin- 2-one (350 mg) obtained in Preparative Example 58 was dissolved in dimethyl sulfoxide (3.5 ml) and sodium hydride (60% in oil, 53.2 mg) was added, which was followed by stirring at room temperature for 30 minutes. Benzyl bromide (158 μl) was added and the mixture was stirred for 1 hour. The reaction mixture was poured into water, neutralized with glacial acetic acid and extracted with ethyl acetate. The organic layer was dried over anhydrous sodium sulfate. After filtration, the residue obtained by concentration under reduced pressure was subjected to silica gel column chromatography to give 374 mg of the title compound as an oil.

$^1$H NMR(300 MHz, δ ppm, CDCl$_3$) 3.47(3H,s), 4.62–5.17(4H,m), 7.04–7.57(13H,m)

Preparative Example 60 (Step 22)

3-Benzyl-5-(4-chlorophenyl)-1,3-dihydrobenzo[e][1,2,4]triazepin-2-one

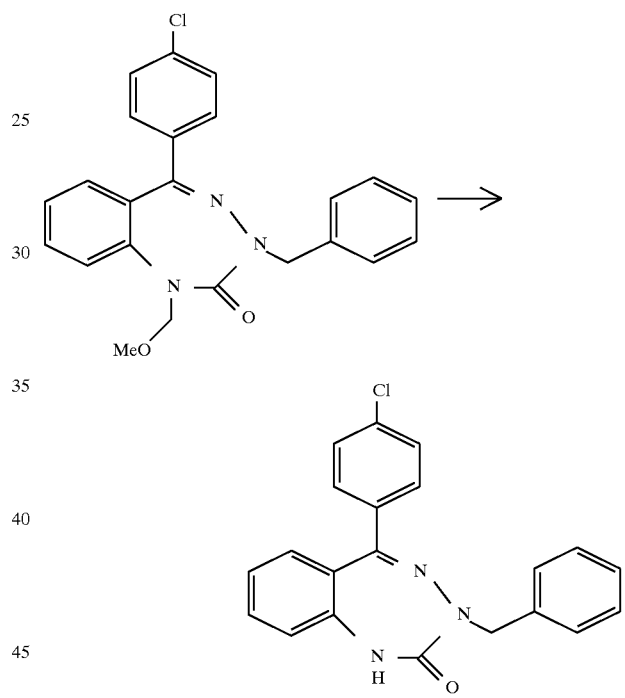

3-Benzyl-5-(4-chlorophenyl)-1-methoxymethyl-1,3-dihydrobenzo[e][1,2,4]triazepin-2-one (370 mg) obtained in Preparative Example 59 was dissolved in ethanol (1 ml) and 5N hydrochloric acid (2 ml) was added, which was followed by reflux under heating for 3 hours. The reaction mixture was cooled to room temperature, added with water and extracted with ethyl acetate. The extract was washed successively with a 5% aqueous sodium hydrogencarbonate solution and water and dried over anhydrous magnesium sulfate. After filtration, the residue obtained by concentration under reduced pressure was washed with diethyl ether to give 260 mg of the title compound as white crystals.

Melting point: 200°–202° C.

Example 204 (Step 23)

3-Benzyl-5-(4-chlorophenyl)-1,3-dihydrobenzo[e][1,2,4]triazepine-2-thione

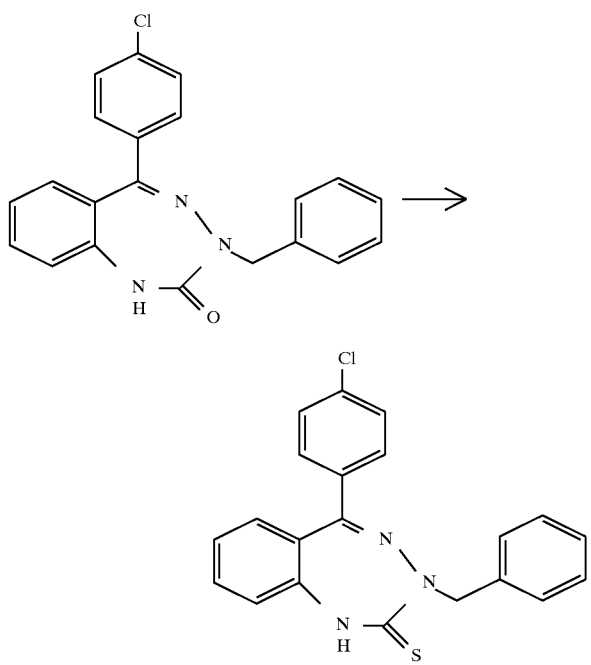

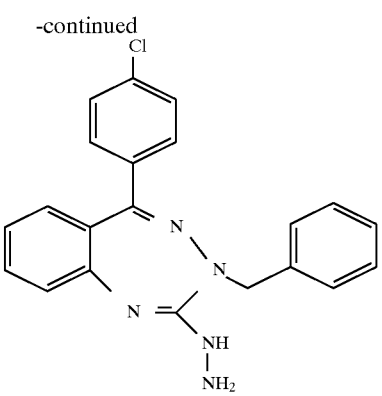

3-Benzyl-5-(4-chlorophenyl)-1,3-dihydrobenzo[e][1,2,4]triazepine-2-thione (40 mg) obtained in Example 204 was dissolved in anhydrous tetrahydrofuran (0.4 ml) and 100% hydrazine hydrate (10 μl) was added, which was followed by stirring at room temperature for 4 hours. The reaction mixture was heated to 40° C. and stirred for 4 hours. The mixture was cooled to room temperature and poured into a saturated aqueous sodium chloride solution. The organic layer was extracted with ethyl acetate and dried over anhydrous magnesium sulfate. After filtration, the residue obtained by concentration under reduced pressure was purified by preparative thin-layer chromatography to give 17 mg of the title compound as a yellow powder.

$^1$H NMR(300 MHz, δ ppm, CDCl$_3$) 4.79(2H ,s), 6.99–7.50(16H,m)

3-Benzyl-5-(4-chlorophenyl)-1,3-dihydrobenzo[e][1,2,4]triazepin-2-one (100 mg) obtained in Preparative Example 60 was suspended in diethylene glycol dimethyl ether (2 ml) and diphosphorus pentasulfide (74 mg) and sodium hydrogencarbonate (74 mg) were added, which was followed by stirring with heating at 100° C. for 22 hours. Diphosphorus pentasulfide (64 mg) was added and the mixture was stirred with heating at 100° C. for 24 hours. The reaction mixture was cooled to room temperature and poured into a 5% aqueous sodium hydrogencarbonate solution. The mixture was extracted with ethyl acetate. The organic layer was washed with a saturated aqueous sodium chloride solution and dried over anhydrous magnesium sulfate. After filtration, the residue obtained by concentration under reduced pressure was purified by preparative thin-layer chromatography to give 60 mg of the title compound as yellow crystals.

Melting point: 159°–160° C.

Example 205 (Step 4)

3-Benzyl-5-(4-chlorophenyl)-3H-benzo[e][1,2,4]triazepin-2-ylhydrazine

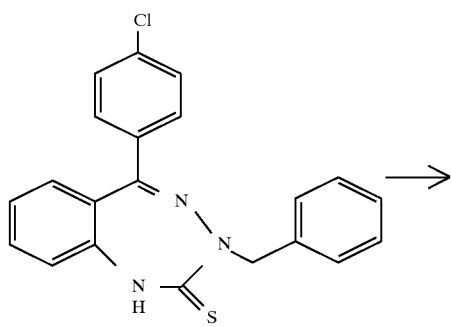

Example 206 (Step 5)

4-Benzyl-6-(4-chlorophenyl)-1-methyl-4H-2,3,4,5,10b-pentaazabenz[e]azulene

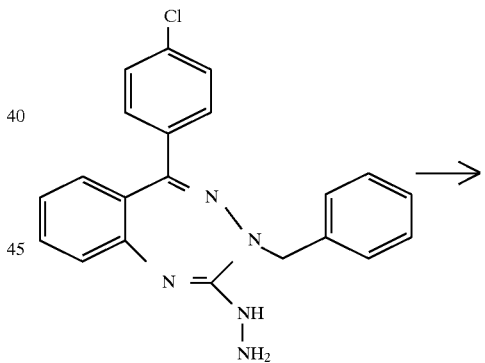

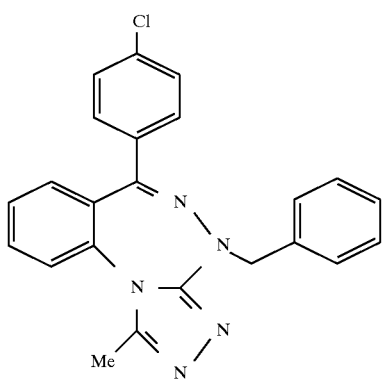

3-Benzyl-5-(4-chlorophenyl)-3H-benzo[e][1,2,4]triazepin-2-ylhydrazine (14 mg) obtained in Example 205 was dissolved in toluene (1 ml) and ethyl orthoacetate (14 μl) was added, which was followed by reflux under heating for 2 days. The reaction mixture was cooled to room temperature, poured into water (10 ml) and extracted with ethyl acetate. The organic layer washed with a saturated aqueous sodium chloride solution and dried over anhydrous sodium sulfate. After filtration, the residue obtained by concentration under reduced pressure was purified by preparative thin-layer chromatography to give 5 mg of the title compound as white crystals.

Melting point: 234°–238° C.

Preparative Example 61 (Step 26)

5-(4-Chlorophenyl)-2-(2,2-dimethoxyethylamino)-3-(4-methoxybenzyl)-3H-benzo[e][1,2,4]triazepine

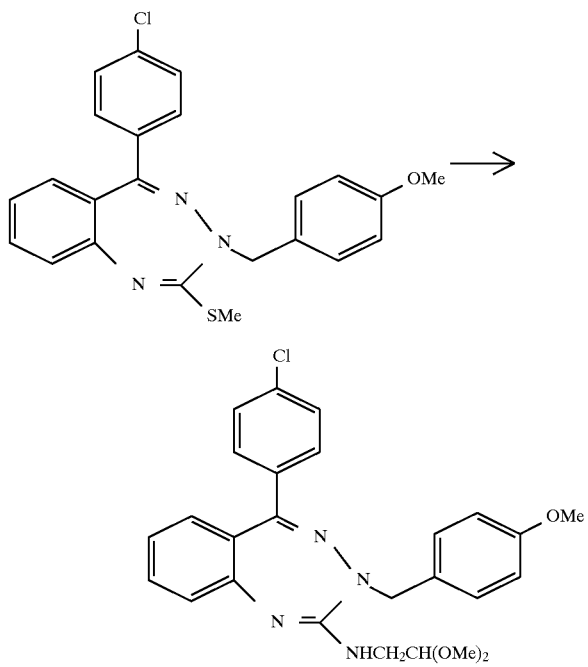

5-(4-Chlorophenyl)-3-(4-methoxybenzyl)-2-methylthio-3H-benzo[e][1,2,4]triazepine (300 mg) obtained in Example 35 was dissolved in 2-ethoxyethanol (1 ml) and aminoacetaldehyde dimethyl acetal (85.2 μl) and p-toluenesulfonic acid (14 mg) were added. The reaction mixture was heated from 80° C. to refluxing temperature over 3 hours and refluxed under heating for 1 hour. After the completion of the reaction, the mixture was allowed to cool to room temperature and added with water (20 ml), followed by extraction with ethyl acetate (30 ml). The organic layer was washed successively with water, a 5% sodium hydrogencarbonate solution and water and dried over anhydrous sodium sulfate. After filtration, the residue obtained by concentration under reduced pressure was crystallized from n-hexane: diethyl ether (5:1) solvent to give 160 mg of the title compound as white crystals.

Melting point: 114°–115° C.

Example 207 (Step 27)

6-(4-Chlorophenyl)-4-(4-methoxybenzyl)-4H-3,4,5,10b-tetraazabenz[e]azulene

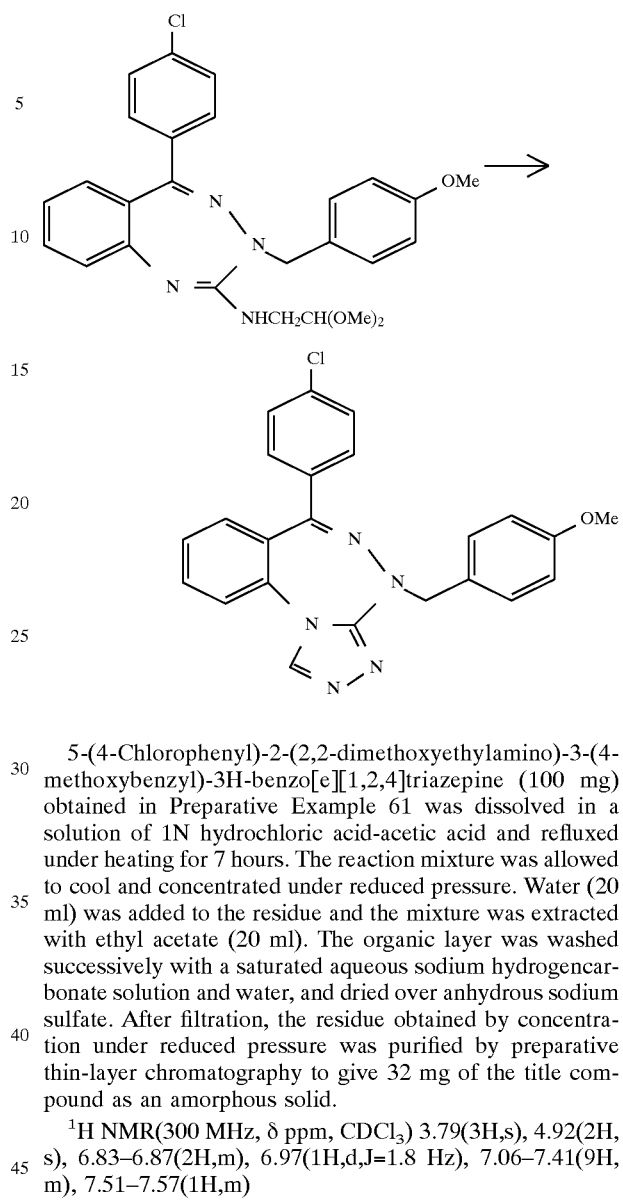

5-(4-Chlorophenyl)-2-(2,2-dimethoxyethylamino)-3-(4-methoxybenzyl)-3H-benzo[e][1,2,4]triazepine (100 mg) obtained in Preparative Example 61 was dissolved in a solution of 1N hydrochloric acid-acetic acid and refluxed under heating for 7 hours. The reaction mixture was allowed to cool and concentrated under reduced pressure. Water (20 ml) was added to the residue and the mixture was extracted with ethyl acetate (20 ml). The organic layer was washed successively with a saturated aqueous sodium hydrogencarbonate solution and water, and dried over anhydrous sodium sulfate. After filtration, the residue obtained by concentration under reduced pressure was purified by preparative thin-layer chromatography to give 32 mg of the title compound as an amorphous solid.

$^1$H NMR(300 MHz, δ ppm, CDCl$_3$) 3.79(3H,s), 4.92(2H, s), 6.83–6.87(2H,m), 6.97(1H,d,J=1.8 Hz), 7.06–7.41(9H, m), 7.51–7.57(1H,m)

Experimental Examples

The results of the tests with respect to the bone resorption-inhibitory action of the triazepine compounds of the above-mentioned formula [I] of the present invention are shown in the following.

Experimental Example 1
Inhibition of bone resorption

The determination of the inhibitory action on the bone resorption was basically in accordance with the method of Raisz [J. Clin. Invest. vol. 44, pp. 103–116 (1965)].

A new born ICR mouse (one or two days old) was intraperitoneally administered with 1.5μ Ci $^{45}$Ca (isotope of calcium as CaCl$_2$ solution) and calvaria was aseptically removed the next day. The calvaria was split into two along the central suture line, and one of them was used as a control and the other was used as a test compound. The calvaria was preincubated at 37° C. for 2 days in BGJb medium [0.5 ml, Fitton-Jackson modification, GIBCO Laboratories, USA, containing bovine serum albumin 1 mg/ml] added with a test compound to the concentrations of 0.04 μM, 0.2 μM and 1 μM and then in the above-mentioned medium containing 50 nM hPTH (1–34) for further 3 days. After the incubation, the $^{45}$Ca radioactivity in the medium and the bone was determined, and the proportion (%) of $^{45}$Ca released from the bone into the medium was calculated by the following formula.

$$\text{Proportion (\%) of } ^{45}\text{Ca released from bone into medium} = \frac{^{45}\text{Ca count in the medium}}{^{45}\text{Ca count in the medium} + ^{45}\text{Ca count in the bone}} \times 100$$

Using the bone obtained from the same mouse and treated in the same manner without adding a test compound, as a control, the proportion (%) relative to the control group was determined according to the following formula.

$$\text{Proportion (\%) relative to control group} = \frac{\text{Proportion (\%) of }^{45}\text{Ca released in the medium from the bone of test group}}{\text{Proportion (\%) of }^{45}\text{Ca released in the medium from the bone of control group}} \times 100$$

The mean of these values obtained using the bones from 4 pairs of respective groups was calculated, based on which $IC_{50}$ was calculated and summarized in Table 36.

TABLE 36

| Example | $IC_{50}$ (μM) | Example | $IC_{50}$ (μM) |
|---|---|---|---|
| 40 | 0.12 | 121 | 0.14 |
| 41 | 0.80 | 122 | 0.72 |
| 46 | 0.42 | 123 | 0.65 |
| 54 | 0.54 | 126 | 0.53 |
| 56 | 0.25 | 128 | 0.93 |
| 57 | 0.72 | 129 | 0.78 |
| 58 | 0.43 | 131 | 0.99 |
| 59 | 0.68 | 134 | 0.18 |
| 61 | 0.81 | 135 | 0.41 |
| 62 | 0.71 | 136 | 0.59 |
| 63 | 0.74 | 139 | 0.018 |
| 68 | 0.33 | 140 | 0.05 |
| 70 | 0.64 | 141 | 0.68 |
| 74 | 0.43 | 142 | 0.45 |
| 76 | 0.56 | 143 | 0.34 |
| 77 | 0.12 | 144 | 0.27 |
| 79 | 0.57 | 145 | 0.12 |
| 81 | 0.59 | 146 | 0.1 |
| 84 | 0.67 | 147 | 0.81 |
| 85 | 0.86 | 148 | 0.68 |
| 88 | 0.59 | 149 | 0.18 |
| 94 | 0.56 | 150 | 0.029 |
| 98 | 0.54 | 184 | 0.56 |
| 100 | 0.71 | 186 | 0.79 |
| 106 | 0.83 | 188 | 0.67 |
| 111 | 0.51 | 189 | 0.26 |
| 112 | 0.38 | 190 | 0.18 |
| 113 | 0.50 | 191 | 0.74 |
| 120 | 0.22 | | |

Experimental Example 2 suppression of bone mass decrease

The suppressive effect of the compound of the present invention on the bone mass decrease was tested using the ovariectomized rats (osteoporosis model rats).

Female SD rats (13 weeks of age) were subjected to bilateral ovariectomies under anesthesia with Nembutal (50 mg/kg/ml, i.p.; Dai-Nippon Pharmaceutical). At the same time, a sham control group that was subjected to sham surgery without removing ovaries was prepared. The next day of the operation, the rats were grouped in such a manner that the bone mineral density (hereinafter abbreviated as BMD) of each group would reach an average. The BMD was determined by their bone mineral density of lumbar spine (L 4–5) that was measured with a DXA bone densitometer (DCS-600 R, Aloka) under ether anesthesia. The test compounds were suspended in 0.5% hydroxypropylmethylcellulose (hereinafter abbreviated as HPMC, Shin-Etsu Chemical Industries, Ltd.) and they were administered orally at the doses of 0.3, 1.0 and 3.0 mg/kg (5 ml/kg:) for 12 weeks daily from the day following the operation. As a positive control, 17 β-estradiol (Sigma) was dissolved in 5% benzyl alcohol and 95% corn oil, and administered subcutaneously at a dose of 50 μg/kg (1 ml/kg) twice a week for 12 weeks. 0.5% HPMC was administered orally to the normal control and the control for 12 weeks at 5 ml/kg. The next day of the final administration, the rats were exsanguinated and killed under ether anesthesia and the lumbar spine (L4–5) was recovered. The soft tissues and processes were removed from the obtained lumbar spine and BMD of the vertebral body (L4–5) was determined with DCS-600 R (Aloka).

The results are shown by mean±S.E. of the respective groups and the statistical evaluations of the effect of respective groups were made by one-way analysis of variance. The significance was ascribed at less than 5%. The results are shown in Table 37.

TABLE 37

| | Dose (mg/kg) | Administ. route | n | BMD (mg/cm$^2$) of body of vertebra |
|---|---|---|---|---|
| Normal control | 0 | p.o. | 8 | 56.3 ± 1.4 |
| Control | 0 | p.o. | 9 | 46.1 ± 0.5 |
| Positive control | 0.05 | s.c. | 8 | 53.5 ± 0.7 |
| Compound of Ex. 131 | 0.3 | p.o. | 9 | 46.5 ± 0.8 |
| " | 1 | p.o. | 8 | 48.5 ± 0.5* |
| " | 3 | p.o. | 9 | 51.3 ± 0.9** |
| Compound of Ex. 54 | 0.3 | p.o. | 9 | 46.2 ± 0.4 |
| " | 1 | p.o. | 8 | 47.3 ± 0.6 |
| " | 3 | p.o. | 9 | 51.6 ± 0.4** |

Mean S.E.:
*p < 0.05
**p < 0.01

Effects of the Invention

The triazepine compounds of the present invention which are expressed by the above-mentioned formula [I] have superior inhibitory action on the bone resorption and are low toxic. The results of the tests on the inhibitory action on bone resorption reveal that these compounds also have an action of reducing the amount of serum calcium caused by bone resorption. Accordingly, these compounds can be used as pharmaceutical agents to effectively suppress bone resorption, prevent bone mass decrease, or prevent or reduce the rise in serum calcium value for the treatment of the diseases such as Paget's disease, hypercalcemia, osteoporosis and so on, as well as for the treatment of the symptoms of advanced bone resorption associated with the inflammatory joint diseases such as chronic rheumatoid arthritis, in which advanced bone resorption are considered to be mainly responsible for the pathogensis.

The compounds of the present invention which are represented by the above-mentioned formulas [II'], [III'] and [IV'] are useful as intermediates to produce the triazepine compounds of the formula [I].

What is claimed is:

1. A method for treating osteoporosis comprising administering to a patient in need thereof, a triazepine compound of the formula [I]

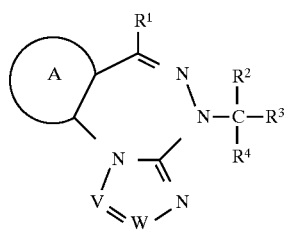

wherein

- $R^1$ is an optionally substituted aryl or an optionally substituted heteroaryl;
- $R^2$ is a hydrogen atom, a hydroxy, a halogen atom or a lower alkyl;
- $R^4$ is a hydrogen atom or a halogen atom, or $R^2$ and $R^4$ are combined together with the carbon atom to which they are bonded to form a carbonyl;
- $R^3$ is a hydrogen atom, a lower alkyl, a lower alkoxy, a cycloalkyl, an optionally substituted aryl, an optionally substituted heteroaryl, —$CR^5$=$CR^6R^7$ wherein $R^5$, $R^6$ and $R^7$ are the same or different and each is hydrogen atom, halogen atom, lower alkyl or optionally substituted aryl, a group of the formula

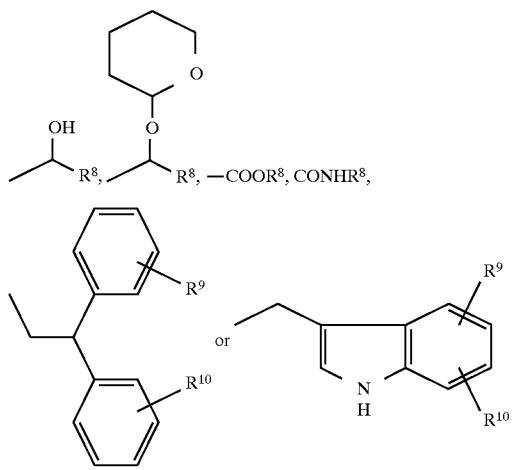

wherein $R^8$ is hydrogen atom, lower alkyl, cycloalkyl, optionally substituted aryl, aralkyl or optionally substituted heteroaryl, and $R^9$ and $R^{10}$ are the same or different and each is hydrogen atom, lower alkyl, lower alkoxy, hydroxy, halogen atom, nitro or amino, —X—Y wherein X is —$(CH_2)_m$— wherein m is an integer of 1 to 4, —CO—, —$COCH_2$—, —NH—, —$NHCH_2$—, —$CH_2NH$—, —$CH_2NHCO$—, —$OCH_2$—, —$(CH_2)_nO$— wherein n is an integer of 1 to 4, or —$CH_2S$—, and Y is halogen atom, cycloalkyl, optionally substituted aryl or optionally substituted heteroaryl, or —$OR^{18}$ wherein $R^{18}$ is optionally substituted aryl;

ring A is a ring selected from the group consisting of the following rings

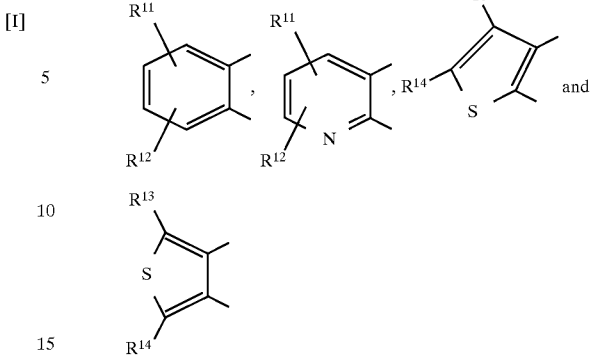

wherein $R^{11}$ and $R^{12}$ are the same or different and each is hydrogen atom, halogen atom, lower alkyl, a lower alkyl substituted by at least one member selected from the group consisting of halogen atom, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl and aralkyloxycarbonyl, lower alkenyl, aralkyl, aralkyl substituted by alkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl or aralkyloxycarbonyl, $R^{13}$ and $R^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and $$-V=W- \text{ is } -\underset{\underset{R^{19}}{|}}{C}=\underset{\underset{H}{|}}{C}-, -\underset{\underset{R^{15}}{|}}{C}=N- \text{ or } -N=N-$$

wherein $R^{15}$ is lower alkyl and $R^{19}$ is hydrogen atom or lower alkyl, or a pharmaceutically acceptable salt thereof; wherein the optionally substituted aryl is an aryl which may have one or more substituents selected from the group consisting of halogen atom, lower alkyl, lower alkoxy, aralkyloxy, methylenedioxy, haloalkyl, haloalkyloxy, halolalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the optionally substituted heteroaryl is an aromatic heterocyclic group selected from the group consisting of pyridyl, thienyl, thiazolyl and isoxazolyl, which may have one or more substituents selected from the group consisting of halogen atom, lower alkyl, lower alkoxy, aralkyloxy, methylenedioxy, haloalkyl, haloalkyloxy, haloalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the cyclic amino is a cyclic amino selected from the group consisting of pyrrolidinyl, piperidino, morpholino, thiomorpholino and piperazinyl, wherein lower alkyl or aralkyl may substitute the 4-position nitrogen atom of piperazinyl; and the cyclic aminocarbonyl is a cyclic aminocarbonyl selected from the group consisting of pyrrolidinylcarbonyl, piperidinocarbonyl, morpholinocarbonyl, thiomorpholinocarbonyl and piperazinylcarbonyl, wherein lower alkyl or aralkyl may substitute the 4-position nitrogen atom of piperazinylcarbonyl.

2. The method for treating osteoporosis of claim 1, wherein, in the formula [I], the ring A is

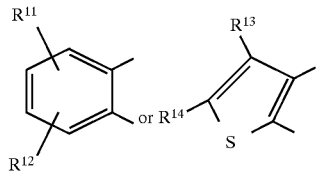

wherein $R^{11}$, $R^{12}$, $R^{13}$ and $R^{14}$ are as defined in claim 1.

3. The method for treating osteoporosis of claim 2, wherein, in the formula [I],

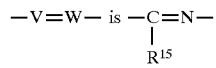

wherein $R^{15}$ is a lower alkyl.

4. The method for treating osteoporosis of claim 3, wherein, in the formula [I], $R^1$ is an optionally substituted aryl.

5. The method for treating osteoporosis of claim 4, wherein $R^1$ is an optionally substituted aryl wherein the aryl is phenyl.

6. The method for treating osteoporosis of claim 5, wherein, in the formula [I], $R^2$ and $R^4$ are both hydrogen atom.

7. A method for treating osteoporosis comprising administering to a patient in need thereof, a triazepine compound which is a member selected from the group consisting of 6-(4-chlorophenyl)-4-(4-methoxybenzyl)-1-methyl-4H-2,3,4,5,10b-pentaazabenz[e]azulene, 6-(4-chlorophenyl)-4-(3,4-dimethoxybenzyl)-1-methyl-4H-2,3,4,5,10b-pentaazabenz[e]azulene, 4-(4-methoxybenzyl)-1-methyl-6-phenyl-4H-2,3,4,5,10b-pentaazabenz[e]azulene, 4-(4-methoxybenzyl)-1,9-dimethyl-6-phenyl-4H-2,3,4,5,10b-pentaazabenz[e]azulene, 8-chloro-4-(4-methoxybenzyl)-1methyl-6-phenyl-4H-2,3,4,5,10b-pentaazabenz[e]azulene, 4-(4-methoxybenzyl)-1-methyl-8-nitro-6-phenyl-4H-2,3,4,5,10b-pentaazabenz[e]azulene, 4-(4-methoxybenzyl)-1-methyl-6-(4-methylphenyl)-4H-2,3,4,5,10b-pentaazabenz[e]azulene, 8-chloro-6-(2-chlorophenyl)-4-(4-methoxybenzyl)-1-methyl-4H-2,3,4,5,10b-pentaazabenz[e]azulene, 4-(4-chlorophenyl)-6-(4-methoxybenzyl)-2,3,9-trimethyl-6H-5,6,7,8,9a-pentaazathien[2,3-e]azulene, 4-(4-chlorophenyl)-2-ethyl-6-(4-methoxybenzyl)-9-methyl-6H-5,6,7,8,9a-pentaazathien[2,3-e]azulene, 6-(4-methoxybenzyl)-2,9-dimethyl-4-phenyl-6H-5,6,7,8,9a-pentaazathien[2,3-e]azulene, 6-(4-methoxybenzyl)-2,3,9-trimethyl-4-phenyl-6H-5,6,7,8,9a-pentaazathien[2,3-e]azulene, 2-ethyl-6-(4-methoxybenzyl)-9-methyl-4-phenyl-6H-5,6,7,8,9a-pentaazathien[2,3-e]azulene, 6-(4-methoxybenzyl)-4-(4-methoxyphenyl)-2,3,9-trimethyl-6H-5,6,7,8,9a-pentaazathien[2,3-e]azulene, 6-(4-chlorophenyl)-1-methyl-4-(pyridin-3-ylmethyl)-4H-2,3,4,5,10b-pentaazabenz[e]azulene, 4-(2-chlorophenyl)-2,3,9-trimethyl-6-(pyridin-4-ylmethyl)-6H-5,6,7,8,9a-pentaazathien[2,3-e]azulene, 6-(4-chlorophenyl)-4-(3-cyanobenzyl)-1-methyl-4H-2,3,4,5,10b-pentaazabenz[e]azulene, 6-(4-chlorophenyl)-4-(2-fluorobenzyl)-1-methyl-4H-2,3,4,5,10b-pentaazabenz[e]azulene, 6-(4-chlorophenyl)-4-(3-fluorobenzyl)-1-methyl-4H-2,3,4,5,10b-pentaazabenz[e]azulene, 6-(4-chlorophenyl)-4-(4-fluorobenzyl)-1-methyl-4H-2,3,4,5,10b-pentaazabenz[e]azulene, 6-(4-chlorophenyl)-4-(2,4-difluorobenzyl)-1-methyl-4H-2,3,4,5,10b-pentaazabenz[e]azulene, 6-(4-chlorophenyl)-4-(2,5-difluorobenzyl)-1-methyl-4H-2,3,4,5,10b-pentaazabenz[e] azulene, 6-(4-chlorophenyl)-4-(3,5-difluorobenzyl)-1-methyl-4H-2,3,4,5,10b-pentaazabenz[e]azulene, 6-(4-chlorophenyl)-4-(3,4-difluorobenzyl)-1-methyl-4H-2,3,4,5,10b-pentaazabenz[e]azulene, 6-(4-chlorophenyl)-1-methyl-4-(2-trifluoromethylbenzyl)-4H-2,3,4,5,10b-pentaazabenz[e]azulene, 6-(4-chlorophenyl)-1-methyl-4-(4-trifluoromethylbenzyl)-4H-2,3,4,5,10b-pentaazabenz[e]azulene, 6-(4-chlorophenyl)-1-methyl-4-(3-trifluoromethylbenzyl)-4H-2,3,4,5,10b-pentaazabenz[e]azulene, 6-(4-chlorophenyl)-1-methyl-4-(4-trifluoromethoxybenzyl)-4H-2,3,4,5,10b-pentaazabenz[e]azulene, 6-(4-chlorophenyl)-1-methyl-4-(3-nitrobenzyl)-4H-2,3,4,5,10b-pentaazabenz[e]azulene, 4-(2-chlorobenzyl)-6-(4-chlorophenyl)-1-methyl-4H-2,3,4,5,10b-pentaazabenz[e]azulene, 4-(3-chlorobenzyl)-6-(4-chloropheny)-1-methyl-4H-2,3,4,5,10b-pentaazabenz[e]azulene, 4-(4-chlorobenzyl)-6-(4-chlorophenyl)-1-methyl-4H-2,3,4,5,10b-pentaazabenz[e]azulene, 6-(4-chlorophenyl)-4-(2-cyanobenzyl)-1-methyl-4H-2,3,4,5,10b-pentaazabenz[e]azulene, 6-(4-chlorophenyl)-4-(4-cyanobenzyl)-1-methyl-4H-2,3,4,5,10b-pentaazabenz[e]azulene, 6-(4-chlorophenyl)-4-(2-methoxybenzyl)-1-methyl-4H-2,3,4,5,10b-pentaazabenz[e]azulene, 6-(4-chlorophenyl)-4-(3-methoxybenzyl)-1-methyl-4H-2,3,4,5,10b-pentaazabenz[e]azulene, 6-(4-chlorophenyl)-4-(4-methoxybenzyl)-1-methyl-4H-2,3,4,5,10b-pentaazabenz[e]azulene, 6-(4-chlorophenyl)-4-(2,5-dimethoxybenzyl)-1-methyl-4H-2,3,4,5,10b-pentaazabenz[e]azulene, 6-(4-chlorophenyl)-1-methyl-4-(3,4,5-trimethoxybenzyl)-4H-2,3,4,5,10b-pentaazabenz[e]azulene, 4-(5-acetyl-2-methoxybenzyl)-6-(4-chlorophenyl)-1-methyl-4H-2,3,4,5,10b-pentaazabenz[e]azulene, 6-(4-chlorophenyl)-1-methyl-4-(3,4-methylenedioxybenzyl)-4H-2,3,4,5,10b-pentaazabenz[e]azulene, 4-(2-chloro-4,5-methylenedioxybenzyl)-6-(4-chlorophenyl)-1-methyl-4H-2,3,4,5,10b-pentaazabenz[e]azulene,.

6-(4-chlorophenyl)-4-(2-ethoxy-5-nitrobenzyl)-1-methyl-4H-2,3,4,5,10b-pentaazabenz[e]azulene, 6-(4-chlorophenyl)-4-(4-methoxy-3-nitrobenzyl)-1-methyl-4H-2,3,4,5,10b-pentaazabenz[e]azulene, 4-(3-chloro-4-methoxybenzyl)-6-(4-chlorophenyl)-1-methyl-4H-2,3,4,5,10b-pentaazabenz[e]azulene, 6-(4-chlorophenyl)-4-(3,5-dichloro-4-methoxybenzyl)-1-methyl-4H-2,3,4,5,10b-pentaazabenz[e]azulene, 6-(4-chlorophenyl)-1-methyl-4-(2-methylbenzyl)-4H-2,3,4,5,10b-pentaazabenz[e]azulene, 6-(4-chlorophenyl)-1-methyl-4-(3-methylbenzyl)-4H-2,3,4,5,10b-pentaazabenz[e]azulene, 6-(4-chlorophenyl)-1-methyl-4-(4-methylbenzyl)-4H-2,3,4,5,10b-pentaazabenz[e]azulene, 4-(4-tert-butylbenzyl)-6-(4-chlorophenyl)-1-methyl-4H-2,3,4,5,10b-pentaazabenz[e]azulene, 6-(4-chlorophenyl)-1-methyl-4-(naphthalen-1-ylmethyl)-4H-2,3,4,5,10b-pentaazabenz[e]azulene, 6-(4-chlorophenyl)-1-methyl-4-(naphthalen-2-ylmethyl)-4H-2,3,4,5,10b-pentaazabenz[e]azulene, 4-(4-benzyloxybenzyl)-6-(4-chlorophenyl)-1-methyl-4H-2,3,4,5,10b-pentaazabenz[e]azulene, 4-benzyl-6-(4-chlorophenyl)-1-methyl-4H-2,3,4,5,10b-pentaazabenz[e]azulene, 6-(4-chlorophenyl)-1-methyl-4-(4-phenylbenzyl)-4H-2,3,4,5,10b-pentaazabenz[e]azulene, 4-(4-chlorophenoxymethyl)-6-(4-chlorophenyl)-1-methyl-4H-2,3,4,5,10b-pentaazabenz[e]azulene, 6-(4-chlorophenyl)-1-methyl-4-(pyridin-2-ylmethyl)-4H-2,3,4,5,10b-pentaazabenz[e]azulene, 6-(4-chlorophenyl)-1-methyl-4-(pyridin-3-ylmethyl)-4H-2,3,4,5,10b-pentaazabenz[e]azulene, 6-(4-chlorophenyl)-4-[2-(indol-3-yl)ethyl]-1-methyl-4H-2,3,4,5,10b-pentaazabenz[e]azulene, 6-(4-chlorophenyl)-4-(2-methyl-1,3-thiazol-4-ylmethyl)-1-methyl-4H-2,3,4,5,10b-pentaazabenz[e]azulene, 6-(4-chlorophenyl)-4-(5-chlorothiophen-2-ylmethyl)-1-methyl-4H-2,3,4,5,10b-pentaazabenz[e]azulene, 6-(4-chlorophenyl)-1-methyl-4-(3,5-dimethylisoxazol-4-ylmethyl)-4H-2,3,4,5,10b-pentaazabenz[e]azulene, 6-(4-chlorophenyl)-1-methyl-4-phenethyl-4H-2,3,4,5,10b-pentaazabenz[e]azulene, 6-(4-chlorophenyl)-1-methyl-4-(3-phenylpropyl)-4H-2,3,4,5,10b-pentaazabenz[e]azulene, 6-(4-chlorophenyl)-4-(3,3-diphenylpropyl)-1-methyl-4H-2,3,4,5,10b-pentaazabenz[e]azulene, 6-(4-chlorophenyl)-4-cyclopropylmethyl-1-methyl-4H-2,3,4,5,10b-pentaazabenz[e]azulene, 6-(4-chlorophenyl)-4-cyclohexylmethyl-1-methyl-4H-2,3,4,5,10b-pentaazabenz[e]azulene, 6-(4-chlorophenyl)-4-(2-cyclohexylethyl)-1-methyl-4H-2,3,4,5,10b-pentaazabenz[e]azulene, 6-(4-chlorophenyl)-1-methyl-4-(3-phenyl-2-propenyl)-4H-2,3,4,5,10b-pentaazabenz[e]azulene, 4-allyl-6-(4-chlorophenyl)-1-methyl-4H-2,3,4,5,10b-pentaazabenz[e]azulene, 6-(4-chlorophenyl)-1-methyl-4-(2-methyl-2-propenyl)-4H-2,3,4,5,10b-pentaazabenz[e]azulene, 6-(4-chlorophenyl)-4-(2-chloro-2-propenyl)-1-methyl-4H-2,3,4,5,10b-pentaazabenz[e]azulene, 4-(2-bromo-2-propenyl)-6-(4-chlorophenyl)-1-methyl-4H-2,3,4,5,10b-pentaazabenz[e]azulene, 6-(4-chlorophenyl)-4-(2,3-dichloro-2-propenyl)-1-methyl-4H-2,3,4,5,10b-pentaazabenz[e]azulene, 6-(4-chlorophenyl)-4-(3,4-dibenzyloxybenzyl)-1-methyl-4H-2,3,4,5,10b-pentaazabenz[e]azulene, 4-benzyloxymethyl-6-(4-chlorophenyl)-1-methyl-4H-2,3,4,5,10b-pentaazabenz[e]azulene, 6-(4-chlorophenyl)-1-methyl-4-(3-phenoxypropyl)-4H-2,3,4,5,10b-pentaazabenz[e]azulene, 6-(4-chlorophenyl)-4-(3,3-dichloro-2-propenyl)-1-methyl-4H-2,3,4,5,10b-pentaazabenz[e]azulene, 6-(4-chlorophenyl)-4-(4-methoxy-3-methylbenzyl)-1-methyl-4H-2,3,4,5,10b-pentaazabenz[e]azulene, 6-(4-chlorophenyl)-1-methyl-4-(pyridin-4-ylmethyl)-4H-2,3,4,5,10b-pentaazabenz[e]azulene, 6-(4-chlorophenyl)-1-methyl-4-(4-methylsulfonylbenzyl)-4H-2,3,4,5,10b-pentaazabenz[e]azulene, 6-(4-chlorophenyl)-1-methyl-4-(4-nitrobenzyl)-4H-2,3,4,5,10b-pentaazabenz[e]azulene, 6-(4-chlorophenyl)-4-(2,6-dichloropyridin-4-ylmethyl)-1-methyl-4H-2,3,4,5,10b-pentaazabenz[e]azulene, 6-(4-chlorophenyl)-4-(2,2,2-trifluoroethyl)-1-methyl-4H-2,3,4,5,10b-pentaazabenz[e]azulene, 6-(4-chlorophenyl)-4-(3,5-dinitrobenzyl)-1-methyl-4H-2,3,4,5,10b-pentaazabenz[e]azulene, 8-chloro-1-methyl-6-phenyl-4-(pyridin-4-ylmethyl)-4H-2,3,4,5,10b-pentaazabenz[e]azulene, 8-chloro-1-methyl-6-phenyl-4-(pyridin-3-ylmethyl)-4H-2,3,4,5,10b-pentaazabenz[e]azulene, 1-methyl-6-phenyl-4-(pyridin-3-ylmethyl)-4H-2,3,4,5,10b-pentaazabenz[e]azulene, 1-methyl-6-phenyl-4-(pyridin-4-ylmethyl)-4H-2,3,4,5,10b-pentaazabenz[e]azulene, 1,9-dimethyl-6-phenyl-4-(pyridin-3-ylmethyl)-4H-2,3,4,5,10b-pentaazabenz[e]azulene, 1,9-dimethyl-6-phenyl-4-(pyridin-4-ylmethyl)-4H-2,3,4,5,10b-pentaazabenz[e]azulene, 4-(3-cyanobenzyl)-1,9-dimethyl-6-phenyl-4H-2,3,4,5,10b-pentaazabenz[e]azulene, 1-methyl-8-nitro-6-phenyl-4-(pyridin-3-ylmethyl)-4H-2,3,4,5,10b-pentaazabenz[e]azulene, 1-methyl-8-nitro-6-phenyl-4-(pyridin-4-ylmethyl)-4H-2,3,4,5,10b-pentaazabenz[e]azulene, 1-methyl-6-(4-methylphenyl)-4-(pyridin-4-ylmethyl)-4H-2,3,4,5,10b-pentaazabenz[e]azulene, 4-(3-cyanobenzyl)-1-methyl-6-(4-methylphenyl)-4H-2,3,4,5,10b-pentaazabenz[e]azulene, 8-chloro-6-(2-chlorophenyl)-1-methyl-4-(pyridin-3-ylmethyl)-4H-2,3,4,5,10b-pentaazabenz[e]azulene, 8-chloro-6-(2-chlorophenyl)-1-methyl-4-(pyridin-4-ylmethyl)-4H-2,3,4,5,10b-pentaazabenz[e]azulene, 4-(4-chlorophenyl)-2,3,9-trimethyl-6-(pyridin-3-ylmethyl)-6H-5,6,7,8,9a-pentaazathien[2,3-e]azulene, 4-(4-chlorophenyl)-2,3,9-trimethyl-6-(pyridin-4-ylmethyl)-6H-5,6,7,8,9a-pentaazathien[2,3-e]azulene, 4-(4-chlorophenyl)-2-ethyl-9-methyl-6-(pyridin-3-ylmethyl)-6H-5,6,7,8,9a-pentaazathien[2,3-e]azulene, 4-(4-chlorophenyl)-2-ethyl-9-methyl-6-(pyridin-4-ylmethyl)-6H-5,6,7,8,9a-pentaazathien[2,3-e]azulene, 2,9-dimethyl-4-phenyl-6-(pyridin-3-ylmethyl)-6H-5,6,7,8,9a-pentaazathien[2,3-e]azulene, 2,9-dimethyl-4-phenyl-6-(pyridin-4-ylmethyl)-6H-5,6,7,8,9a-pentaazathien[2,3-e]azulene, 2,3,9-trimethyl-4-phenyl-6-(pyridin-3-ylmethyl)-6H-5,6,7,8,9a-pentaazathien[2,3-e]azulene, 2,3,9-trimethyl-4-phenyl-6-(pyridin-4-ylmethyl)-6H-5,6,7,8,9a-pentaazathien[2,3-e]azulene, 2-ethyl-9-methyl-4-phenyl-6-(pyridin-3-ylmethyl)-6H-5,6,7,8,9a-pentaazathien[2,3-e]azulene, 2-ethyl-9-methyl-4-phenyl-6-(pyridin-4-ylmethyl)-6H-5,6,7,8,9a-pentaazathien[2,3-e]azulene, 4-(4-methoxyphenyl)-2,3,9-trimethyl-6-(pyridin-3-ylmethyl)-6H-5,6,7,8,9a-pentaazathien[2,3-e]azulene, 4-(4-methoxyphenyl)-2,3,9-trimethyl-6-(pyridin-4-ylmethyl)-6H-5,6,7,8,9a-pentaazathien[2,3-e]azulene, 6-(4-chlorophenyl)-1-methyl-4-(2-nitrobenzyl)-4H-2,3,4,5,10b-pentaazabenz[e]azulene, 6-(4-chlorophenyl)-4-ethoxycarbonylmethyl-1-methyl-4H-2,3,4,5,10b-pentaazabenz[e]azulene,

[6-(4-chlorophenyl)-1-methyl-4H-2,3,4,5,10b-pentaazabenz[e]azulene-4-yl]acetic acid, 6-(4-chlorophenyl)-1-methyl-4-phenylcarbamoylmethyl-4H-2,3,4,5,10b-pentaazabenz[e]azulene, 6-(4-chlorophenyl)-1-methyl-4-(4-methylphenylcarbamoylmethyl)-4H-2,3,4,5,10b-pentaazabenz[e]azulene, 6-(4-chlorophenyl)-4-(2-methoxyphenylcarbamoylmethyl)-1-methyl-4H-2,3,4,5,10b-pentaazabenz[e]azulene, 6-(4-chlorophenyl)-4-(2,5-dimethoxyphenylcarbamoylmethyl)-1-methyl-4H-2,3,4,5,10b-pentaazabenz[e]azulene, 4-(4-chloro-2,5-dimethoxyphenylcarbamoylmethyl)-6-(4-chlorophenyl)-1-methyl-4H-2,3,4,5,10b-pentaazabenz[e]azulene, 6-(4-chlorophenyl)-1-methyl-4-(naphthalen-1-ylcarbamoylmethyl)-4H-2,3,4,5,10b-pentaazabenz[e]azulene, 6-(4-chlorophenyl)-1-methyl-4-(pyridin-3-ylcarbamoylmethyl)-4H-2,3,4,5,10b-pentaazabenz[e]azulene, 6-(4-chlorophenyl)-4-(cyclohexylcarbamoylmethyl)-1-methyl-4H-2,3,4,5,10b-pentaazabenz[e]azulene, 6-(4-chlorophenyl)-1-methyl-4-n-propylcarbamoylmethyl-4H-2,3,4,5,10b-pentaazabenz[e]azulene, 4-bromoacetyl-6-(4-chlorophenyl)-1-methyl-4H-2,3,4,5,10b-pentaazabenz[e]azulene, 6-(4-chlorophenyl)-4-(2-methoxyphenylaminoacetyl)-1-methyl-4H-2,3,4,5,10b-pentaazabenz[e]azulene, 6-(4-chlorophenyl)-1-methyl-4-phenylaminoacetyl-4H-2,3,4,5,10b-pentaazabenz[e]azulene, 6-(4-chlorophenyl)-1-methyl-4-(4-methylphenylaminoacetyl)-4H-2,3,4,5,10b-pentaazabenz[e]azulene, 6-(4-chlorophenyl)-4-(3-fluorophenylaminoacetyl)-1-methyl-4H-2,3,4,5,10b-pentaazabenz[e]azulene, 6-(4-chlorophenyl)-4-(2,5-dimethoxyphenylaminoacetyl)-1-methyl-4H-2,3,4,5,10b-pentaazabenz[e]azulene, 6-(4-chlorophenyl)-1-methyl-4-phenylthioacetyl-4H-2,3,4,5,10b-pentaazabenz[e]azulene, 6-(4-chlorophenyl)-1-methyl-4-phenylacetyl-4H-2,3,4,5,10b-pentaazabenz[e]azulene, 6-(4-chlorophenyl)-1-methyl-4-phenyloxalyl-4H-2,3,4,5,10b-pentaazabenz[e]azulene, 6-(4-chlorophenyl)-4-ethoxymethyl-1-methyl-4H-2,3,4,5,10b-pentaazabenz[e]azulene,

[6-(4-chlorophenyl)-1-methyl-4H-2,3,4,5,10b-pentaazabenz[e]azulene-4-ylmethyl]-phenylamine, 4-benzylcarbamoyl-6-(4-chlorophenyl)-1-methyl-4H-2,3,4,5,10b-pentaazabenz[e]azulene, 6-(4-chlorophenyl)-1-methyl-4-(3-methylphenylcarbamoyl)-4H-2,3,4,5,10b-pentaazabenz[e]azulene, 6-(4-chlorophenyl)-4-(4-hydroxybenzyl)-1-methyl-4H-2,3,4,5,10b-pentaazabenz[e]azulene, 6-(4-chlorophenyl)-4-(3,4-dihydroxybenzyl)-1-methyl-4H-2,3,4,5,10b-pentaazabenz[e]azulene, 6-(4-chlorophenyl)-4-(4-ethoxybenzyl)-1 methyl-4H-2,3,4,5,10b-pentaazabenz[e]azulene, 6-(4-chlorophenyl)-1-methyl-4-(4-methylsulfonylphenyl)hydroxymethyl-4H-2,3,4,5,10b-pentaazabenz[e]azulene, 4-(4-aminobenzyl)-6-(4-chlorophenyl)-1-methyl-4H-2,3,4,5,10b-pentaazabenz[e]azulene, 6-(4-chlorophenyl)-4-(4-formylaminobenzyl)-1-methyl-4H-2,3,4,5,10b-pentaazabenz[e]azulene, 4-(4-acetylaminobenzyl)-6-(4-chlorophenyl)-1-methyl-4H-2,3,4,5,10b-pentaazabenz[e]azulene, 6-(4-chlorophenyl)-4-(4-methylsulfonylaminobenzyl)-1 methyl-4H-2,3,4,5,10b-pentaazabenz[e]azulene, 4-[4-bis(methylsulfonyl)aminobenzyl]-6-(4-chlorophenyl)-4H-2,3,4,5,10b-pentaazabenz[e]azulene, 6-(4-chlorophenyl)-4-(4-dimethylaminobenzyl)-1-methyl-4H-2,3,4,5,10b-pentaazabenz[e]azulene, 6-(4-chlorophenyl)-4-(2-hydroxy-2-phenylethyl)-1-methyl-4H-2,3,4,5,10b-pentaazabenz[e]azulene, 6-(4-chlorophenyl)-4-(2-oxo-2-phenylethyl)-1-methyl-4H-2,3,4,5,10b-pentaazabenz[e]azulene, 6-(4-chlorophenyl)-1-methyl-4-[3-phenyl-2-(tetrahydropyran-2-yloxy)propyl]-4H-2, 3,4,5,10b-pentaazabenz[e]azulene, 6-(4-chlorophenyl)-4-[2-(2-methoxyphenyl)-2-(tetrahydropyran-2-yloxy)ethyl]-1-methyl-4H-2,3,4,5,10b-pentaazabenz[e]azulene, 6-(4-chlorophenyl)-4-(2-hydroxy-3-phenylpropyl)-1-methyl-4H-2,3,4,5,10b-pentaazabenz[e]azulene, 6-(4-chlorophenyl)-4-(2-oxo-3-phenylpropyl)-4H-2,3,4,5,10b-pentaazabenz[e]azulene, 6-(4-chlorophenyl)-4-[2-(4-chlorophenyl)-2-oxoethyl]-1-methyl-4H-2,3,4,5,10b-pentaazabenz[e]azulene, 6-(4-chlorophenyl)-1-methyl-4-[2-(4-methylphenyl)-2-oxoethyl]-4H-2,3,4,5,10b-pentaazabenz[e]azulene, 6-(4-chlorophenyl)-4-[2-(2-methoxyphenyl)-2-oxoethyl]-1-methyl-4H-2,3,4,5,10b-pentaazabenz[e]azulene, 6-(4-chlorophenyl)-4-[2-(2,5-dimethoxyphenyl)-2-oxoethyl]-1-methyl-4H-2, 3,4,5,10b-pentaazabenz[e]azulene, 6-(4-chlorophenyl)-4-[3-(2-methoxyphenyl)-2-oxopropyl]-1-methyl-4H-2,3,4,5,10b-pentaazabenz[e]azulene, 6-(4-chlorophenyl)-4-[3-(2,5-dimethoxyphenyl)-2-oxopropyl]-1-methyl-4H-2, 3,4,5,10b-pentaazabenz[e]azulene, 4-benzyl-6-(4-chlorophenyl)-1-methyl-4H-2,3,4,5,10b-pentaazabenz[e]azulene, and 6-(4-chlorophenyl)-4-(4-methoxybenzyl)-4H-3,4,5,10b-tetraazabenz[e]azulene, or a pharmaceutically acceptable salt thereof.

8. A triazepine compound of the formula [I']

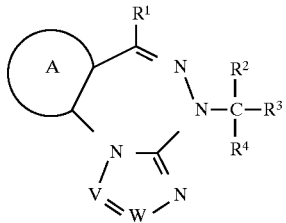

wherein $R^1$ is an optionally substituted aryl or an optionally substituted heteroaryl;

$R^2$ is a hydrogen atom, a hydroxy or a halogen atom;

$R^4$ is a hydrogen atom or a halogen atom, or $R^2$ and $R^4$ are combined together with the carbon atom to which they are bonded to form a carbonyl;

$R^3$ is a lower alkoxy, a cycloalkyl, an optionally substituted aryl, an optionally substituted heteroaryl, —$CR^5$=$CR^6R^7$ wherein $R^5$, $R^6$ and $R^7$ are the same or different and each is hydrogen atom, halogen atom, lower alkyl or optionally substituted aryl, a group of the formula

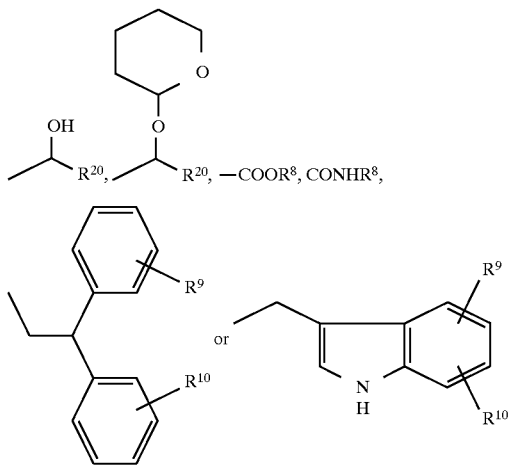

wherein $R^8$ is hydrogen atom, lower alkyl, cycloalkyl, optionally substituted aryl, aralkyl or optionally substituted heteroaryl, and $R^9$ and $R^{10}$ are the same or different and each is hydrogen atom, lower alkyl, lower alkoxy, hydroxy, halogen atom, nitro or amino, $R^{20}$ is optionally substituted aryl, aralkyl or optionally substituted heteroaryl, —X—Y wherein X is —$(CH_2)_m$— wherein m is an integer of 1 to 4, —CO—, —$COCH_2$—, —NH—, —$NHCH_2$—, —$CH_2NH$—, —$CH_2NHCO$—, —$OCH_2$—, —$(CH_2)_nO$— wherein n is an integer of 1 to 4, or —$CH_2S$—, and Y is halogen atom, cycloalkyl, optionally substituted aryl or optionally substituted heteroaryl, or —$OR^{18}$ wherein $R^{18}$ is optionally substituted aryl;

ring A is a ring selected from the group consisting of the following rings

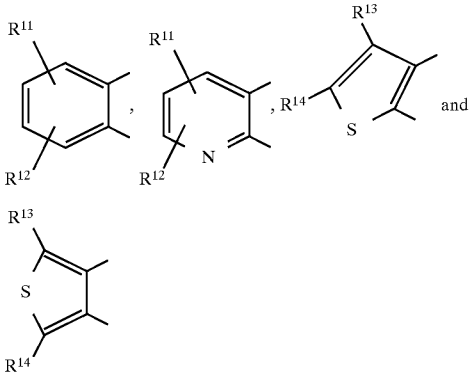

wherein $R^{11}$ and $R^{12}$ are the same or different and each is hydrogen atom, halogen atom, lower alkyl, a lower alkyl substituted by at least one member selected from the group consisting of halogen atom, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl and aralkyloxycarbonyl, lower alkenyl, aralkyl, aralkyl substituted by alkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl or aralkyloxycarbonyl, $R^{13}$ and $R^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and $$-V=W- \text{ is } -\underset{R^{19}}{\underset{|}{C}}=\overset{H}{C}-, -\underset{R^{15}}{\underset{|}{C}}=N- \text{ or } -N=N-$$

wherein $R^{15}$ is lower alkyl and $R^{19}$ is hydrogen atom or lower alkyl, or a pharmaceutically acceptable salt thereof; wherein the optionally substituted aryl is an aryl which may have one or more substituents selected from the group consisting of halogen atom, lower alkyl, lower alkoxy, aralkyloxy, methylenedioxy, haloalkyl, haloalkyloxy, halolalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the optionally substituted heteroaryl is an aromatic heterocyclic group selected from the group consisting of pyridyl, thienyl, thiazolyl and isoxazolyl, which may have one or more substituents selected from the group consisting of halogen atom, lower alkyl, lower alkoxy, aralkyloxy, methylenedioxy, haloalkyl, haloalkyloxy, haloalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the cyclic amino is a cyclic amino selected from the group consisting of pyrrolidinyl, piperidino, morpholino, thiomorpholino and piperazinyl, wherein lower alkyl or aralkyl may substitute the 4-position nitrogen atom of piperazinyl; and the cyclic aminocarbonyl is a cyclic aminocarbonyl selected from the group consisting of pyrrolidinylcarbonyl, piperidinocarbonyl, morpholinocarbonyl, thiomorpholinocarbonyl and piperazinylcarbonyl, wherein lower alkyl or aralkyl may substitute the 4-position nitrogen atom of piperazinylcarbonyl.

9. The triazepine compound of claim 8, wherein the ring A is

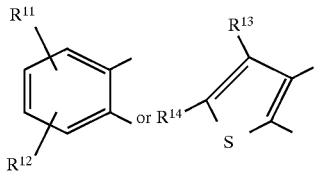

wherein $R^{11}$, $R^{12}$, $R^{13}$ and $R^{14}$ are as defined in claim 8, or a pharmaceutically acceptable salt thereof.

10. The triazepine compound of claim 9, wherein

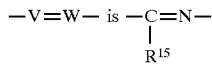

wherein $R^{15}$ is lower alkyl, or a pharmaceutically acceptable salt thereof.

11. The triazepine compound of claim 10, wherein $R^1$ is an optionally substituted aryl, or a pharmaceutically acceptable salt thereof.

12. The triazepine compound of claim 11, wherein $R^1$ is an optionally substituted aryl wherein the aryl is phenyl, or a pharmaceutically acceptable salt thereof.

13. The triazepine compound of claim 12, wherein $R^2$ and $R^4$ are both hydrogen atom, or a pharmaceutically acceptable salt thereof.

14. The triazepine compound of claim 13, wherein $R^3$ is pyridyl or an optionally substituted aryl wherein the aryl is phenyl, or a pharmaceutically acceptable salt thereof.

15. A triazepine compound selected from the group consisting of 6-(4-chlorophenyl)-4-(4-methoxybenzyl)-1-methyl-4H-2,3,4,5,10b-pentaazabenz[e]azulene, 6-(4-chlorophenyl)-4-(3,4-dimethoxybenzyl)-1-methyl-4H-2,3,4,5,10b-pentaazabenz[e]azulene, 4-(4-methoxybenzyl)-1-methyl-6-phenyl-4H-2,3,4,5,10b-pentaazabenz[e]azulene, 4-(4-methoxybenzyl)-1,9-dimethyl-6-phenyl-4H-2,3,4,5,10b-pentaazabenz[e]azulene, 8-chloro-4-(4-methoxybenzyl)-1-methyl-6-phenyl-4H-2,3,4,5,10b-pentaazabenz[e]azulene, 4-(4-methoxybenzyl)-1-methyl-8-nitro-6-phenyl-4H-2,3,4,5,10b-pentaazabenz[e]azulene, 4-(4-methoxybenzyl)-1-methyl-6-(4-methylphenyl)-4H-2,3,4,5,10b-pentaazabenz[e]azulene, 8-chloro-6-(2-chlorophenyl)-4-(4-methoxybenzyl)-1-methyl-4H-2,3,4,5,10b-pentaazabenz[e]azulene, 4-(4-chlorophenyl)-6-(4-methoxybenzyl)-2,3,9-trimethyl-6H-5,6,7,8,9a-pentaazathien[2,3-e]azulene, 4-(4-chlorophenyl)-2-ethyl-6-(4-methoxybenzyl)-9-methyl-6H-5,6,7,8,9a-pentaazathien[2,3-e]azulene, 6-(4-methoxybenzyl)-2,9-dimethyl-4-phenyl-6H-5,6,7,8,9a-pentaazathien[2,3-e]azulene, 6-(4-methoxybenzyl)-2,3,9-trimethyl-4-phenyl-6H-5,6,7,8,9a-pentaazathien[2,3-e]azulene, 2-ethyl-6-(4-methoxybenzyl)-9-methyl-4-phenyl-6H-5,6,7,8,9a-pentaazathien[2,3-e]azulene, 6-(4-methoxybenzyl)-4-(4-methoxyphenyl)-2,3,9-trimethyl-6H-5,6,7,8,9a-pentaazathien[2,3-e]azulene, 6-(4-chlorophenyl)-1-methyl-4-(pyridin-3-ylmethyl)-4H-2,3,4,5,10b-pentaazabenz[e]azulene, 4-(2-chlorophenyl)-2,3,9-trimethyl-6-(pyridin-4-ylmethyl)-6H-5,6,7,8,9a-pentaazathien[2,3-e]azulene, 6-(4-chlorophenyl)-4-(3-cyanobenzyl)-1-methyl-4H-2,3,4,5,10b-pentaazabenz[e]azulene, 6-(4-chlorophenyl)-4-(2-fluorobenzyl)-1-methyl-4H-2,3,4,5,10b-pentaazabenz[e]azulene, 6-(4-chlorophenyl)-4-(3-fluorobenzyl)-1-methyl-4H-2,3,4,5,10b-pentaazabenz[e]azulene, 6-(4-chlorophenyl)-4-(4-fluorobenzyl)-1-methyl-4H-2,3,4,5,10b-pentaazabenz[e]azulene, 6-(4-chlorophenyl)-4-(2,4-difluorobenzyl)-1-methyl-4H-2,3,4,5,10b-pentaazabenz[e]azulene, 6-(4-chlorophenyl)-4-(2,5-difluorobenzyl)-1-methyl-4H-2,3,4,5,10b-pentaazabenz[e]azulene, 6-(4-chlorophenyl)-4-(3,5-difluorobenzyl)-1-methyl-4H-2,3,4,5,10b-pentaazabenz[e]azulene, 6-(4-chlorophenyl)-4-(3,4-difluorobenzyl)-1-methyl-4H-2,3,4,5,10b-pentaazabenz[e]azulene, 6-(4-chlorophenyl)-1-methyl-4-(2-trifluoromethylbenzyl)-4H-2,3,4,5,10b-pentaazabenz[e]azulene, 6-(4-chlorophenyl)-1-methyl-4-(4-trifluoromethylbenzyl)-4H-2,3,4,5,10b-pentaazabenz[e]azulene, 6-(4-chlorophenyl)-1-methyl-4-(3-trifluoromethylbenzyl)-4H-2,3,4,5,10b-pentaazabenz[e]azulene, 6-(4-chlorophenyl)-1-methyl-4-(4-trifluoromethoxybenzyl)-4H-2,3,4,5,10b-pentaazabenz[e]azulene, 6-(4-chlorophenyl)-1-methyl-4-(3-nitrobenzyl)-4H-2,3,4,5,10b-pentaazabenz[e]azulene, 4-(2-chlorobenzyl-6-(4-chlorophenyl)-1-methyl- 4H-2,3,4,5,10b-pentaazabenz[e]azulene, 4-(3-chlorobenzyl)-6-(4-chlorophenyl)-1-methyl-4H-2,3,4,5,10b-pentaazabenz[e]azulene, 4-(4-chlorobenzyl)-6-(4-chlorophenyl)-1-methyl-4H-2,3,4,5,10b-pentaazabenz[e]azulene, 6-(4-chlorophenyl)-4-(2-cyanobenzyl)-1-methyl-4H-2,3,4,5,10b-pentaazabenz[e]azulene, 6-(4-chlorophenyl)-4-(4-cyanobenzyl)-1-methyl-4H-2,3,4,5,10b-pentaazabenz[e]azulene, 6-(4-chlorophenyl)-4-(2-methoxybenzyl)-1-methyl-4H-2,3,4,5,10b-pentaazabenz[e]azulene, 6-(4-chlorophenyl)-4-(3-methoxybenzyl)-1-methyl-4H-2,3,4,5,10b-pentaazabenz[e]azulene, 6-(4-chlorophenyl)-4-(4-methoxybenzyl)-1-methyl-4H-2,3,4,5,10b-pentaazabenz[e]azulene, 6-(4-chlorophenyl)-4-(2,5-dimethoxybenzyl)-1-methyl-4H-2,3,4,5,10b-pentaazabenz[e]azulene, 6-(4-chlorophenyl)-1-methyl-4-(3,4,5-trimethoxybenzyl)-4H-2,3,4,5,10b-pentaazabenz[e]azulene, 4-(5-acetyl-2-methoxybenzyl)-6-(4-chlorophenyl)-1-methyl-4H-2,3,4,5,10b-pentaazabenz[e]azulene, 6-(4-chlorophenyl)-1-methyl-4-(3,4-methylenedioxybenzyl)-4H-2,3,4,5,10b-pentaazabenz[e]azulene, 4-(2-chloro-4,5-methylenedioxybenzyl)-6-(4-chlorophenyl)-1-methyl-4H-2,3,4,5,10b-pentaazabenz[e]azulene, 6-(4-chlorophenyl)-4-(2-methoxy-5-nitrobenzyl)-1-methyl-4H-2,3,4,5,10b-pentaazabenz[e]azulene, 6-(4-chlorophenyl)-4-(4-methoxy-3-nitrobenzyl)-1-methyl-4H-2,3,4,5,10b-pentaazabenz[e]azulene, 4-(3-chloro-4-methoxybenzyl)-6-(4-chlorophenyl)-1-methyl-4H-2,3,4,5,10b-pentaazabenz[e]azulene, 6-(4-chlorophenyl)-4-(3,5-dichloro-4-methoxybenzyl)-1-methyl-4H-2,3,4,5,10b-pentaazabenz[e]azulene, 6-(4-chlorophenyl)-1-methyl-4-(2-methylbenzyl)-4H-2,3,4,5,10b-pentaazabenz[e]azulene, 6-(4-chlorophenyl)-1-methyl-4-(3-methylbenzyl)-4H-2,3,4,5,10b-pentaazabenz[e]azulene, 6-(4-chlorophenyl)-1-methyl-4-(4-methylbenzyl)-4H-2,3,4,5,10b-pentaazabenz[e]azulene, 4-(4-tert-butylbenzyl)-6-(4-chlorophenyl)-1-methyl-4H-2,3,4,5,10b-pentaazabenz[e]azulene, 6-(4-chlorophenyl)-1-methyl-4-(naphthalen-1-ylmethyl)-4H-2,3,4,5,10b-pentaazabenz[e]azulene, 6-(4-chlorophenyl)-1-methyl-4-(naphthalen-2-ylmethyl)-4H-2,3,4,5,10b-pentaazabenz[e]azulene, 4-(4-benzyloxybenzyl)-6-(4-chlorophenyl)-1-methyl-4H-2,3,4,5,10b-pentaazabenz[e]azulene, 4-benzyl-6-(4-chlorophenyl)-1-methyl-4H-2,3, 4,5,10b-pentaazabenz[e]azulene, 6-(4-chlorophenyl)-1-methyl-4-(4-phenylbenzyl)-4H-2,3,4,5,10b-pentaazabenz[e]azulene, 4-(4-chlorophenoxymethyl)-6-(4-chlorophenyl)-1-methyl-4H-2,3,4,5,10b-pentaazabenz[e]azulene, 6-(4-chlorophenyl)-1-methyl-4-(pyridin-2-ylmethyl)-4H-2,3, 4,5,10b-pentaazabenz[e]azulene, 6-(4-chlorophenyl)-1-methyl-4-(pyridin-3-ylmethyl)-4H-2,3,4,5,10b-pentaazabenz[e]azulene, 6-(4-chlorophenyl)-4-[2-(indol-3-yl)ethyl]-1-methyl-4H-2,3,4,5,10b-pentaazabenz[e]azulene, 6-(4-chlorophenyl)-4-(2-methyl-1,3-thiazol-4-ylmethyl)-1-methyl-4H-2,3,4,5,10b-pentaazabenz[e]azulene, 6-(4-chlorophenyl)-4-(5-chlorothiophen-2-ylmethyl)-1-methyl-4H-2,3,4,5,10b-pentaazabenz[e]azulene, 6-(4-chlorophenyl)-1-methyl-4-(3,5-dimethylisoxazol-4-ylmethyl)-4H-2,3,4,5,10b-pentaazabenz[e]azulene, 6-(4-chlorophenyl)-1-methyl-4-phenethyl-4H-2,3,4,5,10b-pentaazabenz[e]azulene, 6-(4-chlorophenyl)-1-methyl-4-(3-phenylpropyl)-4H-2,3,4,5,10b-pentaazabenz[e]azulene, 6-(4-chlorophenyl)-4-(3,3-diphenylpropyl)-1-methyl-4H-2,3,4,5,10b-pentaazabenz[e]azulene, 6-(4-chlorophenyl)-4-cyclopropylmethyl-1-methyl-4H-2,3,4,5,10b-pentaazabenz[e]azulene, 6-(4-chlorophenyl)-4-cyclohexylmethyl-1-methyl-4H-2,3,4,5,10b-pentaazabenz[e]azulene, 6-(4-chlorophenyl)-4-(2-cyclohexylethyl)-1-methyl-4H-2,3,4,5,10b-pentaazabenz[e]azulene, 6-(4-chlorophenyl)-1-methyl-4-(3-phenyl-2-propenyl)-4H-2,3,4,5,10b-pentaazabenz[e]azulene, 4-allyl-6-(4-chlorophenyl)-1-methyl-4H-2,3,4,5,10b-pentaazabenz[e]azulene, 6-(4-chlorophenyl)-1-methyl-4-(2-methyl-2-propenyl)-4H-2, 3,4,5,10b-pentaazabenz[e]azulene, 6-(4-chlorophenyl)-4-(2-chloro-2-propenyl)-1-methyl-4H-2, 3,4,5,10b-pentaazabenz[e]azulene, 4-(2-bromo-2-propenyl)-6-(4-chlorophenyl)-1-methyl-4H-2,3,4,5,10b-pentaazabenz[e]azulene, 6-(4-chlorophenyl)-4-(2,3-dichloro-2-propenyl)-1-methyl-4H-2,3,4,5,10b-pentaazabenz[e]azulene, 6-(4-chlorophenyl)-4-(3, 4-dibenzyloxybenzyl)-1-methyl-4H-2,3,4,5,10b-pentaazabenz[e]azulene, 4-benzyloxymethyl-6-(4-chlorophenyl)-1-methyl-4H-2,3,4,5,10b-pentaazabenz[e]azulene, 6-(4-chlorophenyl)-1-methyl-4-(3-phenoxypropyl)-4H-2,3,4,5,10b-pentaazabenz[e]azulene, 6-(4-chlorophenyl)-4-(3,3-dichloro-2-propenyl)-1-methyl-4H-2,3,4,5,10b-pentaazabenz[e]azulene, 6-(4-chlorophenyl)-4-(4-methoxy-3-methylbenzyl)-1-methyl-4H-2,3,4,5,10b-pentaazabenz[e]azulene, 6-(4-chlorophenyl)-1-methyl-4-(pyridin-4-ylmethyl)-4H-2,3,4,5,10b-pentaazabenz[e]azulene, 6-(4-chlorophenyl)-1-methyl-4-(4-methylsulfonylbenzyl)-4H-2,3,4,5,10b-pentaazabenz[e]azulene, 6-(4-chlorophenyl)-1-methyl-4-(4-nitrobenzyl)-4H-2,3,4,5,10b-pentaazabenz[e]azulene, 6-(4-chlorophenyl)-4-(2,6-dichloropyridin-4-ylmethyl)-1-methyl-4H-2,3,4,5,10b-pentaazabenz[e]azulene, 6-(4-chlorophenyl)-4-(2,2,2-trifluoroethyl)-1-methyl-4H-2,3,4,5,10b-pentaazabenz[e]azulene, 6-(4-chlorophenyl)-4-(3,5-dinitrobenzyl)-1-methyl-4H-2,3,4,5,10b-pentaazabenz[e]azulene, 8-chloro-1-methyl-6-phenyl-4-(pyridin-4-ylmethyl)-4H-2,3,4,5,10b-pentaazabenz[e]azulene, 8-chloro-1-methyl-6-phenyl-4-(pyridin-3-ylmethyl)-4H-2,3,4,5,10b-pentaazabenz[e]azulene, 1-methyl-6-phenyl-4-(pyridin-3-ylmethyl)-4H-2,3,4,5,10b-pentaazabenz[e]azulene, 1-methyl-6-phenyl-4-(pyridin-4-ylmethyl)-4H-2,3,4,5,10b-pentaazabenz[e]azulene, 1,9-dimethyl-6-phenyl-4-(pyridin-3-ylmethyl)-4H-2, 3,4,5,10b-pentaazabenz[e]azulene, 1,9-dimethyl-6-phenyl-4-(pyridin-4-ylmethyl)-4H-2, 3,4,5,10b-pentaazabenz[e]azulene, 4-(3-cyanobenzyl)-1,9-dimethyl-6-phenyl-4H-2,3, 4,5, 10b-pentaazabenz[e]azulene, 1-methyl-8-nitro-6-phenyl-4-(pyridin-3-ylmethyl)-4H-2, 3,4,5,10b-pentaazabenz[e]azulene, 1-methyl-8-nitro-6-phenyl-4-(pyridin-4-ylmethyl)-4H-2, 3,4,5,10b-pentaazabenz[e]azulene, 1-methyl-6-(4-methylphenyl)-4-(pyridin-4-ylmethyl)-4H-2, 3,4,5,10b-pentaazabenz[e]azulene, 4-(3-cyanobenzyl)-1-methyl-6-(4-methylphenyl)-4H-2, 3,4,5,10b-pentaazabenz[e]azulene, 8-chloro-6-(2-chlorophenyl)-1-methyl-4-(pyridin-3-ylmethyl)-4H-2,3,4,5,10b-pentaazabenz[e]azulene, 8-chloro-6-(2-chlorophenyl)-1-methyl-4-(pyridin-4-ylmethyl)-4H-2,3,4,5,10b-pentaazabenz[e]azulene, 4-(4-chlorophenyl)-2,3,9-trimethyl-6-(pyridin-3-ylmethyl)-6H-5,6,7,8,9a-pentaazathien[2,3-e]azulene, 4-(4-chlorophenyl)-2,3,9-trimethyl-6-(pyridin-4-ylmethyl)-6H-5,6,7,8,9a-pentaazathien[2,3-e]azulene, 4-(4-chlorophenyl)-2-ethyl-9-methyl-6-(pyridin-3-ylmethyl)-6H-5,6,7,8,9a-pentaazathien[2,3-e]azulene, 4-(4-chlorophenyl)-2-ethyl-9-methyl-6-(pyridin-4-ylmethyl)-6H-5,6,7,8,9a-pentaazathien[2,3-e]azulene, 2,9-dimethyl-4-phenyl-6-(pyridin-3-ylmethyl)-6H-5,6,7, 8,9a-pentaazathien[2,3-e]azulene, 2, 9-dimethyl-4-phenyl-6-(pyridin-4-ylmethyl)-6H-5,6,7, 8,9a-pentaazathien[2,3-e]azulene, 2,3,9-trimethyl-4-phenyl-6-(pyridin-3-ylmethyl)-6H-5,6, 7,8,9a-pentaazathien[2,3-e]azulene, 2,3,9-trimethyl-4-phenyl-6-(pyridin-4-ylmethyl)-6H-5,6, 7,8,9a-pentaazathien[2,3-e]azulene, 2-ethyl-9-methyl-4-phenyl-6-(pyridin-3-ylmethyl)-6H-5, 6,7,8, 9a-pentaazathien[2,3-e]azulene, 2-ethyl-9-methyl-4-phenyl-6-(pyridin-4-ylmethyl)-6H-5, 6,7,8,9a-pentaazathien[2,3-e]azulene, 4-(4-methoxyphenyl)-2,3,9-trimethyl-6-(pyridin-3-ylmethyl)-6H-5,6,7,8,9a-pentaazathien[2,3-e]azulene, 4-(4-methoxyphenyl)-2,3,9-trimethyl-6-(pyridin-4-ylmethyl)-6H-5,6,7,8,9a-pentaazathien[2,3-e]azulene, 6-(4-chlorophenyl)-1-methyl-4-(2-nitrobenzyl)-4H-2,3,4, 5,10b-pentaazabenz[e]azulene, 6-(4-chlorophenyl)-4-ethoxycarbonylmethyl-1-methyl-4H-2,3,4,5,10b-pentaazabenz[e]azulene,

[6-(4-chlorophenyl)-1-methyl-4H-2,3,4,5,10b-pentaazabenz[e]azulene-4-yl]acetic acid, 6-(4-chlorophenyl)-1-methyl-4-phenylcarbamoylmethyl-4H-2, 3,4,5,10b-pentaazabenz[e]azulene, 6-(4-chlorophenyl)-1-methyl-4-(4-methylphenylcarbamoylmethyl)-4H-2,3,4,5,10b-pentaazabenz[e]azulene, 6-(4-chlorophenyl)-4-(2-methoxyphenylcarbamoylmethyl)-1-methyl-4H-2,3,4, 5,10b-pentaazabenz[e]azulene, 6-(4-chlorophenyl)-4-(2,5-dimethoxyphenylcarbamoylmethyl)-1-methyl-4H-2, 3,4,5, 10b-pentaazabenz[e]azulene, 4-(4-chloro-2,5-dimethoxyphenylcarbamoylmethyl)-6-(4-chlorophenyl)-1-methyl-4H-2,3,4,5,10b-pentaazabenz[e]azulene, 6-(4-chlorophenyl)-1-methyl-4-(naphthalen-1-ylcarbamoylmethyl)-4H-2,3,4,5,10b-pentaazabenz[e]azulene, 6-(4-chlorophenyl)-1-methyl-4-(pyridin-3-ylcarbamoylmethyl)-4H-2,3,4,5,10b-pentaazabenz[e]azulene, 6-(4-chlorophenyl)-4-(cyclohexylcarbamoylmethyl)-1-methyl-4H-2,3,4,5,10b-pentaazabenz[e]azulene, 6-(4-chlorophenyl)-1-methyl-4-n-propylcarbamoylmethyl-4H-2,3,4,5,10b-pentaazabenz[e]azulene, 4-bromoacetyl-6-(4-chlorophenyl)-1-methyl-4H-2,3,4,5, 10b-pentaazabenz[e]azulene, 6-(4-chlorophenyl)-4-(2-methoxyphenylaminoacetyl)-1-methyl-4H-2,3,4,5,10b-pentaazabenz[e]azulene, 6-(4-chlorophenyl)-1-methyl-4-phenylaminoacetyl-4H-2, 3,4,5,10b-pentaazabenz[e]azulene, 6-(4-chlorophenyl)-1-methyl-4-(4-methylphenylaminoacetyl)-4H-2,3,4,5,10b-pentaazabenz[e]azulene, 6-(4-chlorophenyl)-4-(3-fluorophenylaminoacetyl)-1-methyl-4H-2,3,4,5,10b-pentaazabenz[e]azulene, 6-(4-chlorophenyl)-4-(2,5-dimethoxyphenylaminoacetyl)-1-methyl-4H-2,3,4,5,10b-pentaazabenz[e]azulene, 6-(4-chlorophenyl)-1-methyl-4-phenylthioacetyl-4H-2,3, 4,5,10b-pentaazabenz[e]azulene, 6-(4-chlorophenyl)-1-methyl-4-phenylacetyl-4H-2, 3,4,5, 10b-pentaazabenz[e]azulene, 6-(4-chlorophenyl)-1-methyl-4-phenyloxalyl-4H-2,3,4,5, 10b-pentaazabenz[e]azulene, 6-(4-chlorophenyl)-4-ethoxymethyl-1-methyl-4H-2,3,4, 5,10b-pentaazabenz[e]azulene,

[6-(4-chlorophenyl)-1-methyl-4H-2,3,4,5,10b-pentaazabenz[e]azulene-4-ylmethyl]-phenylamine, 4-benzylcarbamoyl-6-(4-chlorophenyl)-1-methyl-4H-2,3, 4,5,10b-pentaazabenz[e]azulene, 6-(4-chlorophenyl)-1-methyl-4-(3-methylphenylcarbamoyl)-4H-2,3,4,5,10b-pentaazabenz[e]azulene, 6-(4-chlorophenyl)-4-(4-hydroxybenzyl)-1-methyl-4H-2, 3,4,5,10b-pentaazabenz[e]azulene, 6-(4-chlorophenyl)-4-(3,4-dihydroxybenzyl)-1-methyl-4H-2,3,4,5,10b-pentaazabenz[e]azulene, 6-(4-chlorophenyl)-4-(4-ethoxybenzyl)-1-methyl-4H-2,3, 4,5,10b-pentaazabenz[e]azulene, 6-(4-chlorophenyl)-1-methyl-4-(4-methylsulfonylphenyl) hydroxymethyl-4H-2,3,4,5,10b-pentaazabenz[e] azulene, 4-(4-aminobenzyl)-6-(4-chlorophenyl)-1-methyl-4H-2, 3,4,5,10b-pentaazabenz[e]azulene, 6-(4-chlorophenyl)-4-(4-formylaminobenzyl)-1-methyl-4H-2,3,4,5,10b-pentaazabenz[e]azulene, 4-(4-acetylaminobenzyl)-6-(4-chlorophenyl)-1-methyl-4H-2, 3,4,5,10b-pentaazabenz[e]azulene, 6-(4-chlorophenyl)-4-(4-methylsulfonylaminobenzyl)-1-methyl-4H-2,3,4,5,10b-pentaazabenz[e]azulene, 4-[4-bis(methylsulfonyl)aminobenzyl]-6-(4-chlorophenyl)-4H-2,3,4,5,10b-pentaazabenz[e] azulene, 6-(4-chlorophenyl)-4-(4-dimethylaminobenzyl)-1-methyl-4H-2,3,4,5,10b-pentaazabenz[e]azulene, 6-(4-chlorophenyl)-4-(2-hydroxy-2-phenylethyl)-1-methyl-4H-2,3,4,5,10b-pentaazabenz[e]azulene, 6-(4-chlorophenyl)-4-(2-oxo-2-phenylethyl)-1-methyl-4H-2,3,4,5,10b-pentaazabenz[e]azulene, 6-(4-chlorophenyl)-1-methyl-4-[3-phenyl-2-(tetrahydropyran-2-yloxy)propyl]-4H-2,3,4,5,10b-pentaazabenz[e]azulene, 6-(4-chlorophenyl)-4-[2-(2-methoxyphenyl)-2-(tetrahydropyran-2-yloxy)ethyl]-1-methyl-4H-2,3,4,5,10b-pentaazabenz[e]azulene, 6-(4-chlorophenyl)-4-(2-hydroxy-3-phenylpropyl)-1-methyl-4H-2,3,4,5,10b-pentaazabenz[e]azulene, 6-(4-chlorophenyl)-4-(2-oxo-3-phenylpropyl)-1-methyl-4H-2,3,4,5,10b-pentaazabenz[e]azulene, 6-(4-chlorophenyl)-4-[2-(4-chlorophenyl)-2-oxoethyl]-1-methyl-4H-2,3,4,5,10b-pentaazabenz[e]azulene, 6-(4-chlorophenyl)-1-methyl-4-[2-(4-methylphenyl)-2-oxoethyl]-4H-2,3,4,5,10b-pentaazabenz[e]azulene, 6-(4-chlorophenyl)-4-[2-(2-methoxyphenyl)-2-oxoethyl]-1-methyl-4H-2,3,4,5,10b-pentaazabenz[e]azulene, 6-(4-chlorophenyl)-4-[2-(2,5-dimethoxyphenyl)-2-oxoethyl]-1-methyl-4H-2,3,4,5,10b-pentaazabenz[e]azulene, 6-(4-chlorophenyl)-4-[3-(2-methoxyphenyl)-2-oxopropyl]-1-methyl-4H-2,3,4,5,10b-pentaazabenz[e]azulene, 6-(4-chlorophenyl)-4-[3-(2,5-dimethoxyphenyl)-2-oxopropyl]-1-methyl-4H-2,3,4,5,10b-pentaazabenz[e]azulene, 4-benzyl-6-(4-chlorophenyl)-1-methyl-4H-2,3,4,5,10b-pentaazabenz[e]azulene, and 6-(4-chlorophenyl)-4-(4-methoxybenzyl)-4H-3,4,5,10b-tetraazabenz[e]azulene, or a pharmaceutically acceptable salt thereof.

16. A pharmaceutical composition comprising a triazepine compound of claim 8 having the formula [I']

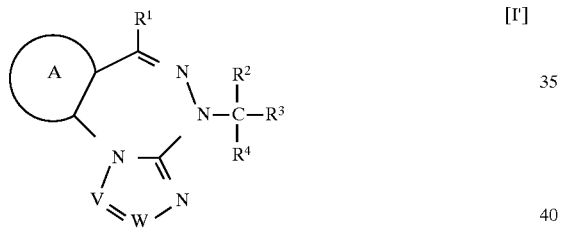

wherein $R^1$, $R^2$, $R^3$, $R^4$, ring A and —V=W— are as defined in claim 8, or a pharmaceutically acceptable salt thereof, and a pharmaceutically acceptable carrier.

17. The pharmaceutical composition of claim 16, wherein, in the formula [I'], the ring A is

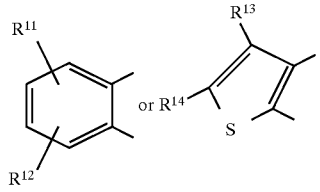

wherein $R^{11}$, $R^{12}$, $R^{13}$ and $R^{14}$ are as defined in claim 16.

18. The pharmaceutical composition of claim 17, wherein, in the formula [I']

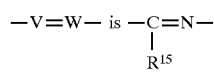

wherein $R^{15}$ is a lower alkyl.

19. The pharmaceutical composition of claim 18, wherein, in the formula [I'], $R^1$ is an optionally substituted aryl.

20. The pharmaceutical composition of claim 19, wherein, in the formula [I'], $R^1$ is an optionally substituted aryl wherein the aryl is phenyl.

21. The pharmaceutical composition of claim 20, wherein, in the formula [I'], $R^2$ and $R^4$ are both hydrogen atom.

22. The pharmaceutical composition of claim 21, wherein, in the formula [I'], $R^3$ is pyridyl or an optionally substituted aryl wherein the aryl is phenyl.

23. A pharmaceutical composition comprising a triazepine compound selected from the group consisting of the compounds of claim 5, or a pharmaceutically acceptable salt thereof, and a pharmaceutically acceptable carrier.

24. A triazepinethione compound of the formula [II']

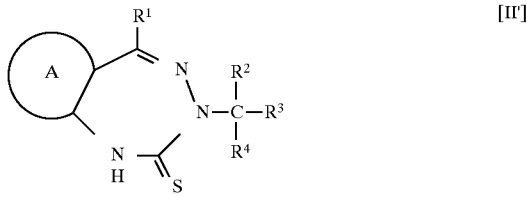

wherein $R^1$ is an optionally substituted aryl or an optionally substituted heteroaryl;

$R^2$ is a hydrogen atom, a hydroxy or a halogen atom;

$R^4$ is a hydrogen atom or a halogen atom, or $R^2$ and $R^4$ are combined together with the carbon atom to which they are bonded to form a carbonyl;

$R^3$ is a lower alkoxy, a cycloalkyl, an optionally substituted aryl, an optionally substituted heteroaryl, —CR$^5$=CR$^6$R$^7$ wherein $R^5$, $R^6$ and $R^7$ are the same or different and each is hydrogen atom, halogen atom, lower alkyl or optionally substituted aryl, a group of the formula

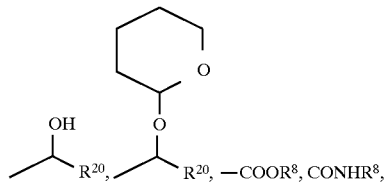

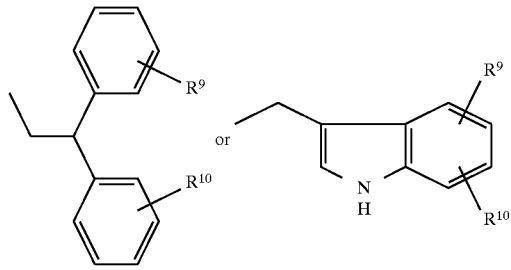

wherein $R^8$ is hydrogen atom, lower alkyl, cycloalkyl, optionally substituted aryl, aralkyl or optionally substituted heteroaryl, and $R^9$ and $R^{10}$ are the same or different and each is hydrogen atom, lower alkyl, lower alkoxy, hydroxy, halogen atom, nitro or amino, $R^{20}$ is optionally substituted aryl, aralkyl or optionally substituted heteroaryl, —X—Y wherein X is —(CH$_2$)$_m$— wherein m is an integer of 1 to 4, —CO—, —COCH$_2$—, —NH—, —NHCH$_2$—, —CH$_2$NH—, —CH$_2$NHCO—, —OCH$_2$—, —(CH$_2$)$_n$O— wherein n is an integer of 1 to 4, or —CH$_2$S—, and Y is halogen atom, cycloalkyl, optionally substituted aryl or optionally substituted heteroaryl, or —OR$^{18}$ wherein R$^{18}$ is optionally substituted aryl;

ring A is a ring selected from the group consisting of the following rings

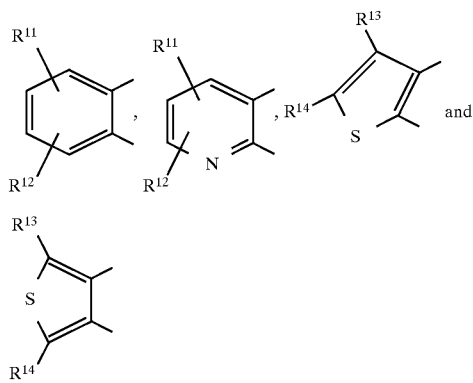

wherein R$^{11}$ and R$^{12}$ are the same or different and each is hydrogen atom, halogen atom, lower alkyl, a lower alkyl substituted by at least one member selected from the group consisting of halogen atom, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl and aralkyloxycarbonyl, lower alkenyl, aralkyl, aralkyl substituted by alkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl or aralkyloxycarbonyl, R$^{13}$ and R$^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and

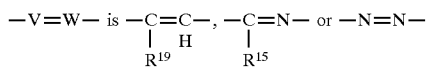

wherein R$^{15}$ is lower alkyl and R$^{19}$ is hydrogen atom or lower alkyl, or a salt thereof; wherein the optionally substituted aryl is an aryl which may have one or more substituents selected from the group consisting of halogen atom, lower alkyl, lower alkoxy, aralkyloxy, methylenedioxy, haloalkyl, haloalkyloxy, halolalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the optionally substituted heteroaryl is an aromatic heterocyclic group selected from the group consisting of pyridyl, thienyl, thiazolyl and isoxazolyl, which may have one or more substituents selected from the group consisting of halogen atom, lower alkyl, lower alkoxy, aralkyloxy, methylenedioxy, haloalkyl, haloalkyloxy, haloalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the cyclic amino is a cyclic amino selected from the group consisting of pyrrolidinyl, piperidino, morpholino, thiomorpholino and piperazinyl, wherein lower alkyl or aralkyl may substitute the 4-position nitrogen atom of piperazinyl; and the cyclic aminocarbonyl is a cyclic aminocarbonyl selected from the group consisting of pyrrolidinylcarbonyl, piperidinocarbonyl, morpholinocarbonyl, thiomorpholinocarbonyl and piperazinylcarbonyl, wherein lower alkyl or aralkyl may substitute the 4-position nitrogen atom of piperazinylcarbonyl.

25. The triazepinethione compound of claim 24, wherein the ring A is

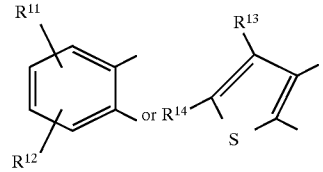

wherein R$^{11}$, R$^{12}$, R$^{13}$ and R$^{14}$ are as defined in claim 24, R$^1$ is an optionally substituted aryl wherein the aryl is phenyl, and R$^2$ and R$^4$ are both hydrogen atom, or a salt thereof.

26. An alkylthiotriazepine compound of the formula [III']

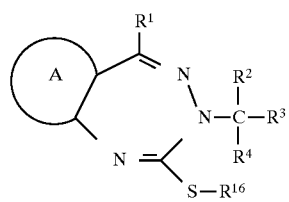

wherein

R$^1$ is an optionally substituted aryl or an optionally substituted heteroaryl;

R$^2$ is a hydrogen atom, a hydroxy or a halogen atom;

R$^4$ is a hydrogen atom or a halogen atom, or R$^2$ and R$^4$ are combined together with the carbon atom to which they are bonded to form a carbonyl;

R$^3$ is a lower alkoxy, a cycloalkyl, an optionally substituted aryl, an optionally substituted heteroaryl, —CR$^5$=CR$^6$R$^7$ wherein R$^5$, R$^6$ and R$^7$ are the same or different and each is hydrogen atom, halogen atom, lower alkyl or optionally substituted aryl, a group of the formula

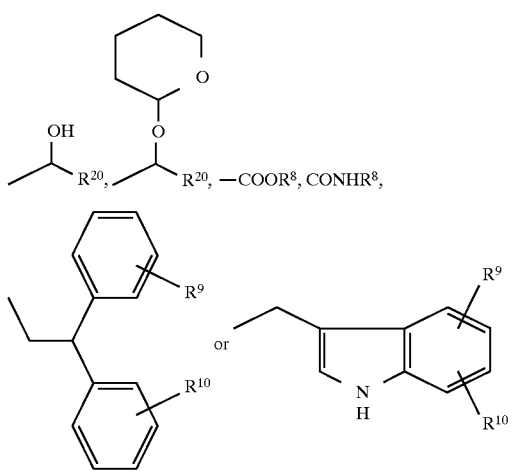

wherein R⁸ is hydrogen atom, lower alkyl, cycloalkyl, optionally substituted aryl, aralkyl or optionally substituted heteroaryl, and R⁹ and R¹⁰ are the same or different and each is hydrogen atom, lower alkyl, lower alkoxy, hydroxy, halogen atom, nitro or amino, R²⁰ is optionally substituted aryl, aralkyl or optionally substituted heteroaryl, —X—Y wherein X is —(CH₂)$_m$— wherein m is an integer of 1 to 4, —CO—, —COCH₂—, —NH—, —NHCH₂—, —CH₂NH—, —CH₂NHCO—, —OCH₂—, —(CH₂)$_n$O— wherein n is an integer of 1 to 4, or —CH₂S—, and Y is halogen atom, cycloalkyl, optionally substituted aryl or optionally substituted heteroaryl, or —OR¹⁸ wherein R¹⁸ is optionally substituted aryl;

ring A is a ring selected from the group consisting of the following rings

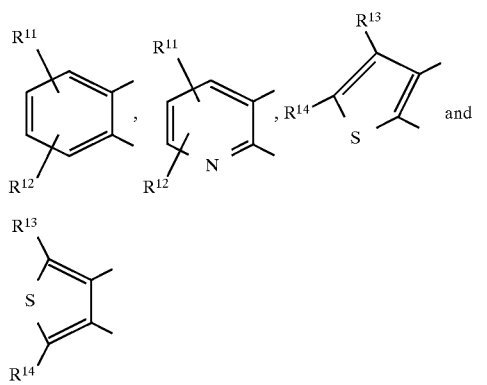

wherein R¹¹ and R¹² are the same or different and each is hydrogen atom, halogen atom, lower alkyl, a lower alkyl substituted by at least one member selected from the group consisting of halogen atom, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl and aralkyloxycarbonyl, lower alkenyl, aralkyl, aralkyl substituted by alkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl or aralkyloxycarbonyl, R¹³ and R¹⁴ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and

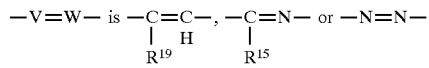

wherein R¹⁵ and R¹⁶ are each lower alkyl and R¹⁹ is hydrogen atom or lower alkyl, or a salt thereof; wherein the optionally substituted aryl is an aryl which may have one or more substituents selected from the group consisting of halogen atom, lower alkyl, lower alkoxy, aralkyloxy, methylenedioxy, haloalkyl, haloalkyloxy, halolalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the optionally substituted heteroaryl is an aromatic heterocyclic group selected from the group consisting of pyridyl, thienyl, thiazolyl and isoxazolyl, which may have one or more substituents selected from the group consisting of halogen atom, lower alkyl, lower alkoxy, aralkyloxy, methylenedioxy, haloalkyl, haloalkyloxy, haloalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the cyclic amino is a cyclic amino selected from the group consisting of pyrrolidinyl, piperidino, morpholino, thiomorpholino and piperazinyl, wherein lower alkyl or aralkyl may substitute the 4-position nitrogen atom of piperazinyl; and the cyclic aminocarbonyl is a cyclic aminocarbonyl selected from the group consisting of pyrrolidinylcarbonyl, piperidinocarbonyl, morpholinocarbonyl, thiomorpholinocarbonyl and piperazinylcarbonyl, wherein lower alkyl or aralkyl may substitute the 4-position nitrogen atom of piperazinylcarbonyl.

27. The alkylthiotriazepine compound of claim 26, wherein the ring A is

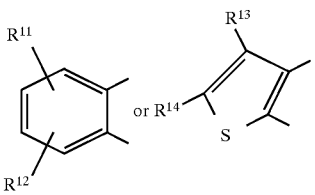

wherein $R^{11}$, $R^{12}$, $R^{13}$ and $R^{14}$ are as defined in claim 26, $R^1$ is an optionally substituted aryl wherein the aryl is phenyl, and $R^2$ and $R^4$ are both hydrogen atom, or a salt thereof.

28. An acylhydrazotriazepine compound of the formula [IV']

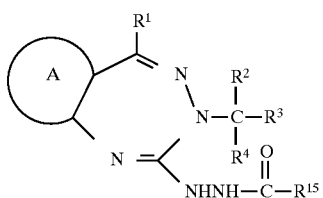

wherein

R' is an optionally substituted aryl or an optionally substituted heteroaryl;

$R^2$ is a hydrogen atom, a hydroxy or a halogen atom;

$R^4$ is a hydrogen atom or a halogen atom, or $R^2$ and $R^4$ are combined together with the carbon atom to which they are bonded to form a carbonyl;

$R^3$ is a lower alkoxy, a cycloalkyl, an optionally substituted aryl, an optionally substituted heteroaryl, —$CR^5$=$CR^6R^7$ wherein $R^5$, $R^6$ and $R^7$ are the same or different and each is hydrogen atom, halogen atom, lower alkyl or optionally substituted aryl, a group of the formula

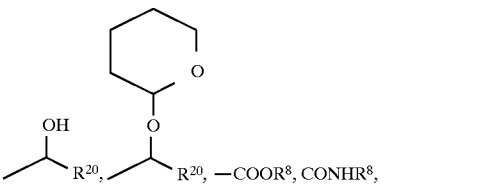

wherein $R^8$ is hydrogen atom, lower alkyl, cycloalkyl, optionally substituted aryl, aralkyl or optionally substituted heteroaryl, and $R^9$ and $R^{10}$ are the same or different and each is hydrogen atom, lower alkyl, lower alkoxy, hydroxy, halogen atom, nitro or amino, $R^{20}$ is optionally substituted aryl, aralkyl or optionally substituted heteroaryl, —X—Y wherein X is —$(CH_2)_m$— wherein m is an integer of 1 to 4, —CO—, —COCH$_2$—, —NH—, —NHCH$_2$—, —CH$_2$NH—, —CH$_2$NHCO—, —OCH$_2$—, —$(CH_2)_n$O— wherein n is an integer of 1 to 4, or —CH$_2$S—, and Y is halogen atom, cycloalkyl, optionally substituted aryl or optionally substituted heteroaryl, or —$OR^{18}$ wherein $R^{18}$ is optionally substituted aryl;

ring A is a ring selected from the group consisting of the following rings

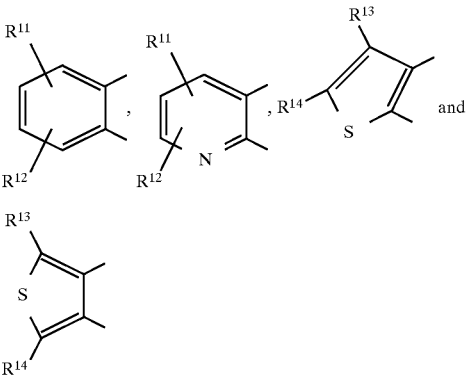

wherein $R^{11}$ and $R^{12}$ are the same or different and each is hydrogen atom, halogen atom, lower alkyl, a lower alkyl substituted by at least one member selected from the group consisting of halogen atom, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl and aralkyloxycarbonyl, lower alkenyl, aralkyl, aralkyl substituted by alkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl or aralkyloxycarbonyl, $R^{13}$ and $R^{14}$ are the same or different and each is hydrogen atom, halogen atom, lower alkyl, lower alkenyl, lower alkynyl, haloalkyl, lower alkoxy, nitro, amino, amino substituted by lower alkyl, cyclic amino, hydroxy, acyloxy selected from alkanoyloxy or benzoyloxy, cyano, carbamoyl, carbamoyl substituted by lower alkyl, cyclic aminocarbonyl, carboxy, lower alkoxycarbonyl, aralkyloxycarbonyl, cycloalkyl or lower alkylcarbonyl; and

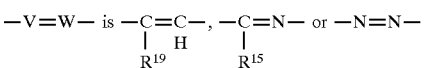

wherein $R^{15}$ is lower alkyl and $R^{19}$ is hydrogen atom or lower alkyl, or a salt thereof; wherein the optionally substituted aryl is an aryl which may have one or more substituents selected from the group consisting of halogen atom, lower alkyl, lower alkoxy, aralkyloxy, methylenedioxy, haloalkyl, haloalkyloxy, halolalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the optionally substituted heteroaryl is an aromatic heterocyclic group selected from the group consisting of pyridyl, thienyl, thiazolyl and isoxazolyl, which may have one or more substituents selected from the group consisting of halogen atom, lower alkyl, lower alkoxy, aralkyloxy, methylenedioxy, haloalkyl, haloalkyloxy, haloalkylsulfonylamino, hydroxy, nitro, amino, alkylamino, dialkylamino, formylamino, acylamino wherein the acyl moiety is alkanoyl or benzoyl, alkylsulfonylamino, bisalkylsulfonylamino, cyano, alkylsulfonyl, acyl which is alkanoyl or benzoyl, acyloxy wherein the acyl moiety is alkanoyl or benzoyl optionally having, on the ring, 1 to 3 substituents selected from the group consisting of halogen atom, lower alkyl, lower alkoxy, haloalkyl and hydroxy, and aralkyl optionally having, on the ring, 1 to 3 substituents selected from the group consisting of halogen atom, lower alkyl, lower alkoxy and hydroxy;

the cyclic amino is a cyclic amino selected from the group consisting of pyrrolidinyl, piperidino, morpholino, thiomorpholino and piperazinyl, wherein lower alkyl or aralkyl may substitute the 4-position nitrogen atom of piperazinyl; and the cyclic aminocarbonyl is a cyclic aminocarbonyl selected from the group consisting of pyrrolidinylcarbonyl, piperidinocarbonyl, morpholinocarbonyl, thiomorpholinocarbonyl and piperazinylcarbonyl, wherein lower alkyl or aralkyl may substitute the 4-position nitrogen atom of piperazinylcarbonyl.

29. The acylhydrazotriazepine compound of claim 28, wherein the ring A is

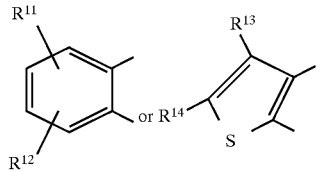

wherein $R^{11}$, $R^{12}$, $R^{13}$ and $R^{14}$ are as defined in claim 28, $R^1$ is an optionally substituted aryl wherein the aryl group is phenyl, and $R^2$ and $R^4$ are both hydrogen atom, or a salt thereof.

30. An alkylthiotriazepine compound of, which is a member selected from the group consisting of 5-(4-chlorophenyl)-3-(3,4-dimethoxybenzyl)-2-methylthio-3H-benzo [e][1,2,4]triazepine, 3-(4-methoxybenzyl)-2-methylthio-5-phenyl-3H-benzo [e][1,2,4]triazepine, 7-chloro-3-(4-methoxybenzyl)-2-methylthio-5-phenyl-3H-benzo[e][1,2,4]triazepine, 3-(4-methoxybenzyl)-8-methyl-2-methylthio-5-phenyl-3H-benzo[e][1,2,4]triazepine 3-(4-methoxybenzyl)-7-nitro-2-methylthio-5-phenyl-3H-benzo[e][1,2,4]triazepine, 3-(4-methoxybenzyl)-5-(4-methylphenyl)-2-methylthio-3H-benzo[e][1,2,4]triazepine, 7-chloro-5-(2-chlorophenyl)-3-(4-methoxybenzyl)-2-methylthio-3H-benzo[e][1,2,4]triazepine, 5-(4-chlorophenyl)-2-methylthio-3-(pyridin-3-ylmethyl)-3H-benzo [e][1,2,4]triazepine, 4-(4-chlorophenyl)-6-(4-methoxybenzyl)-2,3-dimethyl-7-methylthio-6H-1-thia-5,6,8-triazaazulene, 4-(4-chlorophenyl)-2-ethyl-6-(4-methoxybenzyl)-7-methylthio-6H-1-thia-5,6,8-triazaazulene, 6-(4-methoxybenzyl)-2-methyl-7-methylthio-4-phenyl-6H-1-thia-5,6,8-triazaazulene, 6-(4-methoxybenzyl)-2,3-dimethyl-7-methylthio-4-phenyl-6H-1-thia-5,6,8-triazaazulene, 2-ethyl-6-(4-methoxybenzyl)-7-methylthio-4-phenyl-6H-1-thia-5,6,8-triazaazulene, 6-(4-methoxybenzyl)-4-(4-methoxyphenyl)-2,3-dimethyl-7-methylthio-6H-1-thia-5,6,8-triazaazulene, 4-(2-chlorophenyl)-2,3-dimethyl-7-methylthio-6-(pyridin-4-ylmethyl)-6H-1-thia-5,6,8-triazaazulene, and 5-(4-chlorophenyl)-3-(4-methoxybenzyl)-2-methylthio-3H-benzo[e][1,2,4]triazepine, or a salt thereof.

31. A triazepinethione compound of, which is a member selected from the group consisting of 5-(4chlorophenyl)-3-(3,4-dimethoxybenzyl)-1,3-dihydrobenzo[e][1,2,4]triazepine-2-thione, 3-(4-methoxybenzyl)-5-phenyl-1,3-dihydrobenzo[e][1,2,4]triazepine-2-thione, 5-(4-chlorophenyl)-3-(4-methoxybenzyl)-1,3-dihydrobenzo[e][1,2,4]-triazepine-2-thione, 7-chloro-3-(4-methoxybenzyl)-5-phenyl-1,3-dihydrobenzo[e][1,2,4]-triazepine-2-thione, 3-(4-methoxybenzyl)-7-nitro-5-phenyl-1,3-dihydrobenzo [e][1,2,4]-triazepine-2-thione, 3-(4-methoxybenzyl)-5-(4-methylphenyl)-1,3-dihydrobenzo[e][1,2,4]-triazepine-2-thione, 7-chloro-5-(2-chlorophenyl)-3-(4-methoxybenzyl)-1,3-dihydrobenzo[e][1,2,4]triazepine-2-thione, 5-(4-chlorophenyl)-3-(pyridin-3-ylmethyl)-1,3-dihydrobenzo[e][1,2,4]triazepine-2-thione, 4-(4-chlorophenyl)-6-(4-methoxybenzyl)-2,3-dimethyl-6,8-dihydro-1-thia-5,6,8-triazaazulene-7-thione, 4-(4-chlorophenyl)-2-ethyl-6-(4-methoxybenzyl)-6,8-dihydro-1-thia-5,6,8-triazaazulene-7-thione, 6-(4-methoxybenzyl)-2-methyl-4-phenyl-6,8-dihydro-1-thia-5,6,8-triazaazulene-7-thione, 6-(4-methoxybenzyl)-2,3-dimethyl-4-phenyl-6,8-dihydro-1-thia-5,6,8-triazaazulene-7-thione, 2-ethyl-6-(4-methoxybenzyl)-4-phenyl-6,8-dihydro-1-thia-5,6,8-triazaazulene-7-thione, 6-(4-methoxybenzyl)-4-(4-methoxyphenyl)-2,3-dimethyl-6,8-dihydro-1-thia-5,6,8-triazaazulene-7-thione, 4-(2-chlorophenyl)-2,3-dimethyl-6-(pyridin-4-ylmethyl)-6,8-dihydro-1-thia-5,6,8-triazaazulene-7-thione, 3-(4-methoxybenzyl)-8-methyl-5-phenyl-1,3-dihydrobenzo[e][1,2,4]-triazepine-2-thione, and 3-benzyl-5-(4-chlorophenyl)-1,3-dihydrobenzo[e][1,2,4] triazepine-2-thione, or a salt thereof.

32. A acylhydrazotriazepine compound of, which is a member selected from the group consisting of acetic acid N'-[5-(4-chlorophenyl)-3-(3,4-dimethoxybenzyl)-3H-benzo[e][1,2,4]triazepin-2-yl]hydrazide, acetic acid N'-[3-(4-methoxybenzyl)-5-phenyl-3H-benzo [e][1,2,4]-triazepin-2-yl]hydrazide, and acetic acid N'-[3-(4-methoxybenzyl)-8-methyl-5-phenyl-3H-benzo[e][1,2,4]triazepin-2-yl]hydrazide, or a salt thereof.

* * * * *